US010258730B2

(12) United States Patent
Franano et al.

(10) Patent No.: US 10,258,730 B2
(45) Date of Patent: Apr. 16, 2019

(54) BLOOD PUMP SYSTEMS AND METHODS

(71) Applicant: Flow Forward Medical, Inc., Olathe, KS (US)

(72) Inventors: F. Nicholas Franano, Olathe, KS (US); Howard M. Loree, II, Lowell, MA (US); Geoff Tansley, Gold Coast (AU); Steve Woodard, Los Gatos, CA (US); Barrett Hutto, Los Gatos, CA (US)

(73) Assignee: Flow Forward Medical, Inc.

( * ) Notice: Subject to any disclaimer, the term of this patent is extended or adjusted under 35 U.S.C. 154(b) by 0 days.

(21) Appl. No.: 15/607,198

(22) Filed: May 26, 2017

(65) Prior Publication Data
US 2017/0258981 A1 Sep. 14, 2017

Related U.S. Application Data

(63) Continuation of application No. 14/421,767, filed as application No. PCT/US2013/055221 on Aug. 15, (Continued)

(51) Int. Cl.
*A61M 1/36* (2006.01)
*A61M 5/142* (2006.01)
(Continued)

(52) U.S. Cl.
CPC .......... *A61M 1/3653* (2013.01); *A61M 1/101* (2013.01); *A61M 1/1013* (2014.02);
(Continued)

(58) Field of Classification Search
CPC .. A61M 1/3653; A61M 1/1013; A61M 1/101; A61M 1/14236; A61M 1/1008;
(Continued)

(56) References Cited

U.S. PATENT DOCUMENTS 3,487,784 A 1/1970 Rafferty et al.
3,771,910 A 11/1973 Laing
(Continued)

FOREIGN PATENT DOCUMENTS

CN 1228140 A 9/1999
CN 1278188 A 12/2000
(Continued)

OTHER PUBLICATIONS

Translation of Notification of Reasons for Refusal dated Jun. 27, 2017 for corresponding Japanese Patent Applicatio No. 2015-527647.
(Continued)

*Primary Examiner* — Catherine Voorhees
*Assistant Examiner* — Roland Dinga
(74) *Attorney, Agent, or Firm* — Polsinelli PC

(57) ABSTRACT

The present invention relates to a rotary blood pump with a double pivot contact bearing system with an operating range between about 50 mL/min and about 1500 mL/min, wherein the force on the upper bearing is less than 3 N during operating speeds up to 6000 rpm. The rotary blood pump is part of a blood pump system that includes blood conduit(s), a control system with optional sensors, and a power source. Embodiments of the present invention may include elements designed to increase the length of time the rotary blood system can operate effectively in vivo, including wear resistant bearing materials, a rotor back plate for magnetic attraction of the rotor to reduce bearing pivot bearing forces and wear, a rotor size and shape and a bearing gap that combine to create a hydrodynamic bearing effect and reduce bearing pivot bearing forces and wear, improved intravascular conduits with increased resistance to thrombosis, conduit insertion site cuffs to resist infection, and conduit side ports amenable to the easy insertion of guidewire and
(Continued)

catheter-based medical devices to treat conduits and related blood vessels to maintain blood pump system function over time.

39 Claims, 74 Drawing Sheets

Related U.S. Application Data 2013, now Pat. No. 9,662,431, application No. 15/607,198, which is a continuation-in-part of application No. 13/968,070, filed on Aug. 15, 2013, now Pat. No. 9,555,174.

(60) Provisional application No. 61/684,534, filed on Aug. 17, 2012.

(51) Int. Cl.
*A61M 5/168* (2006.01)
*A61M 1/10* (2006.01)

(52) U.S. Cl.
CPC ........ *A61M 1/1031* (2014.02); *A61M 1/1086* (2013.01); *A61M 5/14236* (2013.01); *A61M 5/16804* (2013.01); *A61M 5/16831* (2013.01); *A61M 1/1008* (2014.02); *A61M 1/1036* (2014.02); *A61M 1/3655* (2013.01); *A61M 2205/3334* (2013.01)

(58) Field of Classification Search
CPC ............. A61M 1/1031; A61M 1/1036; A61M 1/3655; A61M 2205/3334
USPC .......................................................... 600/16
See application file for complete search history.

(56) References Cited

U.S. PATENT DOCUMENTS

| | | | |
|---|---|---|---|
| 3,864,055 A | 2/1975 | Kletschka et al. | |
| 4,457,673 A | 7/1984 | Conley et al. | |
| 4,507,048 A | 3/1985 | Belenger et al. | |
| 4,557,673 A | 12/1985 | Chen et al. | |
| 4,606,698 A | 8/1986 | Clausen et al. | |
| 4,665,896 A | 5/1987 | LaForge et al. | |
| 4,756,302 A | 7/1988 | Portner et al. | |
| 4,795,446 A | 1/1989 | Fecht | |
| 4,898,518 A | 2/1990 | Hubbard et al. | |
| 4,984,972 A | 1/1991 | Clausen et al. | |
| 4,994,017 A | 2/1991 | Yozu | |
| 5,006,104 A | 4/1991 | Smith et al. | |
| 5,017,103 A | 5/1991 | Dahl | |
| 5,162,102 A | 11/1992 | Nogawa et al. | |
| 5,178,603 A | 1/1993 | Prince | |
| 5,290,236 A | 3/1994 | Mathewson | |
| 5,300,015 A | 4/1994 | Runge | |
| 5,316,440 A | 5/1994 | Kijima et al. | |
| 5,324,177 A | 6/1994 | Golding et al. | |
| 5,360,317 A | 11/1994 | Clausen et al. | |
| 5,399,074 A | 3/1995 | Nose et al. | |
| 5,443,503 A | 8/1995 | Yamane | |
| 5,458,459 A | 10/1995 | Hubbard et al. | |
| 5,509,900 A | 4/1996 | Kirkman | |
| 5,509,908 A | 4/1996 | Hillstead et al. | |
| 5,527,159 A | 6/1996 | Bozeman, Jr. et al. | |
| D372,921 S | 8/1996 | Ijiri et al. | |
| 5,575,630 A | 11/1996 | Nakazawa et al. | |
| 5,588,812 A | 12/1996 | Taylor et al. | |
| 5,658,136 A | 8/1997 | Mendler | |
| 5,662,711 A | 9/1997 | Douglas | |
| 5,683,231 A | 11/1997 | Nakazawa et al. | |
| 5,707,218 A | 1/1998 | Maher et al. | |
| 5,713,730 A | 2/1998 | Nose et al. | |
| 5,746,575 A | 5/1998 | Westphal et al. | |
| 5,766,207 A | 6/1998 | Potter et al. | |
| 5,803,720 A | 9/1998 | Ohara et al. | |
| 5,851,174 A | 12/1998 | Jarvik et al. | |
| 5,858,003 A | 1/1999 | Atala | |
| 5,863,179 A | 1/1999 | Westphal et al. | |
| 5,890,883 A | 4/1999 | Golding et al. | |
| 5,894,011 A | 4/1999 | Prosl et al. | |
| 5,947,703 A | 9/1999 | Nojiri et al. | |
| 5,947,892 A | 9/1999 | Benkowski et al. | |
| 5,957,672 A | 9/1999 | Aber | |
| 5,989,206 A | 11/1999 | Prosl et al. | |
| 6,015,272 A | 1/2000 | Antaki et al. | |
| 6,050,975 A | 4/2000 | Poirier | |
| 6,093,001 A | 7/2000 | Burgreen et al. | |
| 6,110,139 A | 8/2000 | Loubser | |
| 6,116,862 A | 9/2000 | Rau et al. | |
| 6,152,704 A | 11/2000 | Aboul-Hosn et al. | |
| 6,162,017 A | 12/2000 | Raible | |
| 6,171,078 B1 | 1/2001 | Schob | |
| 6,183,220 B1 | 2/2001 | Ohara et al. | |
| 6,183,412 B1 | 2/2001 | Benkowski et al. | |
| 6,189,388 B1 | 2/2001 | Cole et al. | |
| 6,200,260 B1 | 3/2001 | Bolling | |
| 6,201,329 B1 | 3/2001 | Chen | |
| 6,217,541 B1 | 4/2001 | Yu | |
| 6,227,797 B1 | 5/2001 | Watterson et al. | |
| 6,227,817 B1 | 5/2001 | Paden | |
| 6,234,772 B1 | 5/2001 | Wampler et al. | |
| 6,244,835 B1 | 6/2001 | Antaki et al. | |
| 6,264,601 B1 | 7/2001 | Jassawalla et al. | |
| 6,299,575 B1 | 10/2001 | Bolling | |
| 6,346,071 B1 | 2/2002 | Mussivand | |
| 6,368,075 B1 | 4/2002 | Fremerey | |
| 6,439,845 B1 | 8/2002 | Veres | |
| 6,447,265 B1 | 9/2002 | Antaki et al. | |
| 6,447,266 B2 | 9/2002 | Antaki et al. | |
| 6,623,475 B1 | 9/2003 | Siess | |
| 6,652,447 B2 | 11/2003 | Benkowski et al. | |
| 6,688,861 B2 | 2/2004 | Wampler | |
| 6,692,318 B2 | 2/2004 | McBride | |
| 6,719,791 B1 | 4/2004 | Nusser et al. | |
| 6,742,999 B1 | 6/2004 | Nusser et al. | |
| 6,878,140 B2 | 4/2005 | Barbut | |
| 6,884,210 B2 | 4/2005 | Nose et al. | |
| 6,929,777 B1 | 8/2005 | Litwak et al. | |
| 6,969,345 B2 | 11/2005 | Jassawalla et al. | |
| 6,991,595 B2 | 1/2006 | Burke et al. | |
| 7,059,052 B2 | 6/2006 | Okamura et al. | |
| 7,138,776 B1 | 11/2006 | Gauthier et al. | |
| 7,160,242 B2 | 1/2007 | Yanai | |
| 7,172,550 B2 | 2/2007 | Tsubouchi | |
| 7,229,474 B2 | 6/2007 | Hoffmann et al. | |
| 7,357,425 B2 | 4/2008 | Werth | |
| 7,374,574 B2 | 5/2008 | Nuesser et al. | |
| 7,393,181 B2 | 7/2008 | McBride et al. | |
| 7,396,327 B2 | 7/2008 | Morello | |
| 7,467,929 B2 | 12/2008 | Nusser et al. | |
| 7,476,077 B2 | 1/2009 | Woodard et al. | |
| 7,485,104 B2 | 2/2009 | Kieval | |
| 7,491,163 B2 | 2/2009 | Viole et al. | |
| 7,494,477 B2 | 2/2009 | Rakhorst et al. | |
| 7,572,217 B1 | 8/2009 | Koenig et al. | |
| 7,575,423 B2 | 8/2009 | Wampler | |
| 7,578,782 B2 | 8/2009 | Miles et al. | |
| 7,588,530 B2 | 9/2009 | Heilman et al. | |
| 7,614,997 B2 | 11/2009 | Bolling | |
| 7,614,998 B2 | 11/2009 | Gross et al. | |
| 7,699,586 B2 | 4/2010 | LaRose et al. | |
| 7,736,296 B2 | 6/2010 | Siess et al. | |
| 7,762,977 B2 | 7/2010 | Porter et al. | |
| 9,155,827 B2 | 10/2015 | Franano | |
| 9,539,380 B2 | 1/2017 | Franano | |
| 9,555,174 B2 * | 1/2017 | Franano ................ A61M 1/101 |
| 9,662,431 B2 * | 5/2017 | Franano ............... A61M 1/3653 |
| 2001/0001814 A1 | 5/2001 | Estabrook et al. | |
| 2001/0004435 A1 | 6/2001 | Woodard et al. | |
| 2002/0009242 A1 | 1/2002 | Okamura et al. | |
| 2002/0026944 A1 | 3/2002 | Aboul-Hosn et al. | |
| 2002/0076322 A1 | 6/2002 | Maeda et al. | |

(56) References Cited

U.S. PATENT DOCUMENTS

| | | |
|---|---|---|
| 2002/0161274 A1 | 10/2002 | French et al. |
| 2002/0176798 A1 | 11/2002 | Linker et al. |
| 2003/0163078 A1 | 8/2003 | Fallen et al. |
| 2003/0233021 A1 | 12/2003 | Nose et al. |
| 2003/0233144 A1 | 12/2003 | Antaki et al. |
| 2004/0039243 A1 | 2/2004 | Beamson et al. |
| 2004/0047737 A1 | 3/2004 | Nose et al. |
| 2004/0133173 A1 | 7/2004 | Edoga et al. |
| 2004/0171905 A1 | 9/2004 | Yu et al. |
| 2004/0183305 A1 | 9/2004 | Fisher |
| 2004/0186461 A1 | 9/2004 | DiMatteo |
| 2004/0234397 A1 | 11/2004 | Wampler |
| 2005/0033107 A1 | 2/2005 | Tsubouchi |
| 2005/0038408 A1 | 2/2005 | von Segesser |
| 2005/0085684 A1 | 4/2005 | Rakhorst et al. |
| 2005/0113631 A1 | 5/2005 | Bolling et al. |
| 2005/0277964 A1 | 12/2005 | Brenneman et al. |
| 2006/0064159 A1 | 3/2006 | Porter et al. |
| 2006/0122552 A1 | 6/2006 | O'Mahony |
| 2006/0142633 A1 | 6/2006 | Lane et al. |
| 2006/0222533 A1 | 10/2006 | Reeves et al. |
| 2007/0135775 A1 | 6/2007 | Edoga et al. |
| 2007/0249986 A1 | 10/2007 | Smego |
| 2007/0253842 A1 | 11/2007 | Horvath et al. |
| 2008/0114339 A1 | 5/2008 | McBride et al. |
| 2008/0124231 A1 | 5/2008 | Yaegashi |
| 2008/0132748 A1 | 6/2008 | Shifflette |
| 2008/0240947 A1 | 10/2008 | Allaire et al. |
| 2008/0269880 A1 | 10/2008 | Jarvik |
| 2008/0281250 A1 | 11/2008 | Bergsneider et al. |
| 2009/0024072 A1 | 1/2009 | Criado et al. |
| 2009/0041595 A1 | 2/2009 | Garzaniti et al. |
| 2009/0156885 A1 | 6/2009 | Morello et al. |
| 2009/0209921 A1 | 8/2009 | Claude et al. |
| 2009/0234261 A1 | 9/2009 | Singh |
| 2010/0041939 A1 | 2/2010 | Siess |
| 2010/0204539 A1 | 8/2010 | Tansley et al. |
| 2010/0210990 A1 | 8/2010 | Lyons et al. |
| 2010/0222634 A1 | 9/2010 | Poirier |
| 2011/0002794 A1 | 1/2011 | Haefliger et al. |
| 2011/0196190 A1 | 8/2011 | Farnan et al. |
| 2011/0201990 A1 | 8/2011 | Franano |
| 2011/0243759 A1 | 10/2011 | Ozaki et al. |
| 2011/0257577 A1 | 10/2011 | Lane et al. |
| 2012/0065652 A1 | 3/2012 | Cully et al. |
| 2013/0338559 A1 | 12/2013 | Franano et al. |
| 2014/0296615 A1 | 10/2014 | Franano |
| 2014/0296767 A1 | 10/2014 | Franano |
| 2015/0157787 A1 | 6/2015 | Cully et al. |
| 2015/0209498 A1 | 7/2015 | Franano et al. |
| 2016/0030647 A1 | 2/2016 | Franano |
| 2016/0030648 A1 | 2/2016 | Franano |
| 2017/0112993 A1 | 4/2017 | Franano |

FOREIGN PATENT DOCUMENTS

| | | |
|---|---|---|
| CN | 101024098 A | 8/2007 |
| CN | 101932837 A | 12/2010 |
| CN | 102844074 A | 12/2012 |
| EP | 1 825 872 A2 | 8/2007 |
| JP | 04-224760 A | 8/1992 |
| JP | 2696070 B2 | 9/1997 |
| JP | 2874060 B2 | 1/1999 |
| JP | 2000-102604 A | 4/2000 |
| JP | 3689567 B2 | 4/2000 |
| JP | 3085835 B2 | 7/2000 |
| JP | 2000-229125 A | 8/2000 |
| JP | 2005-058617 A | 3/2005 |
| JP | 4440499 B2 | 8/2005 |
| JP | 2007-516740 A | 6/2007 |
| JP | 2007-222670 A | 9/2007 |
| JP | 2011-502560 A | 1/2011 |
| RU | 2368811 C2 | 9/2009 |
| WO | 86/01395 A1 | 3/1986 |
| WO | 91/08783 A1 | 6/1991 |
| WO | 02/28314 A2 | 4/2002 |
| WO | 2004/043519 A1 | 5/2004 |
| WO | 2005/046779 A2 | 5/2005 |
| WO | 2008/136979 A1 | 11/2008 |
| WO | 2009/059371 A2 | 5/2009 |
| WO | 2009/064879 A2 | 5/2009 |
| WO | 2011/103356 A1 | 8/2011 |
| WO | 2013/025821 A2 | 2/2013 |
| WO | 2013/025826 A1 | 2/2013 |
| WO | 2014/028787 A2 | 2/2014 |
| WO | 2017/190155 A2 | 11/2017 |

OTHER PUBLICATIONS

Bennett et al., "Pump-induced haemolysis: a comparison of short-term ventricular assist devices," Perfusion, 2004, pp. 107-111, vol. 19, No. 2.
Choy et al., "A novel strategy for increasing wall thickness of coronary venules prior to retroperfusion," American Journal of Physiology—Heart and Circulatory Physiology, 2006, pp. H972-H978, vol. 291.
Supplementary European Search Report from related European Patent Application No. 11745274.8, dated Aug. 25, 2015; 9 pgs.
Office Action from related European Patent Application No. 11745274.8, dated May 9, 2016; 10 pgs.
Office Action from related European Patent Application No. 11745274.8, dated May 11, 2017; 4 pgs.
Supplementary European Search Report from related European Patent Application No. 12823591.8, dated Feb. 18, 2015; 7 pgs.
Office Action from related European Patent Application No. 12823591.8, dated Oct. 20, 2017; 11 pgs.
Extended European Search Report from related European Patent Application No. 12823758.3, dated Jun. 29, 2015; 10 pgs.
Supplementary European Search Report from related European Patent Application No. 13829746.0, dated May 9, 2016; 7 pgs.
Gujja et al., "Interventional Therapies for Heart Failure," SIS 2007 Yearbook, Chapter 13, pp. 65-75.
International Search Report and Written Opinion from related International Application No. PCT/US2011/025331, dated May 9, 2011; 22 pgs.
International Search Report and Written Opinion from related International Application No. PCT/US2012/050978, dated Feb. 8, 2013; 17 pgs.
International Search Report and Written Opinion from related International Application No. PCT/US2012/050983, dated Jan. 2, 2013; 14 pgs.
International Search Report and Written Opinion from related International Application No. PCT/US2013/055221, dated Feb. 3, 2014; 35 pgs.
International Search Report and Written Opinion from related International Application No. PCT/US2017/030476, dated Oct. 30, 2017; 55 pgs.
James et al., "Evaluation of Hemolysis in the VentrAssist Implantable Rotary Blood Pump," Artificial Organs, 2003, pp. 108-113, vol. 27, No. 1.
Jiang et al., "A novel vein graft model: adaptation to differential flow environments," American Journal of Physiology—Heart and Circulatory Physiology, 2004, pp. H240-H245, vol. 286.
Kawahito et al., "Hemolysis in Different Centrifugal Pumps," Artificial Organs, 1997, pp. 323-326, vol. 21, No. 4.
Kelly et al., "Characteristics of the response of the iliac artery to wall shear stress in the anaesthetized pig," J. Physiol, 2007, pp. 731-743, vol. 585.2.
Moisiuk et al., "Permanent vascular access for haemodialysis: modern lines," Nephrology and Dialysis, 2002, 1, 4, pp. 14-24.
Office Action from related U.S. Appl. No. 13/030,054, dated Aug. 27, 2015; 15 pgs.
Office Action from related U.S. Appl. No. 13/030,054, dated Nov. 6, 2014; 32 pgs.
Office Action from related U.S. Appl. No. 13/030,054, dated Jun. 6, 2013; 28 pgs.
Office Action from related U.S. Appl. No. 13/030,054, dated Nov. 21, 2012; 19 pgs.

(56) References Cited

OTHER PUBLICATIONS

Office Action from related U.S. Appl. No. 13/968,070, dated Feb. 5, 2016; 18 pgs.
Office Action from related U.S. Appl. No. 13/968,070, dated Jul. 8, 2015; 14 pgs.
Office Action from related U.S. Appl. No. 14/239,251, dated Feb. 8, 2016; 13 pgs.
Office Action from related U.S. Appl. No. 14/421,767, dated Jan. 21, 2016; 34 pgs.
Office Action from related U.S. Appl. No. 14/239,248, dated Sep. 8, 2017; 16 pgs.
Office Action from related U.S. Appl. No. 15/607,198, dated Nov. 13, 2017; 8 pgs.
Office Action from related Australian Patent Application No. 2011217974, dated Jul. 4, 2014; 5 pgs.
Office Action from related Australian Patent Application No. 2012296568, dated Apr. 13, 2016; 3 pgs.
Office Action from related Australian Patent Application No. 2012296563, dated Apr. 14, 2016; 3 pgs.
Office Action from related Australian Patent Application No. 2013302455, dated Oct. 17, 2016; 4 pgs.
Office Action from related Australian Patent Application No. 2015258177, dated Apr. 6, 2017; 4 pgs.
Office Action from related Australian Patent Application No. 2017210640, dated Nov. 2, 2017; 3 pgs.
Office Action from related Canadian Patent Application No. 2,790,194, dated Feb. 8, 2017; 4 pgs.
First Office Action from related Chinese Patent Application No. 201180019380.8, dated Mar. 19, 2014; 8 pgs.
Second Office Action and Search Report from related Chinese Patent Application No. 201180019380.8, dated Oct. 23, 2014; 21 pgs.
Third Office Action from related Chinese Patent Application No. 201180019380.8, dated Jun. 26, 2015; 8 pgs.
Fourth Office Action from related Chinese Patent Application No. 201180019380.8, dated Dec. 22, 2015; 7 pgs.
First Office Action and Search Report from related Chinese Patent Application No. 2013103357853, dated Mar. 30, 2015; 23 pgs.
Second Office Action from related Chinese Patent Application No. 2013103357853, dated Feb. 2, 2016; 7 pgs.
Third Office Action from related Chinese Patent Application No. 201310335785.3, dated Sep. 19, 2016; 6 pgs.
First Office Action and Search Report from related Chinese Patent Application No. 201280050718.0, dated Nov. 4, 2015; 27 pgs.
Second Office Action and Search Report from related Chinese Patent Application No. 201280050718.0, dated Sep. 14, 2016; 24 pgs.
First Office Action and Search Report from related Chinese Patent Application No. 2012800507123, dated Apr. 5, 2016; 18 pgs.

Second Office Action from related Chinese Patent Application No. 2012800507123, dated Mar. 14, 2017; 6 pgs.
First Office Action from related Chinese Patent Application No. 201380053944.9, dated Jul. 5, 2016; 8 pgs.
Second Office Action and Search Report from related Chinese Patent Application No. 201380053944.9, dated May 3, 2017; 21 pgs.
Office Action from related Israel Patent Application No. 221503, dated May 15, 2015; 3 pgs.
Office Action from related Israel Patent Application No. 230992, dated Apr. 6, 2017; 3 pgs.
Office Action from related Israel Patent Application No. 230991, dated May 6, 2017; 3 pgs.
Office Action from related Japanese Patent Application No. 2012-554038, dated Nov. 4, 2014; 7 pgs.
Office Action from related Japanese Patent Application No. 2014-526181, dated Jun. 28, 2016; 6 pgs.
Office Action from related Japanese Patent Application No. 2014-526181, dated Jan. 31, 2017; 8 pgs.
Office Action from related Japanese Patent Application No. 2014-526178, dated Jun. 28, 2016; 5 pgs.
Office Action from related Japanese Patent Application No. 2015-214417, dated Sep. 27, 2016; 7 pgs.
Office Action from related Japanese Patent Application No. 2015-214417, dated Aug. 22, 2017; 11 pgs.
Office Action from related Korean Patent Application No. 10-2012-7022798, dated May 22, 2017; 2 pgs.
Office Action from related Russian Patent Application No. 2014109960, dated Aug. 3, 2016; 8 pgs.
Office Action from related Russian Patent Application No. 2014110029, dated Aug. 28, 2015; 3 pgs.
Office Action from related Russian Patent Application No. 2014110029, dated Dec. 14, 2016; 8 pgs.
Decision of Grant from related Russian Patent Application No. 2014110029, dated Nov. 24, 2017; 18 pgs.
Office Action from related Russian Patent Application No. 2015108946, dated May 27, 2015; 4 pgs.
Office Action from related Russian Patent Application No. 2015108946, dated Jul. 27, 2017; 5 pgs.
Office Action and Search Report from related Russian Patent Application No. 2015108946, dated Oct. 31, 2017; 14 pgs.
Office Action and Search Report from related Taiwan Patent Application No. 102129610, dated Jun. 14, 2017; 12 pgs.
Pries et al., "Remodeling of Blood Vessels: Responses of Diameter and Wall Thickness to Hemodynamic and Metabolic Stimuli," Hypertension, 2005, pp. 725-731, vol. 46.
Wiedeman, "Dimensions of Blood Vessels from Distributing Artery to Collecting Vein," Circulation Research, 1963, pp. 375-378, vol. 12.

* cited by examiner

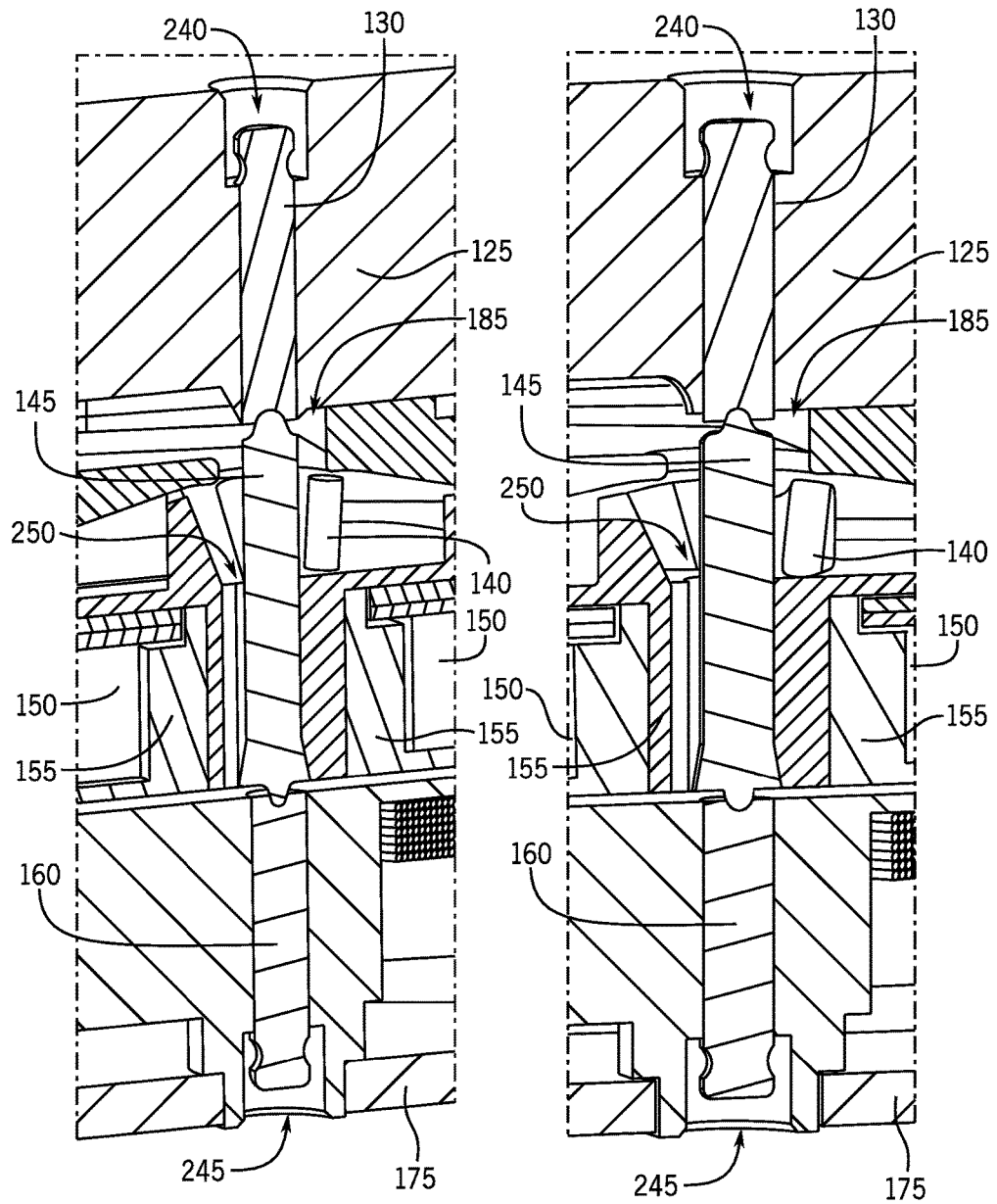

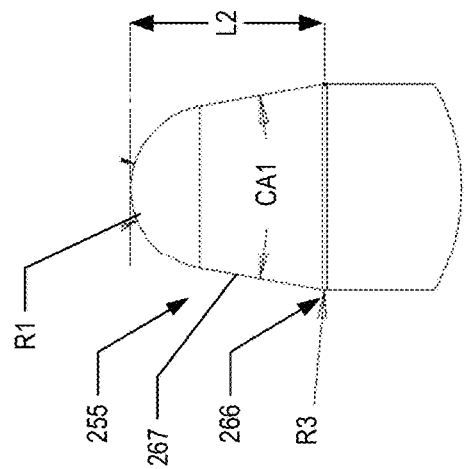
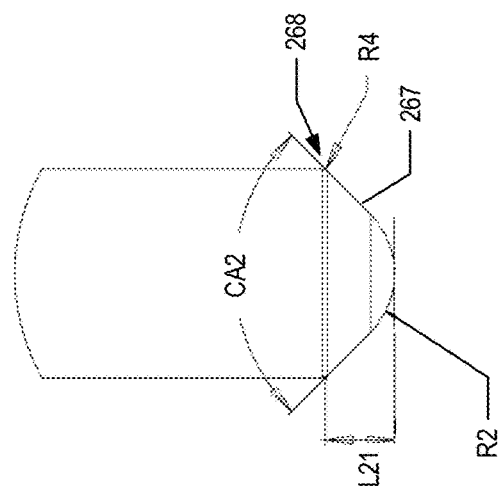
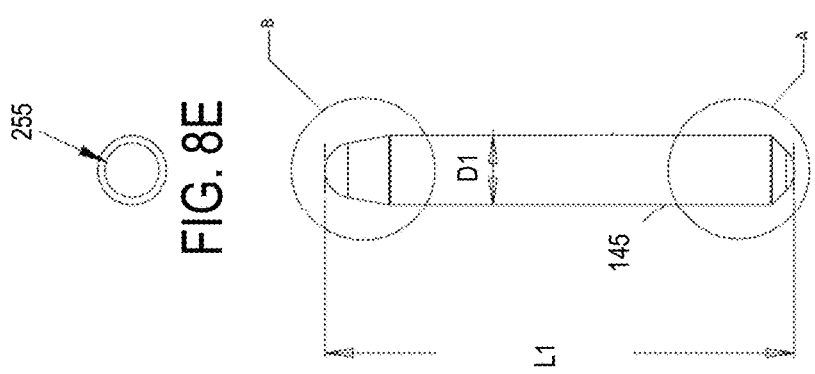

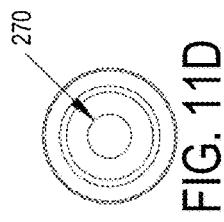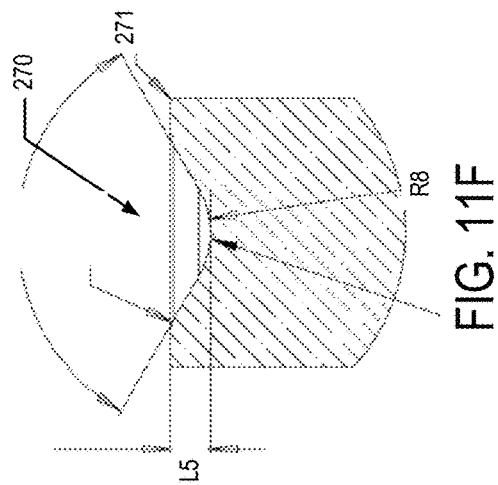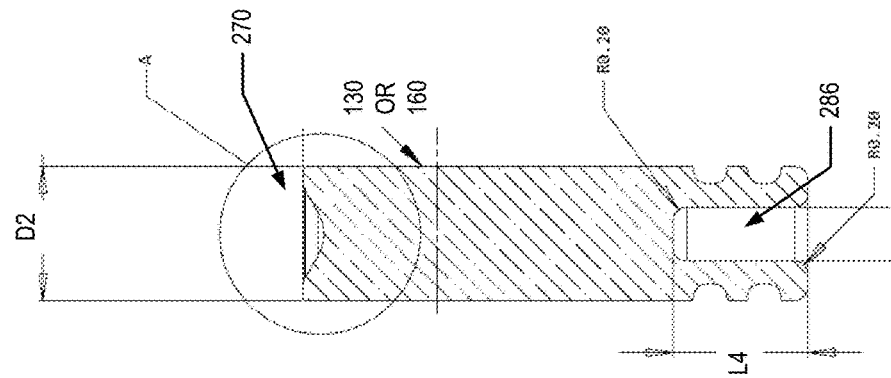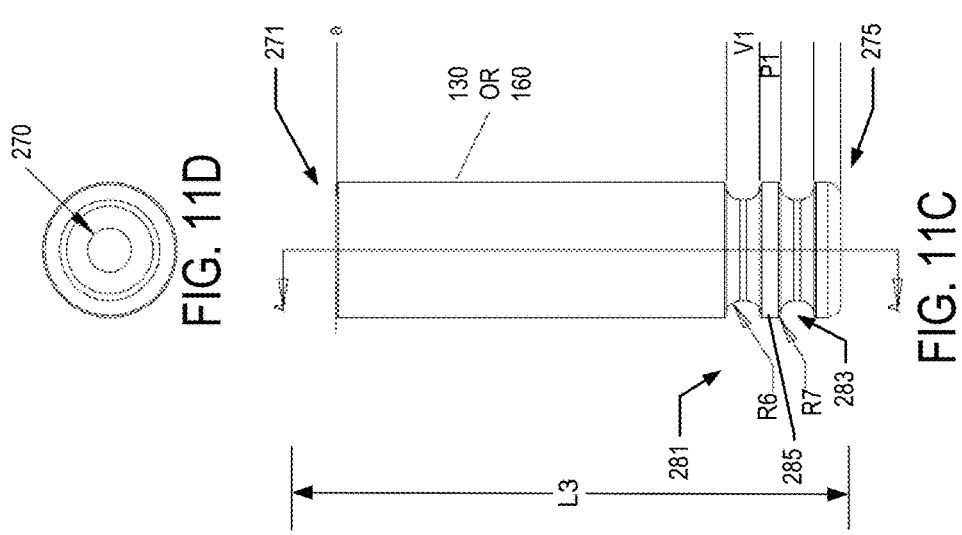

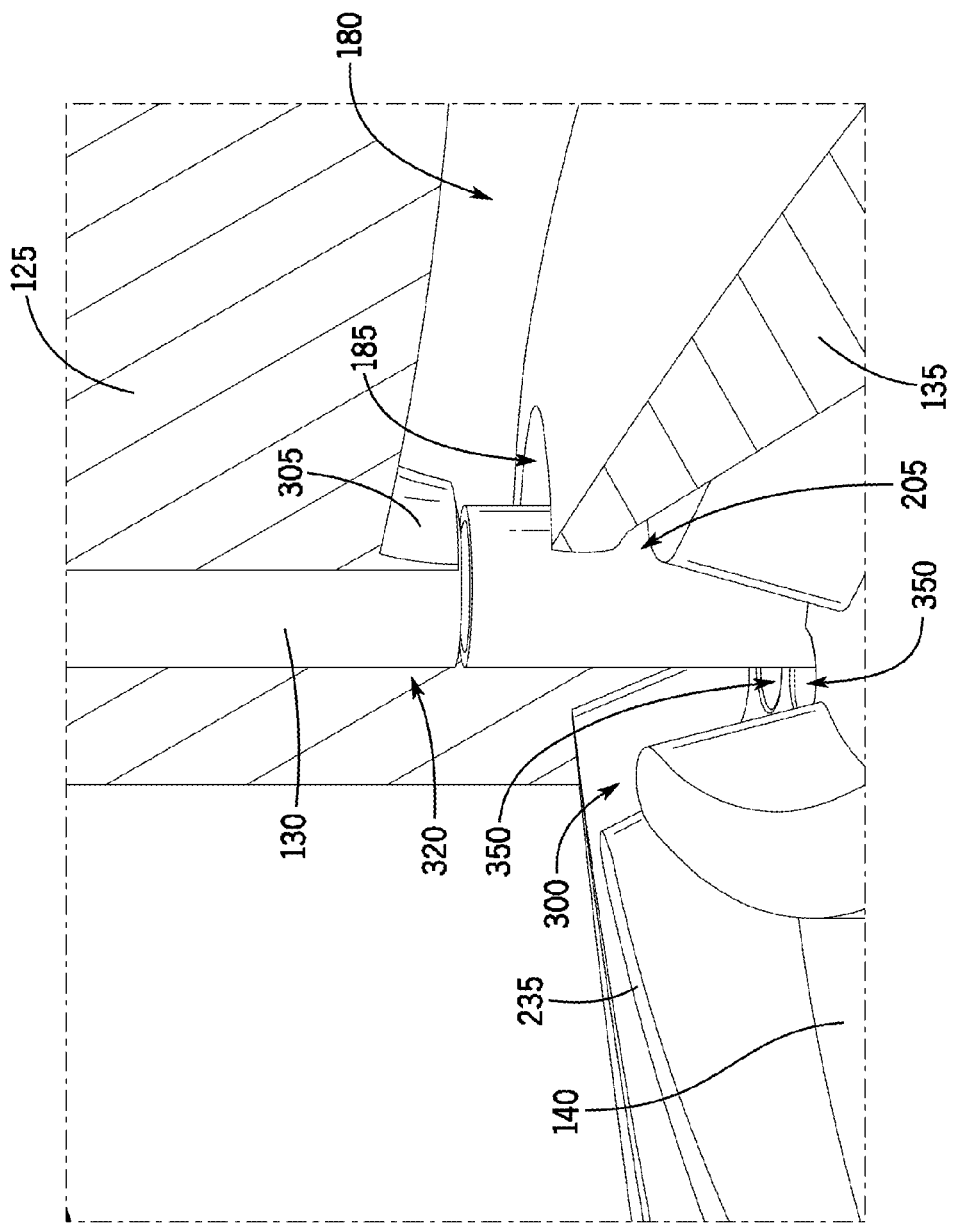

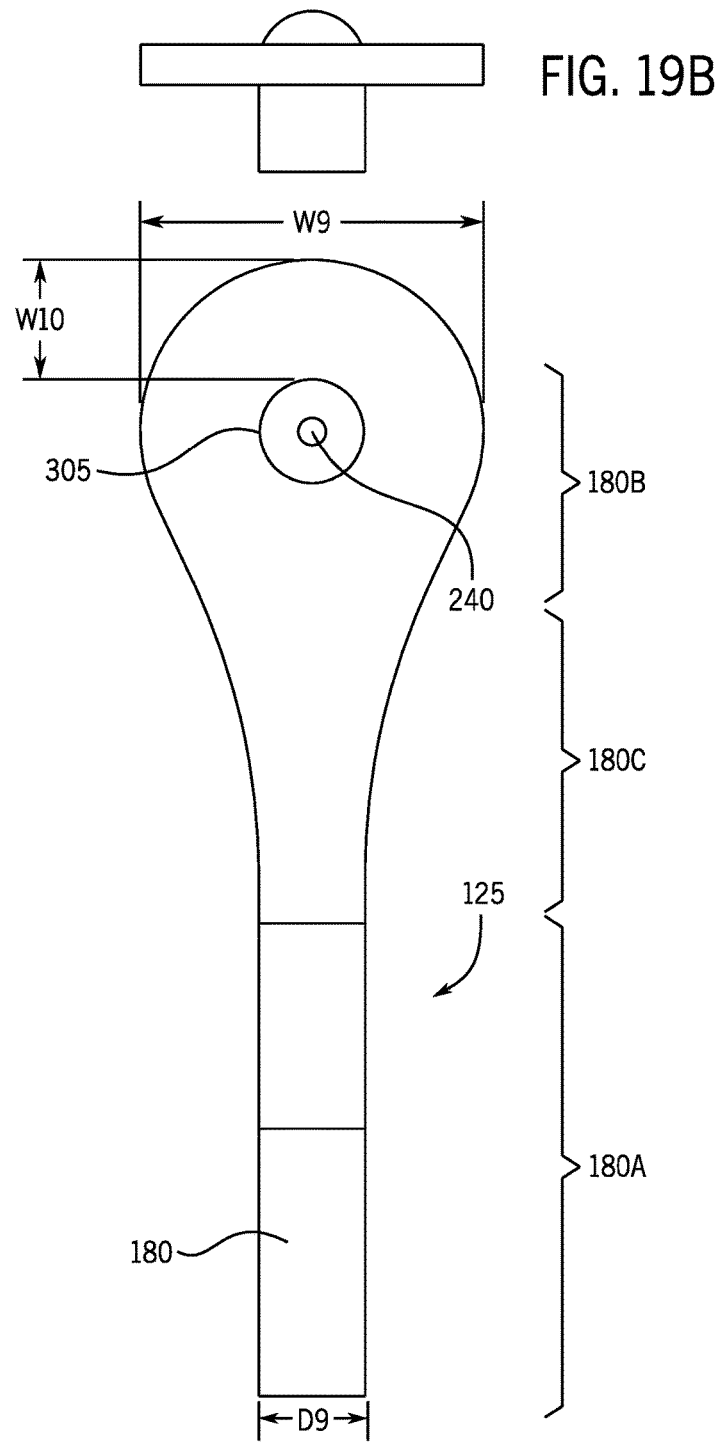

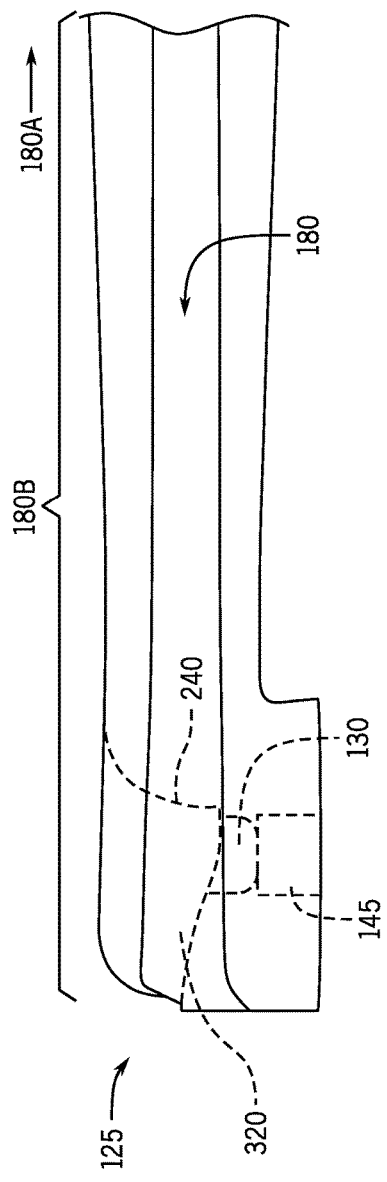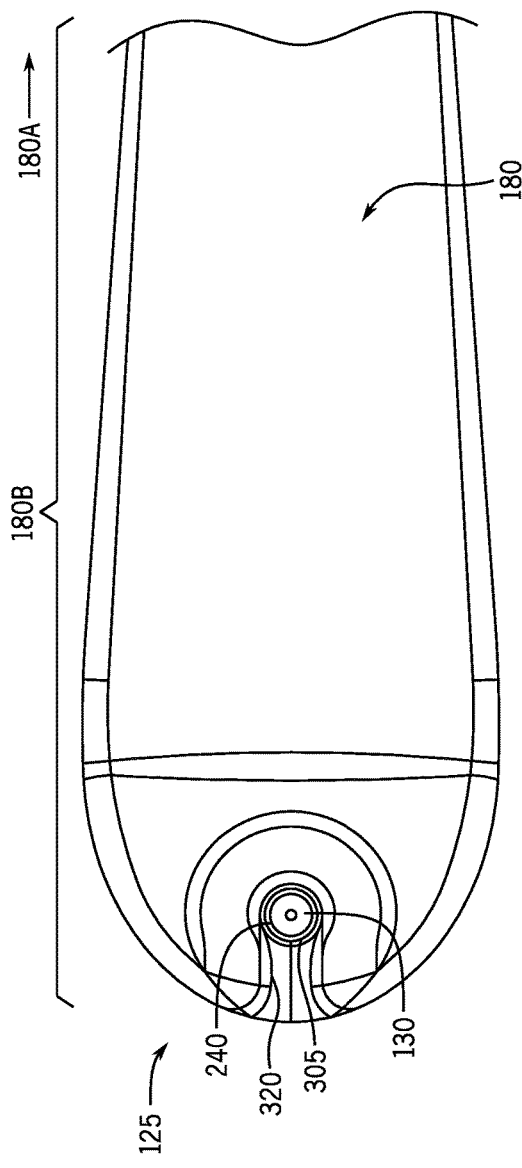

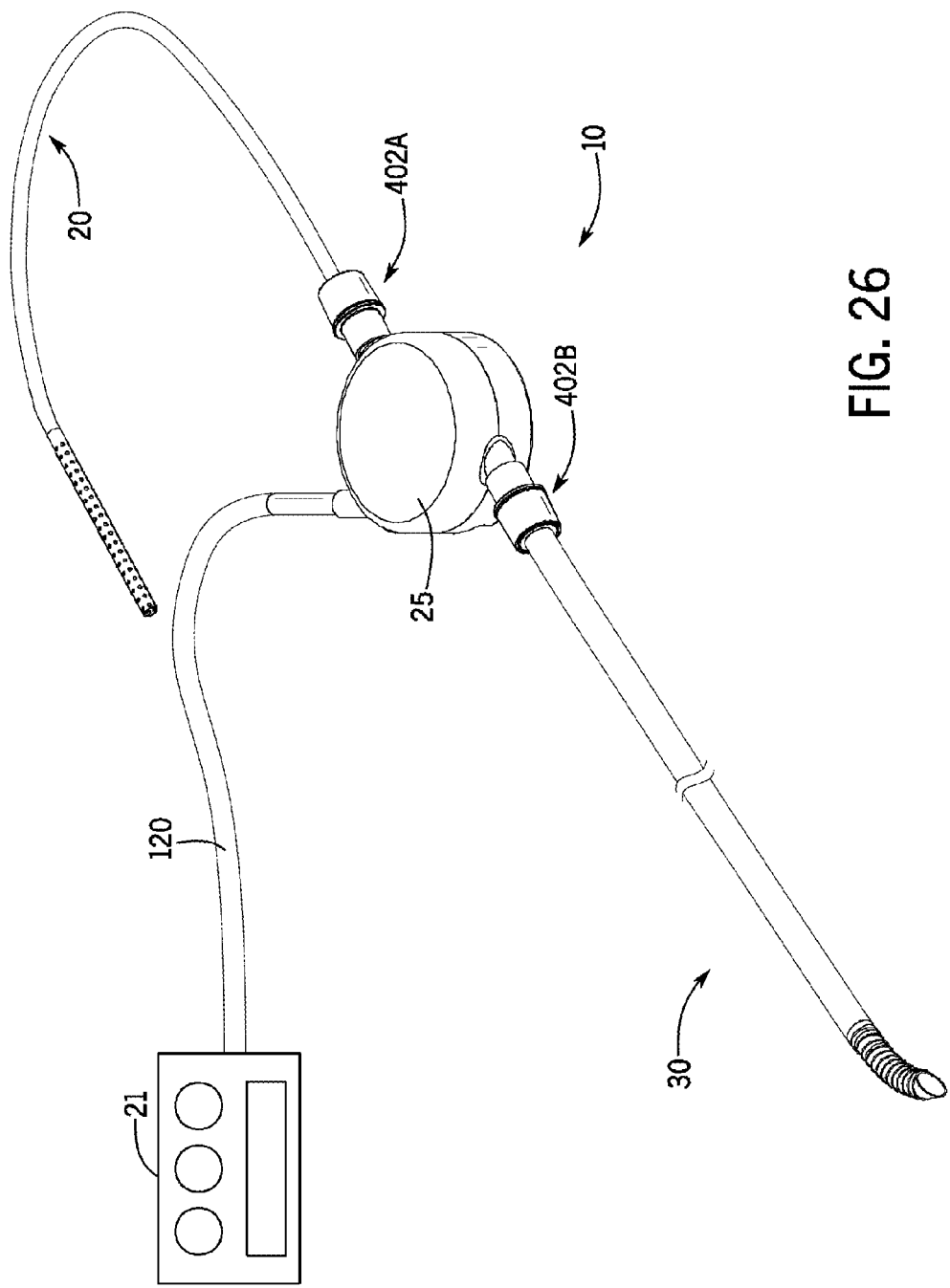

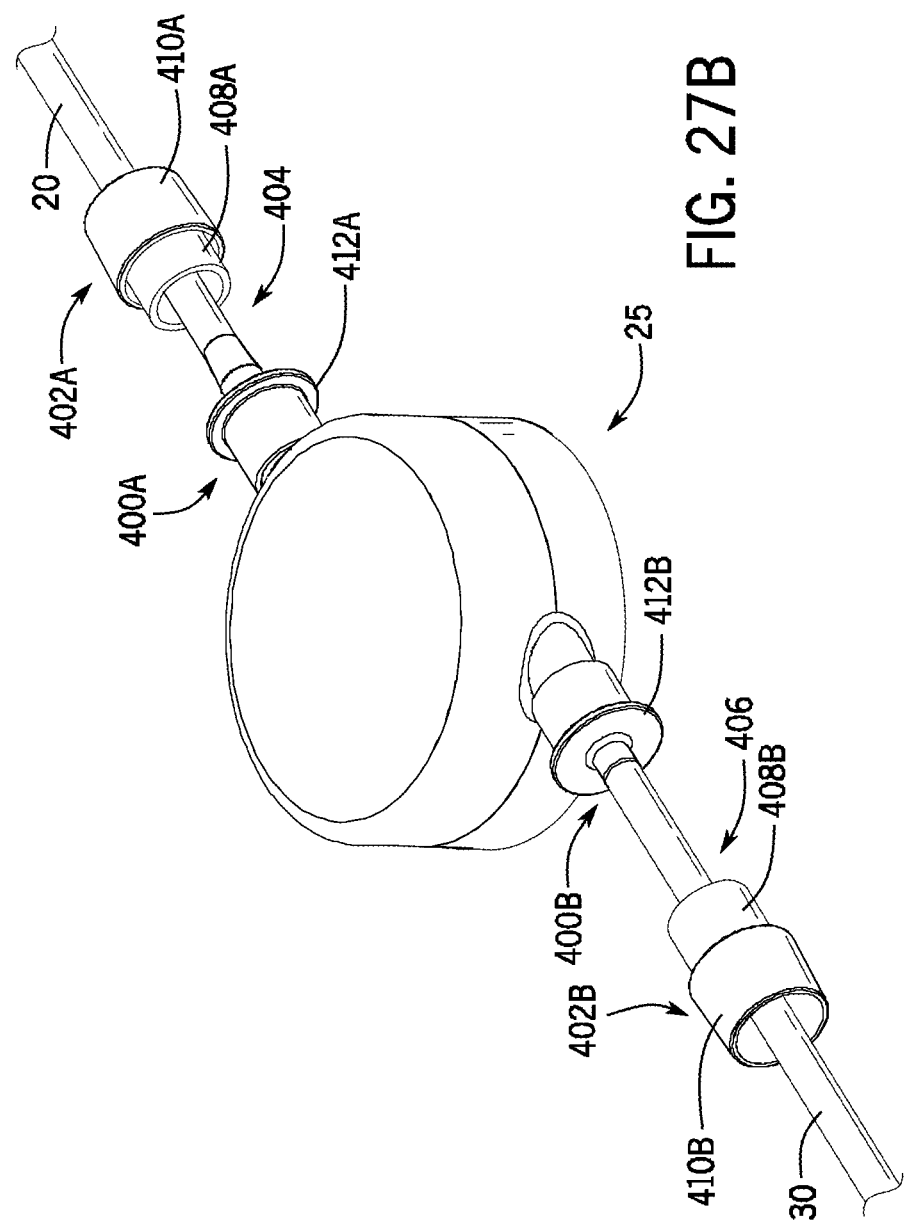

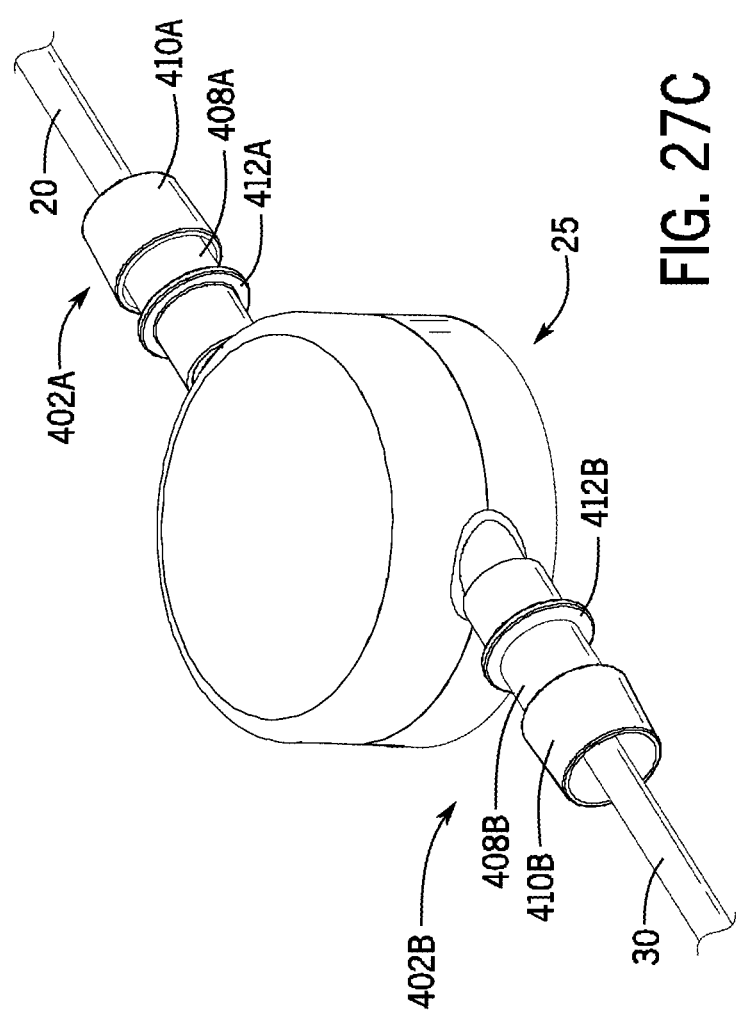

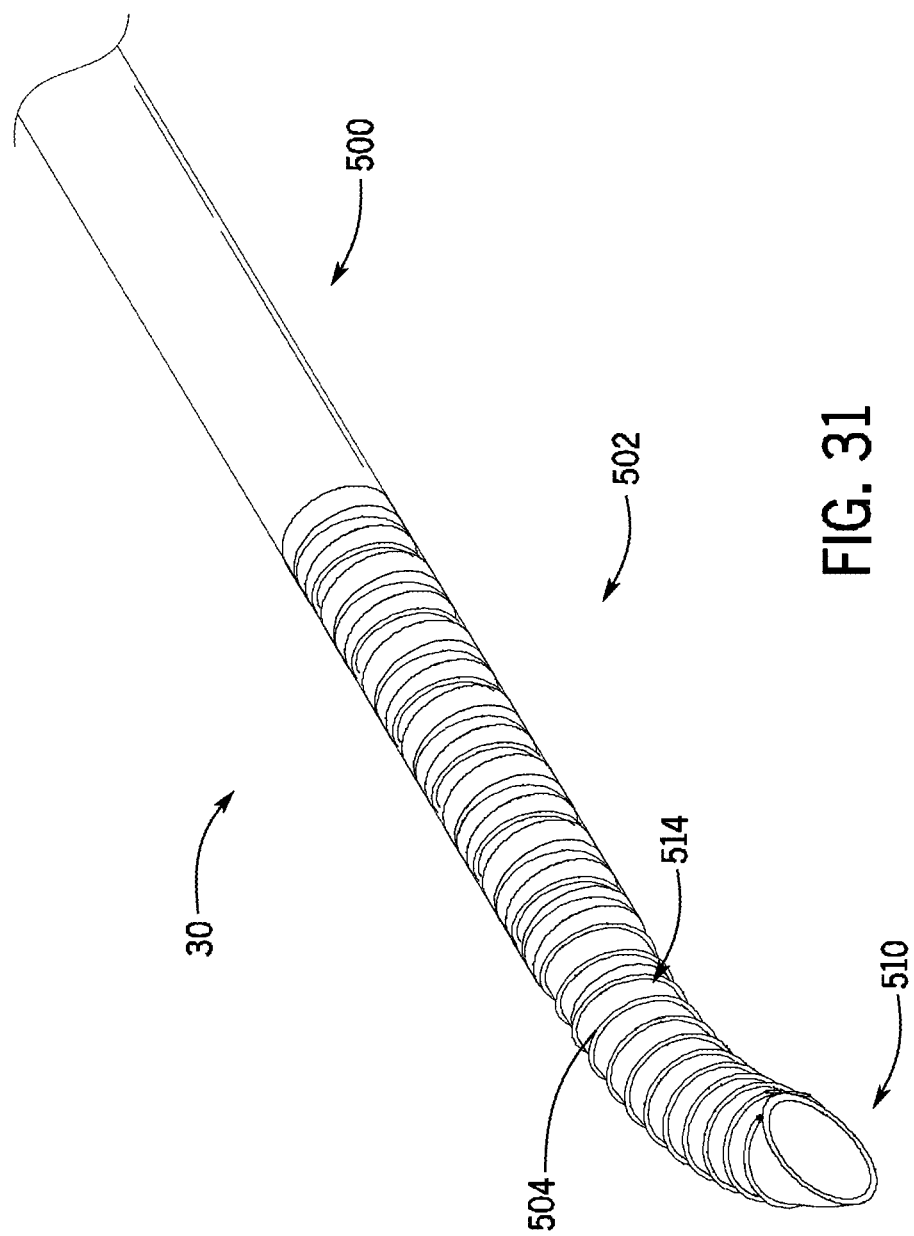

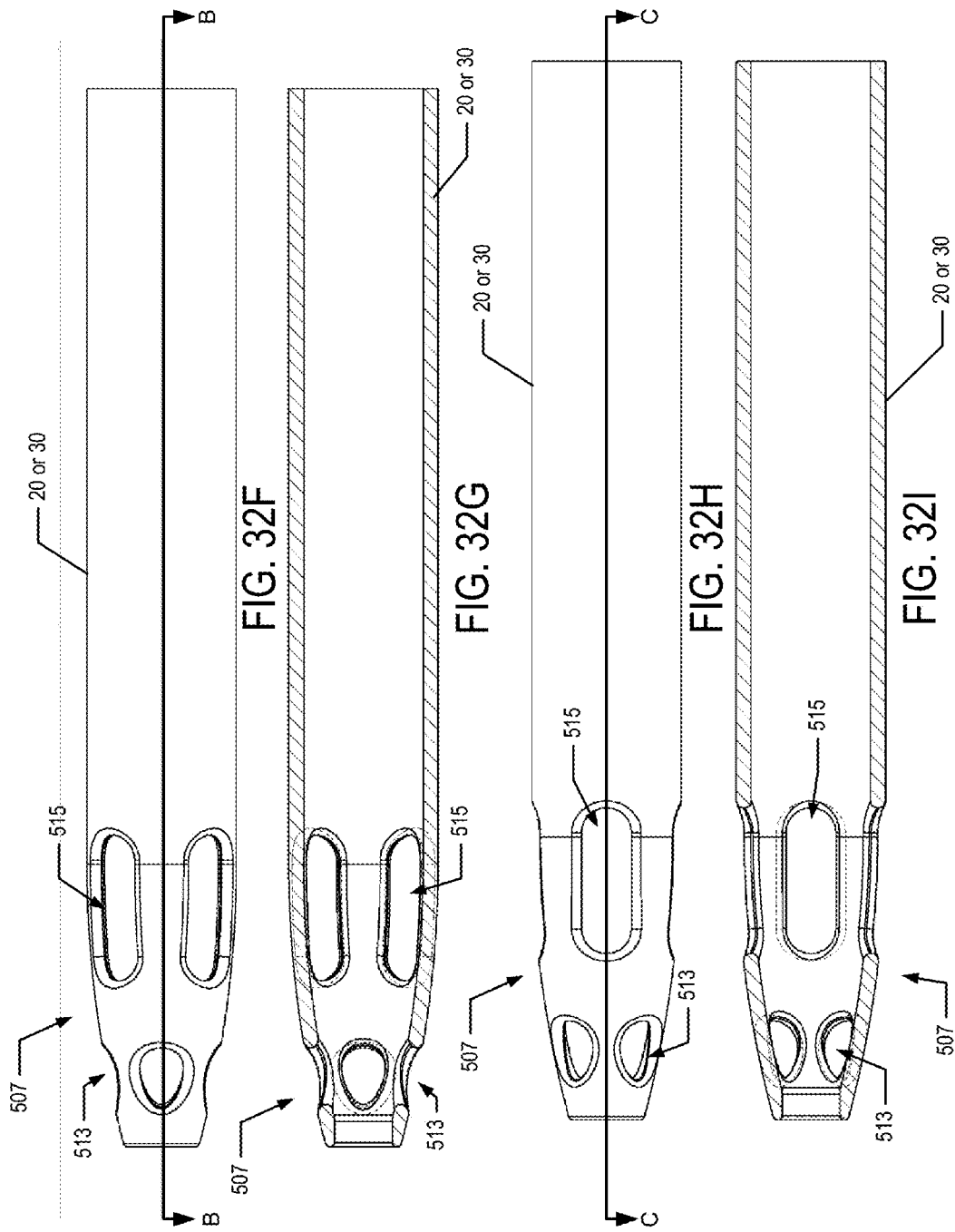

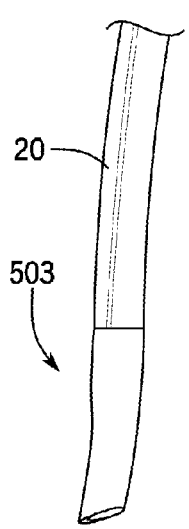 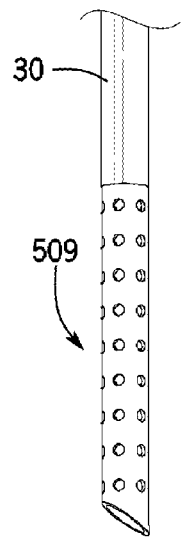 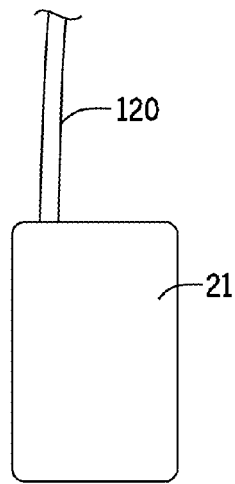
FIG. 45A   FIG. 45B   FIG. 46A
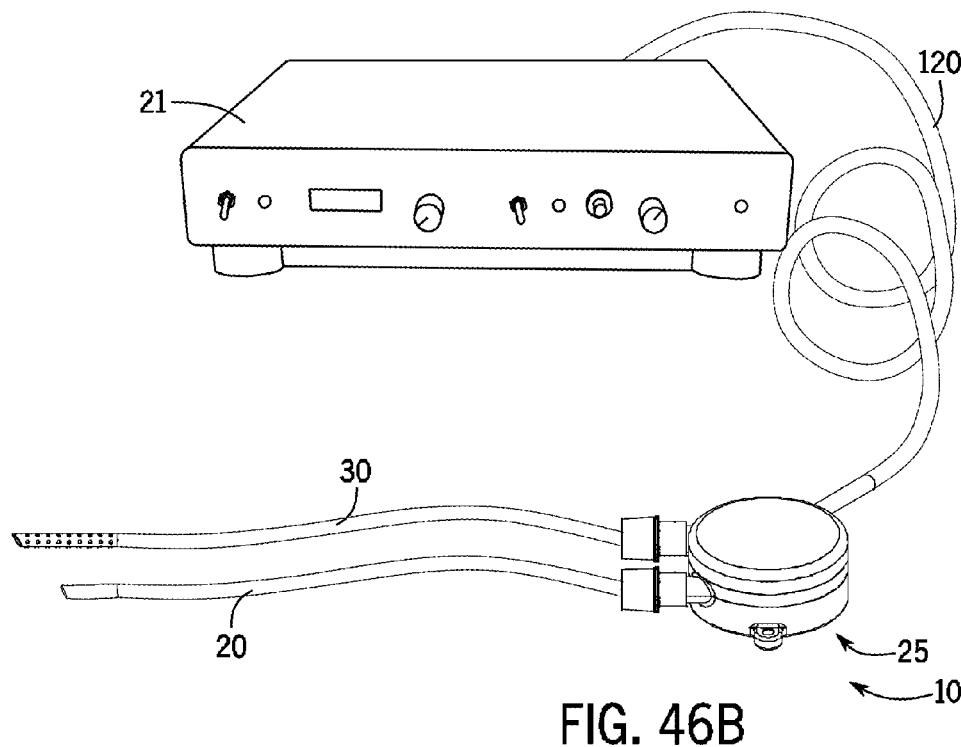
FIG. 46B

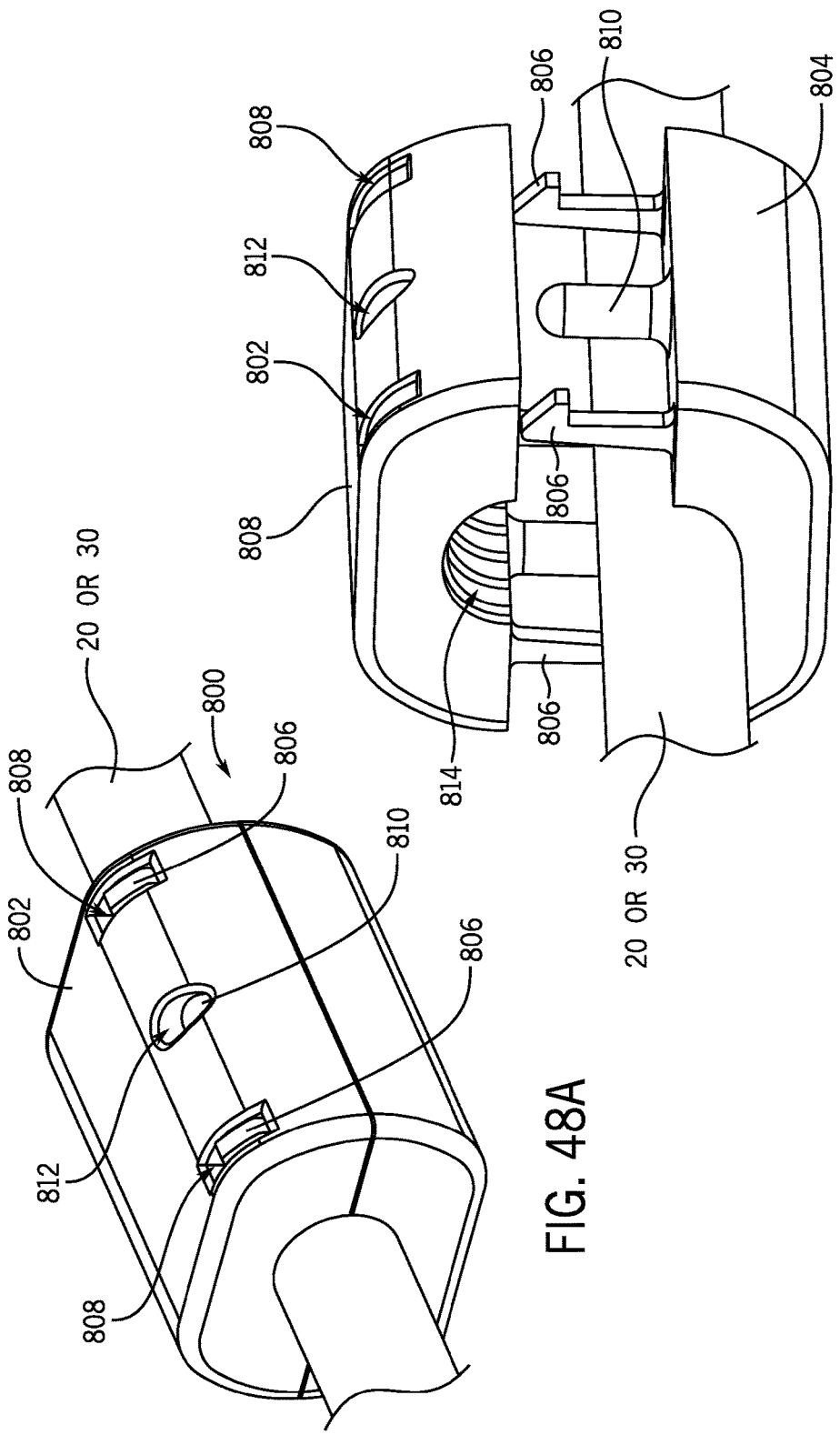

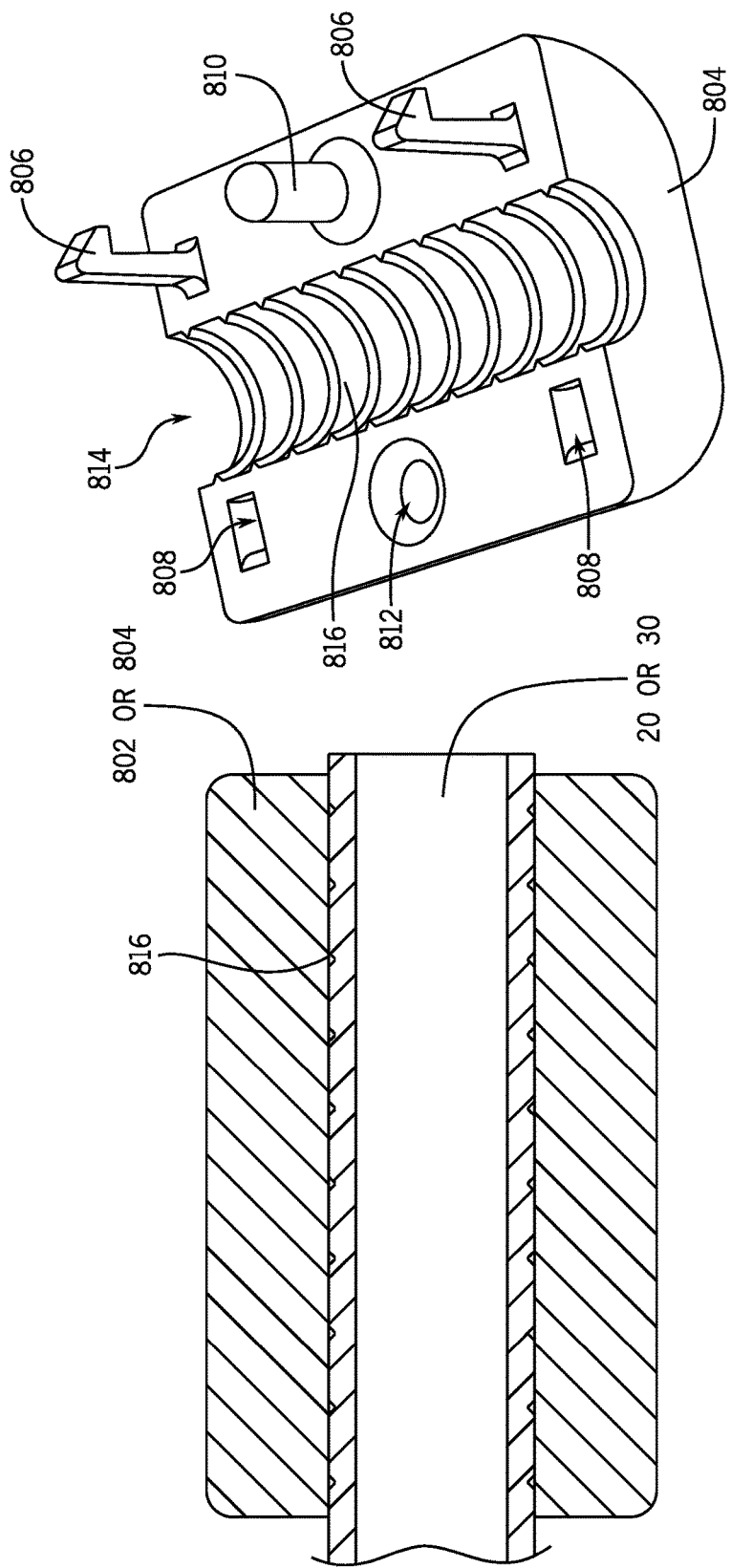

Results 9-Day AFE System Treatment of Porcine Saphenous Vein: A) Angiography Showing Dilation and Absence of Stenosis, B) Histology of Mid Portion of Anastomosis Showing Very Minimal Intimal Hyperplasia

BLOOD PUMP SYSTEMS AND METHODS

CROSS REFERENCE TO RELATED APPLICATIONS

This application is a continuation of U.S. patent application Ser. No. 14/421,767 entitled "Blood Pump Systems and Methods", filed on Feb. 13, 2015, which is a U.S. national stage entry of PCT Application No. PCT/US2013/55221 entitled "Blood Pump Systems and Methods", filed on Aug. 15, 2013. The present application is also a continuation-in-part to U.S. patent application Ser. No. 13/968,070 entitled "Blood Pump Systems and Methods", filed on Aug. 15, 2013 which further claims priority to U.S. Provisional Patent Application No. 61/684,534 entitled "Blood Pump Systems and Methods," filed on Aug. 17, 2012. All of the above-identified applications are incorporated herein by reference in their entireties.

FIELD OF THE INVENTION

The present invention relates to a blood pump system that includes a pump, conduits, a control unit, and a source of power, whereby the system may be used for a variety of peripheral vascular clinical indications. Specifically, this invention may be useful for persistently increasing the overall diameter and lumen diameter of veins and arteries in patients needing a vascular access site for hemodialysis, a bypass graft, or other type of surgery or procedure where a larger vein or artery diameter is desired. This invention may also be useful for increasing lower extremity venous return and reducing lower extremity venous pressure in patients with lower extremity venous hypertension, including those patients with skin discoloration and ulceration. This invention may be further useful for providing increased local blood flow to organs and tissues in need thereof, such as the lower extremities of patients with peripheral arterial disease (PAD).

BACKGROUND INFORMATION

There are over half a million chronic kidney disease (CKD) patients in the United States, with over 100,000 new CKD patients each year. There is a four percent annual increase in projected prevalence population due to such driving factors as, for example, high blood pressure, diabetes, and an aging population.

Hemodialysis is the treatment of choice for 92% of CKD patients, because without hemodialysis or some other form of treatment those CKD patients would die. A typical CKD patient undergoing hemodialysis treatment must have his or her vascular system connected to a hemodialysis machine two to three times per week. For hemodialysis, there are three common vascular access site options. The preferred access site option is an arteriovenous fistula (AVF), which is a direct, surgically created connection between an artery and a vein, preferably in the wrist, or alternatively, in the forearm, upper arm, leg, or groin. Another access site option is an arteriovenous graft (AVG), which is a surgically created connection between an artery and vein using an interposed synthetic conduit. The final major access site option is a catheter inserted into a large vein in the neck, chest, leg, or other anatomic location.

Patients with an AVF have less morbidity, less mortality, and a lower cost of care compared with patients with an AVG or a catheter; therefore, an AVF in the wrist is the preferred form of vascular access for hemodialysis. Patients with an AVG or catheter have substantially higher rates of infection and death than patients having an AVF, with catheter patients having the worst outcomes. In addition, patients having an AVG or catheter have a higher average cost of care, with catheter patients having the highest costs. If a patient is eligible for an AVF, the wrist or forearm is generally preferred over an AVF in the upper arm due to higher rates of hand ischemia and the generally shorter and deeper vein segments of the upper arm.

Unfortunately, about 85 percent of patients are ineligible for an AVF in the wrist, mostly due to vein and artery diameters that are too small. Furthermore, about 60 percent of all AVFs created are not useable without additional surgical and interventional procedures due to an occurrence commonly referred to as "maturation failure," which is correlated with small vein and artery diameter. The availability of veins and arteries with larger diameters is correlated with higher AVF eligibility and lower rates of maturation failure.

Currently, there are few options for permanently and persistently increasing the diameter of a vein or artery. All current methods use mechanical methods of dilation, such as balloon angioplasty, that can lead to vein or artery injury. Since a patient needs to have peripheral veins and arteries of a certain size for a physician to create an AVF, it is desirable to have a method and system for persistently and permanently increasing the size or diameter of peripheral veins or arteries.

Approximately 7 million people in the US suffer from chronic venous insufficiency and hypertension, which can progress to venous ulceration. Lower extremity ulcer is the most common form of chronic wound, with an estimated prevalence of 1% of the US population. About 2.5 million people in the US have a lower extremity ulceration and about 600,000 people seek treatment for a venous ulceration of the lower extremity each year in the US. The incidence of venous ulceration is expected to rise as the population ages.

In a survey of patients with venous ulcers, 81% of patients reported an adverse effect on mobility, 56% reported spending up to 8 hours per week on ulcer care, 68% reported a negative emotional impact, including fear, social isolation, anger, depression, and negative self-image. In the survey, 80% of patients are not working outside the home; and of the 20% employed, leg ulceration correlated with time lost from work, job loss, and adverse effects on finances.

Lower extremity venous hypertension and ulceration is costly to treat and places a substantial burden on health care providers and systems. In a study of 78 venous ulcer patients at the Cleveland Clinic, median ulcer size was 2.8 cm2 (mean=9.4 cm2) and 5% had bilateral ulcers. The median time to ulcer healing was 77 days (mean=108 days) and the mean cost of treatment was $2,400 per month. The mean total cost of treatment to heal an ulcer was $9,685 per patient. For patients requiring more than a year to heal, the average total cost per patient was $18,534.

In a majority of cases, venous hypertension and ulceration results from valvular incompetence secondary to deep vein thrombosis or an unknown cause. In a substantial minority of cases, venous hypertension and ulceration results from femoral or pelvic venous obstruction secondary to deep vein thrombosis, vein injury, or extrinsic vein compression. Chronic tissue exposure to localized venous hypertension leads to dilation of capillaries with increased permeability and leakage of plasma and erythrocytes, trapping and activation of leukocytes in the microcirculation, and the release of free radicals and other toxic products, such as tumor necrosis factors and collagenase, which can promote cell death and tissue damage. Leakage of fibrinogen into surrounding tissues binds or "traps" growth factors and cytokines, and renders them unavailable for maintenance and repair of tissue integrity.

Lower extremity venous hypertension presents clinically as leg redness and discoloration, swelling, pain, edema, pruritus, scaling, discharge, and lipodermatosclerosis. Ulcers generally develop on the medial aspect of the leg and possess irregular borders and can be associated with severe pain. Venous ulcers are often complicated by superimposed bacterial infection. The arterial circulation is usually adequate. Current treatments for lower extremity venous hypertension and ulcer are often inadequate. Patients are mostly offered palliative treatments, with the goal of healing ulcers and preventing recurrence, including aggressive wound care, compression therapy to decrease lower extremity venous pressure and increase venous return, lower extremity vein stripping or ablation, and skin grafting. However, current treatments often fail to heal ulcers and recurrence rates for healed ulcers are high.

Currently, small "heart pumps" exist; however, such pumps are costly and not designed and dimensioned for use in an extremity or for the uses described herein. As such, there is a need in the art for systems, components, methods, and pump devices that can increase the diameter of peripheral veins and arteries at a reasonable cost. Additionally, there is a need for a systems, components, methods, and pump devices that can increase lower extremity venous return, reduce lower extremity venous hypertension, and heal venous ulcers.

SUMMARY OF THE INVENTION

The present application relates to blood pump systems, including blood pump systems with wide operating ranges, low cost-of-goods-sold (COGS), and intermediate duty times. These blood pump systems are designed for use in a variety of clinical situations and for a variety of clinical indications, as described herein.

The blood pump systems described herein can be used for increasing the diameter of veins and arteries, preferably peripheral veins and arteries. The system will function to move blood in such a way as to cause an increase in vein or artery diameters. This can be accomplished by discharging ("pushing") blood into a vein or artery or by removing ("pulling") blood from a vein or artery. By either method, the system increases the flow of blood in a vessel, which ultimately leads to a persistent increase in vessel diameter. As such, the system and, more particularly, the pump use mechanical means to activate biological response pathways resulting in the enlargement or "remodeling" of veins or arteries. The system has a blood pump, conduits to carry or convey blood to and from the blood pump, a control system to monitor the blood pump and modify the operation of the blood pump, and a power source. As such, the system comprises a group of members that can be, for example, fluidly connected to an artery at one end and fluidly connected to a vein at the other, whereby, when activated, blood is pumped at a rate such that wall shear stress (WSS) on the endothelium of the vein, artery, or both is elevated for a period of time sufficient to causes a persistent enlargement in the vein or artery. Any of a variety of pumps and pump systems may be used so long as the flow of blood through the pump system can be controlled to produce the desired blood vessel diameter increase.

The blood pump systems described herein can be used to increase lower extremity venous return, reduce lower extremity venous hypertension, and heal venous ulcers. The system will function to move blood from a vein in the affected lower extremity, such as a femoral, saphenous vein, or iliac vein, to a location in the venous circulation such that the return of venous blood from the lower extremity to the heart is improved. Locations for return to the venous circulation include the jugular vein, the axillary vein, the subclavian vein, the brachiocephalic vein, the superior vena cava, and the right atrium. The system has a blood pump, one or more conduits to carry or convey blood to and from the blood pump, a control system to monitor the blood pump and modify the operation of the blood pump, and a power source. As such, the system comprises a group of members that can be, for example, fluidly connected at one end to a peripheral vein and fluidly connected to a peripheral, central vein, or right atrium at the other end, whereby, when activated, blood is pumped at a rate such that venous blood pressure is lowered in the treated lower extremity for a period of time sufficient to cause partial or complete healing of a venous ulcer to occur. Any of a variety of pumps and pump systems may be used so long as the flow of blood through the pump system can be controlled to produce the desired effect.

Various types of blood pumps may be employed, including positive displacement and rotary pumps, with rotary type pumps being preferred. In one embodiment, a rotary blood pump system includes a pump having a housing defining an inlet to receive blood and an outlet to discharge blood. The pump housing is designed and dimensioned to house a rotating impeller suspended on bearings. The pump housing can have a first bearing at the inlet portion of the housing and a second bearing at the outlet portion of the housing. Blood enters and exits the rotating impeller, whereby the impeller increases the exit velocity of the blood. This increased velocity is recovered or translated as increased pressure as the blood decelerates within the pump diffuser, which terminates in the pump outlet.

In other embodiments, various types of rotary blood pumps may be used. For example, an axial flow pump, a mixed flow pump, or preferably, a centrifugal blood pump may be used. In addition, a variety of pump impeller bearings may be used, including, but not limited to magnetic bearings, hydrodynamic bearings, and, preferably pivot (contact) types. Similarly, various types of pump diffusers may be used, including but not limited to a collector diffuser, or preferably a volute diffuser.

In one embodiment, a centrifugal blood pump with pivot bearings includes a pump housing defining a pump inlet having an inflow diffuser to receive blood and direct blood onto an impeller, the pump housing having a top bezel and top pivot bearing extending from a top of the housing into the inlet, and a bottom bezel and bottom pivot bearing extending from a bottom of the housing into the interior space of the housing. The pump also includes the impeller suspended within the housing, the impeller further having a bearing lumen to receive an impeller pivot. The impeller pivot has a first end to engage the inlet portion (top) pivot bearing and a second end to engage the outlet portion (bottom) pivot bearing. In one embodiment, the ends of the impeller pivot are convex and at least one end of each pivot bearing is concave. In another embodiment, the ends of the impeller pivot are concave and the pivot bearings are convex. The impeller can include a variety of fin or blade constructions designed to contact and accelerate blood into the volute. For example, the impeller defines a plurality of blades on the top surface of the impeller and extending radially from a center of the impeller to an outer edge of the impeller. The blades accelerate blood from the impeller's central inlet to its peripheral outlet. In another option, the impeller does not include blades or fins, but does include means to move or propel blood. The impeller optionally includes at least one washout lumen, cut-away, or bore extending generally parallel to a central axis of the impeller from a bottom surface through the impeller to a top surface. The lumen is designed to prevent stagnation of blood under the impeller and around the bottom pivot bearing.

The blood pump includes a motor, preferably electric, designed to actuate the impeller. In one embodiment, the blood pump includes a drive motor having at least one magnet mechanically attached to the impeller and at least one armature mechanically attached to the housing. The armature induces an electromotive force on the at least one magnet attached to the impeller. The pump motor can be an axial-gap brushless direct current (DC) torque motor with sensorless back electromotive force (back-EMF) commutation. The motor employs a sintered alloy of neodymium iron boron (NdFeB) for the magnets in the impeller and a 3-phase planar "racetrack" coil configuration in the stator. The motor has a pancake aspect ratio, with a very small axial length in comparison to its diameter.

In one embodiment, the blood pump system includes a centrifugal blood pump with an operating range between about 50 milliliters per minute and about 1500 milliliters per minute. The system also includes a pump housing defining a pump inlet to receive blood and direct blood onto an impeller. The pump housing has a top pivot bearing extending from a top of the housing into the inlet, and a bottom pivot bearing extending from a bottom of the housing into the interior space of the housing. The pump also includes an impeller suspended within the housing wherein a first gap between the impeller and a top portion of the housing is in a first range between about 0.05 mm and about 0.2 mm.

The impeller includes an impeller pivot having a first end to engage the top pivot and a second end to engage the bottom pivot and a plurality of blades on the top surface of the impeller and extending radially away from a center of the impeller, the blades to force blood received at the inlet through the pump housing and to the outlet. The impeller also includes at least one lumen extending parallel to a central axis of the impeller from the bottom surface through the impeller to a top surface.

The pump further includes at least one magnet mechanically engaged to the impeller and an electric motor to magnetically engage the at least one magnet, wherein the electric motor rotates the at least one magnet and the impeller. In other embodiments, the pump also includes a ferromagnetic backplate to magnetically engage the at least one magnet.

The blood pump system has one or more conduits including a first (inflow) conduit having two ends, a first end that is fluidly connected to a location in the vascular system and receives blood from that location, and a second end that is fluidly connected to the pump. The inflow conduit delivers blood to the pump. The blood pump system has a second (outflow) conduit having two ends, a first end that is fluidly connected to the pump and receives blood from the pump, and a second end that is fluidly connected to a location in the vascular system. The outflow delivers blood to a location in the vascular system.

In various embodiments, the conduits of the blood pump system have an individual length of between 2 cm and 110 cm and a combined length between 4 cm and 220 cm, and may be trimmed to a desired length by a surgeon or other physician, including during implantation of the pump system. The conduits each have an inner diameter between 2 mm and 10 mm, and preferably between 4 mm and 6 mm. The conduits may be formed at least in part from polyurethane (such as Pellethane® or Carbothane®), polyvinyl chloride, polyethylene, silicone elastomer, polytetrafluoroethylene (PTFE), expanded polytetrafluoroethylene (ePTFE), polyethylene terephthalate (PET, e.g. Dacron), and combinations thereof. The conduits may further include an elastic reservoir.

All or portions of the conduits may be reinforced with a braided or spiral coiled shape memory material, such as nitinol, or other self-expanding or radially expansive material, such as stainless steel. For pump systems designed for the treatment of lower extremity venous hypertension and venous ulcers, the conduit that conveys blood from a lower extremity vein to the pump portion of the pump system may further comprise a distal segment of ePTFE or Dacron such this segment can be fluidly connected to the lower extremity vein by a surgical anastomosis. Further, this ePTFE or Dacron segment may comprise an external reinforcement, such as additional ePTFE or Dacron material, or with a self-expanding or radially expansile material such as nitinol or stainless steel. This external reinforcement may take the form of a spiral or a braid, or may comprise a more completely circumferential and uniform support structure, or may be configured in another manner that resists collapse, compression, or coaption when the pressure within the conduits is low or negative. The conduits may have chamfered ends that fluidly connect to the vascular system. The ends can be chamfered at an angle between 10 degrees and 80 degrees. One or more of the conduits may have a number of holes or fenestrations in the walls of the distal ends, when configured for placement within the lumen of a blood vessel or other intravascular location. The conduits may be secured to the pump using radially-compressive connectors.

In another embodiment a blood pump system a centrifugal blood pump and a pump housing defining a pump inlet to receive blood and direct blood onto an impeller. The pump housing has a top pivot bearing extending from a top of the housing into the inlet, and a bottom pivot bearing extending from a bottom of the housing into the interior space of the housing. The pump also includes an impeller suspended within the housing wherein a first gap between the impeller and a top portion of the housing is in a first range between about 0.05 mm and about 0.2 mm.

The impeller includes an impeller pivot having a first end to engage the top pivot and a second end to engage the bottom pivot and a plurality of blades on the top surface of the impeller and extending radially away from a center of the impeller, the blades to force blood received at the inlet through the pump housing and to the outlet. The impeller also includes at least one lumen extending parallel to a central axis of the impeller from the bottom surface through the impeller to a top surface.

The pump further includes at least one magnet mechanically engaged to the impeller and an electric motor to magnetically engage the at least one magnet, wherein the electric motor rotates the at least one magnet and the impeller. The blood pump also includes having at least one conduit having an end in communication with the pump inlet or pump outlet and a distal end for insertion into a blood vessel. The distal end includes a tapered, non-chamfered distal tip defining an generally circular end opening coaxial with a central longitudinal axis of the distal end. The distal end also includes a first plurality of side holes symmetrically arranged about a circumference of the distal tip, where the first plurality of side holes are proximal to the circular end opening and oriented at an angle relative to the central longitudinal axis. The distal tip also includes a second plurality of side holes symmetrically arranged about a circumference of the distal tip.

In various other embodiments, the conduits of the blood pump systems also include one or more side ports in communication with the conduits. The blood pump systems also include one or more attachable conduit cuffs to engage the at least one conduit.

In one embodiment, a blood pump system includes a blood pump and a control system to monitor the blood pump system and modify the operation of the blood pump to maintain an increased mean wall shear stress within an artery or vein fluidly connected to the blood pump. The control system is further configured to maintain mean wall shear stress within a vein in the range of 0.76 to 23 Pa, or preferably in the range of 2.5 to 10 Pa. In another embodiment, the control system monitors and maintains an increased mean blood velocity within an artery or vein fluidly connected to the blood pump. In this embodiment, the control system is configured to maintain mean blood velocity within an artery or vein in the range of 10 cm/s and 120 cm/s, or preferably in the range of 25 cm/s and 100 cm/s. In either embodiment, the blood pump system is configured to maintain increased mean wall shear stress or increased mean blood velocity for at least 1 day, 7 days, 14 days, 28 days, 42 days, 56 days, 84 days, or 112 days. As used herein, term velocity may refer to speed of the blood regardless of directional component or vector.

The blood pump system has a control system to achieve and maintain the desired flow rate, which can optionally include a control device for receiving information and controlling the operation of the pump of the blood pumping system. At a minimum, the control system can be manually actuated to adjust speed of the motor. Alternately, an automatic (i.e. "smart") control system can be used. Optionally, the control system includes sensors that can be located in the pump, the conduits, or in the vascular system of the patient. The control device can measure the rotational speed of the motor based on the zero-crossings of the back-EMF waveform. These zero crossings indicate magnetic pole reversals of the impeller. The speed of the motor is controlled by pulse width modulation (PWM) of the input voltage, and torque is controlled by PWM of the input current. The control device also monitors other state variables of the pump motor, such as current and voltage, from which both the flow rate through the blood pumping system and the wall shear stress in the peripheral blood vessel can be estimated and controlled.

The control device preferably includes a "processor", which comprises a sensing stage, processing stage, and power stage to drive and control the pump motor. The processor energizes the motor windings and controls the motor speed by analyzing the back-EMF in the motor windings, as well as information from optional sensors. The processor can execute control algorithms encoded on a computer-readable medium. The blood pump system includes a cable for electrically connecting the control device to the pump and optional sensors. The blood pump system also includes a power source that, in various embodiments, may be integrated into the control device. In various embodiments, the power source for the blood pump system may be mobile (e.g. a rechargeable battery or fuel cell) or stationary (e.g. a power base unit connected to AC mains).

The control system may acquire information from various sources. The motor drive electronics within the control device can measure at least one of the motor speed, input power, or current required to operate the pump. In other embodiments, the control system includes sensors in the blood pump or conduits that measure at least one of a blood velocity, a blood flow rate, a resistance to blood flow in a peripheral blood vessel, a blood pressure, a pulsatility index, and combinations thereof. In other embodiments, the control system includes sensors in the vascular system of the patient that measure at least one of a blood velocity, a blood flow rate, a blood pressure, a pulsatility index, a vessel diameter, and combinations thereof.

In various embodiments, the control system may estimate and maintain a desired and elevated level of wall shear stress in a target vessel or a donating artery or vein, using the information from the control device and/or sensors, such as a motor speed, motor input power, pump flow rate, pump pressure head, pressure near the junction of the outflow conduit, and the target vessel, pressure drop across a blood vessel, and combinations thereof. For the purpose of this application, "target vessel", "target blood vessel", "target vein", or "target artery" refers to a specific segment of an artery or a vein that is intended to achieve a persistently increased overall diameter and lumen diameter when a pump-conduit assembly is implanted, configured, and operated in such a manner as to result in the persistent increase in the overall diameter and lumen diameter.

Various control system methods may be used to automatically control the operation of the blood pump system. In one embodiment, a method of determining and controlling a wall shear stress in a blood vessel includes the steps of measuring a blood viscosity, measuring a blood flow rate in a blood pump system or the blood vessel, and measuring a radius of the blood vessel. The steps also include determining the wall shear stress in the blood vessel from the measured blood viscosity, the measured flow rate, and the radius of the blood vessel, comparing the determined wall shear stress to a predetermined reference value, and adjusting a blood pump speed when the determined wall shear stress does not approximate the predetermined reference value. The steps are repeated until the determined wall shear stress approximates the predetermined reference value.

In another embodiment, a method of computing and controlling a wall shear stress in a blood vessel includes the steps of estimating a blood viscosity, measuring a blood flow rate in a blood pump system or the blood vessel, and measuring a radius of the blood vessel. The steps also include determining the wall shear stress from the estimated blood viscosity, the measured blood flow rate, and the radius of the blood vessel, comparing the determined wall shear stress with a predetermined reference value, and adjusting a blood pump speed when the determined wall shear stress does not approximate the predetermined reference value. The steps are repeated until the determined wall shear stress approximates the predetermined reference value.

In one embodiment, a method of estimating and controlling a wall shear stress in a blood vessel includes the steps of estimating a blood viscosity, measuring at least one motor state variable of a blood pump system selected from a voltage, a current, or a pump speed, and estimating a blood flow rate in the blood pump system. The steps also include measuring a pressure in the blood vessel, determining a vascular resistance of the blood vessel from the estimated blood flow rate and the measured pressure in the blood vessel, estimating a radius of the blood vessel. The steps further include determining the wall shear stress from the estimated blood viscosity, the estimated blood flow rate, and the radius of the blood vessel, comparing the determined wall shear stress with a predetermined reference value, and adjusting the pump speed when the determined wall shear stress does not approximate the predetermined reference value. The steps are repeated until the determined wall shear stress approximates the predetermined reference value.

In another embodiment, a method of estimating and controlling a wall shear stress in a blood vessel using a blood pump system includes the steps of estimating a blood viscosity, measuring at least one motor state variable of the blood pump system selected from a voltage, a current, or a pump speed, and estimating a blood flow rate and a pressure head in the blood pump system. The steps also include calculating a vascular resistance of the blood vessel from the estimated blood flow rate and the estimated pressure head, estimating a radius of the blood vessel, and determining the wall shear stress from the estimated blood viscosity, the estimated blood flow rate, and the estimated radius of the blood vessel. The steps further include comparing the determined wall shear stress with a predetermined reference value and adjusting the pump speed when the determined wall shear stress does not approximate the predetermined reference value. The steps are repeated the determined wall shear stress approximates the predetermined reference value.

In one embodiment, a method of estimating and controlling a wall shear stress in a blood vessel using a blood pump system includes the steps of estimating at least one member selected from a group consisting of a blood viscosity, a blood flow rate, a pressure head in the blood pump system, and a radius of the blood vessel, measuring at least one motor state variable of the blood pump system selected from a group consisting of a voltage, a current, and a pump speed, and determining the wall shear stress in the blood vessel. The steps also include comparing the determined wall shear stress with a predetermined reference value and adjusting the pump speed when the determined wall shear stress does not approximate the predetermined reference value. The steps are repeated until the determined wall shear stress approximates the predetermined reference value.

In yet another embodiment, a sensorless method to avoid a collapse or coaption of a blood vessel or atrial chamber fluidly connected to a blood pump system upon detecting an imminence of the collapse at an inlet of the blood pump system includes the steps of measuring a blood pump motor current and continually determining a spectral analysis representation of the blood pump motor current in a form of a Fourier series. The steps also include providing a detection indication when an amplitude of the second harmonic term of the Fourier series exceeds a reference value and decrementing a pump speed when the amplitude of the second harmonic term of the Fourier series exceeds the reference value. The steps are repeated until the amplitude of the second harmonic term falls below the reference value.

In another embodiment, a blood pump system includes a blood pump and a control system to monitor the blood pump system and modify the operation of the blood pump to maintain a reduction in venous blood pressure in the treated lower extremity. The blood pump is also configured to maintain the lumen area of the inflow conduit and the fluidly connected peripheral vein segment during changes in body position, such as a change from standing to lying down. In one embodiment, the control system monitors blood pressure in the lower extremity vein fluidly connected to the inflow conduit of the blood pump system and adjusts the pump speed to maintain vein pressure in a desired range that is low enough to result in adequate venous return through the blood pump system while simultaneously avoiding vein wall collapse, coaption, or prolapse. In this embodiment, the control system is configured to maintain a pressure in the lower extremity vein segment adjacent to the inflow conduit in the range of 5 mmHg and 100 mmHg, or preferably in the range of 10 mmHg and 50 mmHg or the range of 10 mmHg and 25 mmHg. In either embodiment, the blood pump system is configured to generally maintain this lower extremity vein segment pressure range for at least 7 days, 28 days, 56 days, 112 days, 224 days, or 356 days.

The blood pump system has a control system to generally achieve and maintain the desired lower extremity vein segment pressure range, which can optionally include a control device for receiving information and controlling the operation of the pump of the blood pumping system. At a minimum, the control system can be manually actuated to adjust speed of the motor. Alternately, an automatic (i.e. "smart") control system can be used. Optionally, the control system includes sensors that can be located in the pump, the conduits, or the vascular system of the patient. The sensors, including but not limited to position sensors, may be located in or on the patient at various other locations. The control device can measure the rotational speed of the motor based on the zero-crossings of the back-EMF waveform. These zero crossings indicate magnetic pole reversals of the impeller. The speed of the motor is controlled by pulse width modulation (PWM) of the input voltage, and torque is controlled by PWM of the input current. The control device also monitors other state variables of the pump motor, such as current and voltage, from which both the flow rate through the blood pumping system can be estimated and controlled. The control device preferably includes a memory, a processor for controlling the pump motor speed, analyzing the information coming from the motor drive electronics and optional sensors, and executing instructions encoded on a computer-readable medium. The blood pump system includes a cable for electrically connecting the control device to the pump and optional sensors. The blood pump system also includes a power source that, in various embodiments, may be integrated into the control device. In various embodiments, the power source for the blood pump system may be mobile (e.g. a rechargeable battery or fuel cell) or stationary (e.g. a power base unit connected to AC mains).

The control system may acquire information from various sources. The motor drive electronics within the control device can measure at least one of the motor speed, input power, or current required to operate the pump. In other embodiments, the control system includes sensors in the blood pump or conduits that measure at least one of a blood velocity, a blood flow rate, a blood pressure, a body position, and combinations thereof. In other embodiments, the control system includes sensors in the vascular system of the patient that measure at least one of a blood velocity, a blood flow rate, a blood pressure, and combinations thereof.

Various control system methods may be used to automatically control the operation of the blood pump system. In one embodiment, a method of reducing lower extremity vein segment pressure includes the steps of estimating body position and adjusting the speed of the pump based on body position. In another embodiment, a method of reducing lower extremity vein segment pressure includes the steps of estimating body position, measuring a blood pressure in the inflow conduit or the segment of vein fluidly connected to the inflow conduit, and adjusting the speed of the pump based on body position and blood pressure in the inflow conduit or the segment of vein fluidly connected to the inflow conduit. In another embodiment, a method of reducing lower extremity vein segment pressure includes the steps of measuring at least one motor state variable of the blood pump system selected from a group consisting of a voltage, a current, and a pump speed, and setting the speed of the blood pump system to provide at least a certain minimum flow of blood through the blood pump system. In another embodiment, a method of reducing lower extremity vein segment pressure includes the steps of measuring a blood flow through the pump system, and setting the speed of the blood pump system to provide at least a certain minimum flow of blood through the blood pump system.

In yet another embodiment, a sensorless method to avoid a collapse or coaption of a lower extremity vein segment fluidly connected to a blood pump system upon detecting an imminence of the collapse of the vein or an inflow conduit at or near an inlet of the blood pump system includes the steps of measuring a blood pump motor current and continually determining a spectral analysis representation of the blood pump motor current in a form of a Fourier series. The steps also include providing a detection indication when an amplitude of the second harmonic term of the Fourier series exceeds a reference value and decrementing a pump speed when the amplitude of the second harmonic term of the Fourier series exceeds the reference value. The steps are repeated until the amplitude of the second harmonic term falls below the reference value.

In various other embodiments, the systems and methods disclosed herein may be encoded on computer-readable media that may be executed by a processing device. Any reference values or predetermined standards used by the systems and methods may be stored in a database or other suitable storage medium.

BRIEF DESCRIPTION OF THE FIGURES

FIGS. 5A-B are enlarged views of the pivot axis area of FIGS. 3B and 4B.

FIG. 8C is a side elevation view of an embodiment of the impeller pivot.

FIGS. 8D-E are plan views of the top and the bottom surface, respectively, of an embodiment of the impeller pivot.

FIGS. 8F-G are close up plan views of the top and the bottom pivots, respectively, of an embodiment of the impeller pivot.

FIG. 11C is a side elevation view of a representative bearing pin.

FIG. 11D is a plan view of one end of a representative bearing pin.

FIGS. 11E-F are cross sectional views of the representative bearing pin and bearing surface, respectively, of the representative bearing pin taken along section line A-A in FIG. 11C.

FIG. 17 is an isometric partial cross section of the impeller chamber inlet orifice.

FIGS. 19A and 19B are the same respective views as FIGS. 18A and 18B, except of another embodiment.

FIGS. 24A and 24B are, respectively, plan and side elevation views of another embodiment of the inlet cap and inlet channel similar to that described in FIG. 21, except further including an arcuate wedged portion.

FIG. 26 is a perspective view of a blood pump system according to one embodiment.

FIGS. 27A-27D are perspective views of the connection between the pump and conduits according to one embodiment.

FIG. 31 is a view of the distal portion of the outflow conduit according to one embodiment.

FIG. 32F is a plan view of the intravascular portion of an inflow or outflow conduit according to one embodiment.

FIG. 32G is a cross-sectional view of the intravascular portion of the inflow or outflow conduit of FIG. 32F along line B-B according to one embodiment.

FIG. 32H is a plan view of the intravascular portion of an inflow or outflow conduit according to one embodiment.

FIG. 32I is a cross-sectional view of the intravascular portion of the inflow or outflow conduit of FIG. 32H along line C-C according to one embodiment.

FIG. 45A is a photograph of a portion of a conduit configured for fluid connection to the vascular system by surgical anastomosis.

FIG. 45B is a photograph of a portion of a conduit configured for insertion into the lumen of a portion of the vascular system.

FIGS. 46A-B are photographs of a wearable control device and a fixed or table-mounted control device, respectively.

FIGS. 48A-D are perspective views of a portion of a cuff device that may be attached to the external surface of a segment of a conduit.

DETAILED DESCRIPTION OF THE INVENTION

Figure 1:
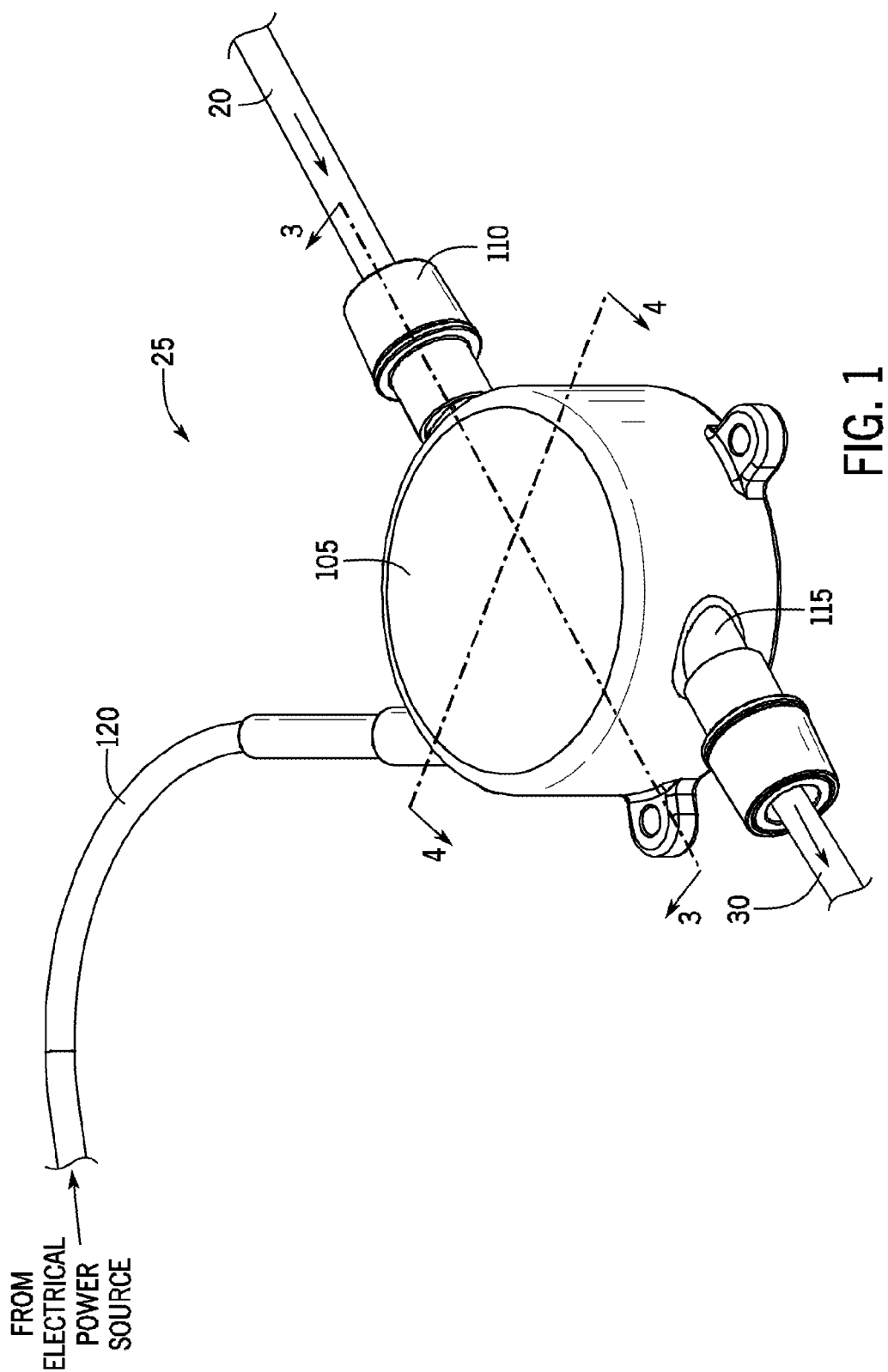
FIG. 1 is an isometric view of the pump.

The systems and components of the present application relate to a blood pump system. In various embodiments, the present application relates to a blood pump designed and dimensioned to discharge blood into a target vessel or withdraw blood from a target vessel in such a way and for such a period of time that the diameter of the target vessel (vein or artery) is persistently increased. Even more specifically, the present application relates to a rotary blood pump system configured to persistently increase the mean and/or peak blood velocity and mean and/or peak wall shear stress in selected segments of veins or arteries for a period of time sufficient to persistently increase the overall diameter and the lumen diameter of selected segments of veins or arteries. The term "persistent increase" or "persistent dilation" when used to describe dilation or an increase in the overall diameter and lumen diameter of an artery or vein, is used herein to mean that even if the pump is turned off, an increase in the overall diameter or lumen diameter of a vessel can still be demonstrated when compared to the overall diameter or lumen diameter of the vessel prior to the period of blood pumping. That is, the overall diameter or lumen diameter of the vessel has become larger independent of the pressure generated by the pump. The blood pump system may therefore be useful to certain patients, including CKD patients in need of a vascular access site for hemodialysis. The blood pump system can include a rotary blood pump, one or more blood-carrying conduits, a control system, and a power source. The blood pump system withdraws blood from one location in the vascular system and discharges blood to another location in the vascular system. During operation, such a blood pump system may persistently increase mean and/or peak blood velocity and mean and/or peak WSS in a target blood vessel to a level and for a period of time sufficient to persistently increase the overall diameter and lumen diameter of the target blood vessel. The system functions in configurations where blood is withdrawn from the target blood vessel or in configurations where blood is discharged into the target blood vessel. Further, the system can be used simultaneously to increase the size of the donating and receiving vessels.

In various other embodiments, the present application relates to a blood pump designed and dimensioned to move venous blood from a lower extremity to the heart or to another location in the venous system where it can more easily return to the heart, in order to reduce venous blood pressure in the lower extremity, and in some instances to reduce swelling or increase the rate of healing of an associated skin ulceration. Even more specifically, the present application relates to a rotary blood pump system configured to move venous blood from a lower extremity to the heart or to another location in the venous system where it can more easily return to the heart in order to reduce venous blood pressure in the lower extremity, and in some instances to reduce swelling or increase the rate of healing of an associated skin ulceration. The blood pump system may therefore be useful to certain patients including those with venous hypertension and/or venous ulceration of one or both lower extremities, such as patients with lower extremity venous obstruction or patients with damaged or incompetent venous valves in one or both lower extremities. The blood pump system can include a rotary blood pump, one or more blood-carrying conduits, a control system, and a power source. The blood pump system withdraws blood from a lower extremity vein segment and discharges blood to another location in the venous system. Locations for the return of blood to the venous circulation include the jugular vein, the axillary vein, the subclavian vein, the brachiocephalic vein, the superior vena cava, and the right atrium.

The optional blood-carrying conduits can include an inflow conduit to carry blood from a location in the vascular system (such as a donating vein, a donating artery, or the right atrium) to the blood pump and an outflow conduit to carry blood from the blood pump to a location in the vascular system (such as an accepting peripheral vein or artery, or an accepting location such as the right atrium). The blood pump system also includes a control system. A preferred control system is designed to collect information on the operating parameters and performance of the blood pump system, and changes in the vascular system, such as changes in the diameter of a donating artery, donating vein, accepting artery, or accepting vein of a patient. The blood pump system is primarily configured to pump a sufficient amount of blood such that a desired mean and/or peak wall shear stress (WSS) is achieved within a blood vessel segment (the "target blood vessel" or "target vessel") and for a sufficient period of time such that the permanent or persistent overall diameter and lumen diameter of the blood vessel segment is increased. The mean WSS can be calculated using the measured, estimated, or assumed vessel diameter and the measured, estimated, or assumed average blood flow rate through the blood pump system.

The diameter of blood vessels can be determined by measuring the diameter of the void within the center of the blood vessel. For the purpose of this application, this measurement is referred to as "lumen diameter". The diameter of blood vessels can be determined by measuring the diameter in a manner that includes the void within the center of the blood vessel and the wall of the blood vessel. For the purpose of this application, this measurement is referred to as "overall diameter". The invention relates to simultaneously and persistently increasing the overall diameter and lumen diameter of a peripheral vein by moving blood (preferably with low pulsatility) into the peripheral accepting vein, thereby increasing the velocity of the blood in the peripheral accepting vein and increasing the WSS on the endothelium of the peripheral accepting vein. Systems and methods are described wherein the velocity of the blood in a peripheral accepting vein and the WSS on the endothelium of the peripheral accepting vein is increased by using a pump. Systems and methods are also described that withdraw or "pull" blood such that the velocity of the blood and the WSS is increased in the donating vessel, either an artery or a vein. Preferably, the pump actively discharges blood into the peripheral accepting vein, wherein the pumped blood has reduced pulsatility, such as when the pulse pressure is lower than blood in a peripheral artery.

Blood pump systems described herein may have one or a group of characteristics that differ from many other blood pump systems. For example, a blood pump system described herein may operate safely within a wide operating range of blood flow, such as a range from 50 mL/min to 1500 mL/min. In another example, a blood pump system described herein can be fabricated with a low cost-of-goods-sold (COGS), such as in the range of $1,000 to $5,000. In yet another example, a blood pump system described herein is designed to operate reliably outside of a hospital or clinic setting for an intermediate period of time, such as for 1 hour to 12 months, or such as for 7 days to 12 months. In some examples, a blood pump system described herein can have one, several, or all of these factors, as one or more blood pump systems described herein can operate safely over a wide operating range of blood flow including from 50 mL/min to 1500 mL/min, have low COGS of $1,000 to $5,000, and can operate reliably outside of a hospital or clinic setting for an intermediate period of time, such as for 1 hour to 12 months, or such as for 7 days to 12 months.

To begin a detailed discussion of the blood pump 25 of the system 10, reference is made to FIG. 1, which is an isometric view of the blood pump 25. In one embodiment, the blood pump 25 is a miniaturized centrifugal pump having a magnetic drive wherein the impeller of the pump is rotationally driven by rotating magnetic fields. For example, the rotating magnetic fields may be generated by energizing a number of electromagnets in a particular sequence. In another example, the rotating magnetic fields may be generated by rotating a number of permanent magnets or energized electromagnets. The pump can have a diameter approximately equal to that of a coin on the order of, for example, a United States quarter, a United States half dollar, or a larger diameter, as need be. For example, the pump 25 has a diameter in a range between about 2.0 cm and about 5.0 cm, according to various embodiments. As shown in FIG. 1, the blood pump 25 includes a body 105, an inlet 110, an outlet 115, and a power cable 120. The power cable 120 connects the blood pump 25 to the control device 21 of a control system 14 and power source. The power source can be part of the control device 21 or separate. The power cable allows for communication between the control device 21 and the motor of the blood pump 25. The cable can also be used to transfer power from a power source to the motor or pump. More particularly, the power cable 120 connects the electrical components of the magnetic drive inside the body 105 to an electrical power source (e.g., a battery).

The inlet 110 is capable of being fluidly coupled to the inflow conduit 20 via a coupling arrangement (e.g., a barbed-end, a flange, and a locking collar). The inlet 110 provides a fluid pathway into the intake region (i.e. center) of the pump impeller. The intake region of the impeller can be of a variety of constructions so long as blood is received out of the outlet at a velocity greater than the intake. The outlet 115 is capable of being fluidly coupled to the outflow conduit 30 via a coupling arrangement similar to the inlet (e.g., a barbed-end, a flange, and a locking collar). The outlet 115 provides a fluid pathway from the outlet region (i.e. periphery) of the pump impeller.

Figure 2:
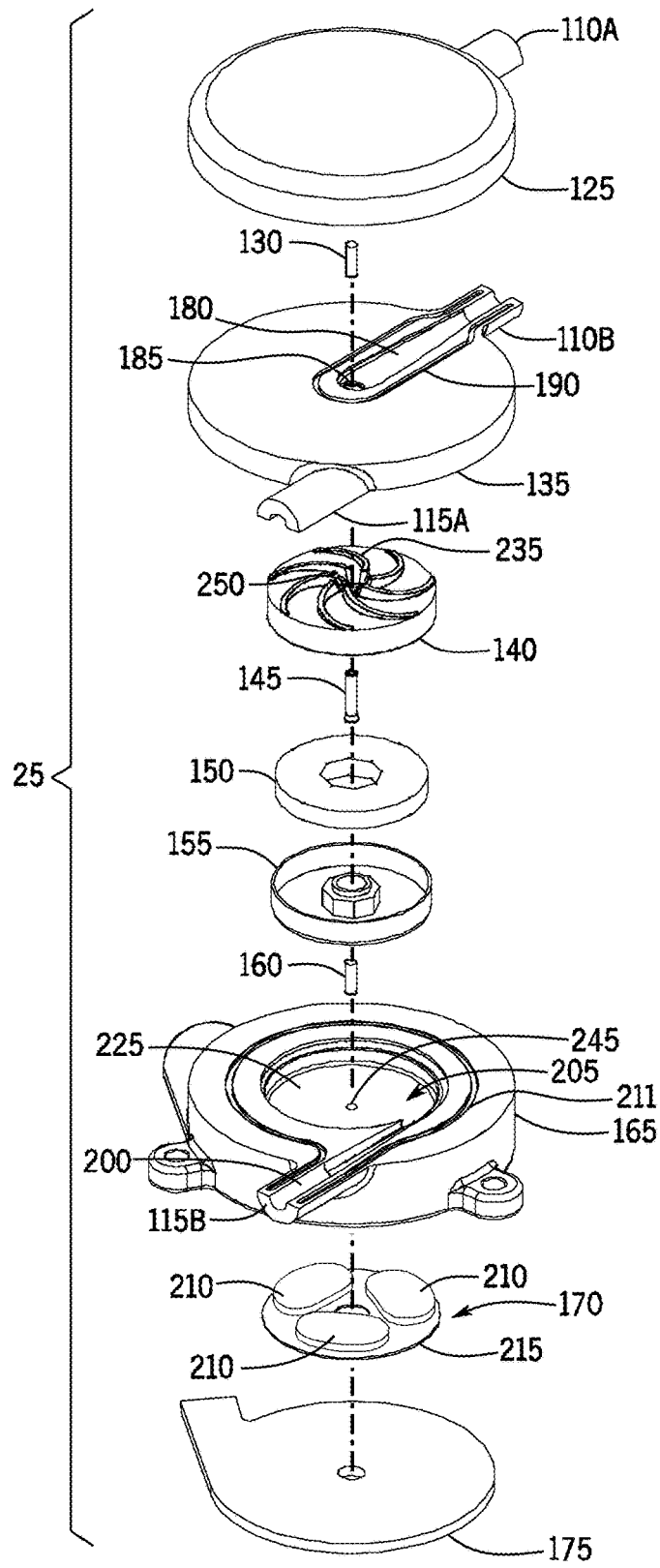
FIG. 2 is an exploded isometric view of the pump showing its components contained in the body identified in FIG. 1.

As illustrated in FIG. 2, which is an exploded isometric view of the blood pump 25 showing its components contained in the body 105 identified in FIG. 1, the blood pump 25 includes an inlet cap 125, a top bearing pin 130, a top impeller casing 135, an impeller 140, an impeller pivot 145, a magnet assembly 150, a magnet enclosure 155, a bottom bearing pin 160, a bottom impeller casing 165, an electrical coil assembly 170, and a coil assembly enclosure lid 175. The inlet cap 125 and top impeller casing 135 each include approximately half of the inlet 110.

Figure 3A:
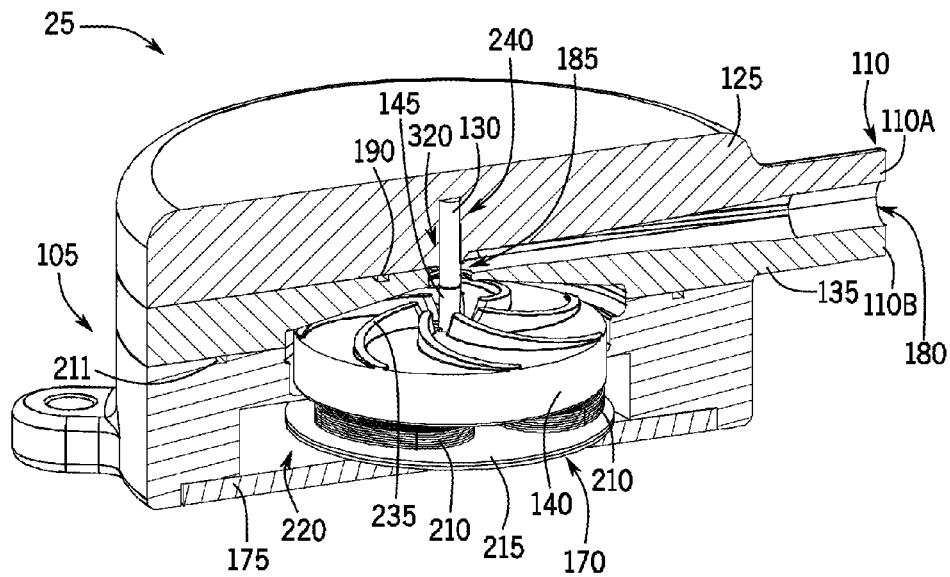
FIGS. 3A and 3B are, respectively, partial and full cross sectional elevations of the pump as taken along section line 3-3 in FIG. 1.
Figure 3B:
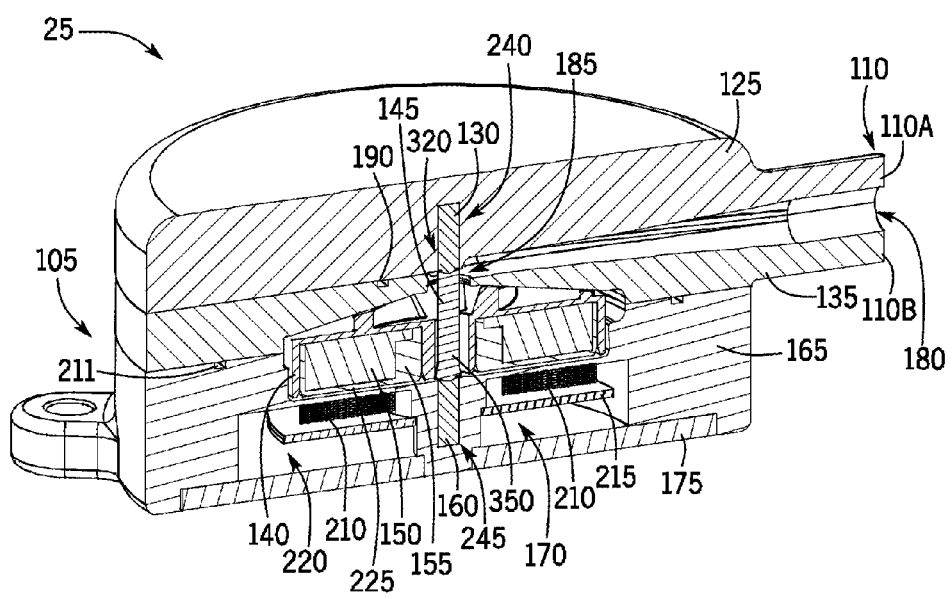

As shown in FIGS. 3A and 3B, which are, respectively, partial and full cross sectional elevations of the blood pump 25 as taken along section line 3-3 in FIG. 1, the components mentioned with respect to FIG. 2 generally sandwich together to form the pump. For example, as can be understood from FIGS. 2-3A, the inlet cap 125 and top impeller casing 135 respectively include a top horizontally extending inlet portion 110A and a bottom horizontally extending inlet portion 110B. Typically, the inlet and outlet are opposed and located in different planes. When the inlet cap 125 and top impeller casing 135 are sandwiched together, they define an inlet fluid channel 180 leading through the inlet 110 to the impeller inlet orifice 185. The inlet cap 125 and top impeller casing 135 respectively define approximately a top half and a bottom half of the channel 180. A seal groove 190 is defined in the top impeller casing 135 adjacent to the border of the channel 180 and is adapted to receive a resilient fluid seal member for creating a fluid tight seal between the inlet cap 125 and top impeller casing 135.

Figure 4A:
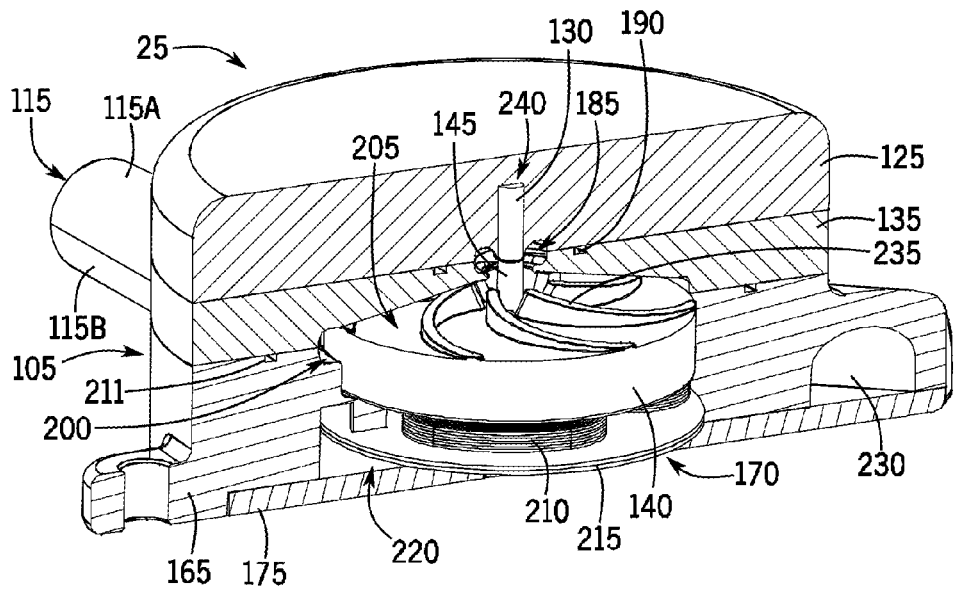
FIGS. 4A and 4B are, respectively, partial and full cross sectional elevations of the pump as taken along section line 4-4 in FIG. 1.
Figure 4B:
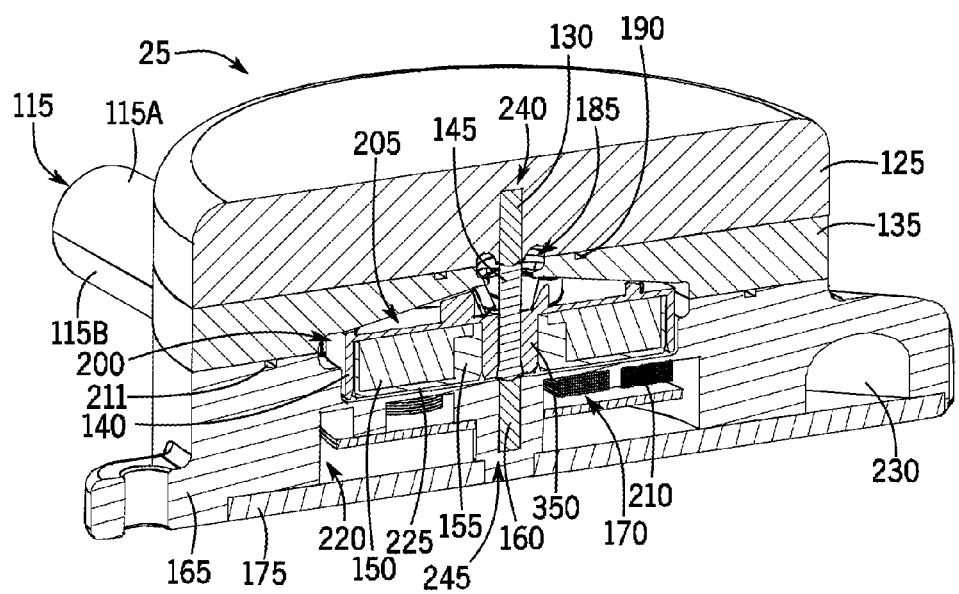
Figure 4C:
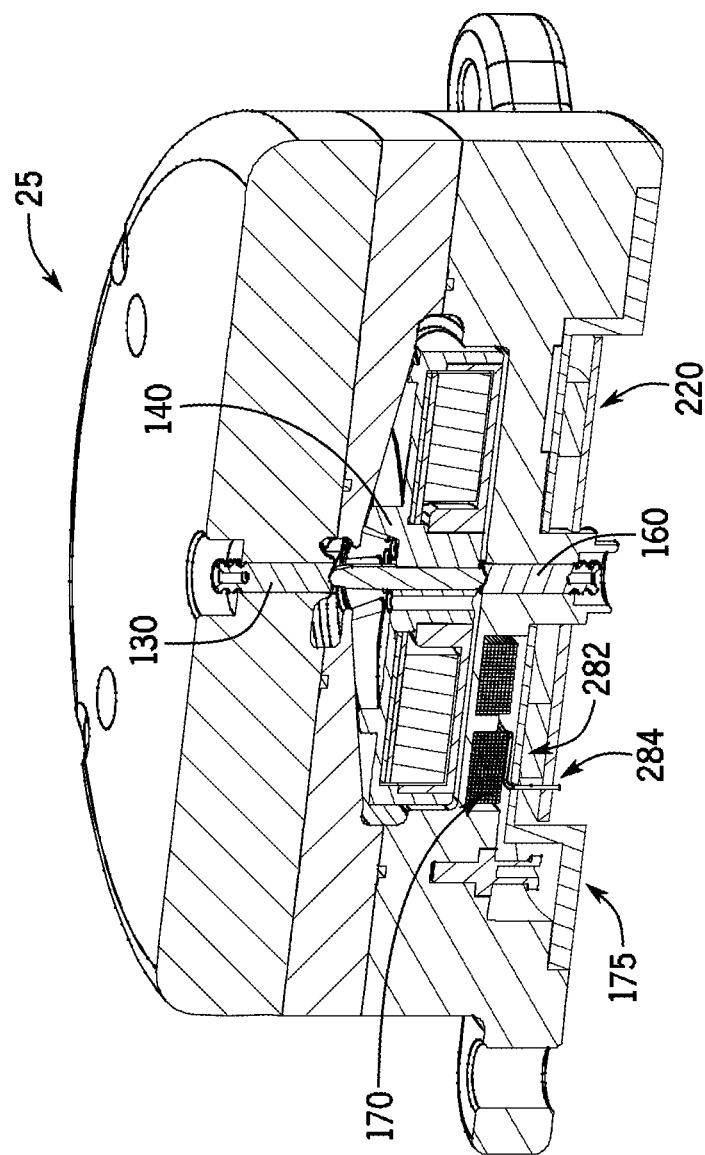
FIG. 4C is a cross sectional elevation of another embodiment of the pump.

FIGS. 4A and 4B are, respectively, partial and full cross sectional elevations of the blood pump 25 as taken along section line 4-4 in FIG. 1. As can be understood from FIGS. 2, 4A, and 4B, the top impeller casing 135 and bottom impeller casing 165 respectively include a top horizontally extending outlet portion 115A and a bottom horizontally extending outlet portion 115B. When top impeller casing 135 and bottom impeller casing 165 are sandwiched together, they define an outlet fluid channel 200 (i.e. volute) leading from the impeller chamber 205 to the outlet 115. The top impeller casing 135 and bottom impeller casing 165 respectively define approximately a top half and a bottom half of the channel 200. A seal groove 211 is defined in the bottom impeller casing 165 adjacent to the border of the channel 200 and impeller chamber 205 and is adapted to receive a resilient fluid seal member for creating a fluid tight seal between the top impeller casing 135 and bottom impeller casing 165.

As indicated in FIGS. 2-4B, the impeller magnet assembly 150 is a plurality of magnets in the form of a ring or disk. The magnets 150 are located in the volume of the magnet enclosure 155 and the volume of the impeller 140. The magnet enclosure 155 is received in the impeller 140. The magnet enclosure 155 and the impeller 140 respectively form the bottom and top portions of the volume in which the magnets 150 are located. The magnet enclosure 155, magnets 150, and impeller 140 are coupled together in a fixed integral assembly that rotates as a unit within the impeller chamber 205. Alternative constructions can be used that cause rotation of the impeller.

As illustrated in FIGS. 2-4B, the electrical coil assembly 170 is a plurality of electrical coils 210 arranged in a circular pattern on the lower impeller casing and optionally capped by a support disk 215. The electrical coil assembly 170 is fixed within the coil chamber 220 defined in the bottom impeller casing 165 and capped by the coil enclosure lid 175. An internal floor structure 225 separates the impeller chamber 205 from the coil chamber 220. In one embodiment, the coil chamber 220 also contains one or more voids or spaces, spacers 282, and a ferrous backplate 284, as shown in FIG. 4C. An attractive magnetic force is generated between the impeller magnet 150 and the backplate 284, which counteracts the upward force imposed by the increased pressure of blood flowing in the gap 542 between the bottom face of the impeller 140 and the bottom impeller casing 165, as shown in FIG. 4E, and the decrease pressure at the impeller chamber inlet orifice 185 above the impeller. The net effect is an unloading of the top bearing pin 130. Depending upon the position of the backplate 284 and the speed of the pump 25, the axial load can be shared between the top and bottom bearing pins 130 and 160 or it can be borne solely by the bottom bearing pin or the top bearing pin. For example, the force at the top bearing pin 130 may be less than approximately 3 N during operating speeds up to approximately 6000 rpm. Similarly, the force on the bottom bearing pin 160 was less than approximately 4 N when operating at speeds up to approximately 6000 rpm. Conversely, when at rest (i.e. 0 rpm), the axial force experienced at the bottom force is at least 0.1 N and may be up to 10 N or greater.

A number of studies were performed to measure the load at the top and bottom bearing pins 130 and 160 with various pump speeds and backplate 284 orientations. The speed at which the load changes from the bottom bearing pin 160 to the top bearing pin 130 can be tuned by varying the distance between the impeller 140 and backplate 284, such as with one or more spacers 282. Similarly, the load on the top and the bottom bearing pins 130 and 160 at a particular impeller speed can be tuned by varying the distance between the impeller 140 and backplate 284. The ferrous backplate 284 also functions to increase the motor performance and motor torque, as the backplate causes the magnetic flux to penetrate deeper into the coils 210 thereby providing a higher axial flux density.

Figure 4D:
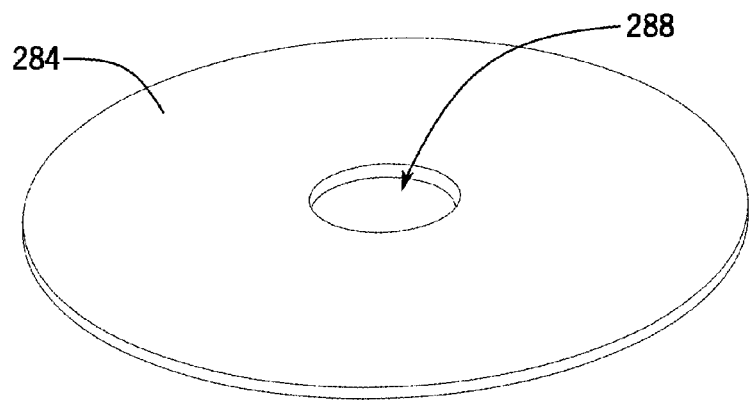
FIG. 4D is a perspective view of a backplate according to one embodiment.
Figure 4E:
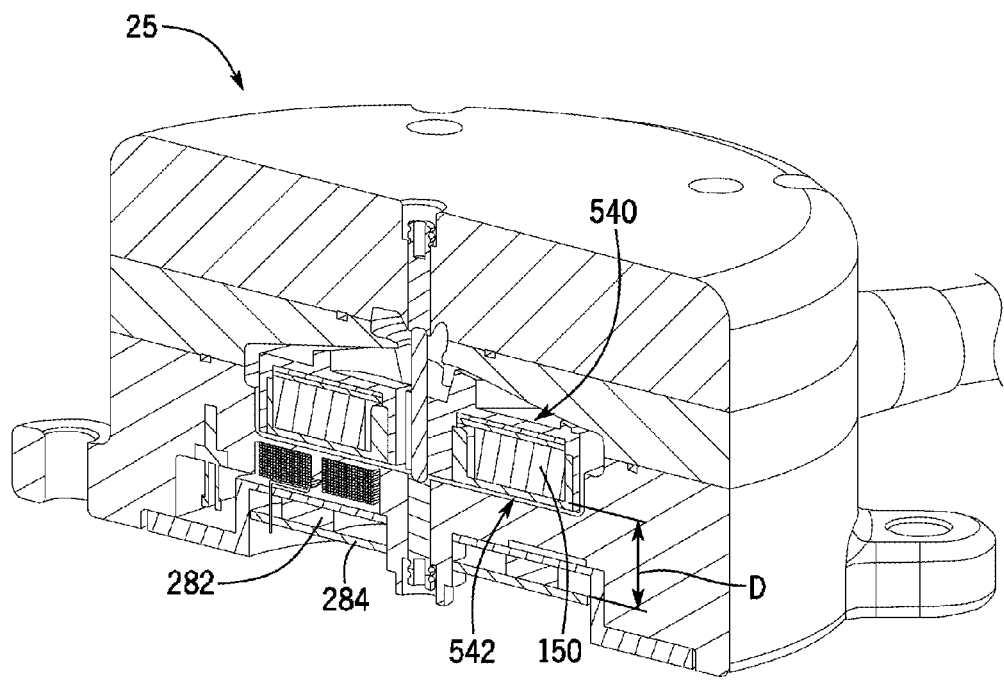
FIG. 4E is a cross sectional elevation of the pump according to one embodiment.

One embodiment of the backplate 284 is shown in FIG. 4D. As shown, the backplate 284 has a general disc shape and is composed of a ferrous metal or alloy. In one embodiment, the backplate 284 is composed of an iron-cobalt-vanadium soft magnetic alloy, such as Hiperco® 50, produced by Carpenter Technology. The backplate 284 has a thickness in a range from approximately 0.04 mm to about 0.07 mm and an outer diameter in a range from approximately 20 mm to approximately 40 mm. In a preferred embodiment, the backplate 284 is a solid disc having a thickness of approximately 0.53 mm and an outer diameter of approximately 31 mm. The backplate 284 may include a central opening 288 to accommodate the structural features of the pump 25; however, in other embodiments a solid disc without the opening 288 may be used. FIG. 4E is illustration of an embodiment of the pump 25. As shown, in one embodiment, the backplate 284 is positioned a distance "D" away from the magnet 150. In one embodiment, the distance "D" is in a range between approximately 4 mm and 8 mm. In a preferred embodiment, the distance "D" is equal to approximately 6 mm. In other embodiments, the backplate 284 may be positioned closer to or farther from the magnets 150 to achieve the desired gap 540 between the top face of the impeller 140 and the top impeller casing 135 and the gap 542 between the bottom of the impeller and the bottom impeller casing 165.

Figure 4F:
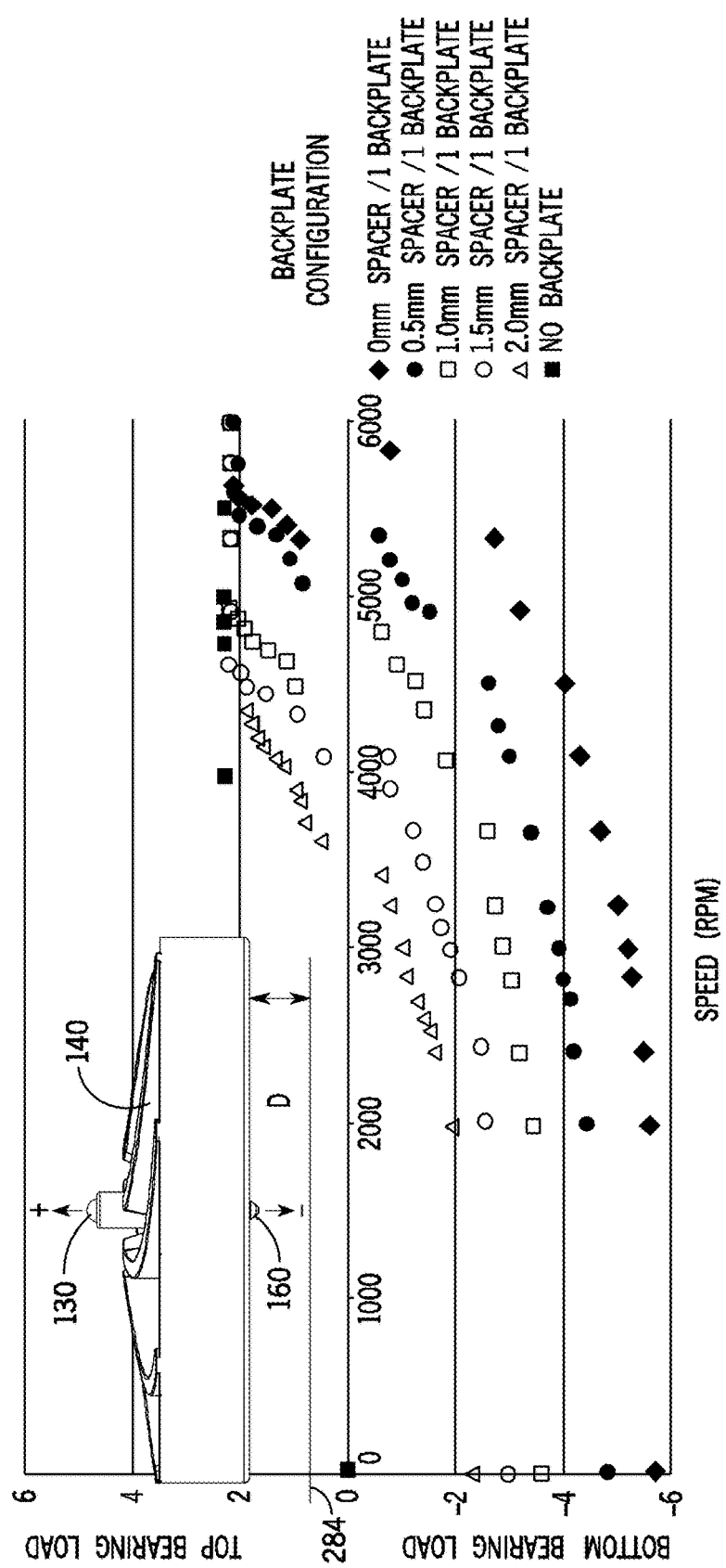
FIG. 4F is a chart and illustration depicting the loads at the top and bottom bearings as a function of the backplate arrangement according to one embodiment.
Figure 4G:
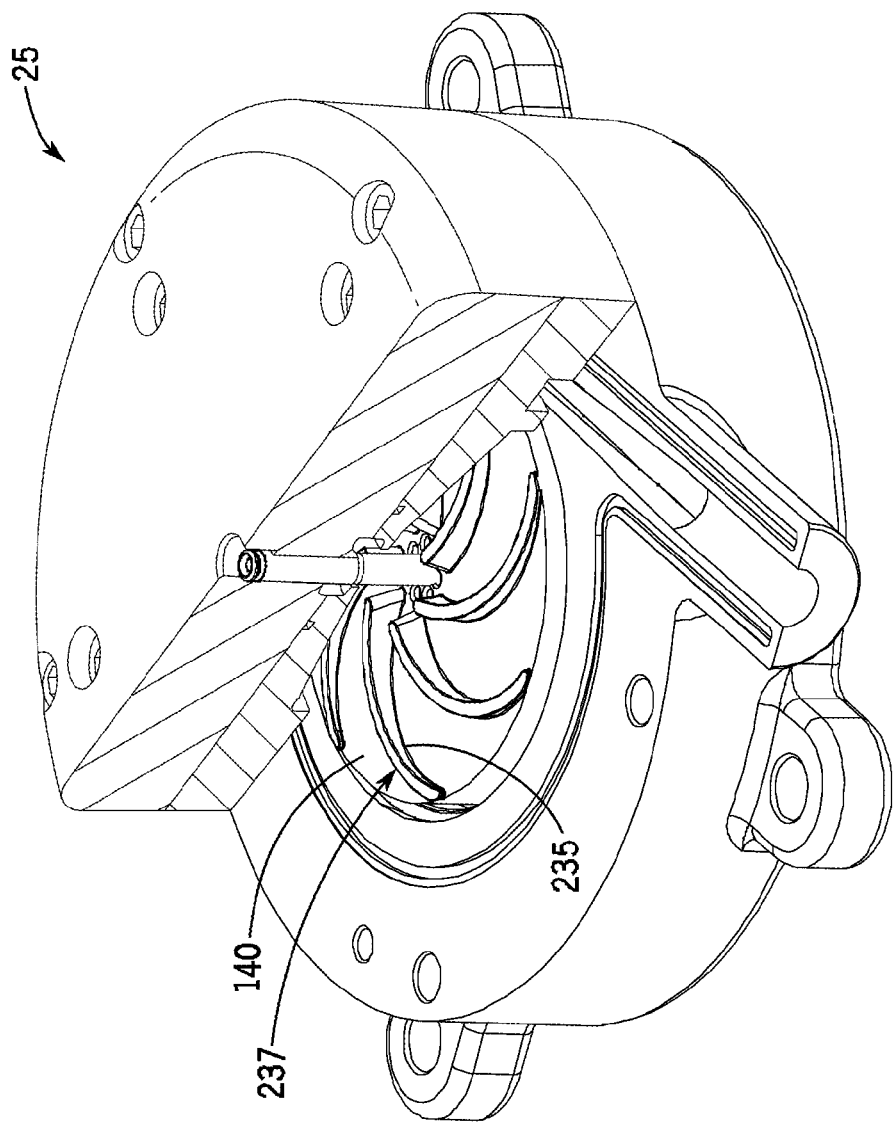
FIG. 4G is partial-section view of a blood pump illustrating the surface area of the impeller that provides a hydrodynamic bearing according to one embodiment.
Figure 4H:
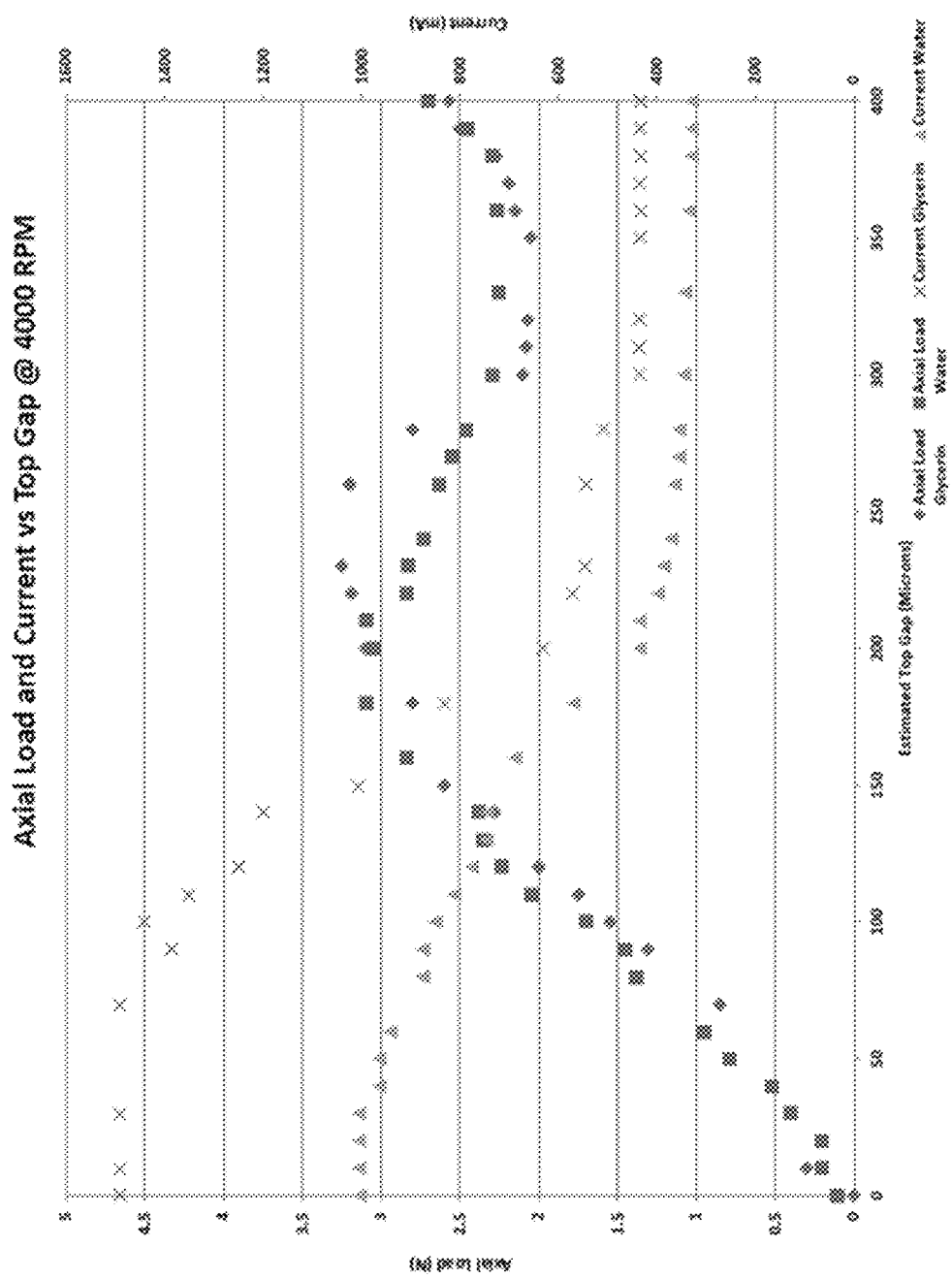
FIG. 4H is a chart depicting the axial load at the top bearing as a function of the top gap between the impeller and the top casing as at 4000 RPM.

FIG. 4F is an illustration of the impeller 140 and the backplate 284 and a graph depicting experimental results of the load measured at both the top pin and the bottom pin as a function of the backplate 284 position relative to the magnets 150. The effective position of the backplate 284 is configurable based on different arrangements of spacers 282 and the thickness of the backplate 284. As shown, a preferred embodiment includes a single backplate 284 positioned approximately 6 mm away from the motors using a 1.5 mm spacer 282. Depending upon the desired or tolerable loads at the top and bottom bearings other backplate and spacer combinations may be used. Similarly, FIG. 4H is a chart depicting the axial load at the top bearing as a function of the top gap 540 between the impeller 140 and the top casing 135 when the pump 25 is operating at approximately 4000 RPM.

The electrical cable 120 (see FIG. 1) extends through passage 230 in the bottom impeller casing 165 to the coil chamber 220 and the coils 210. Electrical power supplied to the coils 210 via the electrical cable 120 generates rotating magnetic fields, which act on the magnets 150 to cause the magnets, and the impeller 140 coupled to the magnets to rotate. The impeller rotation causes the impeller blades 235 to act upon the fluid (e.g., blood) present in the impeller chamber, resulting in momentum being transferred to the fluid that is recovered as a pressure increase in the outlet fluid channel 200. The fluid is thus drawn into the inlet 110 at low pressure and discharged from the outlet 115 at a higher pressure.

As shown in FIGS. 3A-4B, the pivot axis for the impeller 140, magnets 150, and enclosure 155 is the impeller pivot 145. As depicted in FIGS. 5A-B, the impeller pivot 145 is pivotally supported (i.e. restrained in all degrees of freedom except rotation about a single axis) via a top bearing pin 130 and a bottom bearing pin 160. The top bearing pin 130 is received and fixed in a cylindrical recess 240 in the inlet cap 125, while the bottom bearing pin 160 is received and fixed in a cylindrical recess 245 in the bottom impeller casing 165. The impeller pivot 145 extends through and is fixed to a center cylindrical opening 250 in the impeller 140.

In one embodiment of the impeller assembly, the impeller pivot 145, the top bearing pin 130, and the bottom bearing pin 160 are formed from high purity alumina ($Al_2O_3$), such as CoorsTek® AD-998. In another embodiment of the impeller assembly, the impeller pivot 145, the top bearing pin 130, and the bottom bearing pin 160 are formed from silicon carbide whisker-reinforced alumina, such as Greenleaf® WG-300. In yet another embodiment, the impeller pivot 145, the top bearing pin 130, and the bottom bearing pin 160 are each formed from alumina toughened zirconia (ATZ), which may provide a bearing more resistant to wear than bearings formed from alumina. Forming bearing components from ATZ may also yield a smoother surface finish than bearing components formed from alumina. In all three embodiments, the dimensions of the impeller pivot 145, the top bearing pin 130, and the bottom bearing pin 160 are designed to limit the contact stresses to permissible levels for high purity alumina, silicon carbide toughened alumina, or ATZ, respectively, in view of peak thrust loads generated by hydrostatic forces and shock loads. In another embodiment of the impeller assembly, the impeller pivot 145 is formed from silicon carbide whisker-reinforced alumina, such as Greenleaf® WG-300 or from high purity alumina, such as CoorsTek® AD-998, while the top bearing pin 130, the bottom bearing pin 160, or both are formed from ultrahigh molecular weight polyethylene. In various other embodiments, portions or all of the top bearing pin 130, and the bottom bearing pin 160 can be formed from polyethylene. Additionally, the geometry of each component of the impeller assembly has been selected to limit fatigue and wear in order to satisfy the safety and durability requirements of the system 10. A number of studies have been conducted to illustrate the superior wear characteristics of ATZ over an experimental lifetime of the pump 25, which results in reduced changes to the overall height of the bearing stack when compared with bearing systems comprised of alumina and polyethylene.

Figures 6A, 6B:
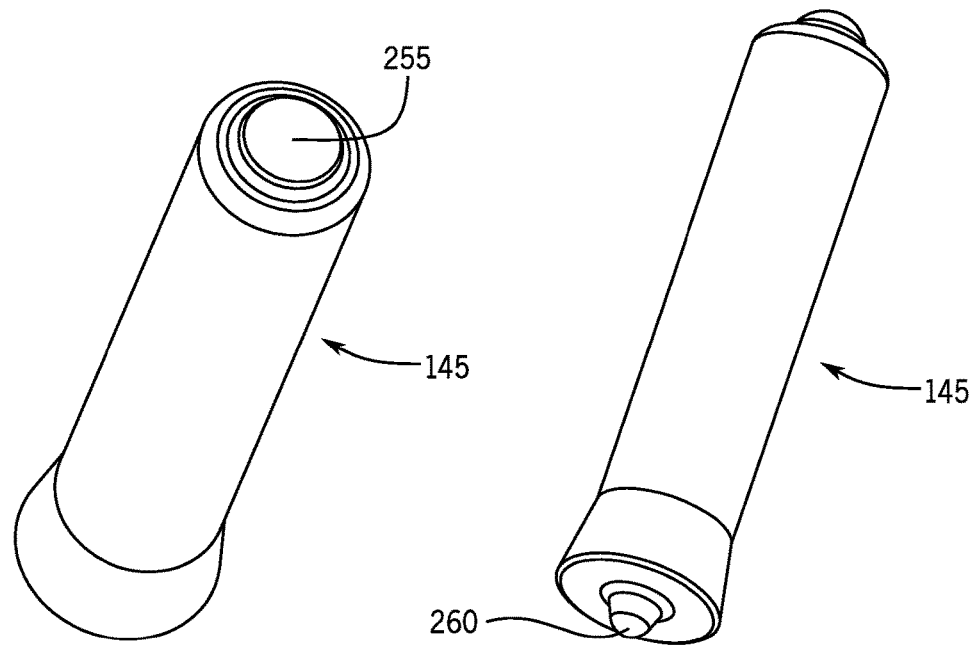
FIGS. 6A-B, respectively, are top and bottom isometric views of the impeller pivot.
Figures 7A, 7B:
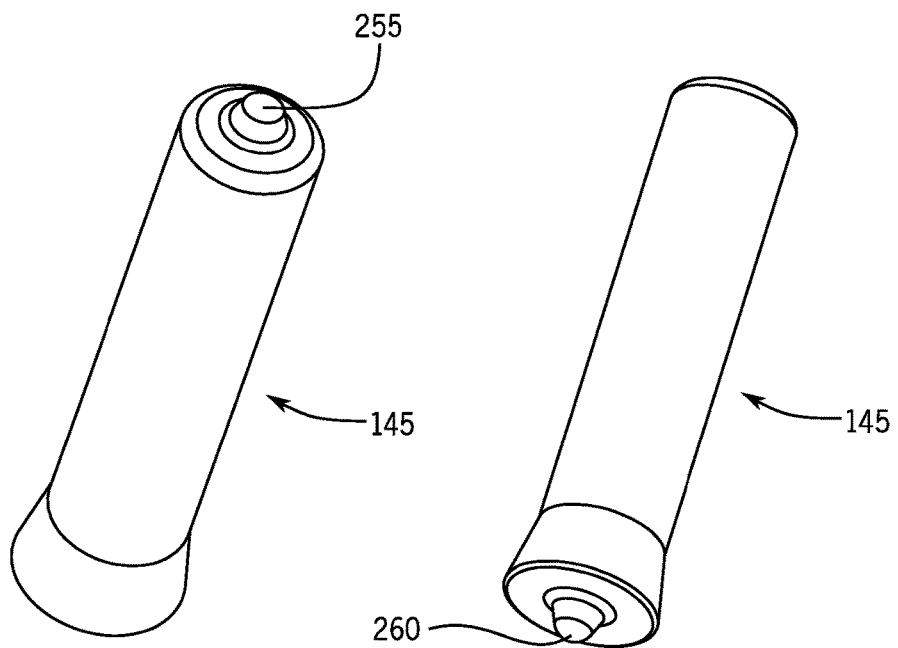
FIGS. 7A-B, respectively, are top and bottom isometric views of the impeller pivot
Figure 8A:
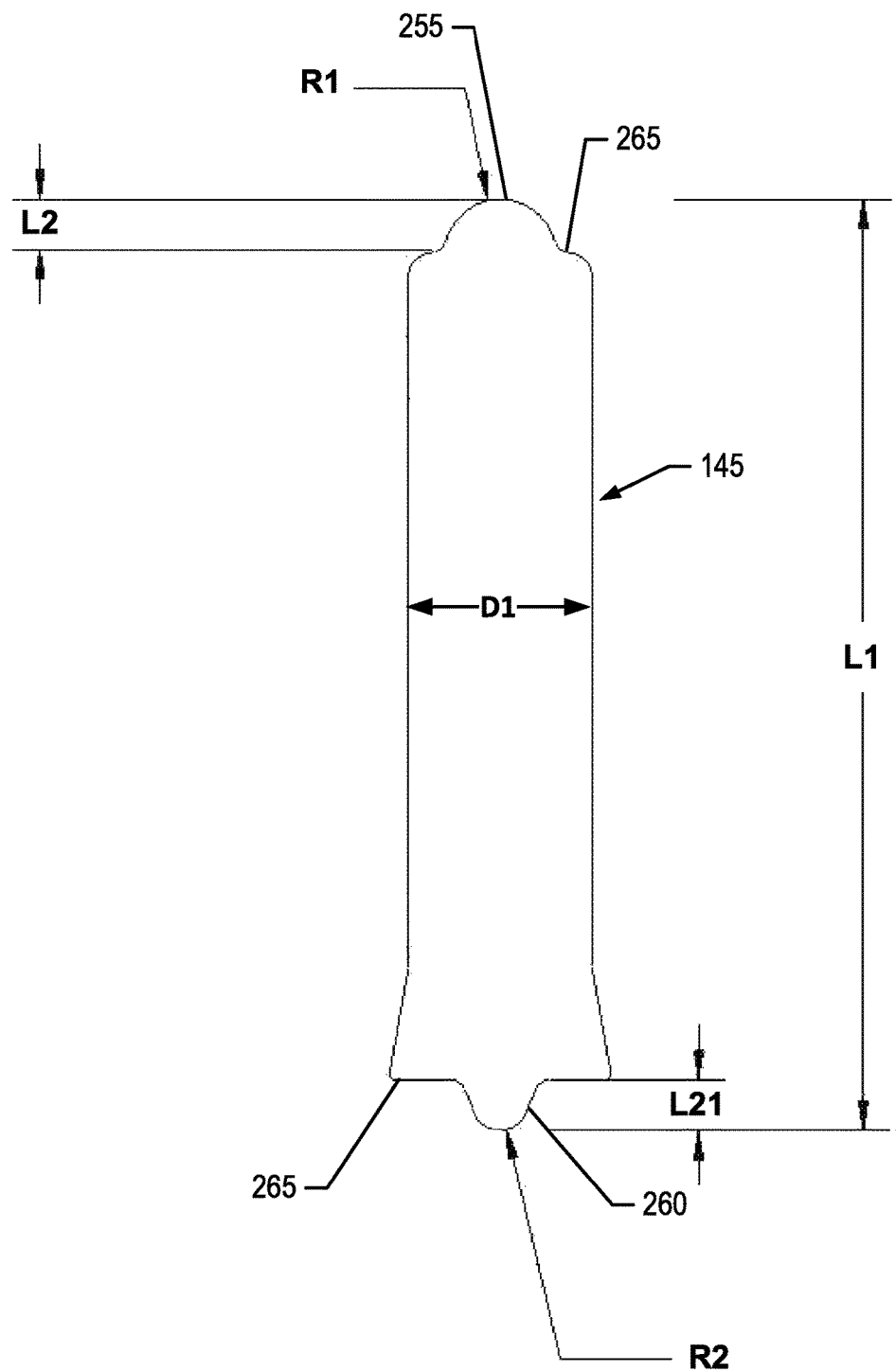
FIGS. 8A-B are side elevation views of embodiments of the impeller pivot.
Figure 8B:
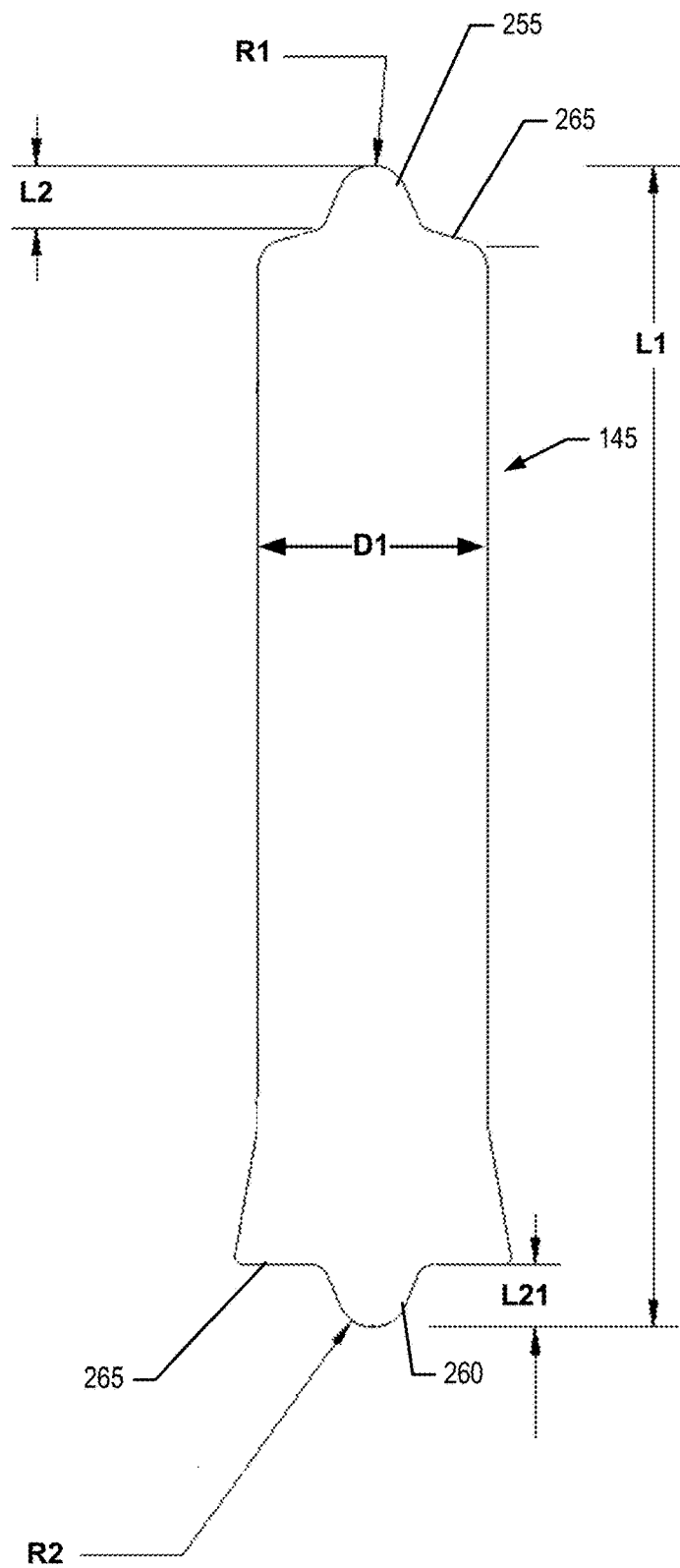

As illustrated in FIGS. 6A-7B, the impeller pivot includes an upper hemispherical convex bearing surface 255 and a bottom hemispherical convex bearing surface 260. As indicated in FIGS. 6A, 6B, and 8A, one embodiment of the impeller pivot has an overall length L1 of approximately 10.15 mm, plus or minus 0.05 mm, and a pivot diameter D1 of approximately 2 mm, plus or minus approximately 0.01 mm. The upper bearing surface 255 has a radius R1 of approximately 0.61 mm, plus or minus 0.02 mm and extends a length L2 past an adjacent lip 265 by approximately 0.55 mm, plus or minus 0.02 mm. The lower bearing surface 260 has a radius R2 of approximately 0.31 mm, plus or minus 0.02 mm and extends a length L21 past an adjacent lip 265 by approximately 0.55 mm, plus or minus 0.02 mm. Similarly, an alternate embodiment of the impeller pivot 145, as indicated in FIGS. 7A, 7B, and 8B, has an overall length L1 of approximately 10.15 mm, plus or minus 0.05 mm, and a pivot diameter D1 of approximately 2 mm, plus or minus approximately 0.01 mm. The upper bearing surface 255 has a radius R1 of approximately 0.31 mm, plus or minus 0.02 mm and extends a length L2 past an adjacent lip 265 by approximately 0.55 mm, plus or minus 0.02 mm. The lower bearing surface 260 has a radius R2 of approximately 0.31 mm, plus or minus 0.02 mm and extends a length L21 past an adjacent lip 265 by approximately 0.55 mm, plus or minus 0.02 mm. Other sizes and dimensions may be used depending upon the size and performance requirements of the pump. The sizes are such that the resultant pump can be used in a patient to increase the diameter of a vessel.

Similarly, an alternate embodiment of the impeller pivot 145, as indicated in FIGS. 7A, 7B, and 8B, has an overall length L1 of approximately 10.15 mm, plus or minus 0.05 mm, and a pivot diameter D1 of approximately 2 mm, plus or minus approximately 0.01 mm. The upper bearing surface 255 has a radius R1 of approximately 0.31 mm, plus or minus 0.02 mm and extends a length L2 past an adjacent lip 265 by approximately 0.55 mm, plus or minus 0.02 mm. The lower bearing surface 260 has a radius R2 of approximately 0.31 mm, plus or minus 0.02 mm and extends a length L21 past an adjacent lip 265 by approximately 0.55 mm, plus or minus 0.02 mm.

As can be understood from FIGS. 8C-8G, yet another embodiment of the impeller pivot 145 includes an upper hemispherical convex bearing surface 255 and a bottom hemispherical convex bearing surface 260. FIGS. 8D and 8E are plan views of the upper hemispherical convex bearing surface 255 and the bottom hemispherical convex bearing surface 260, respectively as viewed along a longitudinal axis of the impeller pivot 140. FIGS. 8F and 8G are close-up views of the bottom hemispherical convex bearing surface 260 and the upper hemispherical convex bearing surface 255, respectively. As indicated in FIG. 8C, one embodiment of the impeller pivot has an overall length L1 of approximately 10.45 mm, plus or minus 0.05 mm, and a pivot diameter D1 of approximately 1.5 mm, plus or minus approximately 0.005 mm. The upper bearing surface 255 has a radius R1 of approximately 0.6 mm, plus or minus 0.02 mm and extends a length L2 past an adjacent taper point 266 by approximately 1.4 mm, plus or minus 0.10 mm. The taper point 266 has a radius R3 of approximately 0.20 mm plus or minus 0.02 mm where the surface 267 of the impeller pivot tapers inward along the length L2 at a conical angle CA1 of approximately 20 degrees. The lower bearing surface 260 has a radius R2 of approximately 0.60 mm, plus or minus 0.02 mm and extends a length L21 past an adjacent taper point 268 by approximately 0.5 mm, plus or minus 0.10 mm. The taper point 268 has a radius R4 of approximately 0.05 mm where the surface 267 of the impeller pivot tapers inward along the length L21 at a conical angle CA2 of approximately 90 degrees.

Figures 9A, 9B:
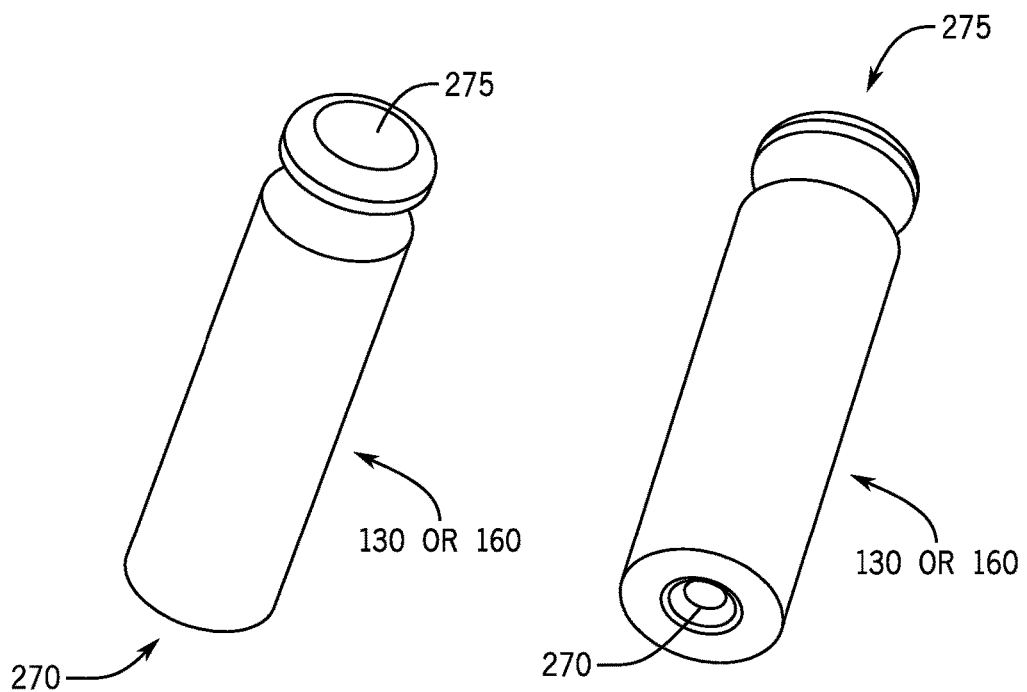
FIGS. 9A-B are, respectively, opposite end views of a representative bearing pin used on either end of the impeller pivot to support and allow rotation of the impeller pivot.
Figure 10:
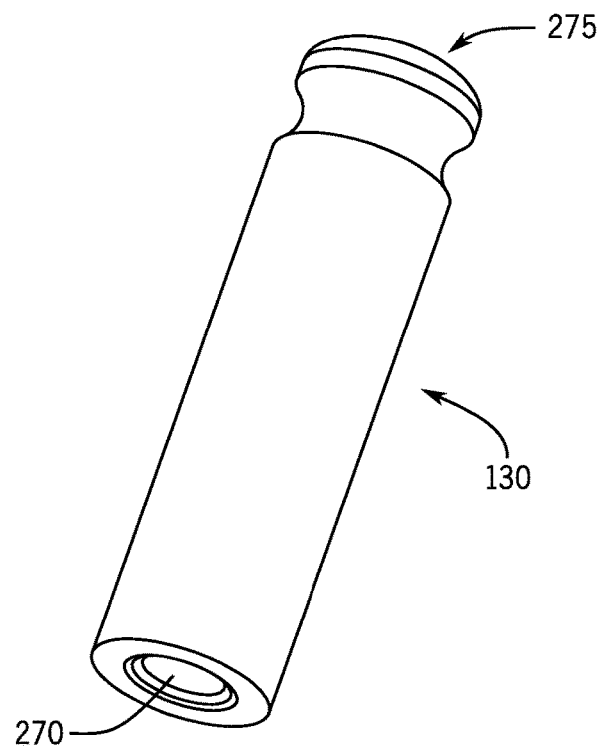
FIG. 10 is a view of an embodiment of the top bearing pin.

As can be understood from FIGS. 5A and 5B, the upper bearings pin 130 and bottom bearing pin 160 generally have the same configuration, but are oppositely oriented. As depicted in FIGS. 9A-B, the top bearing pin 130 and the bottom bearing pin 160, have a tea cup or hemispherical concave bearing surface 270 on one end and a generally planar surface 275 on the opposite end. Similarly, FIG. 10 depicts a particular embodiment of the top bearing pin 130, which has a tea cup or hemispherical concave bearing surface 270 on one end and a generally planar surface 275 on the opposite end. In this embodiment, the hemispherical concave bearing surface 270 of the top bearing pin 130 has a larger radius than the concave bearing surface on the bottom bearing pin 160.

Figure 11A:
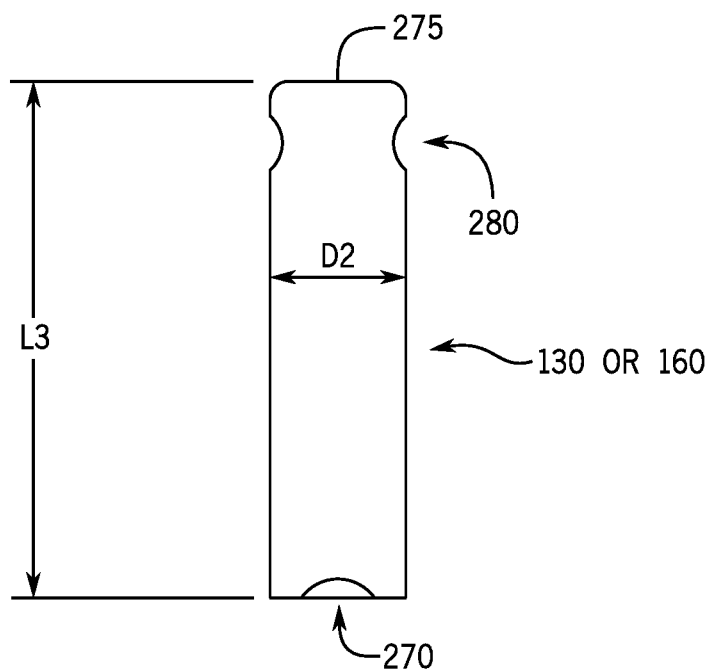
FIGS. 11A-B are side elevation views of embodiments of the representative bearing pin.
Figure 11B:
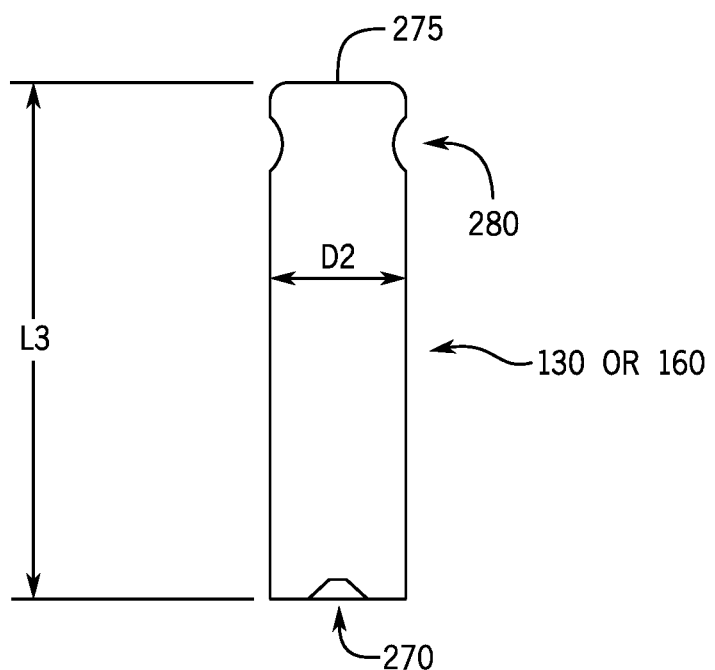

As illustrated in FIG. 11A, one embodiment of the bearing pin 130, 160 has an overall length L3 of approximately 7.5 mm, plus or minus 0.1 mm, a minimum pivot diameter D2 of approximately 2 mm, plus or minus 0.01 mm, and a radius of approximately 0.6 mm at the edge near the bearing surface 270. Near the non-bearing end 275 of the bearing pin 130, 160, a groove 280 extends circumferentially around the pin to provide a mechanical interlock for bonding the bearing pin in place within the blood pump 25. Similarly, an alternate embodiment of the bearing pins 130, 160, as illustrated in FIG. 11B, has an overall length L3 of approximately 7.5 mm, plus or minus 0.1 mm, a minimum pivot diameter D2 of approximately 3 mm, plus or minus 0.01 mm, and a radius of approximately 0.2 mm at the edge near the planar end 275. Near the non-bearing end of the bearing pin 130, 160 there is a groove 280 circumferentially extending around the pivot used to provide a mechanical interlock for bonding the bearing pin in place. Other sizes and dimensions may be used depending upon the size of the pump, the materials of the bearing pin, and the forces acting on the bearing pin.

As can be understood from FIGS. 3B, 4B, and 5A-11B, the convex upper bearing surface 255 of the impeller pivot 145 is rotationally received against the concave bearing surface 270 of the top bearing pin 130, and the convex lower bearing surface 260 of the impeller pivot 145 is rotationally received against the concave bearing surface 270 of the bottom bearing pin 160. Thus, the convex bearing ends 255, 260 of the impeller pivot 145 are pivotally supported by complementary concave bearing surfaces 270 of the top and bottom bearing pins 130 and 160, respectively. Accordingly, the impeller assembly may freely rotate in the impeller chamber 205 on the impeller pivot 145, which is supported end to end with the bearing pins 130 and 160, in a configuration commonly known as a "double pin bearing."

As can be understood from FIGS. 11C-11F, yet another embodiment of the bearing pin 130, 160 has an overall length L3 of approximately 7.5 mm, plus or minus 0.1 mm and a minimum pivot diameter D2 of approximately 2.0 mm, plus or minus 0.01 mm. The bearing end 271 has a radius R5 of approximately 0.3 mm at the edge near the bearing surface 270. Near the non-bearing end 275 of the bearing pin 130, 160, a series of grooves 281 extends circumferentially around the pin to provide a mechanical interlock for bonding the bearing pin in place within the blood pump 25. The series of grooves 281 may be defined by one or more valleys 283 having a radius R6 of approximately 0.20 mm and a plateau 285 having an edge radius R7 of approximately 0.03 mm. The distance V1 across each valley is approximately 0.5 mm, while the distance P1 across the plateau 285 is approximately 0.3 mm. The bearing pins 130 and 160 may also include a recess 286 having a diameter D3 of approximately 0.8 mm plus or minus 0.01 mm and a length L4 of approximately 2.0 mm, as shown in the cross section view of FIG. 11E. FIG. 11D is a view of the bearing surface 270 as viewed along a longitudinal axis of the bearing pin 130, 160. The bearing surface 270 may have a radius R8 of approximately 0.65 mm plus or minus 0.01 mm and a depth L5 of approximately 0.3 mm, as shown in the cross section view of FIG. 11F.

In yet another embodiment of the impeller assembly, the impeller assembly is a composite of the impeller shaft 145, top bearing pin 130, and bottom bearing pin 160. The composite design is beneficial with regard to the simplicity, tolerances, and cost of the machined bearing components. All of these constructions are designed to allow the motor to function in a continuous state for around a day to 1-12 weeks or longer, without breakdown.

Figure 12:
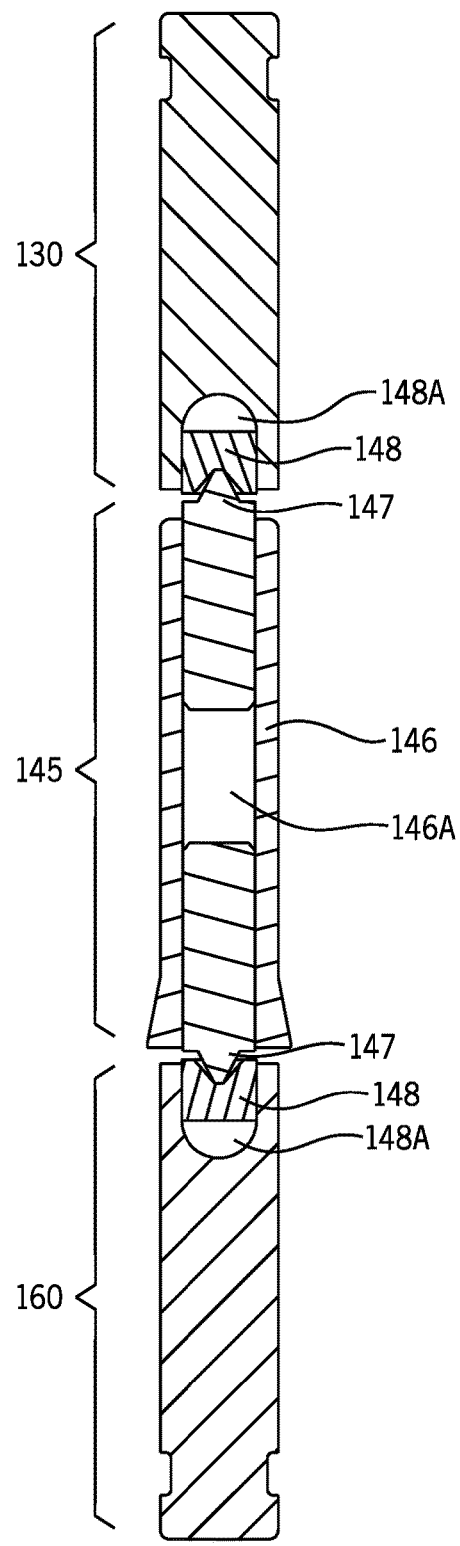
FIG. 12 is a longitudinal cross section of a representative bearing pin assembly.

As illustrated in FIG. 12, the impeller shaft 145 comprises an impeller pivot body 146 and two impeller pivot inserts 147. The impeller pivot body 146 comprises a machinable metal, such as stainless steel, and the impeller pivot inserts 147 comprise a high purity alumina ($Al_2O_3$), such as CoorsTek AD-998, a silicon carbide whisker-reinforced alumina, such as Greenleaf WG-300, or alumina toughened zirconia (ATZ). The impeller pivot inserts 147 are affixed to the impeller pivot body 146 by an adhesive and/or an interference fit. Optionally, the chamber 146A may be filled with an adhesive or other potting material that is resistant to compression. The aforementioned composite configuration and materials can be applied to embodiments of both the top bearing pin 130 and bottom bearing pin 160, where the pin inserts 148 engage the impeller pivot inserts 147. Optionally, the chambers 148A for each bearing pin 130 and 160, may be filled with an adhesive or other potting material that is resistant to compression.

The inlet cap 125 and its inlet channel 180 may have a variety of configurations, depending on the embodiment of the blood pump 25. For example, the inlet cap 125 depicted in FIG. 2 is shown as being generally coextensive with the top impeller casing 135. In other embodiments, the inlet cap 125 may be substantially smaller than, and not coextensive with, the top impeller casing 135, as depicted in FIGS. 13-15, which are views of the inlet cap and impeller casing.

Figure 13:
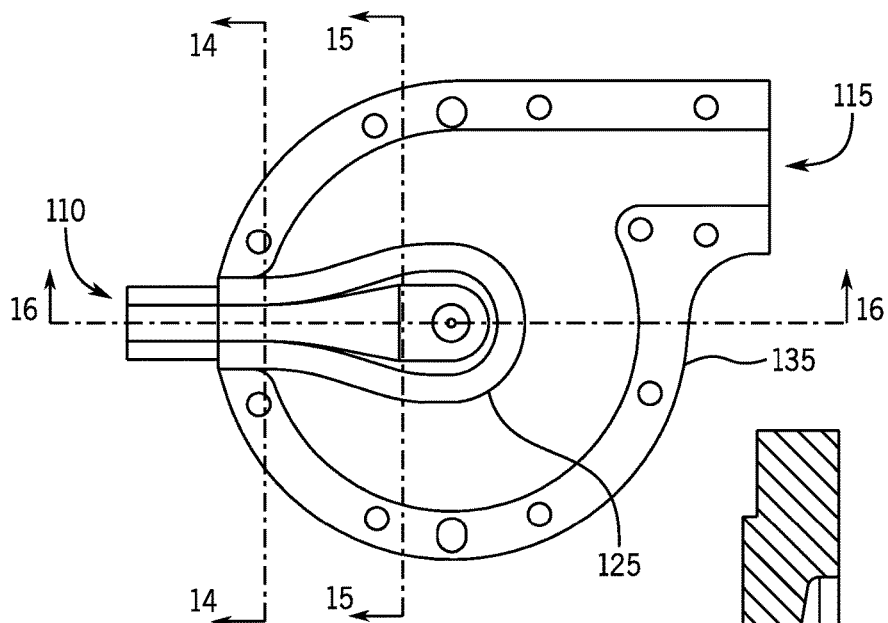
FIG. 13 is a plan view of the inlet cap and impeller casing.
Figure 14:
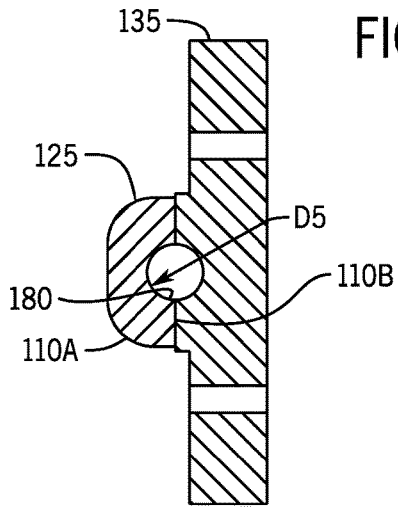
FIGS. 14-16 are, respectively, cross sectional elevations taken along section lines 14-14, 15-15, and 16-16 in FIG. 13.
Figure 15:
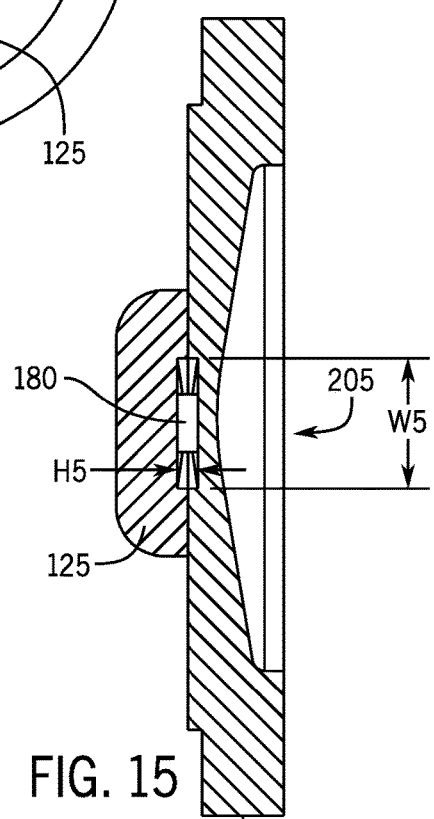
Figure 16:
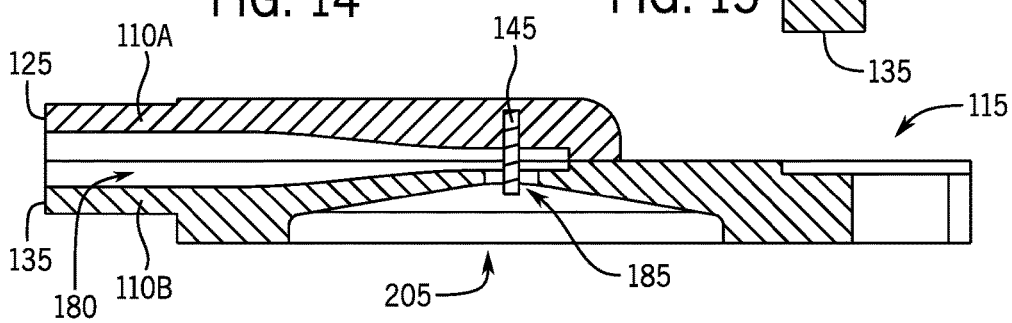

As shown in FIGS. 14-16, which are, respectively, cross sectional elevations taken along section lines 14-14, 15-15, and 16-16 in FIG. 13, the inlet 110 is a two part construction having portions 110A and 110B that each form approximately half of the inlet 110 and are respectively part of the inlet cap 125 and top impeller casing 135. Each portion 110A and 110B has defined therein approximately half of the inlet channel 180. As illustrated in FIG. 14, the inlet channel 180 initially has a circular diameter D5 of approximately 4 mm. As indicated in FIG. 15, the inlet channel 180 transitions from a circular cross section to a generally rectangular cross section having a width W5 of approximately 8.4 mm and a height H5 of approximately 1.5 mm. Again, as dimensions change so will the listed measurements.

As depicted in FIG. 16, the inlet channel 180 surrounds the impeller chamber inlet orifice 185, which extends around the top bearing 145 received in, and affixed to, the inlet cap 125. As shown in FIG. 17, which is an isometric partial cross section of the impeller chamber inlet orifice 185, the impeller chamber inlet orifice 185 leads to the impeller chamber 205 near the intake region 300 of the impeller 140. The upper bearing end of the impeller pivot 145 extends up through the orifice 185 to pivotally interface with the top bearing pin 130 supported in the inlet cap 125. Impeller blades 235 extend radially outward from the intake region 300 of the impeller 140.

Figure 18B:
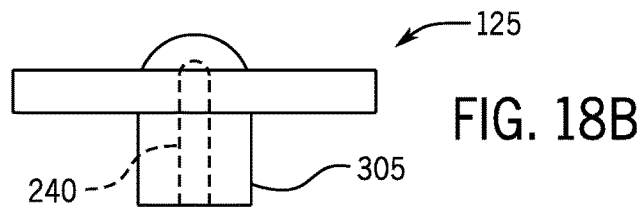
FIGS. 18A and 18B are, respectively, a plan view of the inlet cap portion defining the inlet channel and an end elevation view of the same.
Figure 18A:
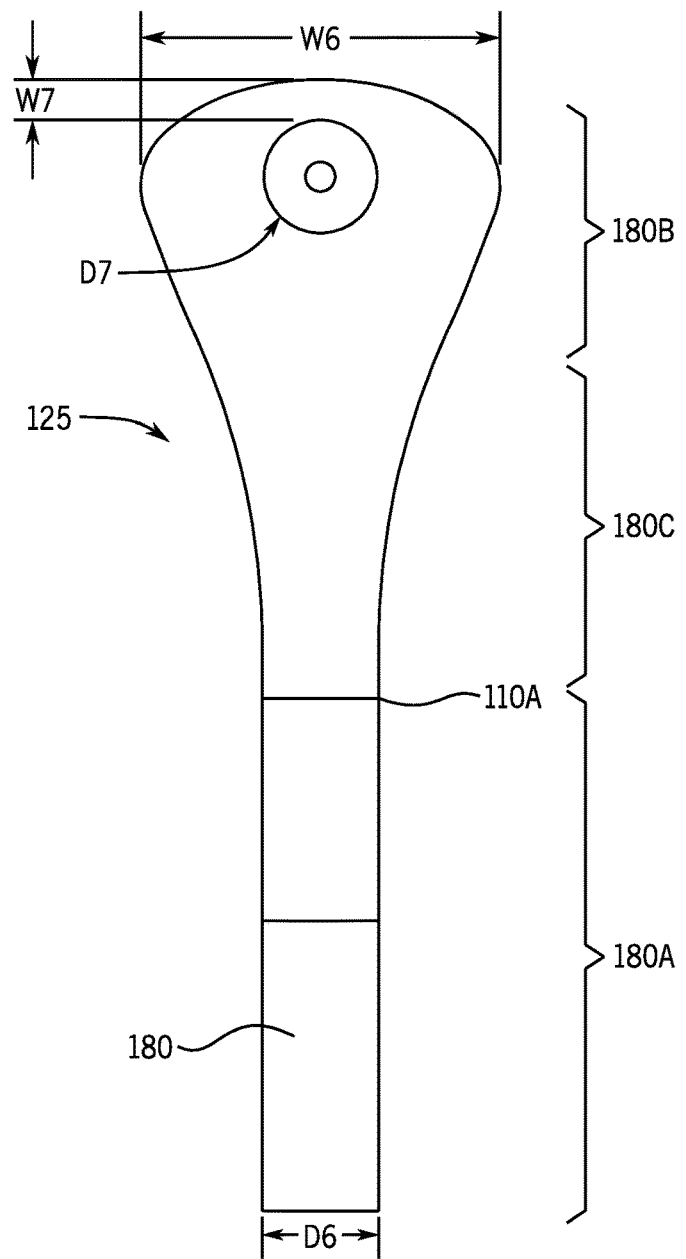

As depicted in FIGS. 18A and 18B, which are, respectively, a plan view of the inlet cap portion 110A defining the inlet channel 180 and an end elevation view of the same, in one embodiment, the inlet channel 180 may be said to have an elliptic configuration. Specifically, a cylindrical channel portion 180A transitions in portion 180C into an elliptical channel portion 180B. A cylindrical island portion or bezel 305 supporting the top bearing pin 130 is generally centered in the elliptical channel portion 180B and includes a cylindrical hole 240 that receives the top bearing pin 130 similar to as illustrated in FIG. 17. In one embodiment, the cylindrical channel portion 180A has a diameter D6 of approximately 4 mm. The elliptical channel portion 180B has a width W6 of approximately 12.4 mm. The distal distance W7 between the wall of the bezel 305 and the distal end of the wall defining the elliptical channel portion 180B is approximately 1.5 mm. In other embodiments, the cylindrical channel portion 180A has a diameter D6 of approximately 5 mm or 6 mm.

As depicted in FIGS. 19A and 19B, which are the same respective views as FIGS. 18A and 18B, except of another embodiment, the inlet channel 180 may be said to have a circular configuration. Specifically, a cylindrical channel portion 180A transitions in portion 180C into a circular channel portion 180B. A cylindrical island portion or bezel 305 supporting the top bearing pin 130 is generally centered in the circular channel portion 180B and includes a cylindrical hole 240 that receives the top bearing pin 130 similar to as illustrated in FIG. 17. In one embodiment, the cylindrical channel portion 180A has a diameter D9 of approximately 3.5 mm to 4.5 mm, preferably 4 mm. The circular channel portion 180B has a width W9 of approximately 11.5 mm to 13 mm, preferably 12.4 mm. The distal distance W10 between the wall of the bezel 305 and the distal end of the wall defining the circular channel portion 180B is approximately 3.5 mm to 4.5 mm, preferably 4.2 mm. In other embodiments, the cylindrical channel portion 180A has a diameter D6 of approximately 5 mm or 6 mm.

Figures 20A, 20B:
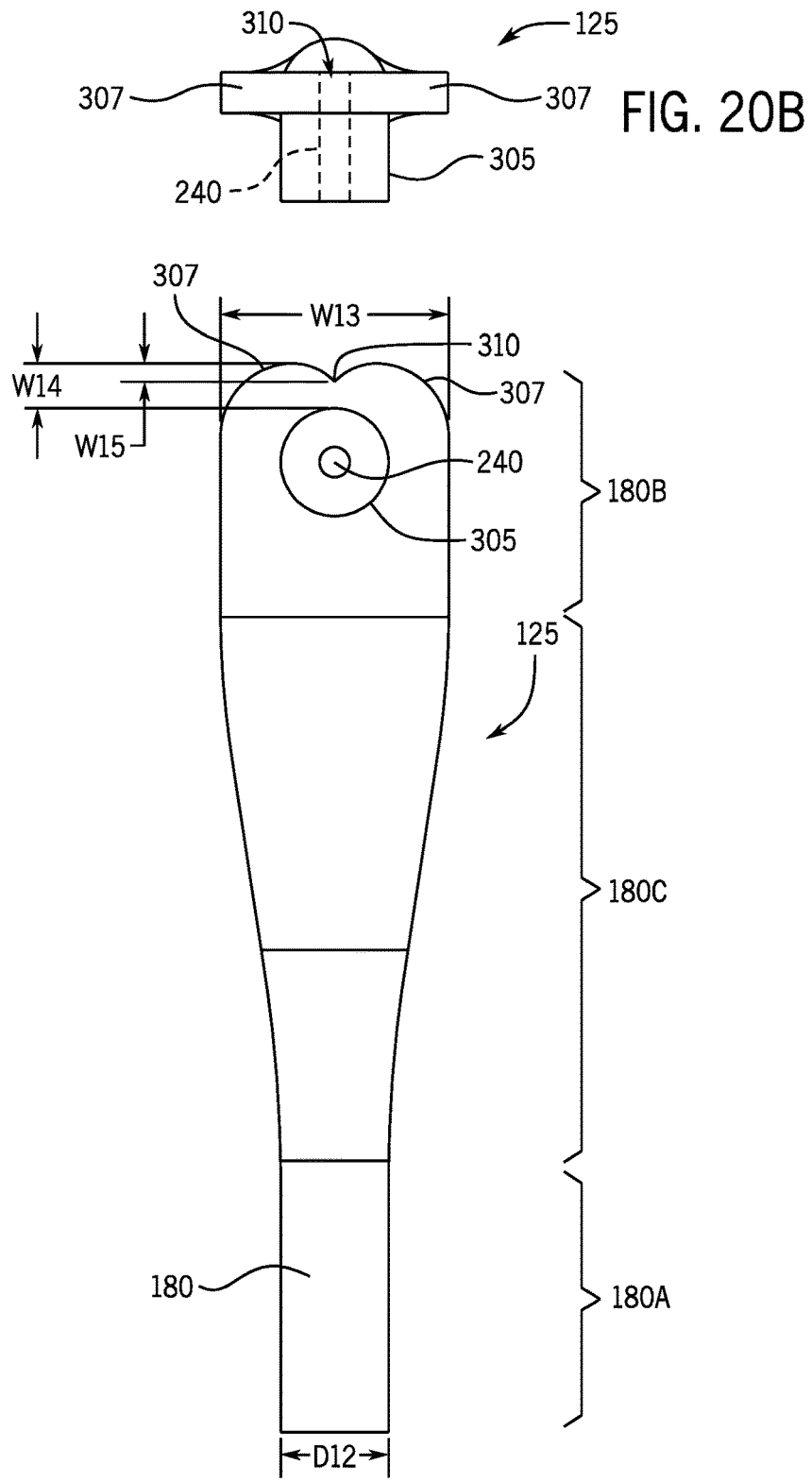
FIGS. 20A and 20B are the same respective views as FIGS. 18A and 18B, except of another embodiment.

As depicted in FIGS. 20A and 20B, which are the same respective views as FIGS. 18A and 18B, except of another embodiment, the inlet channel 180 may be said to have a complex arcuate configuration. Specifically, a cylindrical channel portion 180A transitions in portion 180C into a complex arcuate channel portion 180B. A cylindrical island portion or bezel 305 supporting the top bearing pin 130 is generally centered in the complex arcuate channel portion 180B and includes a cylindrical hole 240 that receives the top bearing pin 130 similar to as illustrated in FIG. 17. In one embodiment, the cylindrical channel portion 180A has a diameter D12 of approximately 4 mm. The complex arcuate channel portion 180B has a width W13 of approximately 8.4 mm. The distal distance W14 between the wall of the bezel 305 and the distal end dome 307 of the wall defining the complex arcuate channel portion 180B is approximately 1.75 mm. The distal distance W15 between the wall of the bezel 305 and the distal end cleft 310 of the wall defining the complex arcuate channel portion 180B is approximately 0.5 mm to 1.5 mm, preferably 1 mm. In other embodiments, the cylindrical channel portion 180A has a diameter D6 of approximately 5 mm or 6 mm.

Figure 21:
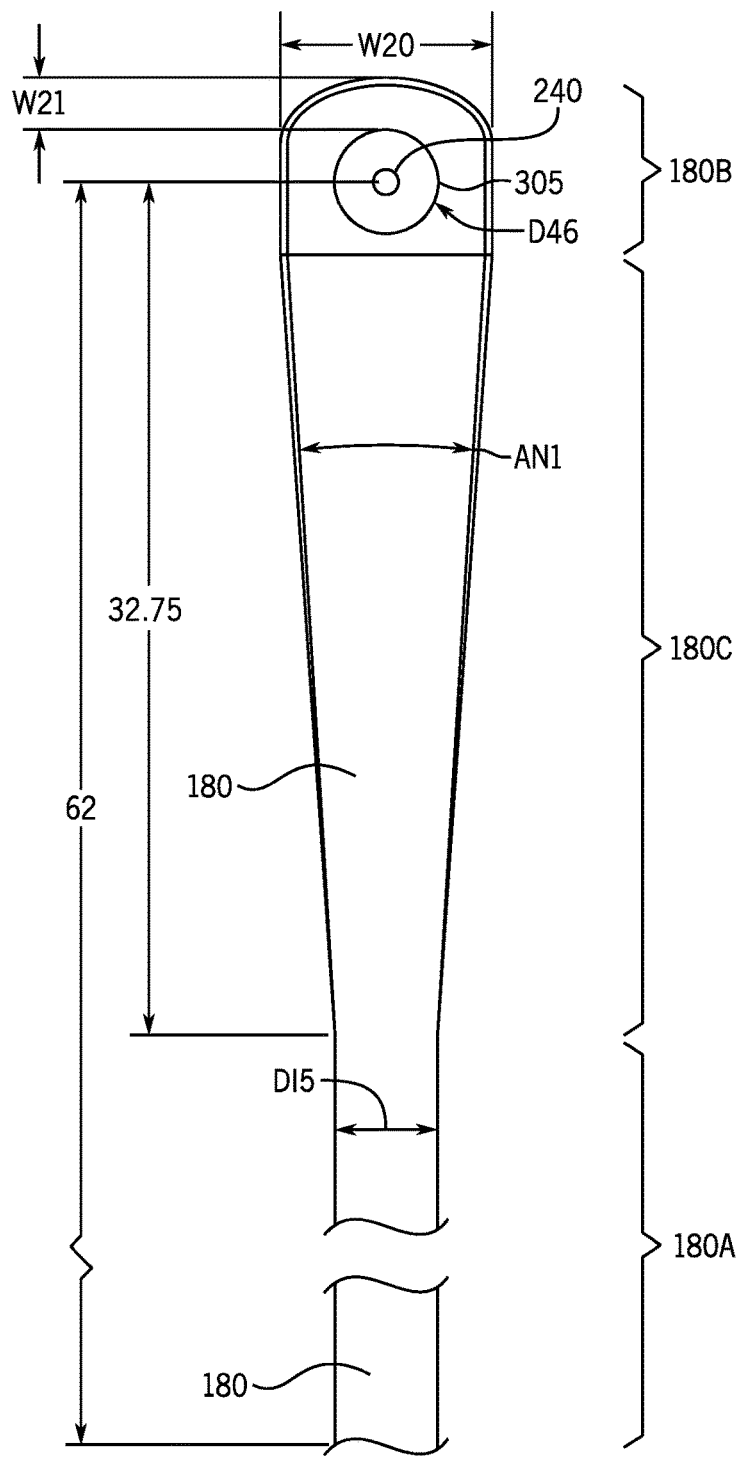
FIGS. 21-23 are the same views as FIG. 18A, except of three other embodiments.
Figures 22, 23:
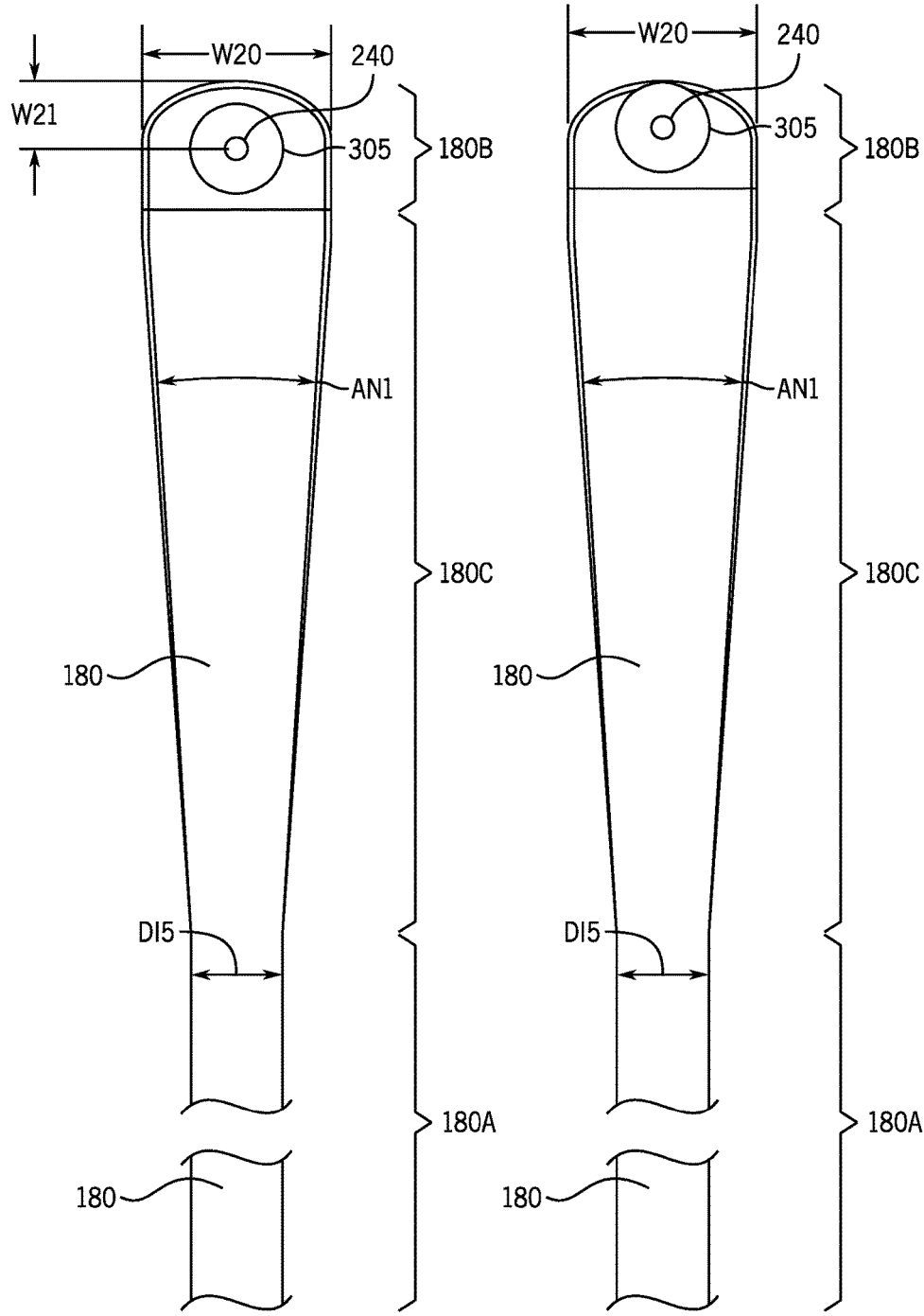

As depicted in FIGS. 21-23, which are the same views as FIG. 18A, except of three other embodiments, the inlet channel 180 may be said to have a tear drop configuration. Specifically, a cylindrical channel portion 180A transitions into a tear drop channel portion 180B. A cylindrical island portion or bezel 305 supporting the top bearing pin 130 is generally centered in the tear drop channel portion 180B and includes a cylindrical hole 240 that receives the top bearing pin 130 similar to as illustrated in FIG. 17. In one embodiment, the cylindrical channel portion 180A has a diameter D15 of approximately 4 mm. The tear drop channel portion 180B has a width W20 of approximately 8 mm. The bezel 305 has a diameter D16 of 4 mm. A transition region 180C of the channel 180 between the tear drop portion 180B and the cylindrical portion 180A has walls that diverge from each other at an angle AN1 of approximately 8 degrees. In other embodiments, the cylindrical channel portion 180A has a diameter D6 of approximately 5 mm or 6 mm.

For the embodiment of FIG. 21, the distal distance W21 between the wall of the bezel 305 and the distal end of the wall defining the tear drop channel portion 180B is approximately 2 mm. For the embodiment of FIG. 22, the distal distance W21 between the wall of the bezel 305 and the distal end of the wall defining the tear drop channel portion 180B is approximately 1 mm. For the embodiment of FIG. 23, the distal distance W21 between the wall of the bezel 305 and the distal end of the wall defining the tear drop channel portion 180B is approximately 0 mm because the bezel intersects the distal end of the wall defining the tear drop channel portion.

As illustrated in FIGS. 24A and 24B, which are, respectively, plan and side elevation views of another embodiment of the inlet cap 110 and inlet channel 180 similar to that described in FIG. 21, an arcuate wedged portion 320 may extend between the distal wall of the tear drop channel portion 180B to the distal side of the bezel 305. In such an embodiment, the cylindrical island portion or bezel 305 is generally centered in the tear drop channel portion 180B and includes a cylindrical hole 240 that receives the top bearing pin 130 similarly to as illustrated in FIG. 17. In one embodiment, the dimensional configuration of the embodiment depicted in FIGS. 24A and 24B is substantially the same as discussed with respect to FIG. 21, the significant difference being the presence of the arcuate wedge portion 320. As can be understood from FIGS. 24A and 24B, the wedge portion 320 has walls that are arcuate to smoothly curve from the roof and adjacent wall of the tear drop channel portion 180B to the vertical extension of the bezel 305. Such a wedged portion 320 may be seen to exist in the embodiment depicted in FIGS. 3A, 3B, and 17 and may reduce areas of inlet channel flow stagnation and facilitate tangential inflow of fluid through the impeller chamber inlet orifice 185.

Figure 25:
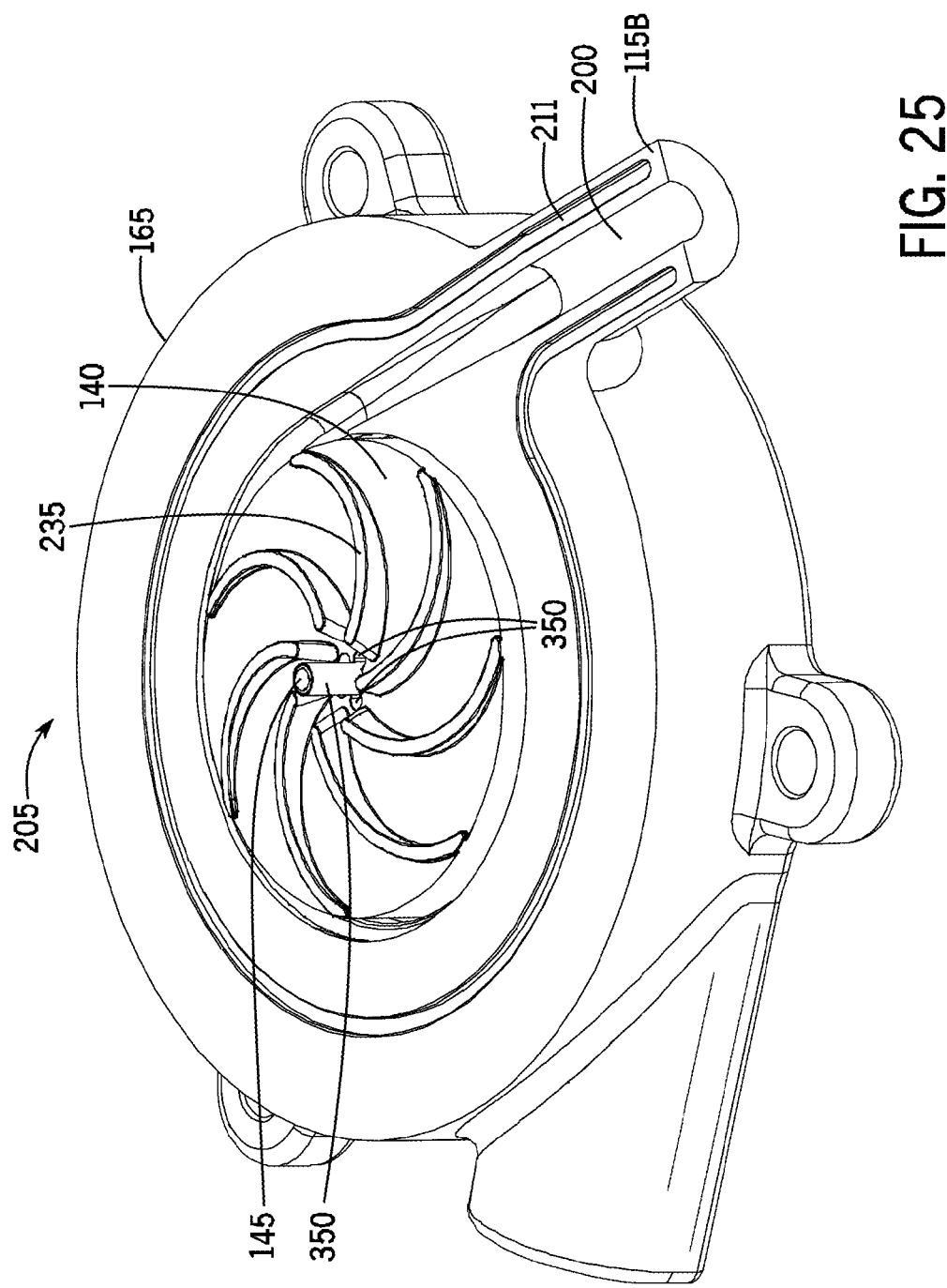
FIG. 25 is an isometric view of the pump with the top impeller casing removed to reveal the impeller occupying the impeller chamber.
Figure 27A:
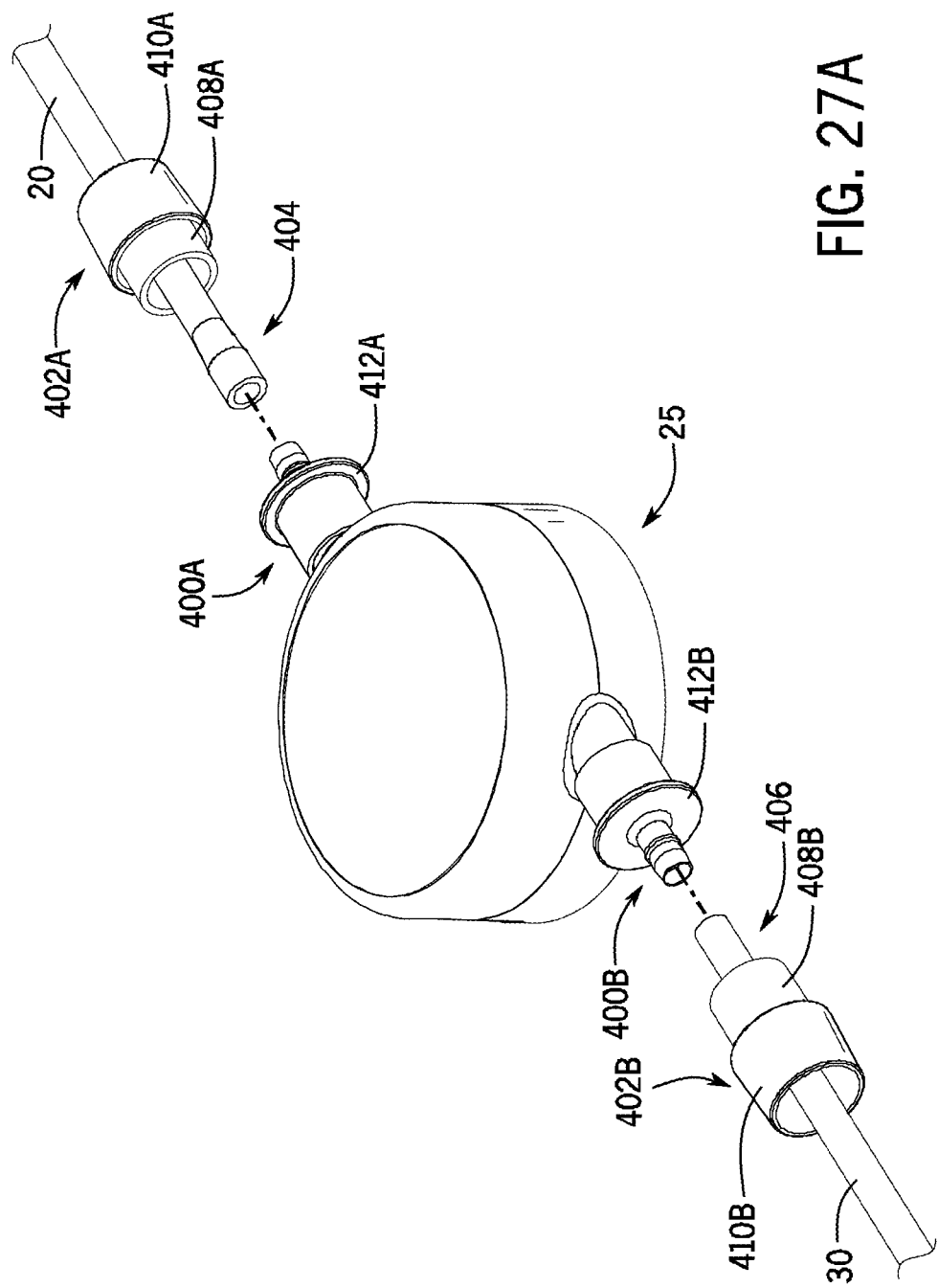
Figure 27D:
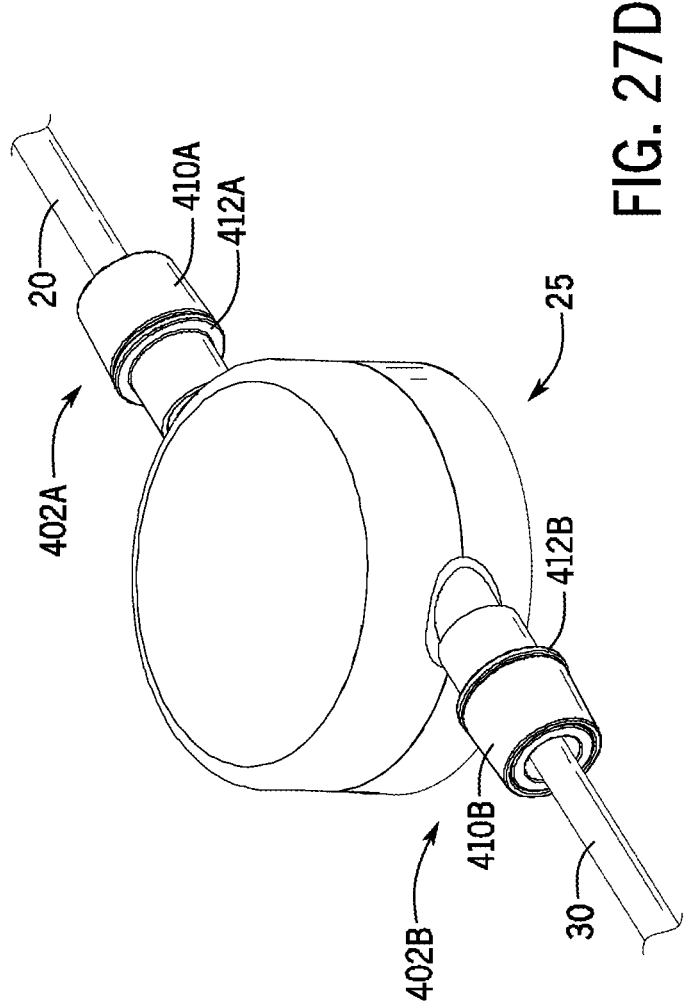

As shown in FIG. 25, which is an isometric view of the blood pump 25 with the top impeller casing removed to reveal the impeller 140 occupying the impeller chamber 205, the outlet fluid channel 200 exits the impeller chamber substantially tangential to the outer circumferential edge of the impeller. As indicated in FIGS. 3B, 4B, 17, and 25, a plurality of bores 350 (i.e. washout holes) are circumferentially distributed about the impeller pivot center hole 250, and the bores 350 are generally parallel to the center hole 250 and extend though the full thickness of the impeller to daylight on both top and bottom boundaries of the impeller. The bottom openings of the bores 350 are located near the bottom bearing interface between the bottom bearing 165 and the impeller pivot bottom bearing surface 260 (see FIG. 8). As a result, a fluid can be flowed through the bores 350 to cleanse the bottom bearing interface. For example, a fluid can be flowed through the impeller chamber inlet hole 185, radially-outward along the impeller blades 235, through the gap 542 under the impeller, and then back to the region of the impeller chamber inlet hole 185. This flow of blood serves to cleanse the underside of the impeller, the bottom bearing interface, the upper bearing interface, and the region behind the bezel 305.

As can be understood from FIGS. 3B, 5, 17, and 25, in one embodiment, the impeller 140 is rotationally supported in the impeller chamber 205 on a shaft 145 extending through a center of the impeller. The shaft has an upper bearing end and a bottom bearing end, each end rotatably operably coupled to the pump housing. The impeller has a top face, a bottom face, and multiple bores 350 extending through the impeller from the top face to the bottom face. The multiple bores are generally evenly distributed radially about center of the impeller. Further, the multiple bores 350 extend through the impeller generally parallel to each other and the shaft. The inlet channel 180 leads to an inlet orifice 185 of the impeller chamber. The inlet channel opens into the impeller chamber generally perpendicular to the inlet channel. The inlet orifice extends along at least a portion of an outer circumferential surface of the shaft near the upper bearing end. The inlet orifice and the holes open in directions that are generally parallel to each other. During operation of the pump, at least a portion of the blood pumped through the impeller chamber circulates along the top and bottom faces of the impeller via the bores. Thus, the bores of the impeller eliminate flow dead ends around the impeller by generally keeping blood flowing along all blood contacting surfaces of the impeller. Accordingly, the bores help to prevent blood accumulation in the vicinity of the shaft/impeller intersection and along the sides and bottom face of the impeller.

In various embodiments, the gap between the top face of the impeller 140 and the top impeller casing 135 is in a range between 0.05 mm and 0.3 mm, with preferred embodiments between 0.075 and 0.125 mm. Although counter to prevailing thoughts, it was determined that a smaller gap between the top face of the impeller 140 and the top impeller casing 135 is preferable as this takes advantage of the hydrodynamic flow behavior of the blood flowing around the impeller, which lowers the axial load applied to the top bearing which, in some instances, can function as a form of hydrodynamic bearing and can either replace the upper bearing or can supplement the upper bearing. The hydrodynamic bearing effectively formed by top surface of the impeller blades 235 with the smaller gap between the top face of the impeller 140 and the top impeller casing 135 reduces the load and therefore wear on the top bearing pin. As a result, the pump 25 may be operated for longer durations before replacement of the bearing is required. By way of example, as shown in FIG. 4G, the total surface area of the top of impeller blades 235, indicated generally as 237, provides a hydrodynamic bearing having an area in a range between about 70 mm$^2$ to about 120 mm$^2$. In one embodiment, the total surface area of the impeller blades 235 that facilitates the hydrodynamic bearing is approximately 96 mm$^2$. In this embodiment, the approximate area of the rotor top surface, excluding the central and washout holes, with the blades removed is approximately 677.7 mm$^2$. Therefore, if the area of the blade top surfaces is approximately 96.1 mm$^2$, then approximately 14% of the surface area is used to form the hydrodynamic bearing. In other embodiments, a greater ratio, such as 20% or more or a smaller ratio such as 10% or less of the impeller surface area may be used to form the hydrodynamic bearing.

In various embodiments, the gap 542 between the bottom face of the impeller and the bottom impeller casing 165 is in a range between approximately 0.1 mm and 0.5 mm, with preferred embodiments having a gap between approximately 0.2 and 0.35 mm. A larger gap 542 between the bottom face of the impeller 140 and the bottom impeller casing 165 is preferred as this improves the washing of the bottom bearing and lowers shear stress on the blood in the bottom gap.

In various embodiments, a balance is made the low design point flow and the broad operating flow range of the blood pump system. The specified ranges of top and bottom rotor-housing gaps enable the system to simultaneously achieve its hydraulic performance, manufacturing cost, blood damage, and service life requirements. These were verified in numerous studies using actual working prototypes through in vitro life tests demonstrating negligible bearing wear over 6 weeks and in vivo studies showing dramatic vein dilation over 9 days of treatment with no clinically significant hemolysis.

The body and impeller of the blood pump 25, including blood-contacting surfaces, are made from a variety of rigid biocompatible materials. Preferred options include injection moldable plastics such as polycarbonate and polyetheretherketone (PEEK). In various embodiments, the blood-contacting surfaces of the blood pump 25 may comprise Ti6Al4V, Ti6Al7Nb, or other commercially pure titanium alloys. In one embodiment, the surfaces of the pump components to be exposed to the patient's blood may have antithrombotic coatings. For example, the luminal surfaces may be coated with Astute®, a heparin based antithrombotic coating by BioInteractions Ltd., or Applause™, a heparin coating by SurModics, Inc.

In other embodiments, the surfaces of the blood pump system components in contact with the patient's tissue may have antimicrobial coatings. For example, the external surfaces of the synthetic conduits 16 and 18 or the external surfaces of the pump or the power cord 120 (which is also known as a "lead") may be coated with Avert®, a surface-active antimicrobial coating by BioInteractions Ltd.

Figure 34:
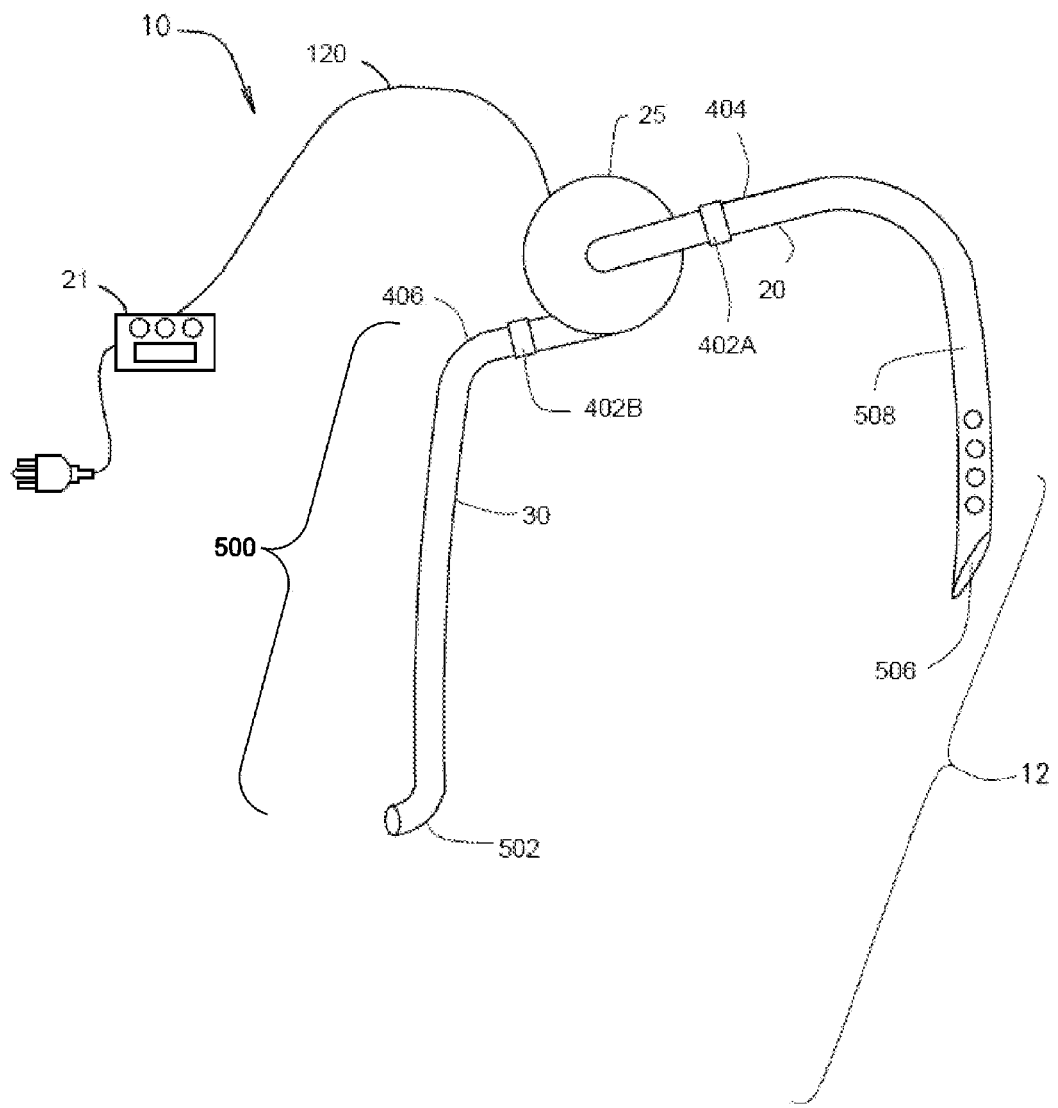
FIG. 34 is a schematic view of the pump system according to another embodiment.

In various embodiments, the blood pump 25 may be implanted within a patient. Conversely, in other embodiments, the blood pump 25 may remain external to the patient. For example, when located externally to the patient, the blood pump 25 may be secured to the patient using tape, sutures, or other suitable means to affix the pump to the patient. The system 10 may be powered by wearable electronics having rechargeable batteries 28, as shown in FIG. 34.

The pump for the pump system 10 disclosed herein may be a rotary pump, including, for example, a centrifugal flow pump, an axial flow pump, a radial flow pump, or a mixed flow pump. As shown in FIGS. 1-15, in one embodiment, the pump is a centrifugal pump. Without recognizing specific limitations, the blood pump 25 can be configured to routinely pump about 0.05 to 1.5 L/min, 0.1 to 1.5 L, or 0.5 to 3.0 L/min, for example.

While the pump configuration discussed above with respect to FIGS. 1-25 is advantageous, other pump configurations may be employed with the pump systems and methods disclosed herein. Accordingly, the systems and methods disclosed herein should not be limited to the pump configuration discussed above with respect to FIGS. 1-25, but should include all types of pumps applicable for the systems and methods disclosed herein.

A preferred embodiment of the pump system 10 disclosed herein with respect to FIGS. 1-25 satisfies several unique needs that cannot be satisfied by any blood pump systems known in the art. Specifically, the Arteriovenous Fistula Eligibility ("AFE") pump system ("AFE System") may be configured for up to 12 weeks of intended use. Further, the AFE pump system may be configured as a centrifugal rotary blood pump system for a low flow rate (e.g., 50 to 1500 mL/min) and medium pressure range (e.g., 25 to 350 mmHg).

A control scheme used with the AFE System pump system may be optimized to maintain a steady and elevated mean WSS of 0.76-23 Pa, or more preferably 2.5 Pa to 10 Pa, in target veins that are directly fluidly connected to the blood pump or a conduit of the blood pump system, or target veins that are fluidly connected to a vein that is directly fluidly connected to the blood pump or a conduit of the blood pump system. With this control scheme, the AFE System is configured to operate for a period of time such that the overall diameter and lumen diameter of the target vein will persistently increase by 25%, 50%, or 100% or more, utilizing sensing of operating parameters and periodic speed adjustment. A control scheme used with the AFE System pump system may be optimized to maintain a steady pressure in the segment of the outflow conduit adjacent to the target vein in a range of 10 mmHg to 350 mmHg, preferably between 25 mmHg to 100 mmHg. With this control scheme, the AFE System is configured to operate for a period of time such that the overall diameter and lumen diameter of the target vein will persistently increase by 25%, 50%, or 100% or more, utilizing sensing of operating parameters and periodic speed adjustment.

For certain embodiments, the inflow conduit may be placed by percutaneous approach, with a portion of the inflow conduit residing in an intravascular location, and the outflow conduit may be placed by surgical approach adaptable to initial vein diameters of between 1-6 mm. In this setting, elevated mean WSS in the target blood vessel results from discharging blood into the target blood vessel.

For other embodiments, the outflow conduit may be placed by percutaneous approach, with a portion of the outflow conduit residing in an intravascular location, and the inflow conduit may be placed by surgical approach adaptable to initial vein or artery diameters of between 1-6 mm. In this setting, elevated mean WSS in the target blood vessel results from removing blood from the target blood vessel. In certain settings, WSS can be elevated in both a blood vessel where blood is removed and a blood vessel where blood is discharged, making both blood vessels target blood vessels. The pump system 10 achieves both ease of insertion/removal and resistance to infection. The pump system 10 is a mobile system with a pump that is adaptable for either implanted or extracorporeal placement. In various embodiments, the pump system 10 is powered by wearable electronics with rechargeable batteries.

The pump system 10 includes an inflow conduit 20 and an outflow conduit 30, as shown in FIG. 26. The inflow conduit 20 is placed in fluid communication with one location in the vascular system, draws blood from this location, and carries it to the blood pump 25. In certain embodiments, the inflow conduit 20 is configured for placement of at least a portion of the inflow conduit within the lumen of the vascular system. In other embodiments, the inflow conduit 20 is joined to a blood vessel by a surgical anastomosis. The outflow conduit 30 is configured for making a fluid communication with another location in the vascular system and directs blood from the blood pump 25 to the other location in the vascular system. In certain embodiments, the outflow conduit 20 is configured for placement of at least a portion of the outflow conduit within the lumen of the vascular system. In other embodiments, the outflow conduit 30 is joined to a blood vessel by a surgical anastomosis.

The conduits 20 and 30 may each have a length that ranges between 2 cm and 110 cm and a total combined length of 4 cm to 220 cm. The length of the each conduit 20 and 30 may be trimmed to a desired length as determined by the location of the blood pump 25 and the location of the connections between the conduits and the vascular system. The conduits 20 and 30 also have thin but compression-resistant and kink-resistant walls that have a thickness of between 0.5 mm and 4 mm and inner diameters that are between 2 mm and 10 mm. Preferably, the inner diameters for the conduits are 4 to 6 mm.

The inflow and outflow conduits 20 and 30 may be connected to the blood pump 25 using any suitable connector that is durable, resists leaks, and is not susceptible to unintentional disengagement. Typically, the leading edge of the connector is thin, in order to minimize the step change in fluid path diameter between the inner diameter of the conduits 20 and 30 and the inner diameter of the connector. Preferably, the step change in fluid path diameter should be less than 0.5 mm. In one embodiment, as shown FIGS. 27A-27D, the conduits 20 and 30 are connected to the blood pump 25 using barb fittings 400A and 400B and radially compressive retainers (i.e. locking collars) 402A and 402B. By way of example, and not limitation, the radially compressive retainers 402A and 402B, may be BarbLock® retainers manufactured by Saint-Gobain Performance Plastics, a division of Saint-Gobain S.A. headquartered in Courbevoie, France. In another embodiment, the conduits 20 and 30 are connected to the blood pump 25 using Pure-Fit® sterile connectors, also manufactured by Saint-Gobain Performance Plastics.

The radial compressive retainers 402A and 402B are placed over the proximal ends 404 and 406 of the inflow and outflow conduits 20 and 30, respectively. The conduits 20 and 30 are then placed over the barb fitting 400A and 400B to form a fluid connection between the conduits and the blood pump 25. Collets 408A and 408B of the radial compressive retainers 402A and 402B are placed along the conduits 20 and 30 to encircle the conduits and the barb-fittings 400A and 400B. Outer sleeves 410A and 410B of the radial compressive retainers 402A and 402B are then moved along a longitudinal axis of the retainers to compressively engage the respective collets 408A and 408B, conduits 20 and 30, and the barb fittings 400A and 400B. In one embodiment, the outer sleeves 410A and 410B are moved by a compressive tool configured to engage the outer sleeves and a support shelf 412A and 412B of the barb fittings 400A and 400B, respectively. The compressive tool may also be configured to remove the radial compressive retainers 402A and 402B.

Figure 28A:
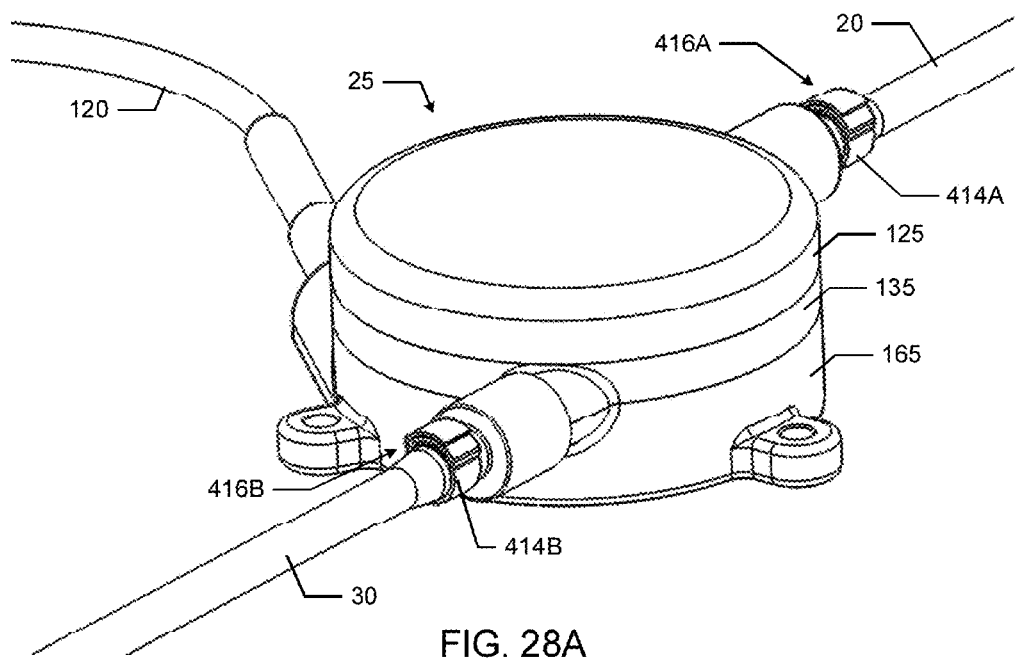
FIGS. 28A and 28B are perspective views of the connection between the pump and conduits according to one embodiment.
Figure 28B:
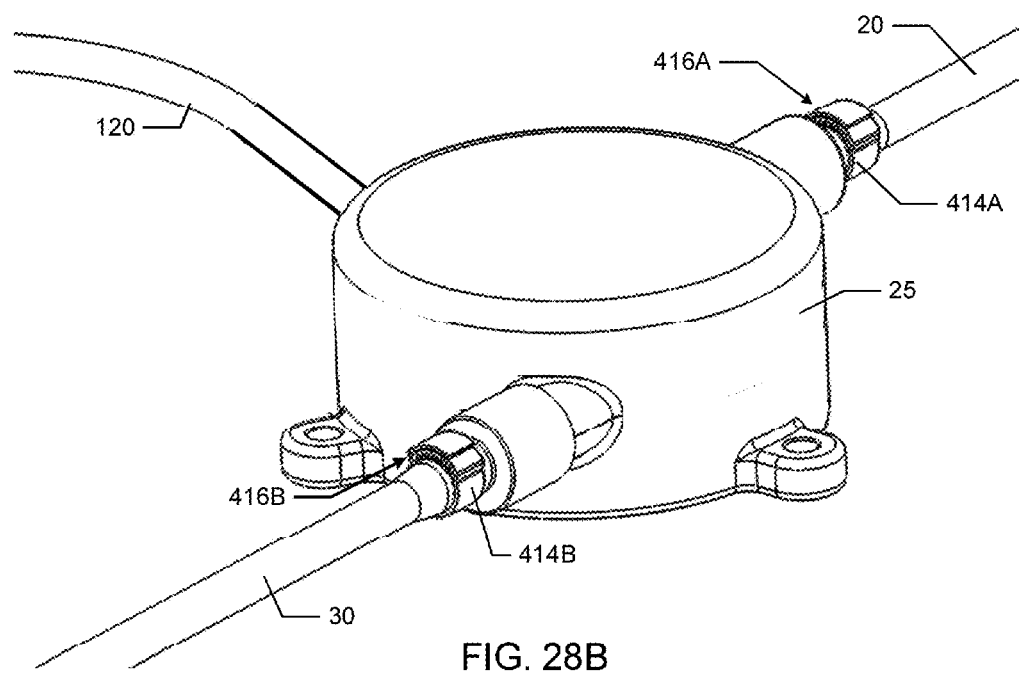

In other embodiments, alternative connectors may be used. Preferably, the alternative connectors are durable, resist leaks, and resist unintentional dislodgment. For example, as shown in FIGS. 28A-B, the conduits 20 and 30 engage barb fittings, similar to barb fittings 400A and 400B, to form a fluid connection between the conduits and the blood pump 25. The conduits 20 and 30 are secured to the barb fittings using circular clips 414A and 414B that apply radial compressive force to the portion of the conduits on the barb fittings by way of a ratcheting mechanism 416A-416B of the clips. The circular clips 414A and 414B provide a leak-resistant and durable connection that may be removed with a removal tool (not shown) which releases the ratcheting mechanisms 416A-416B of the clips.

Figure 29A:
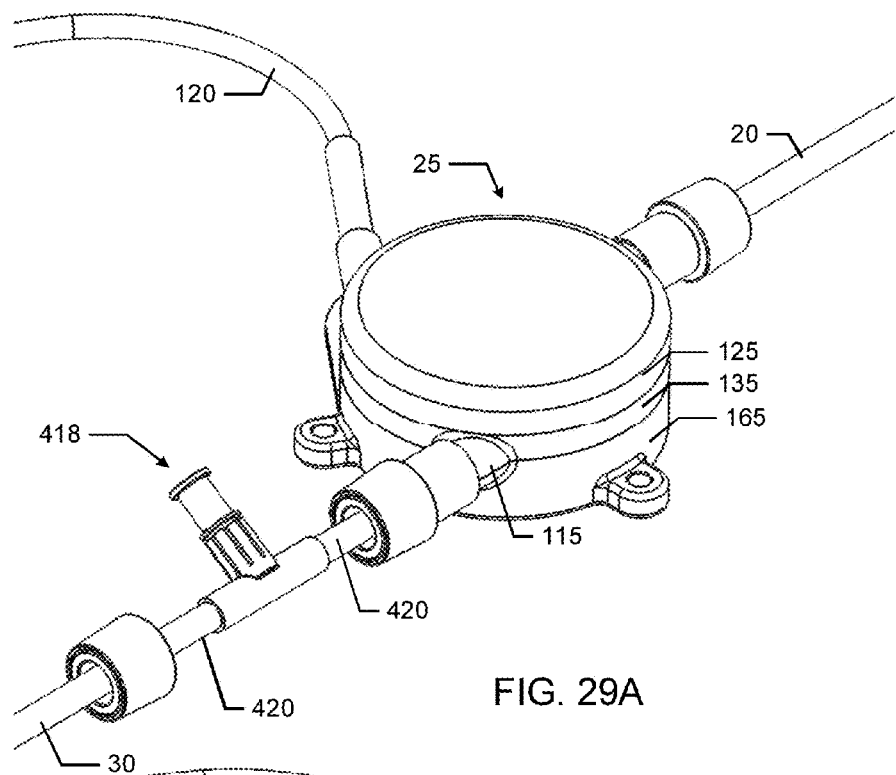
FIGS. 29A and 29B are perspective views of the connection between the pump and conduits that include a side port according to one embodiment.
Figure 29B:
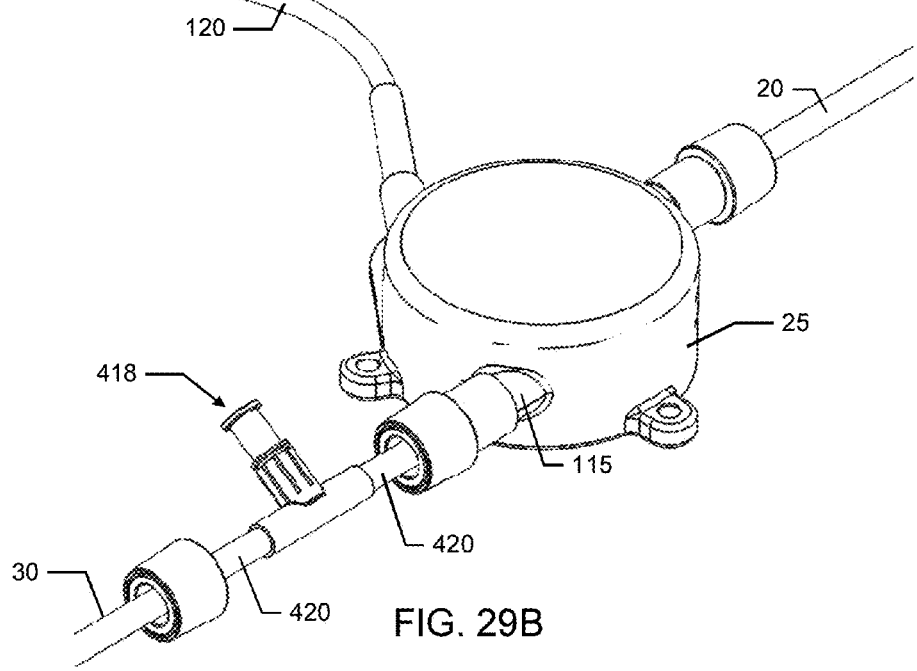

In another embodiment, the inflow conduit 20 and the outflow conduit 30 each contain at least one side port 417, as shown in FIGS. 29A-B, 30A-B, and 50, 51A-B, and 52A-B, that provides controlled access to the fluid path. Side ports 417 may be used periodically to introduce contrast into the fluid path to enable visualization of portions of the AFE System or portions of the vascular system in fluid communication with the conduit(s) of the AFE System by fluoroscopy. The side ports 417 may also be used to remove and return blood from the vascular system of a patient during hemodialysis, plasmapheresis, apheresis, or other clinical indications wherein blood is rapidly removed and returned to a patient. The side ports 417 may also be used to obtain blood samples, to infuse medications, or for other clinically useful purposes. Any side port design that allows periodic access to the fluid path and does not leak or alter the fluid flow path when not accessed is suitable. By way of example, and not limitation, the side port 417 may be a "T" port fitting that includes a check valve that opens when a syringe is inserted and closes when the syringe is removed. As shown in FIGS. 29A-B, a "T" port assembly 418 with auxiliary tubing 420 is in fluid communication with the pump outlet 115 and outflow conduit 30.

Figure 30A:
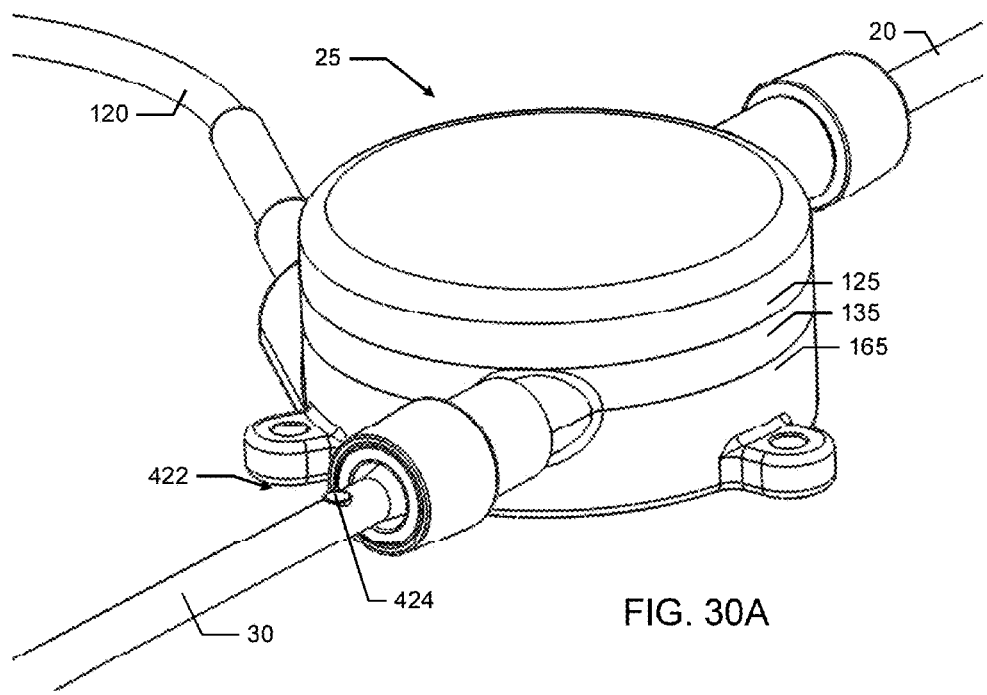
FIGS. 30A and 30B are perspective views of the connection between the pump and conduits that include a septum according to one embodiment.
Figure 30B:
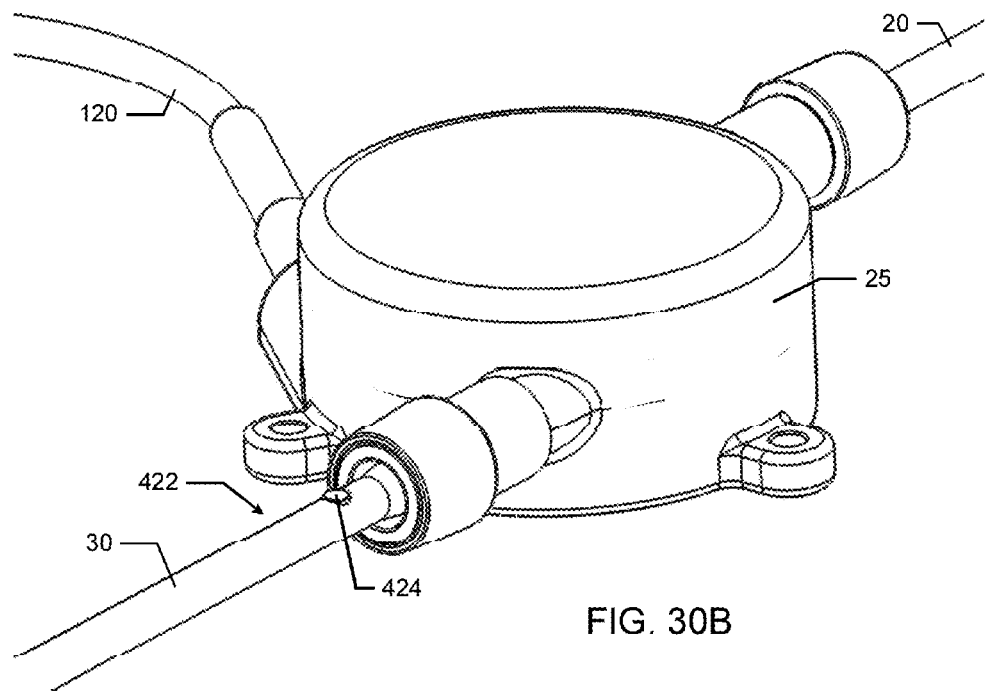

In another embodiment, a side port 417 for the inflow conduit 20, the outflow conduit 30, or both utilizes a septum access port 422 having a septum 424, as shown in FIGS. 30A-B, through which a suitable hypodermic needle can be inserted for access and then removed, after which the septum closes, preventing fluid loss from the conduit. Suitable materials for the septum 424 include, but are not limited to, silicone, polyurethane, and other elastomeric polymers. The segment of the inflow and/or outflow conduit 20 or 30, respectively, which includes the septum 424, is of a suitable thickness to close a hypodermic puncture hole when the needle is removed. As shown in FIGS. 30A-B, the septum access port 422 is shown in which the septum 424 makes up a portion of the outflow conduit 30. By way of example, and not limitation, the septum access port 422 may extend about one centimeter over the length of the outflow conduit 30. The septum 424 may be attached to the outflow conduit 30 by any suitable means including, but not limited to, adhesive attachment, thermal bonding, and thermal bonding between inner and outer layers of the conduit tubing.

In various embodiments, the conduits 20 and 30 may be comprised of materials commonly used to make hemodialysis catheters such as polyurethane, polyvinyl chloride, polyethylene, silicone, and polytetrafluoroethylene (PTFE), and including Pellethane® or Carbothane®. In other embodiments, the conduits may be comprised of materials commonly used to make hemodialysis grafts or synthetic peripheral bypass grafts such as expanded polytetrafluoroethylene (ePTFE) or Dacron. In further embodiments, conduits may be comprised of combinations of polyurethane, polyvinyl chloride, polyethylene, silicone, PTFE, Pellethane®, Carbothane®, Carbothane® PC-3575, ePTFE, or Dacron.

For example, the entire length of the inflow conduit 20 may be composed of polyurethane. In another embodiment, shown in FIG. 31, a segment 500 of the outflow conduit 30 configured to make a fluid communication with the blood pump 25 is composed of polyurethane while a segment 502 of the outflow conduit configured to make a fluid communication with the vascular system is composed of ePTFE.

Figure 41:
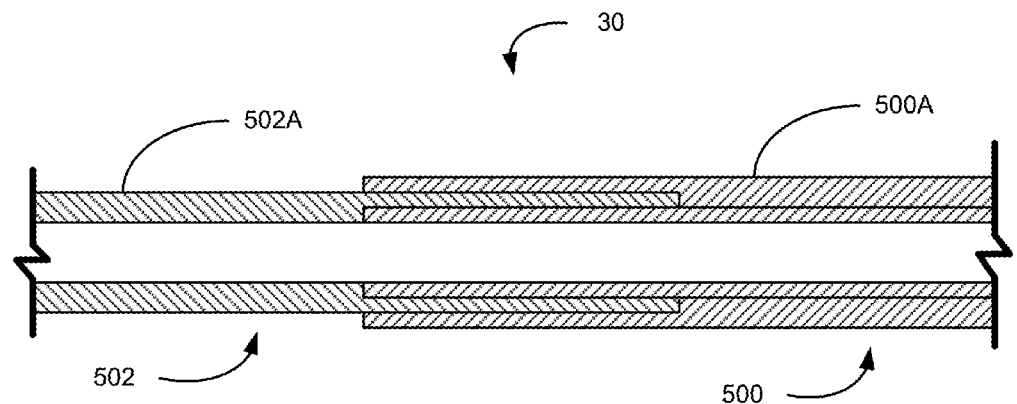
FIG. 41 is a longitudinal cross section of the junction between the proximal segment and distal segment.

By way of example and not limitation, and as shown in FIG. 41, which is a longitudinal cross section of the junction between the proximal segment 500 and distal segment 502, the proximal segment 500 of the outflow conduit 30 is joined to the distal segment 502 of the outflow conduit during the manufacturing process by placing one or more layers 502A of ePTFE from the distal segment between layers 500A of polyurethane from the proximal segment. The overlapping layers of polyurethane and ePTFE are then heat laminated to bond the proximal segment 500 and the distal segments 502 together.

In another example, one or more holes are made within the overlapped sections of the ePTFE of segment 502 prior to heat laminating the conduit. When the outflow conduit 30 is heated to a temperature that is sufficient to melt the polyurethane without melting the ePTFE (e.g. 200° F. to 500° F.), the molten polyurethane fills in and then cools within the holes created in the ePTFE segment 502. The inner and outer polyurethane layers of the segment 500 are joined with in the holes to mechanically join the two segments 500 and 502 together as well as mechanically join the inner and outer layers of polyurethane in the overlapped segment.

The embodiment of the outflow conduit 30 manufactured to have the ePTFE layer 502A sandwiched between the polyurethane layers 500A is advantageous in that the ePTFE layer 502A can be readily sutured to blood vessels using standard techniques. This is also the case for an inflow conduit 20 manufactured as discussed above with respect to FIG. 41.

Figure 42:
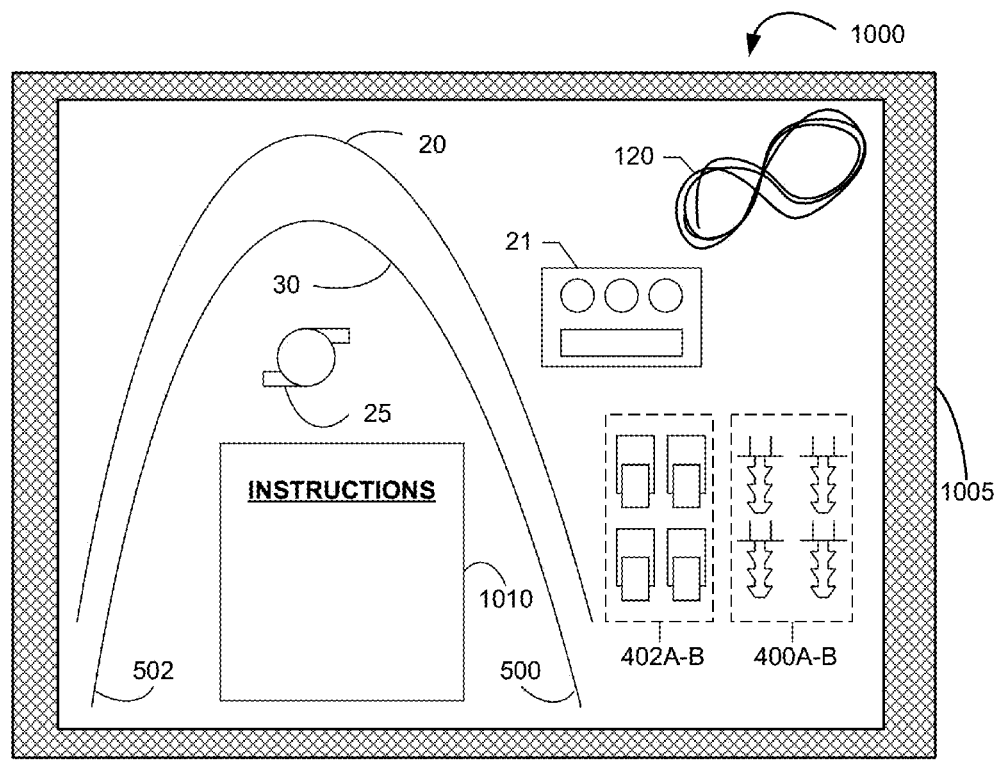
FIG. 42 is a plan view of a medical kit.

As illustrated in FIG. 42, which is a plan view of a medical kit 1000, the blood pump 25, inflow conduit 20, outflow conduit 30, control device 21, and power cord 120 can be provided in a sterile package 1005 with instructions 1010 on how to assemble and implant the pump system in a patient. The medical kit 1000 may also include the barb fittings 400A and 400B and the radially compressive retainers 402A and 402B. In one embodiment, one or both conduits 20, 30 are manufactured as described above with respect to FIG. 41 and enclosed within the sterile package 1005 along with the blood pump 25. The medical kit 1000, at a minimum, includes a system for discharging or removing blood and instructions for implementation and usage.

Figure 43:
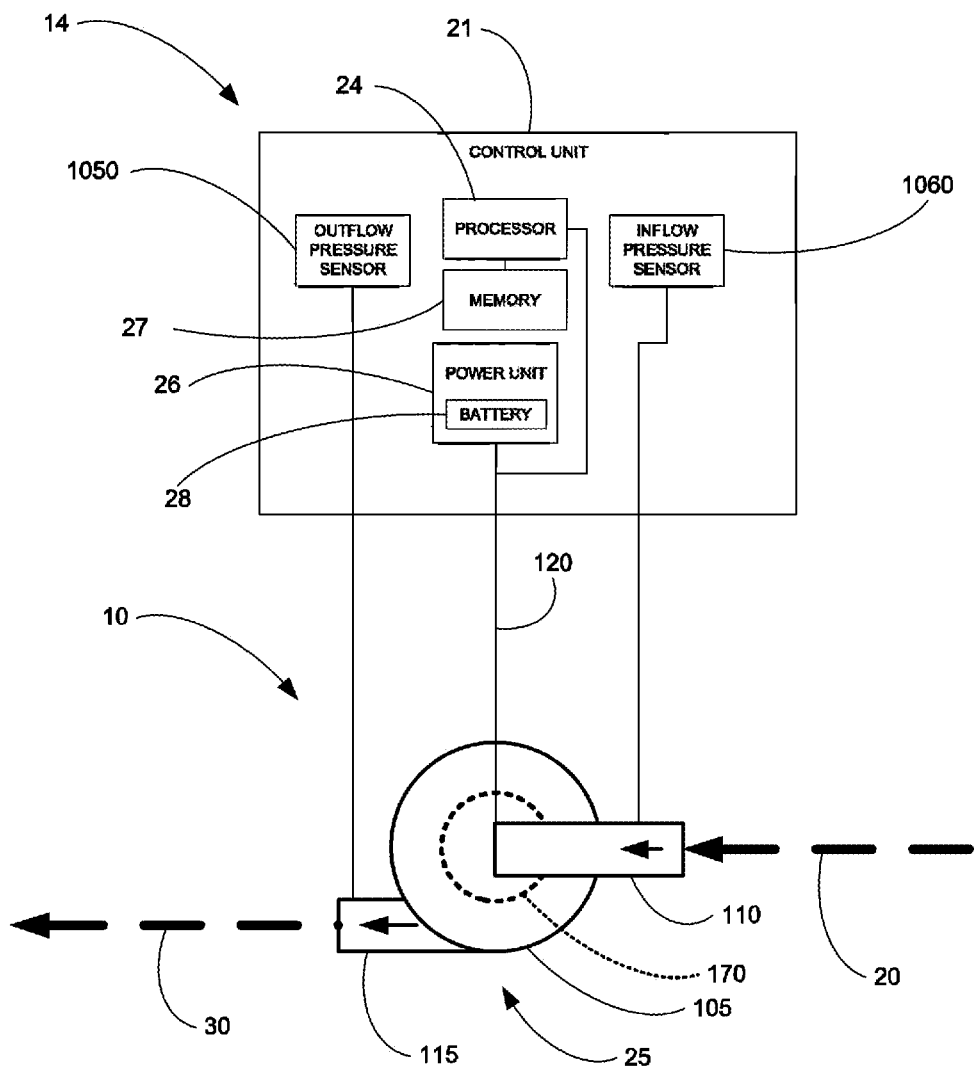
FIG. 43 is a schematic diagram of a pump system controlled according to outflow pressure.

In one embodiment, the operation of the blood pump 25 is controlled via the control unit 21 of a pump control system 14 by reading the outflow pressure and adjusting the pump speed accordingly. For example, as depicted in FIG. 43, which is a schematic diagram of a pump system 10 controlled according to outflow pressure, an outflow pressure sensor 1050 may be operably coupled to the outlet 115 of the blood pump 25 or further downstream, such as, for example, somewhere along the length of the outflow conduit 30. The processor 24 may compare the pressure reading from the outflow pressure sensor 1050 to a range of target outflow pressures stored in the memory 27. The processor will then adjust the speed of the pump drive 170 accordingly to cause the pressure reading from the outflow pressure sensor 1050 to be within the range of target outflow pressures stored in the memory.

In one embodiment, the control system 14 also includes an inflow pressure sensor 1060 that may be operably coupled to the inlet 110 of the blood pump 25 or further upstream, such as, for example, somewhere along the length of the inflow conduit 20. The processor 24 may read both the pressure reading from the outflow pressure sensor 1050 and the pressure reading from the inflow pressure sensor 1060 and calculate a pressure difference. This pressure difference may then be compared to a range of target pressure differences stored in the memory 1055. The processor will then adjust the speed of the pump drive 170 to cause the calculated pressure difference to be within the range of target pressure differences stored in the memory.

In other embodiments, the inflow and outflow conduits 20 and 30 can be any material or combination of materials so long as the conduits 20 and 30 exhibit desirable characteristics, such as flexibility, sterility, resistance to kinking and compression, and can be connected to a blood vessel via an anastomosis or inserted into the lumen of a blood vessel, as needed. In addition, the conduits 20 and 30 preferably exhibit the characteristics needed for subcutaneous tunneling as desired, such as comprising lubricious external surface coatings such as Harmony™ advanced lubricity coatings.

As another example, the inflow and outflow conduits 20 and 30 may have an exterior layer composed of a different material than the interior layer. All or a portion of the external layers of the inflow and outflow conduits 20 and 30 may also be coated with a lubricating agent, such as silicon or a hydrophilic coating to aid in subcutaneous tunneling and removal from the body, and to mitigate possible allergic reactions to latex. In certain embodiments, at least a portion of the surface of the exterior layer of the inflow and outflow conduits 20 and 30 may have an antimicrobial coating. In other embodiments, at least a portion of the surface of the blood pump 25 or the power cord 120 may have an antimicrobial coating. For example, Avert™, a surface active antimicrobial coating may be used. In certain embodiments, a portion of the surface of the exterior layer of an inflow and outflow conduit may include a material to resist infection and encourage tissue incorporation, such as Dacron, polyester velour, or silicone. One such material is the VitaCuff® antimicrobial cuff by Vitaphore Corp. The VitaCuff comprises two concentric layers of material. The internal layer is constructed of medical grade silicone. The external, tissue-interfacing layer comprises a collagen matrix with an anti-microbial activity that is attributable to silver ions bound to the collagen. In certain embodiments, this material absorbs physiological fluids, quickly expands, and helps provide a physical barrier at the exit site. Tissue ingrowth occurs, further securing the conduit in place, and reducing conduit movement to reduce the incidence of exit site infection.

Figure 48E:
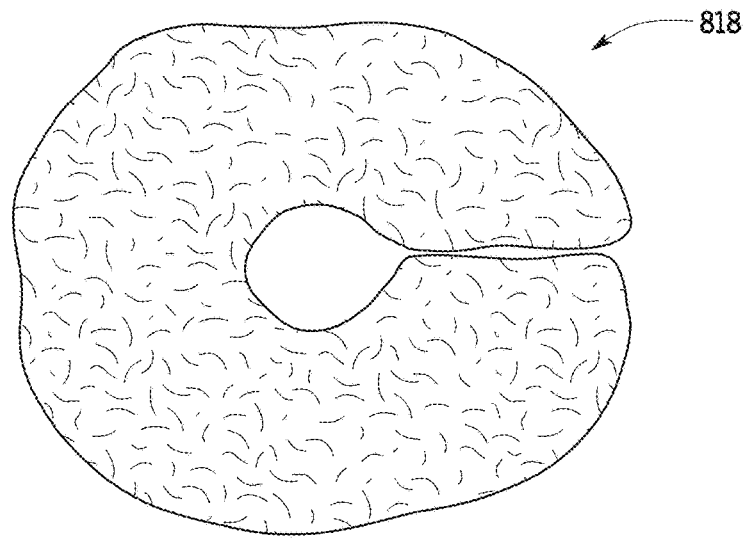
FIGS. 48E-F are photographs of a cuff device that may be attached to the external surface of a segment of a conduit.
Figure 48F:
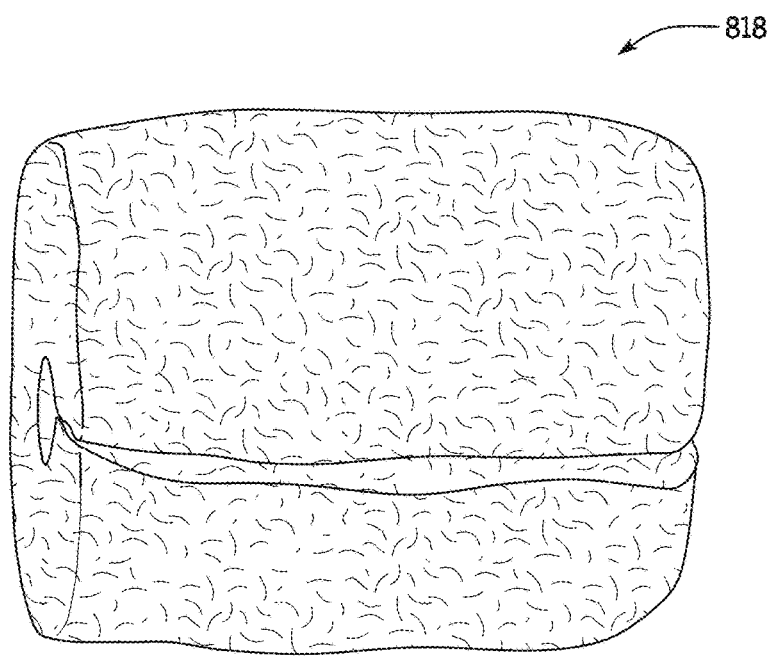

As can be understood from FIGS. 48A-F, an embodiment of a cuff 800 for securing the inflow and outflow conduits 20 and 30 to the patient over time and reducing ingress of foreign matter such as bacteria at the skin insertion site or into the body along the path of the conduits. The cuff 800 may include a two-part design having a detachable upper portion 802 and a detachable lower portion 804 that are mechanically engaged to one another and conduits. As shown in FIGS. 48B and 48D, each of the upper and lower portions 802 and 804 includes one or more latching members 806 and corresponding latching recesses 808. In one embodiment, the upper and lower portions 802 and 804 each include two latching members 806 that are received in latching recesses 808 on the opposing portion to secure the two portions together, as shown in FIGS. 48A-B. Each portion 802 and 804 may also include a guidance member 810 to further align the two halves and a corresponding guidance recess 812 for receiving the guidance member on the opposing portion. The upper and lower portions 802 and 804 each define a channel 814 for receiving a conduit 20 or 30. The channel 814 further defines a series of circumferentially continuous or, alternately, interrupted projections 816 that project into the channel 814. The projections 816 securely engage the conduits 20 or 30 when the cuff 800 is attached to the conduits to prevent movement or slippage of the cuff relative to the conduit. The projections 816 also provide a seal around the exterior surface of the conduits 20 and 30. In various embodiments, the exterior of the cuff may be coated or encased with a material 818 to encourage tissue incorporation or resist infection, such as Dacron, polyester velour, or silicone, as shown in FIG. 48E-F. The material 818 may also comprise agents with antimicrobial properties. The material 818 provides a porous external surface to the cuff 800 to encourage tissue ingrowth, increase adhesion locally between the patient and the conduit 20 or 30, and reduce ingress of foreign matter and bacterial into the skin incision site, the patient's body, or along the conduit path.

A physician may adjust the length of a subcutaneous tunnel for a conduit 20 or 30, such that a cuff 800 affixed to the conduit at a location that is appropriately located within the tunnel. When the cuff 800 is configured for attachment and detachment to a conduit 20 or 30 that may be trimmed to an appropriate length, the cuff 800 can be affixed to the trimmed conduit such that the cuff is appropriately located within the subcutaneous tunnel.

In certain embodiments, at least a portion of the blood-contacting luminal surfaces of the inflow and outflow conduits 20 and 30 may be coated with an antithrombotic agent or material. Similarly, at least a portion of the blood-contacting surfaces of the blood pump 25 may be coated with an antithrombotic agent or material. For example, the surfaces may be coated with the Applause® coating from SurModics, Inc., or the Astute® coating from BioInteractions Ltd., which are both hydrophilic copolymer coatings containing heparin.

In certain embodiments, at least a portion of the inflow conduit 20 and outflow conduit 30 are preferentially reinforced to resist kinking, compression, collapse, and coaption. For example, the conduits 20 and 30 may be reinforced with nitinol or another shape memory alloy or self-expanding or radially expansive material. Preferably, a layer of braided nitinol is wrapped around at least a portion of each of the conduits 20 and 30 or incorporated into the walls of conduits. In one embodiment, the inflow conduit 20 is reinforced by braided nitinol incorporated into the walls of the conduit. In another embodiment, the inflow conduit may be reinforced by braided stainless steel that is incorporated into the wall of the conduits 20 and 30. Alternately, a coil of nitinol or PTFE may be wrapped around portions of the conduits 20 and 30 or incorporated therein. For example, as shown in FIG. 31, the distal segment 502 of the outflow conduit 30 has a PTFE coil 504 incorporated around the ePTFE conduit forming the wall 514 of the conduit. In other embodiments, a coil of nitinol may be wrapped around portions of the conduits 20 and 30 or incorporated therein.

The braid density of the braided nitinol incorporated into both the inflow and the outflow conduits 20 and 30, commonly measured in pixels per inch ("PPI"), is typically between about 10 and 200, and preferably between about 20 and about 60. In various embodiments, the braid density may vary along the lengths of the inflow and the outflow conduits 20 and 30. For example, the braid density may be greater in portions of the conduits 20 and 30 adjacent to the blood pump 25, in order to maintain greater stiffness of the conduits and minimize the risk of external conduit compression or conduit collapse during suction, while allowing for more flexibility in different segments of the conduits.

Figure 32B:
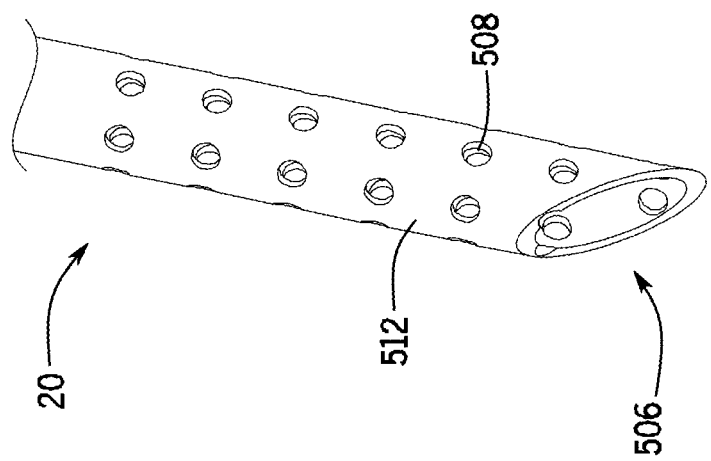
FIGS. 32A and 32B are views of the intravascular portion of an inflow conduit according to one embodiment.
Figure 32A:
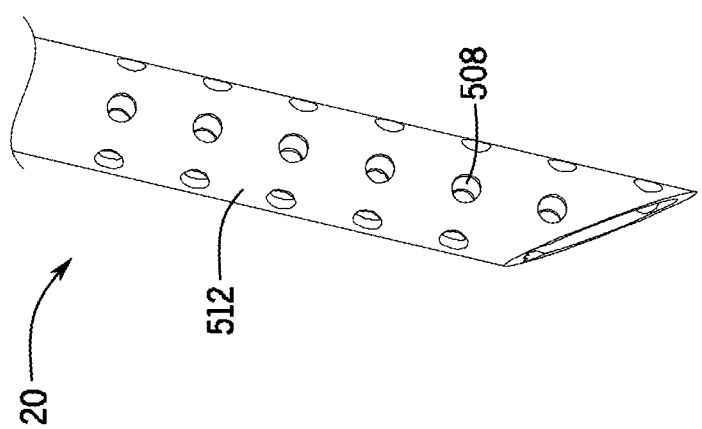
Figure 32C:
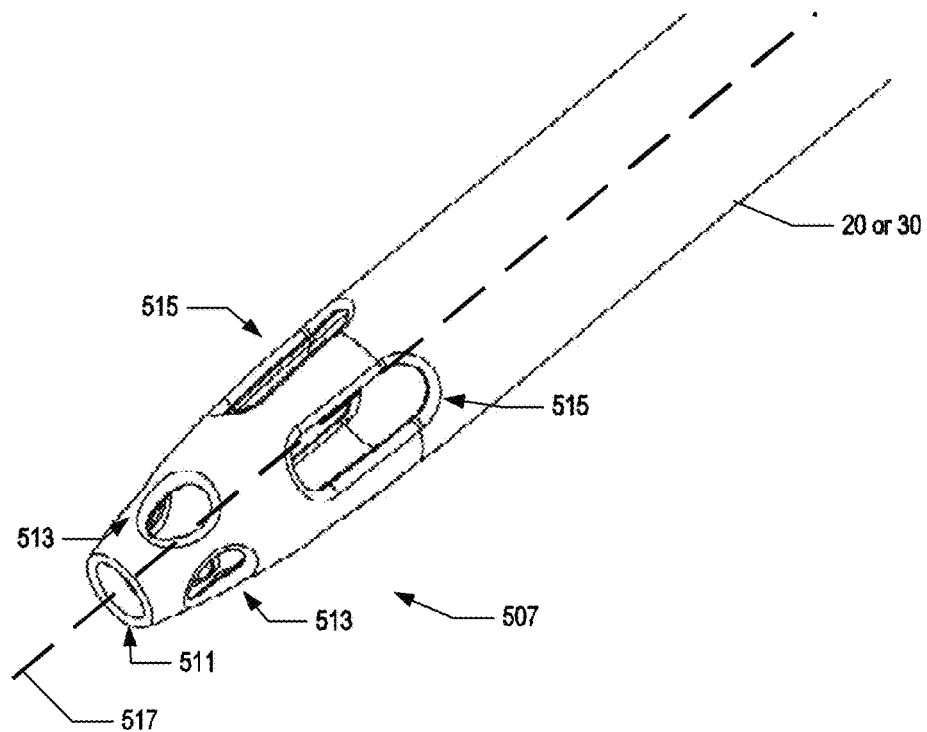
FIG. 32C is perspective view of the intravascular portion of an inflow or outflow conduit according to one embodiment.

In one embodiment, as shown in FIGS. 32A-32B, the intravascular portion 506 of the inflow conduit 20 is fenestrated by means of multiple side holes 508. These side holes enhance blood inflow and reduce the risk of suction of the vein or right atrium wall by the end hole in the event of partial obstruction of the conduit tip. The side holes 508 may be circular and range in diameter from 1.0 mm to 3.0 mm. In preferred embodiments, the side holes 508 may be elliptical, or any other shape and size suitable for the intravascular aspiration of blood.

As shown in FIGS. 31 and 32A-32B, the distal end 506 of the inflow conduit 20 and the distal end 510 of the outflow conduit 30 may be cut and chamfered at an angle between about 10° and 80°. In certain embodiments, the chamfer reduces the risk of suction of the vein or right atrium wall by the end hole in the event of partial obstruction of the tip of the conduit during aspiration of blood. In other embodiments, the chamfer increases the area of the conduit as it joins the vascular system in an anastomotic connection. In certain embodiments, the distal ends 506 and 510 are chamfered at 45°. The inflow and outflow conduits 20 and 30 are adapted for ease of insertion, subcutaneous tunneling, and removal, while also providing a resistance to infection and thrombosis.

In another embodiment, as shown in FIGS. 32C-32I, the intravascular portion 506 of the inflow conduit 20 and/or the outflow cannula 30 has a distal tip 507 that is optimized to reduce stagnant or recirculating flow within the conduit. The distal tip 507 is tapered and non-chamfered, with a circular end hole 511 having a diameter in a range between about 1.0 mm and about 3.0 mm, preferably the diameter is approximately 2.0 mm. The distal tip 507 is fenestrated by means of multiple sets of side holes 513 and 515. The side holes 513 and 515 may be of various sizes, shapes, and orientations. For example, a set of four side holes 513 are symmetrically arranged immediately behind the nose of the tip. Each of the side holes in the set 513 are circular in shape and angled with respect to the center line 517 of the inflow conduit lumen. In one aspect, the side holes 513 have a diameter in a range between approximately 0.8 mm and approximately 2.5 mm and are preferably approximately 1.7 mm in diameter. Moreover, the side holes 513 are oriented at an angle relative to the center line 517 in a range between approximately 30° and approximately 60°; preferably the holes are oriented at approximately 40°. Another set of four side holes 515 are symmetrically arranged approximately 6.5 mm from the nose of the tip 507. The side holes 515 are generally elliptical in shape with a major axis in a range between approximately 2.5 mm and approximately 7.0 mm long; preferably the major axis approximately 4.8 mm in length. The side holes 515 also have a minor axis in a range ranging between approximately 1.0 mm and approximately 2.5 mm long; preferably the minor axis is about 1.7 mm in length. In various aspects, the edges of the side holes 513 and 515 holes are rounded or radiused to avoid blood damage. Studies have demonstrated that embodiments of the cannula tip 507 as disclosed herein, are configured to generate levels of WSS at least one order of magnitude greater than existing cannulas. It is believed that the increase WSS is a function of the hole diameter difference (squared) and is also driven by the overall reduction in cannula diameter.

Figure 32D:
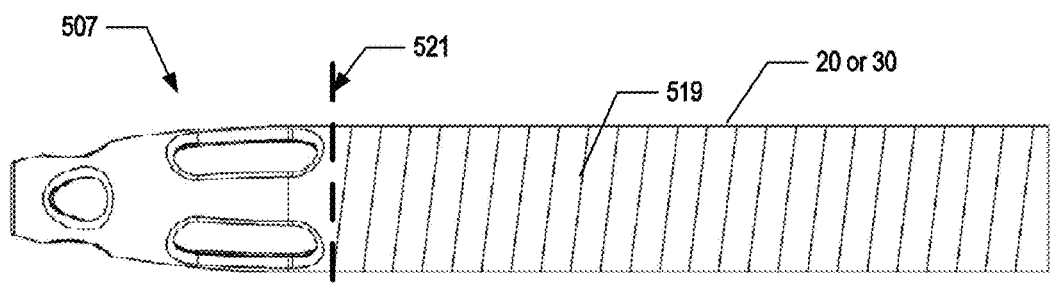
FIG. 32D is a plan view of the intravascular portion of an inflow or outflow conduit and a reinforcement coil of the conduit according to one embodiment.
Figure 32E:
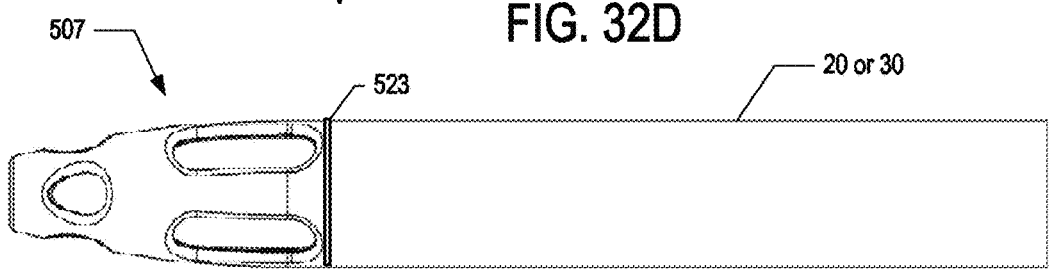
FIG. 32E is a plan view of the intravascular portion of an inflow or outflow conduit and a marker band according to one embodiment.
Figure 32J:
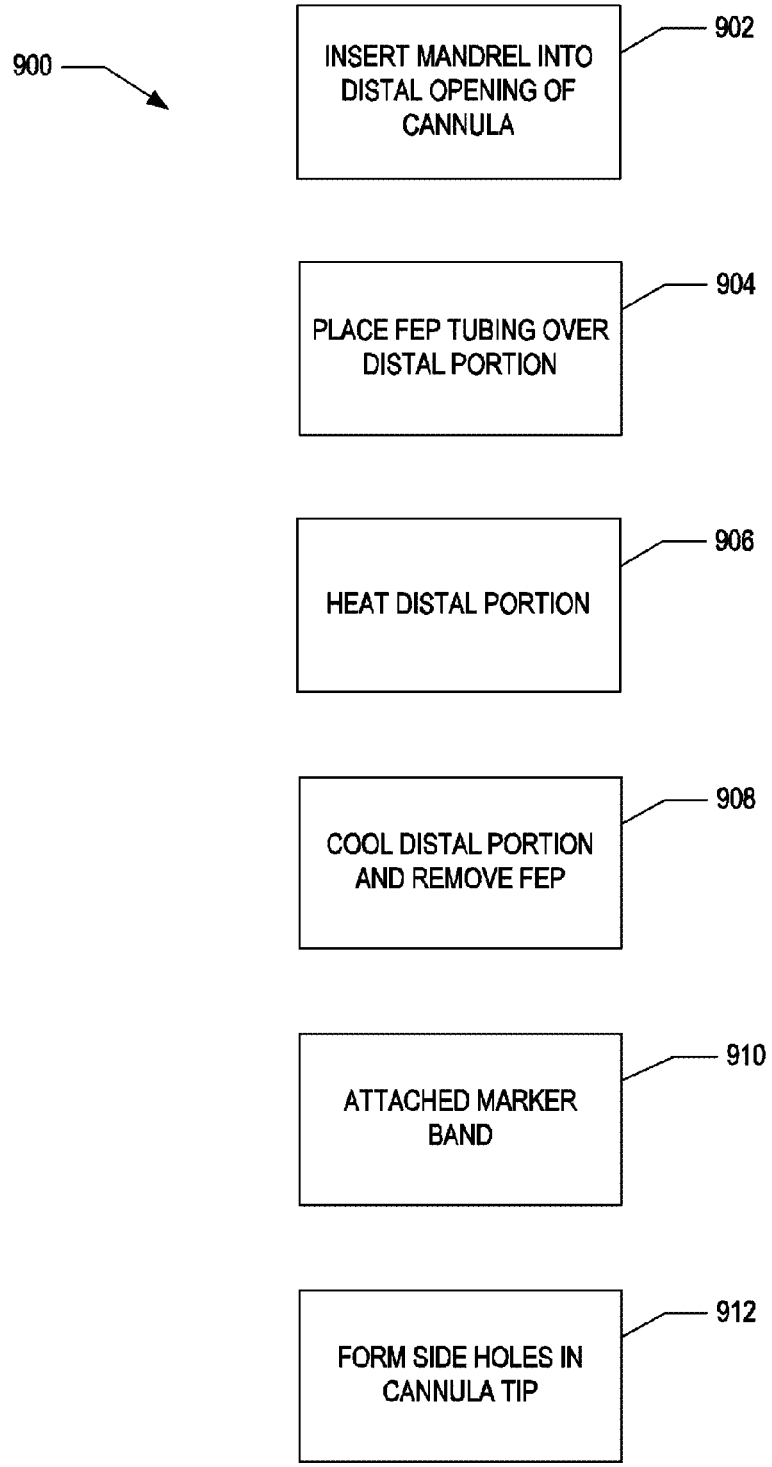
FIG. 32J is a flowchart of a method of manufacturing a cannula tip according to one embodiment.
Figure 33:
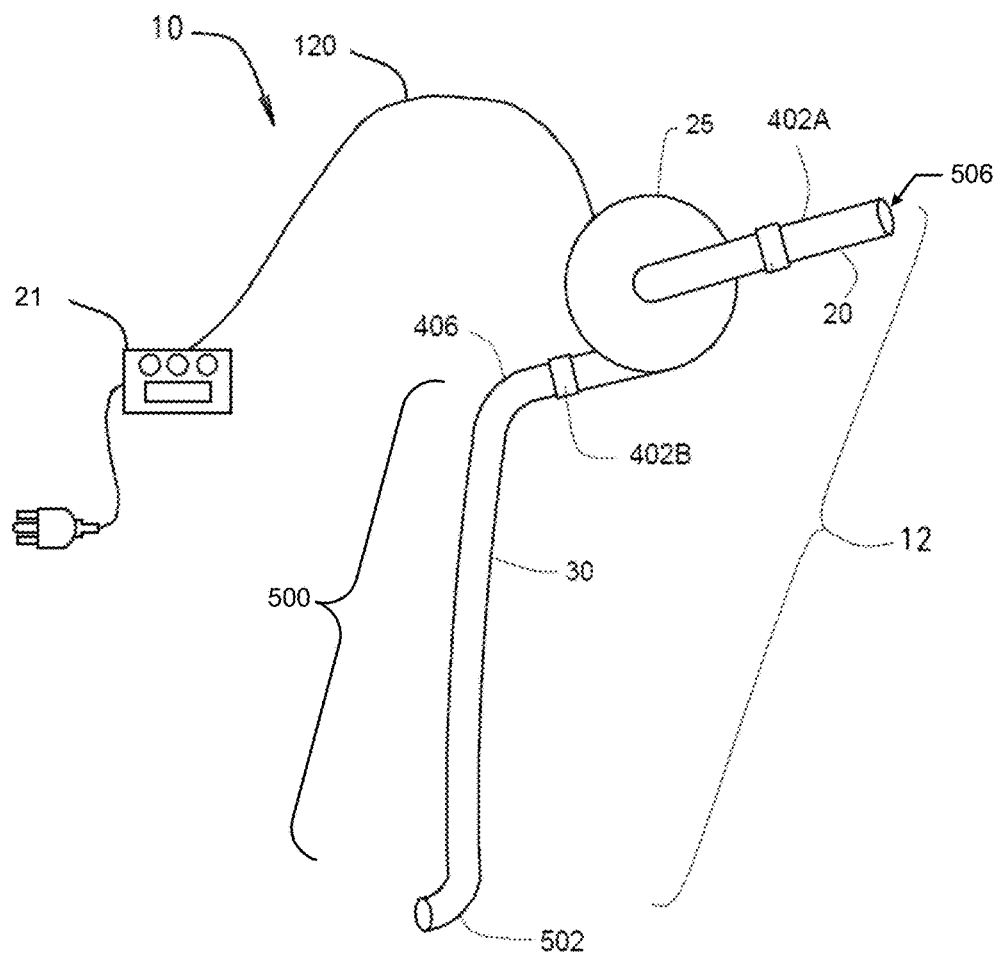
FIG. 33 is a schematic view of the pump system according to one embodiment.

In various embodiments, the cannula tip 507 does not include the reinforcement coils of the inflow conduit 20 or outflow conduit 30. As shown in FIG. 32D, a nitinol braid 519 embedded in the inflow or outflow conduits 20 and 30, respectively, does not extend into cannula tip 507. Rather, the reinforcement coil 519 terminates at or near the cannula tip 507, as indicated by 521. As shown in FIG. 32E, the cannula tip 507 may also include a radiopaque material, such as a ring or band 523. The marker band 523 aids in the positioning of the inflow or outflow conduits 20 and 30 during insertion into a blood vessel with fluoroscopy In one aspect, the present disclosure also relates to a method for manufacturing the cannula distal tip 507 as shown in FIGS. 32C-32I. A flowchart depicting a process 900 for manufacturing the cannula tip 507 is shown in FIG. 32J. At step 902, a rigid mandrel is inserted through the distal tip opening 511 of the non-reinforced distal end of the inflow cannula 20. In example, the cannula tip 507 has an inner diameter of approximately 4.0 mm and an outer diameter of approximately 5.4 mm, while the mandrel has a diameter in a range of approximately 1.5 mm to 2.0 mm. In various aspects, the mandrel may be composed of any rigid material including a metal, such as stainless steel. At step 904, a segment of thin heat-shrink fluorinated ethylene propylene (FEP) tubing is placed over the tip 507 and mandrel assembly. Approximately 0.5 cm to 2.5 cm of the distal portion of the tip 507 is heated to about 400° F. at step 906. In one aspect, the distal portion is positioned within an environment of heated air that softens the cannula tip 507, which may be composed of polyurethane, as well as causing the FEP to shrink and compress the cannula tip against the mandrel and reduce the inner diameter of the distal tip opening 511 to approximately 1.5 mm to 2.0 mm. Moreover, by positioning the distal portion of the tip 507 and mandrel assembly in the heated environment, a thermal gradient is applied across the FEP tubing, which shrinks in differing amounts corresponding to the different temperatures along the thermal gradient. As a result, the polyurethane cannula tip 507 is compressed in a tapered manner, with the greatest compressive force exerted at the distal portion, where the temperature is the greatest, and decreasing in compressive force in a proximal direction.

In various embodiments, the degree of tamper imparted to the distal tip 507 may be varied according to the configuration desired by the manufacturer or user, as well as by changes in process variables, including but not limited to the temperature of the heated environment, the material of the distal tip 507, the length and initial diameter of the FEP tubing. After forming a tapered configuration in the distal tip 507, the cannula tip is allowed to cool and the FEP tubing is removed at step 908, resulting in a smoothly tapered distal tip 507.

In one embodiment, a radiopaque distal ring marker band 522 is adhered to the cannula tip at step 910. In one aspect, the marker band has a diameter less than outer diameter of the distal end of the inflow cannula 20 and is forcibly inserted over the tip 507 of the cannula prior to the application of the FEP tubing and the tapering process of step 904-908. The marker band is preferably attached at a position that will be placed within the heated environment. As the FEP tubing compresses against the marker band, the softened material of the cannula (e.g. polyurethane) flows around and over the band thereby embedding the band within the cannula wall.

At step 912, the side holes 513 and 515 are formed with in the cannula tip 507. In one aspect, the side holes 513 and 515 are formed by piercing the walls of the cannula tip 507 using a length of a rigid conduit, such as but not limited to stainless steel tubing. For example, the round side holes 513 may be formed by piercing the cannula tip 507 side walls with a stainless steel tube having a wall thickness of approximately 0.5 mm. One end of the tubing is sharpened and configured to form a leading inner edge and a bevel surface between the inner and outer surfaces of the tubing of approximately 45°. To form the more elongated side holes 515, sharpened stainless steel tubing similar to that used to form the side holes 513 is used. However, the tubing used to form the side holes 515 typically has a larger diameter and is compressed until the appropriate ellipsoid dimensions are achieved. The compressed tubing now having an elongated oval or elliptical cross-section is used to pierce the side walls of the cannula tip 507.

In yet another aspect, the sharpened tip of the stainless steel tubing used to produce the side holes 513 and 515 may be heated to between about 250° F. and about 400° F. before piercing through the surface of the cannula tip 507 at step 912. In one aspect, the heated tubing heats and at least softens the material of the cannula tip 517 causing it to "flow" and form a smooth, rounded inner surface to the side holes 513 and 515. Conversely, in other embodiments, the side holes 513 and 515 may be formed by any suitable method, including but not limited to being cut by a laser or other precision cutting tool.

In one embodiment, a portion of the inflow conduit 20 may be inserted into the lumen of a blood vessel and advanced to the desired position using a percutaneous approach or an open surgical approach. To aid in the positioning of the inflow and outflow conduits 20 and 30, the conduits may have radiopaque marker bands or other radiopaque materials embedded within the walls 512 and 514 of the inflow and outflow conduits, respectively, that are visible under fluoroscopy. For example, portions of the inflow and outflow conduits 20 and 30 may be composed of Carbothane® PC-3575 polyurethane embedded with barium sulfate salts. In other embodiments the portions of the inflow and outflow conduits 20 and 30 that are configured to be inserted into the lumen of the vascular system may have self-expanding or radially expansive (such as can be accomplished by incorporating nitinol) walls so that the diameter of the intravascular portion of the inflow and outflow conduits 20 and 30 will match the diameter of the vascular system at that location, such as is seen with the self-expanding segment of the GORE® Hybrid Vascular Graft.

Figure 37A:
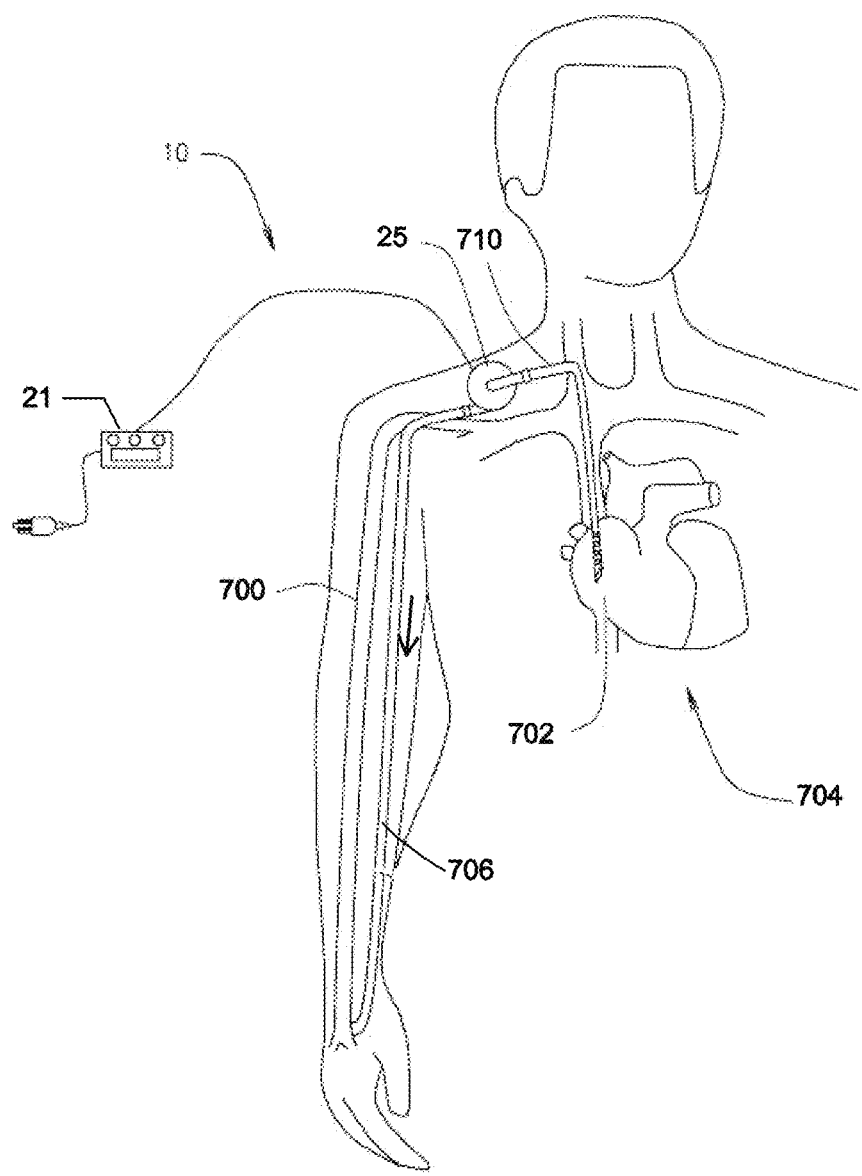
FIG. 37A is a view of the pump system as applied to a circulatory system of a patient according to one embodiment.

In various embodiments, including the embodiment shown in FIG. 37, the inflow and outflow conduits 20 and 30 may be attached to blood vessels using a surgical anastomosis, using suture in a running or divided fashion, henceforth described as an "anastomotic connection." An anastomotic connection can also be made with surgical clips and other standard ways of making an anastomosis. For example, an anastomotic connection may be made between the ePTFE distal segment 502 of the outflow conduit 30 and a blood vessel.

In certain embodiments where an anastomotic connection is made, the outflow conduit 30 is secured to blood vessels having an initial diameter between 1 mm and 20 mm, and preferably vessels having an initial diameter between 1.5 mm and 6 mm.

Conversely, in other embodiments shown in FIGS. 32A-B and 37-40, portions of the inflow and outflow conduits 20 and 30 are placed within a blood vessel or the right atrium. For example, the distal end 506 of the inflow conduit 20 may be positioned within the right atrium or the superior vena cava. As shown in FIGS. 32A-32B, the side holes 508 aid in the aspiration or discharge of blood when the distal end 506 has been placed intravascularly.

In various other embodiments, at least one of the inflow and outflow conduits 20 and 30 may be compatible for use with a hemodialysis machine, or machines used for plasmapheresis or apheresis. For example, a patient using the blood pump system 10 may also need to receive a hemodialysis treatment. In this example, blood may be withdrawn from the blood pump system, passed through a hemodialysis machine, and then discharged back into the blood pump system for delivery back into the vascular system, thereby eliminating the need to create an additional vascular access site in the patient. Side ports 417 on the inflow and outflow conduits 20 and 30 may facilitate the removal and return of blood from the AFE System during hemodialysis, plasmapheresis, apheresis, or other procedures where blood is removed and returned to a patient. In certain embodiments, the side ports 417 may be configured in such a way as to enable the sterile insertion of endovascular devices, such as guidewires, angioplasty balloons, vascular stents, vascular occlusive devices, local drug delivery catheters and thrombolysis catheters, and thrombectomy devices such as Fogarty balloons. In some of these certain embodiments, the long axis of the side port 417 may be formed at an angle to the long axis of the conduit, such as at a 30 degree angle, a 40 degree angle, or at a 45 degree angle, among others. In some of these embodiments, the side port 417 may comprise a hemostatic sheath to facilitate the rapid and simple insertion and removal of endovascular devices.

Figure 50:
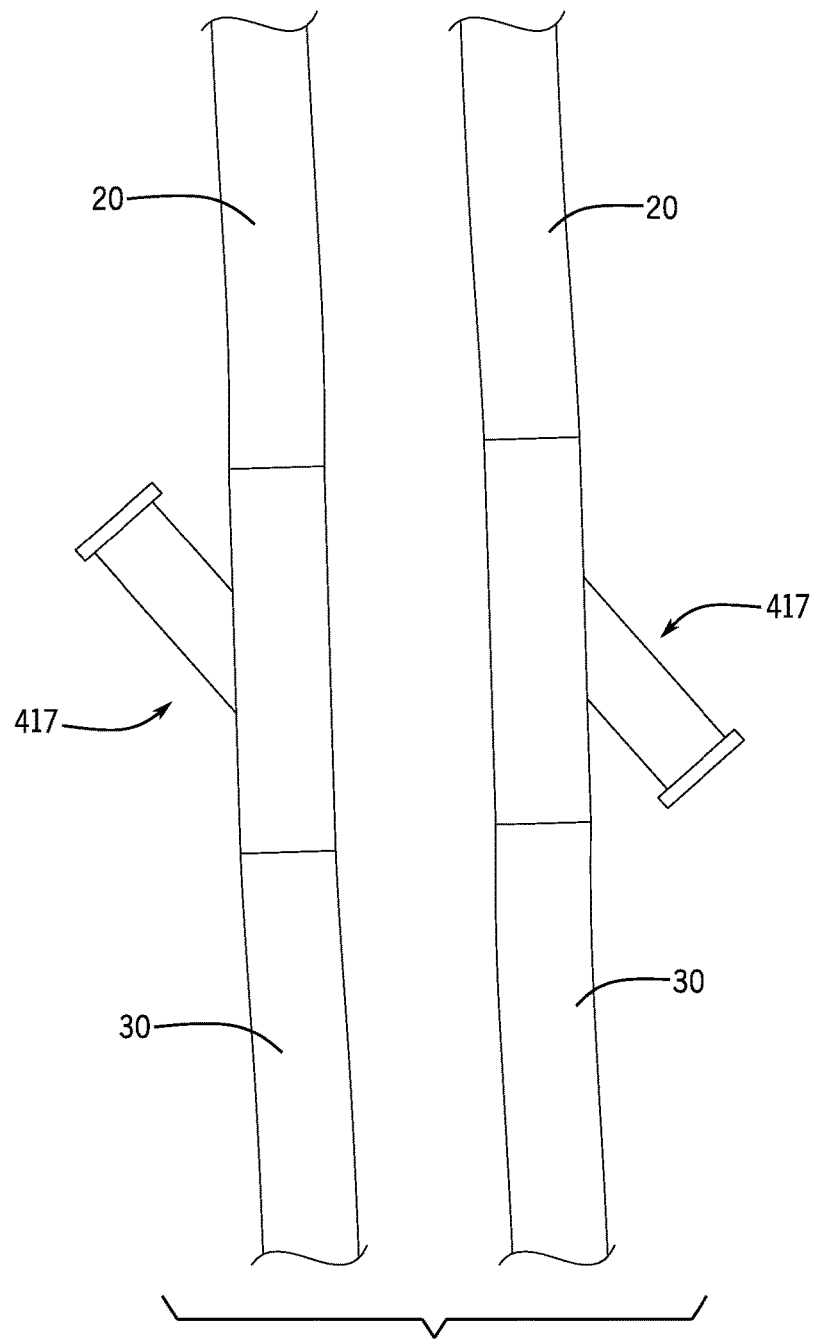
FIG. 50 is a photograph of a side port assembled to inflow and outflow conduits according to one embodiment.

The side ports 417 may be in attached to the inflow and outflow conduits 20 and 30, respectively, by any suitable method. In one embodiment, an adhesive is applied to the surfaces of the side port 417 that will be received within the conduits 20 and 30. The side port 417 is engaged to the conduits and the adhesive is allowed to cure forming a fluid-tight seat, as shown in FIG. 50. In one aspect, the adhesive is an ultraviolet (UV) curable medical-grade adhesive.

Figure 51B:
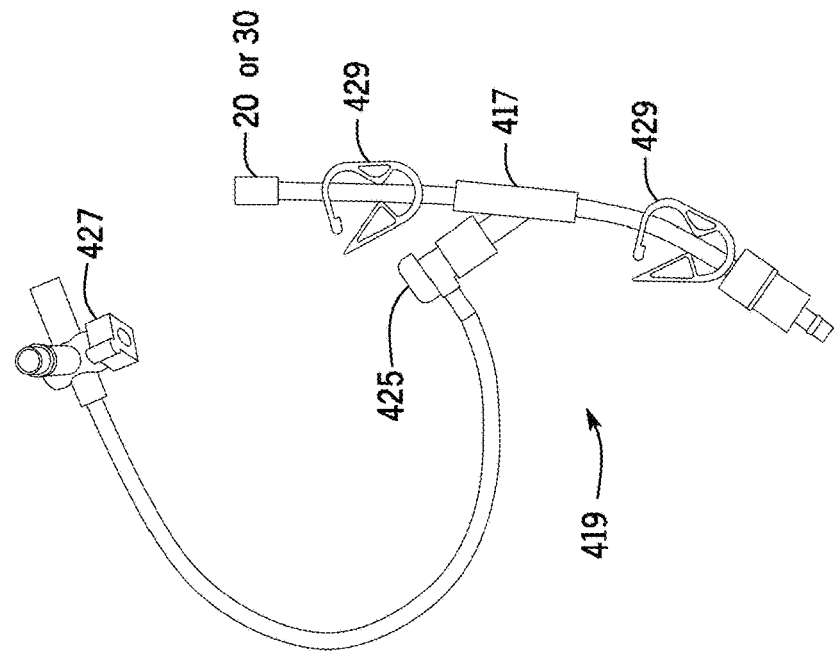
FIGS. 51A-B are photographs of an unassembled and assembled "access capable" side port assembly, respectively, according to one embodiment.
Figure 51A:
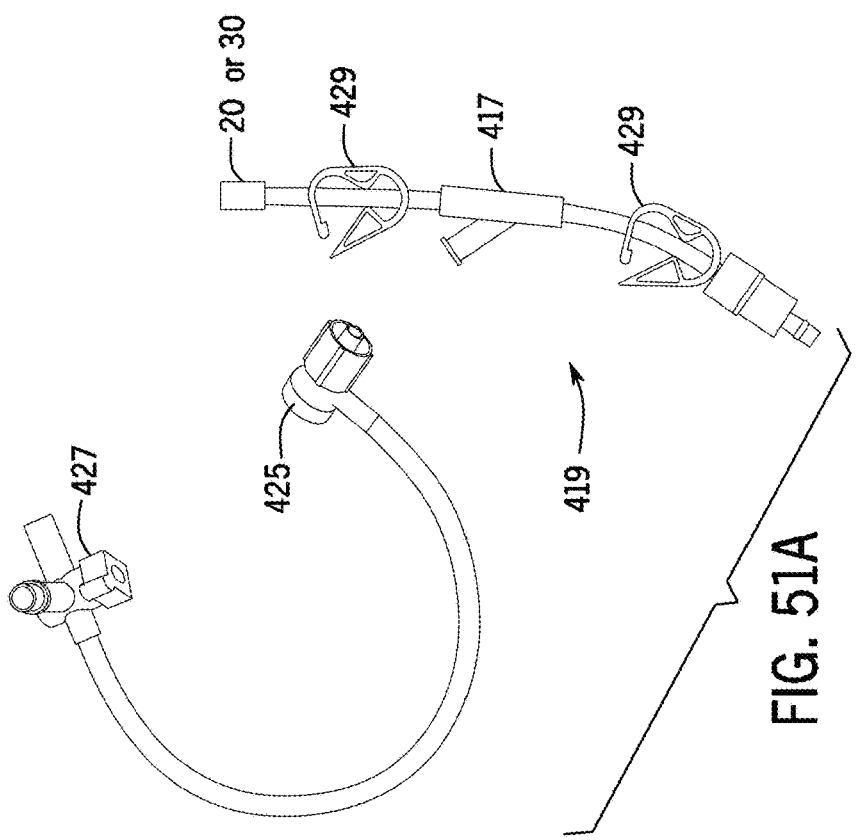
Figure 52A:
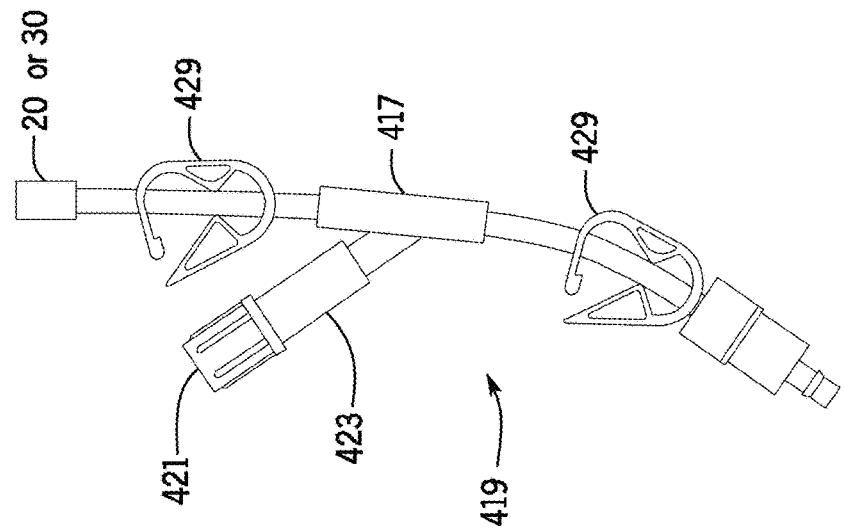
FIGS. 52A-B are photographs of an unassembled and assembled "access capable" side port assembly, respectively, according to another embodiment.
Figure 52B:
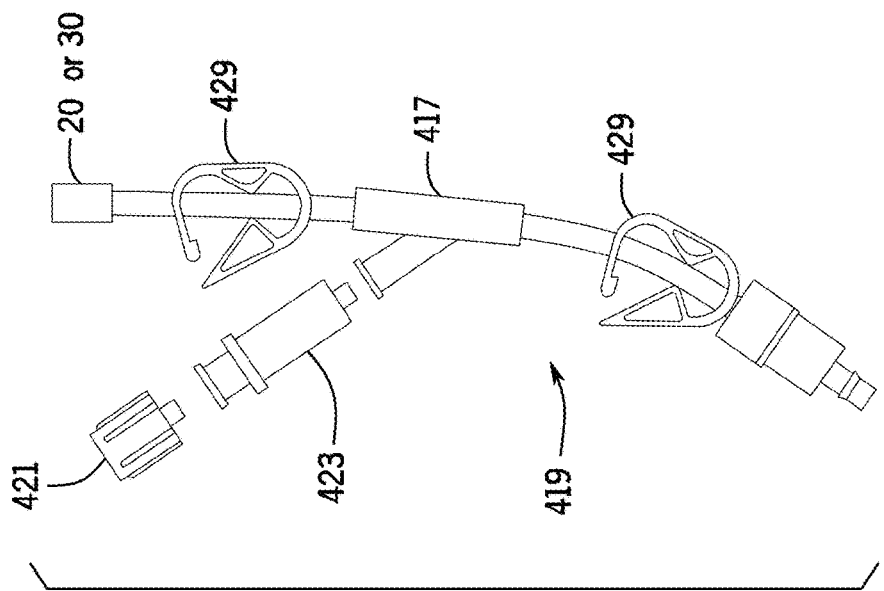

FIGS. 51A-B and 52A-B depict embodiments of a side port assembly 419 that is "access ready" or "access capable" and configured to permit the withdrawal of fluid from the conduits 20 or 30 and to introduce substances and other materials, including but not limited to medical tools and devices, into the conduits. In particular, FIGS. 51A and 52A depict unassembled assemblies 419, while FIGS. 51B and 52B depict corresponding assembled side port assemblies. In various embodiments, the side port 417 includes a cap to seal the side port when desired. By way of example and not limitation, the cap may be a hard or rigid end cap 421 with a threaded luer fitting that can be screwed on and off of the side port. In another example, the cap is an infusion valve 423 that includes a plunger that is normally closed until a syringe is inserted into the cap, for infusion or aspiration. When the syringe is removed, the plunger returns to the closed position to seal the cap. In yet another example, the cap may be a hemostatic valve 425, similar to that in a standard angiography sheath. The hemostatic valve 425 allow the cap to remain closed until a guidewire or catheter is inserted through the valve. This allows the operator to slide wires and catheters into and out of the side port 417 without manually opening or closing the cap. The side port 417 may also include a 3-way side arm 427 that allows for concurrent infusion and/or aspiration. As shown in FIG. 51B, an assembled embodiment of the "access ready" side port 417 includes various combinations of the caps, the 3-way side arm 427, as well as one or more clamps 429. In other embodiments, few or greater caps in various other combinations may also be used.

When a blood pump system is in place with such "access ready" side ports, endovascular procedures can be readily performed on the conduits and the associated vascular system such as thrombectomy of conduits, balloon angioplasty of associated vessels such as the outflow vein of an AFE System, endovascular occlusion of vascular side branches, and local drug delivery in conduits and associated vessels, such as with catheter-directed thrombolysis. In one embodiment, the use of the AFE System is combined with the use of endovascular occlusion devices. For example, during treatment of a target vein with the AFE System, one or more side branches of the target vein may dilate in response to the elevated WSS, thereby reducing the WSS dose in the downstream vessel segment. In this situation, blood flow into these vein side branches can be blocked by placing an endovascular occlusion device into the vein side branches. Devices that could be used for this purpose include standard coils for peripheral vascular occlusion, Amplatz Vascular Plug devices (St. Jude Medical, Inc.), or Blockstent Microcatheters (Metactive Medical, LLC). These devices could be placed through the side port on the outflow conduit 30 or through a separate vascular access, such as a sheath placed in a peripheral vein such as the femoral vein or cephalic vein.

Figure 35:
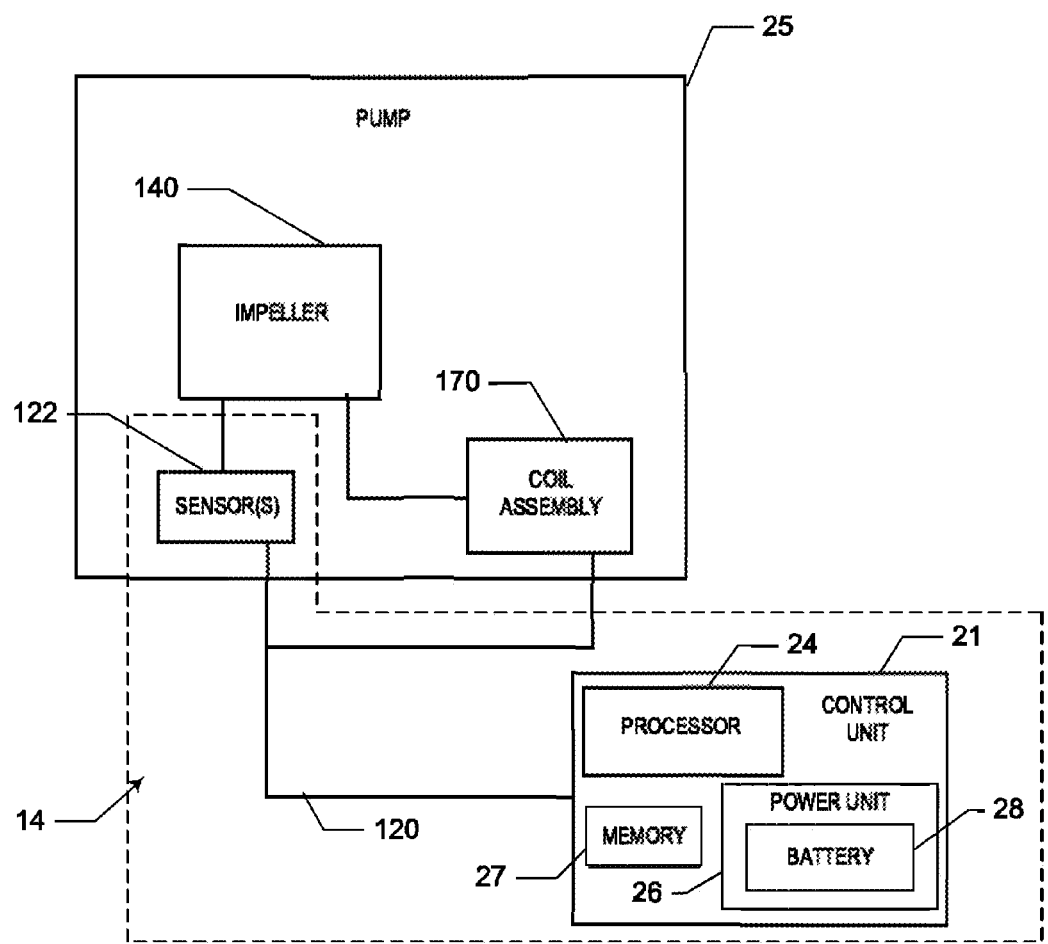
FIG. 35 is a schematic view of a control systems according to one embodiment.

As shown in FIG. 35, one embodiment of the control system 14 includes a control device 21 having at least one processor 24 and memory 27 for delivering power to the pump and receiving information from the blood pump 25, whereby the information is used to set and control pump speed and estimate the flow rate of blood or fluid through the pump system. The processor 24 is configured to read, process, and execute systems, methods, and instructions encoded on a computer-readable medium. The control system 14 then estimates the wall shear stress in the target vessel using the measured or estimated vessel diameter and the measured or estimated average flow rate of the pump system. The control device also includes a power source 26, optionally having a battery 28.

In one embodiment, the control system 14 receives sensor feedback from one or more sensors 122. Any of a variety of suitable sensors may be used to detect any of a variety of changes in a physical quantity of the blood, blood pump 15, the blood pump system 10, and/or the target vessel. In some embodiments, sensors may be used to detect body position or changes in body position. The sensors 122 generate a signal indicative of the change to be analyzed and/or processed. Essentially, the sensors 122 monitor a variety of properties of the blood pump system 10, the blood flowing through the system, and the target blood vessel for changes that can be processed and compared to desired reference values or predetermined standards. The desired reference values or predetermined standards may be stored in a database or other suitable medium.

In various embodiments, one or more sensors 122 may be in communication with the blood pump 25, the inflow conduit 20, the outflow conduit 30, the donating vessel or location, or the accepting vessel or location. In various embodiments, the control system 14 or portions thereof may be located internally within the housing or casing of the blood pump 25. For example, one or more of the sensors 122 may be located in the inlet 110 or outlet 115 of the blood pump 25. In other embodiments, the control system 14 may be external to the pump.

Wall shear stress can be used as a variable to configure the operation of the pump system 10 to result in an increase in the overall diameter and lumen diameter of the target vessel or an increase in the length of the target vessel.

Assuming Hagen-Poiseuille blood flow (i.e. laminar flow with a fully developed parabolic velocity profile) in the lumen of a vessel having a circular cross section, then WSS can be determined using the equation:

$$WSS(Pa) = 4Q\mu/\pi R^3 \qquad [\text{Eqn. 1}]$$

where:
$Q$=flow rate (m³/s)
$\mu$=viscosity of blood (Pa/s)
$R$=radius of vessel (m)

Wall Shear Stress Control Method #1: Manual

Figure 36A:
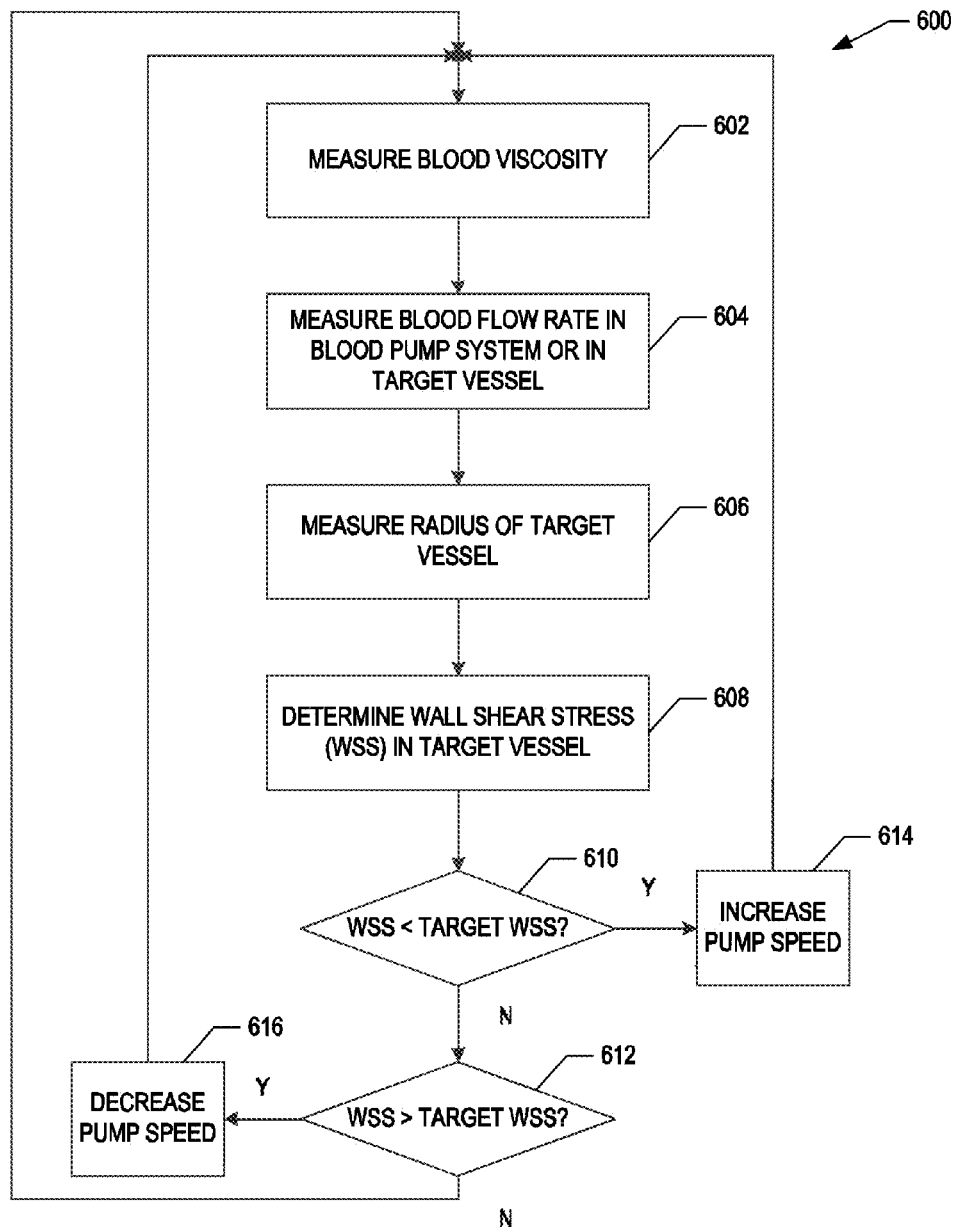
FIGS. 36A-36D are flowcharts of control system methods according to various embodiments.

Mean and/or peak WSS in the target blood vessel can be controlled by adjusting pump speed, which affects the blood flow rate through the pump-conduit system and therefore blood flow through the target vessel. As shown in FIG. 36A, a manual control method 600 may involve the direct measurement of blood viscosity at block 602 (by sampling the patient's blood and analyzing it in a viscometer), blood flow rate in the blood pump system or blood flow rate in the target vessel at block 604 (by placement of an ultrasonic flow sensor on either the inflow or outflow conduit or by ultrasound or thermal dilution methods, respectively) and vessel radius at block 606 (by various imaging methods including angiography, ultrasound, computed tomography, or magnetic resonance imaging). The WSS acting on the vessel wall is determined at block 608, compared to the desired level at blocks 610 or 612, and then the pump flow rate (Q) is adjusted through changes in the rotational speed of the pump impeller at blocks 614 or 616. Changes in pump speed are effected by varying the duty-cycle of the pulse width modulation of the motor input voltage.

Figure 36B:
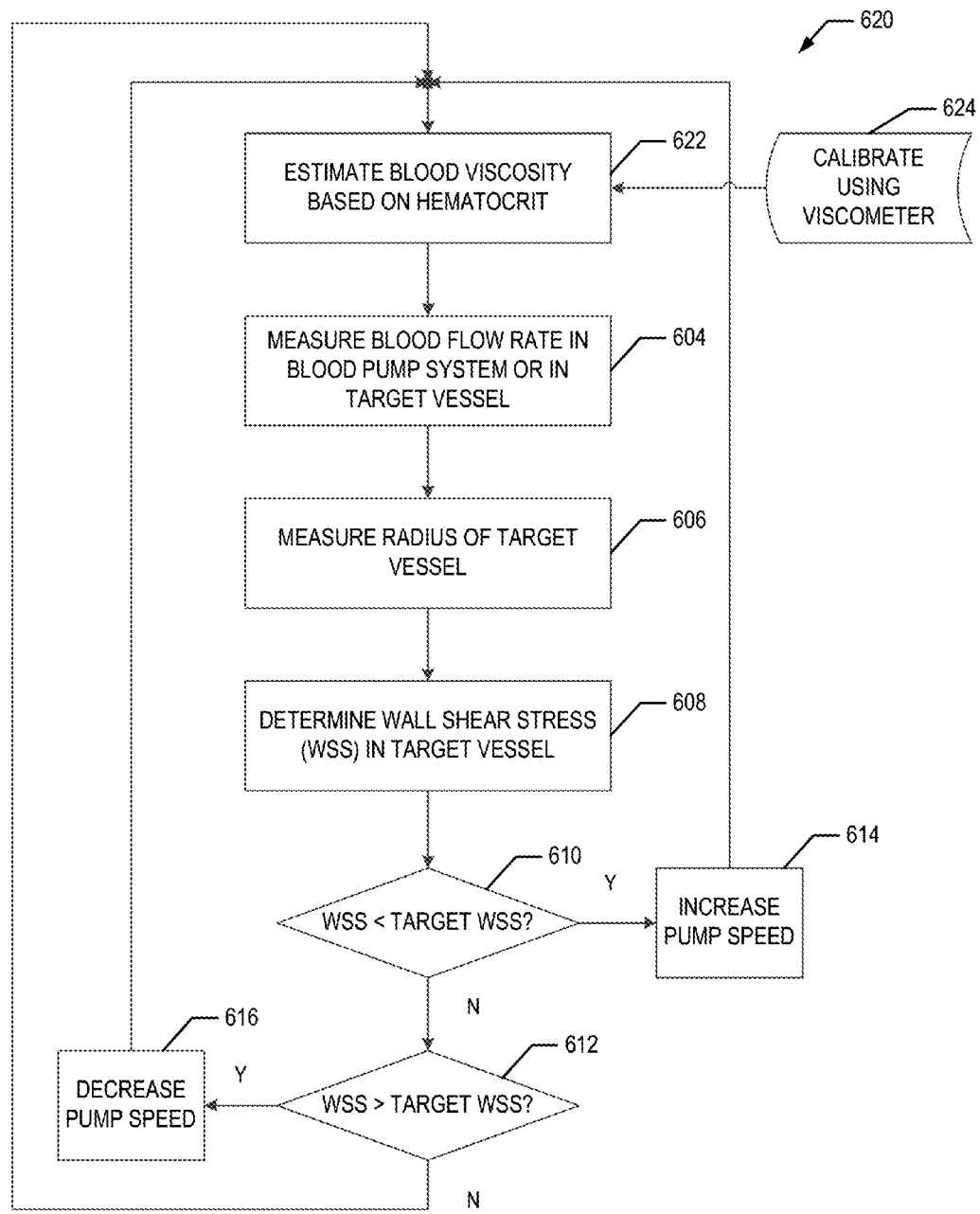

Wall Shear Stress Control Method #2: Automatic with Indirect Blood Viscosity, Direct Blood Flow, and Target Blood Vessel Diameter Measurements An automatic WSS control system may involve direct measurement of blood flow rate in the pump system or the target vessel, and direct measurement of the diameter of the target vessel blood vessel. As shown in FIG. 36B, this automatic WSS control method 620 may involve indirect measurements of blood viscosity at block 622 (estimated based on its known relationship with measured hematocrit and approximate mean WSS). Periodic calibration of the viscosity estimator at block 624 may be performed using direct measurements of viscosity as previously described. In clinical practice, the blood viscosity usually varies slowly.

Figure 36C:
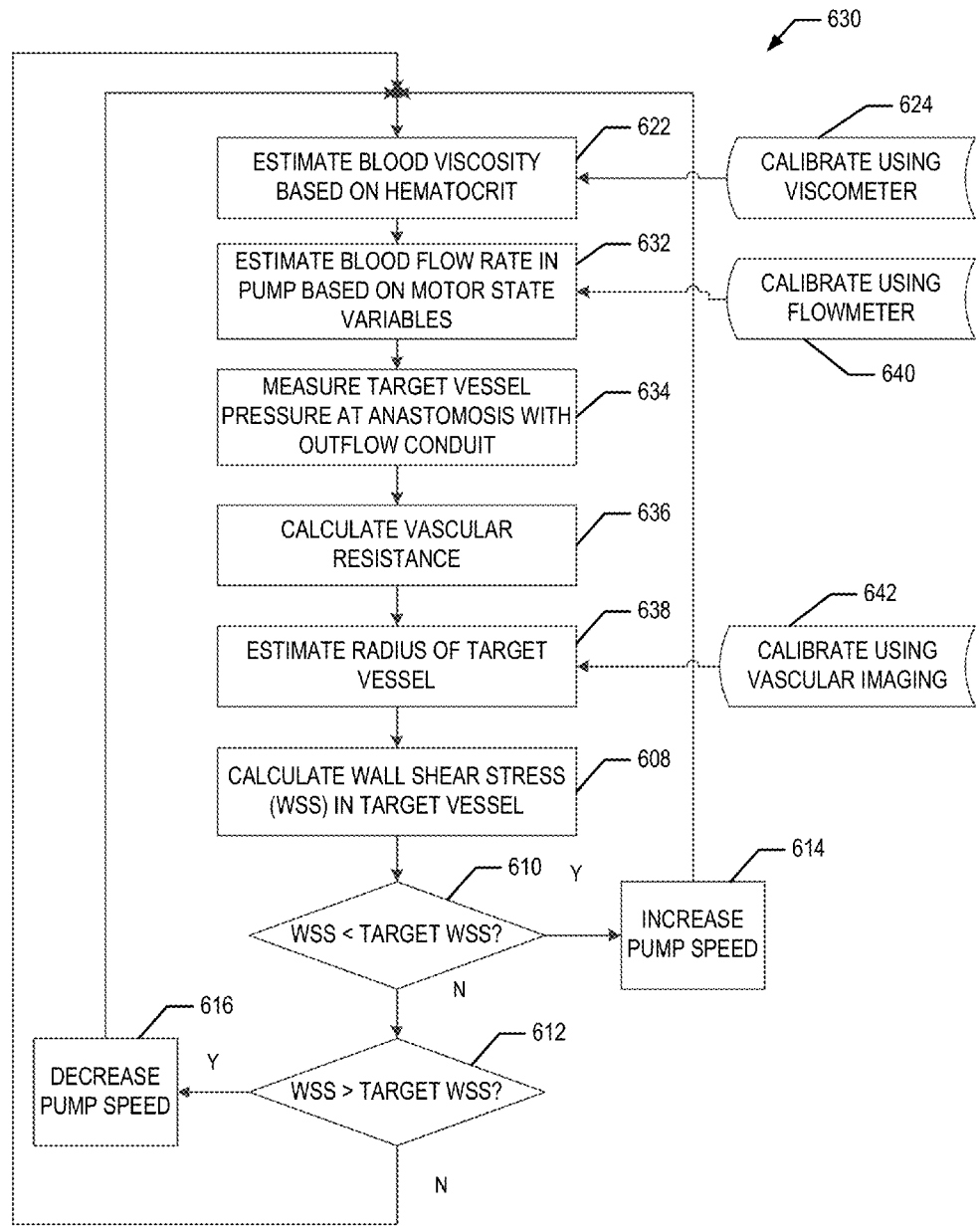

Wall Shear Stress Control Method #3: Automatic with Indirect Blood Viscosity, Blood Flow, Target Blood Vessel Diameter Measurements, and Direct Vein Pressure Measurements As shown in FIG. 36C, an automatic WSS control method 630 may involve indirect measurements of blood viscosity (estimated based on its known relationship with measured hematocrit and approximate mean WSS) at block 622, blood flow rate through the blood pump system (estimated based on its relationship to motor state variables) at block 632, measurements of the target blood vessel pressure at block 634, and measurements of the vessel radius (estimated based on vascular resistance) at block 638. Vascular resistance is calculated at block 636 based on the estimated pump flow rate and the measured blood pressure in the vessel. Periodic calibration of the blood viscosity, pump flow, and target vessel radius estimators respectively, may be performed using direct measurements at blocks 624, 640, and 642, respectively, as previously described.

Figure 36D:
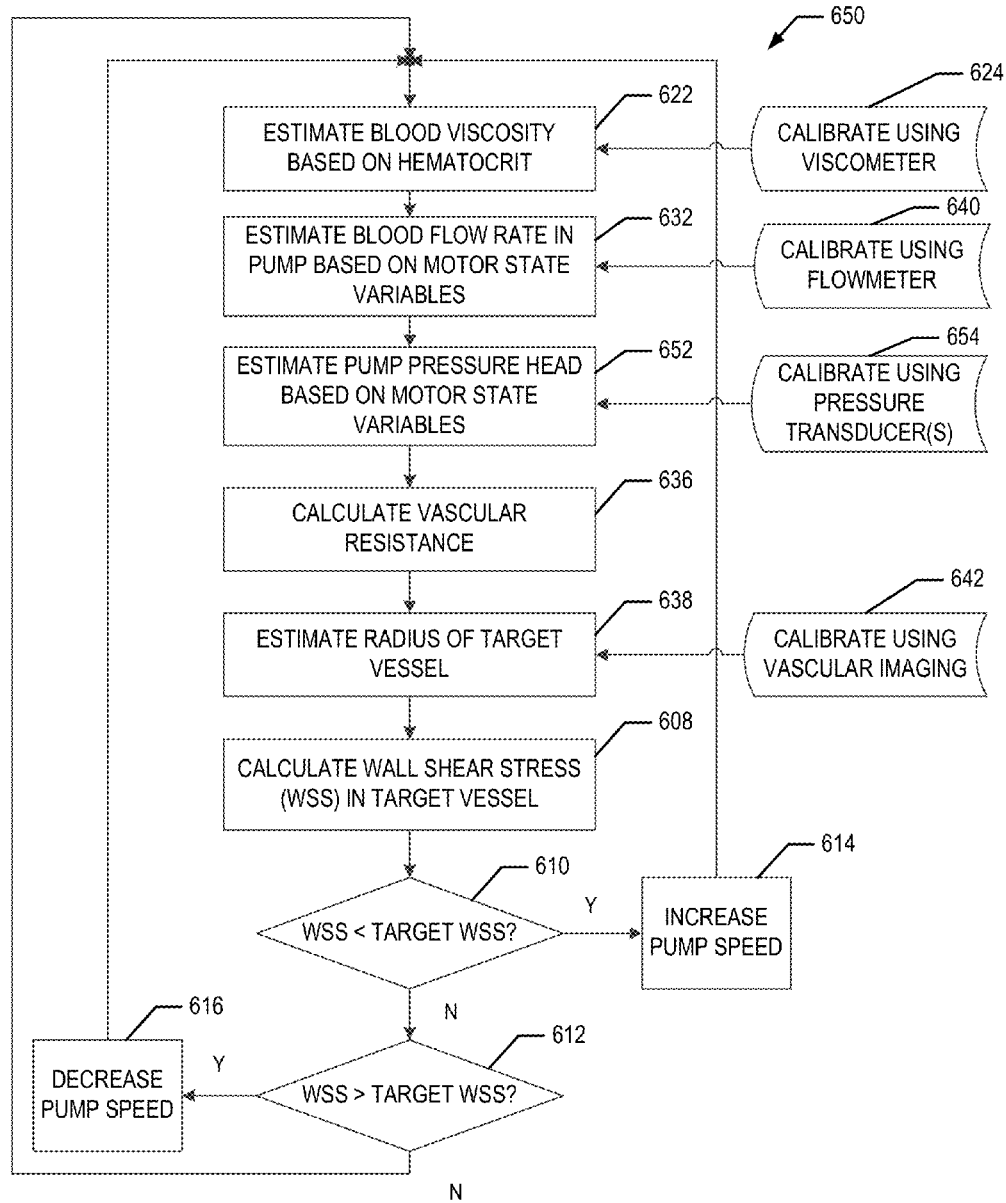

Wall Shear Stress Control Method #4: Automatic with Indirect Blood Viscosity, Blood Flow, Pump Pressure Head, and Target Blood Vessel Diameter Measurements As shown in FIG. 36D, an automatic WSS control method 650 may involve indirect measurements of blood viscosity (estimated based on its known relationship with measured hematocrit and approximate mean WSS) at block 622, blood flow rate through the blood pump system (estimated based on its relationship to motor state variables) at block 632, and vessel radius (estimated based on vascular resistance) at block 638. Vascular resistance is calculated at block 636 based on the pump flow rate estimated at block 632 and pump pressure head, where pump pressure head is also estimated at block 652 based on its relationship to motor state variables. Periodic calibration of the blood viscosity, pump flow, and target vessel radius estimators may be performed using direct measurements at blocks 624, 640, and 642, respectively, as previously described. Periodic calibration of the pump pressure head estimator may be performed by measuring pump inlet and pump outlet pressures with separate pressure transducers and calculating their difference at block 654, or by directly measuring pressure head across the pump with a differential pressure sensor.

Sensorless Determination of Blood Pump System Flow Rate and Pressure Head:

Referring to FIG. 35, the processor 24 is adapted to detect and monitor electric current appearing in one or more of the electric coils of the coil assembly 170 of the pump via the power cable 120 which, in conjunction with monitoring the voltage provided to the coil assembly permits the processor 24 to derive the input power ($P_{in}$) consumed by the blood pump 25 and an actual rotational speed of the impeller 140 ($\omega$). The processor 24 can estimate pump flow rate (Q) or changes in flow rate ($\Delta Q$) as a function of $P_{in}$ and $\omega$. For example, $Q=f[P_{in},\omega]$. More specifically, the following equation is used:

$$Q = a + b \cdot \ln(P_{in}) + c \cdot \omega^{0.5} \quad \text{[Eqn. 2]}$$

where:
Q=flow rate (L/min)
$P_{in}$=Motor input power (W)
µ=Pump speed (rpm)

Motor input power is derived from the measured motor current and voltage. The values for a, b, and c are derived from curve fitting the plot of pump flow rate as a function of motor speed and input power.

The processor 24 can also estimate pump pressure head ($H_p$) or changes in pump pressure head ($\Delta H_p$) as a function of $P_{in}$ and $\omega$. For example, $H_p=f[P_{in},\omega]$. More specifically, the following equation is used:

$$H_p = d + e \cdot \ln(P_{in}) + f \cdot \omega^{2.5} \quad \text{[Eqn. 3]}$$

The values for d, e, and f are derived from curve fitting the plot of pump pressure head as a function of pump speed and motor input power, where $H_p$ is measured across the inflow conduit 20, pump 25, and outflow conduit 30.

Determination of Vascular Resistance and Estimation of Vessel Radius:

Vascular resistance (Rv) is the resistance to flow that must be overcome to push blood through the circulatory system. Resistance is equal to driving pressure ($H_v$) divided by the flow rate. When the blood pump system is connected to a target vessel that is a vein, the vascular resistance is calculated using the following equation:

$$R_v = (P_v - CVP)/Q \quad \text{[Eqn. 4]}$$

where:
$H_v$=pressure head lost across the peripheral vessel on the return path of the blood to the heart (mmHg)
$P_v$=vein pressure at anastomosis (mmHg)
CVP=central venous pressure (mmHg)
$R_v$=vascular resistance ((mmHg·min)/L)

Figure 36E:
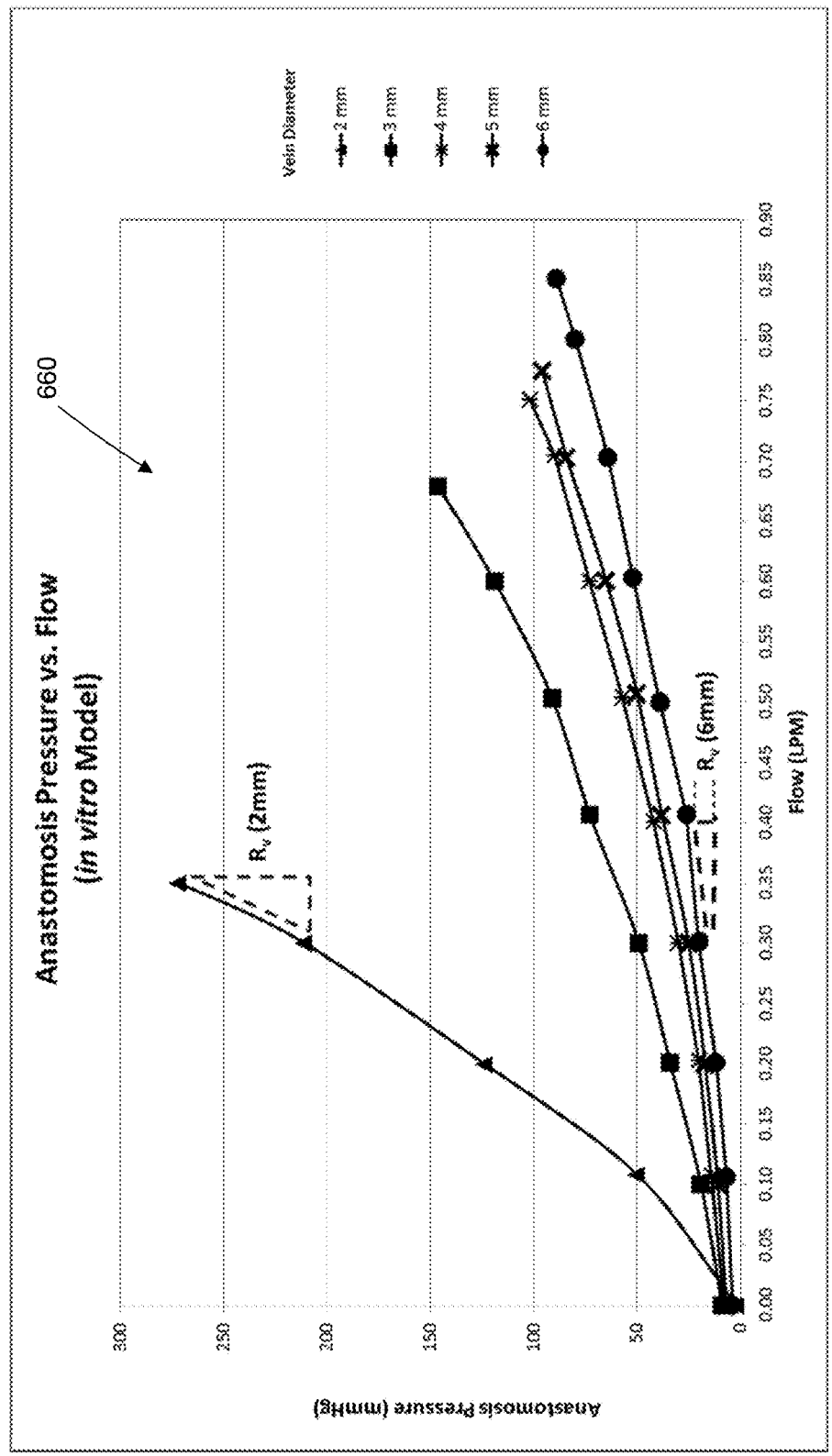
FIG. 36E is a plot of anastomosis pressures and blood flow rates for an in vitro model of the pump system according to one embodiment.

Normally, CVP ranges between 2-8 mmHg and can be neglected in the above equation because the operating ranges of $P_v$ and Q are proportionally much greater. As illustrated in FIG. 36E, vascular resistance can be represented graphically as the slope of various $P_v$ vs. Q curves 660. Since the curves 660 are nonlinear, the slope is a function of Q. As illustrated by the following equation, the vascular resistance may be derived by temporarily increasing speed by several hundred rpm ($\Delta\omega$), measuring the resulting change in vein pressure ($\Delta P_v$), and estimating the resulting change in pump flow ($\Delta Q$):

$$R_v(Q) = \Delta P_v / \Delta Q \quad \text{[Eqn. 5]}$$

It is noted that the vascular resistance is a strong function of vessel diameter or radius, with smaller veins having high vascular resistance. Vascular resistance can be quantified in various units, for example, Wood units ((mmHg·min)/L) can be multiplied by eight to convert to SI units ((Pa·s)/m³).

Alternatively, pump pressure head ($H_p$) may be used as a basis for calculating vascular resistance. When the pump-conduit system is configured to withdraw blood from one location in the vascular system to discharge it into a peripheral artery or vein it is a reasonable assumption that the pressure head gained across the system (Hp) is exactly equal to the pressure head lost across the peripheral vessel on the return path of the blood to the heart ($H_v$):

$$H_v, H_p \quad \text{[Eqn. 6]}$$

The radius of the peripheral vessel is inversely proportional to its vascular resistance ($R_v$), the ratio of $H_v$ to Q. Assuming Hagen-Poiseuille blood flow in the vessel of circular cross section, the vascular resistance can be represented using the equation:

$$R_v(\text{Pa·s/m}^3) = P_v/Q = 8 \cdot \mu L / \pi \cdot R^4 \quad \text{[Eqn. 7]}$$

where:
$P_v$ is expressed in units of Pa
Q is expressed in units of (m³/s)
µ=viscosity of blood (Pa/s)
R=radius of vessel (m)
L=length of vessel (m)

In practice, Eqn. 7 would be refined based upon in vivo measurements of pressure drop across specific veins of known diameter. This provides an empirical form of the equation:

$$R_v(\text{Pa·s/m}^3) = K \cdot \mu / R^4 \quad \text{[Eqn. 8]}$$

where:
K is an empirical constant for the target vein (m)

Determination of Wall Shear Stress:

The wall shear stress in the target vessel can be determined based on the above equations. Using Eqn. 4, the pump flow rate can be expressed according to the following equation:

$$Q = P_v / R_v \quad \text{[Eqn. 9]}$$

Using Eqn. 8, vessel radius can be expressed according to the following equation:

$$R = (K \cdot \mu / R_v)^{0.25} \quad \text{[Eqn. 10]}$$

Using Eqns. 1, 9, and 10, the wall shear stress can be expressed according to the following equation:

$$WSS(Pa) = ((4 \cdot P_v)/(\pi \cdot K^{0.75})) \cdot (\mu/R_v)^{0.25} \quad \text{[Eqn. 11]}$$

In various embodiments, the estimated variables used by the control system are periodically calibrated. For example, the estimates of flow rate and pressure head are periodically calibrated using actual measured values at an interval ranging from 1 minute and up to 30 days. Similarly, the estimate of artery or vein radius is periodically calibrated using actual measured values at an interval ranging from 1 minute and up to 30 days.

Figure 36F:
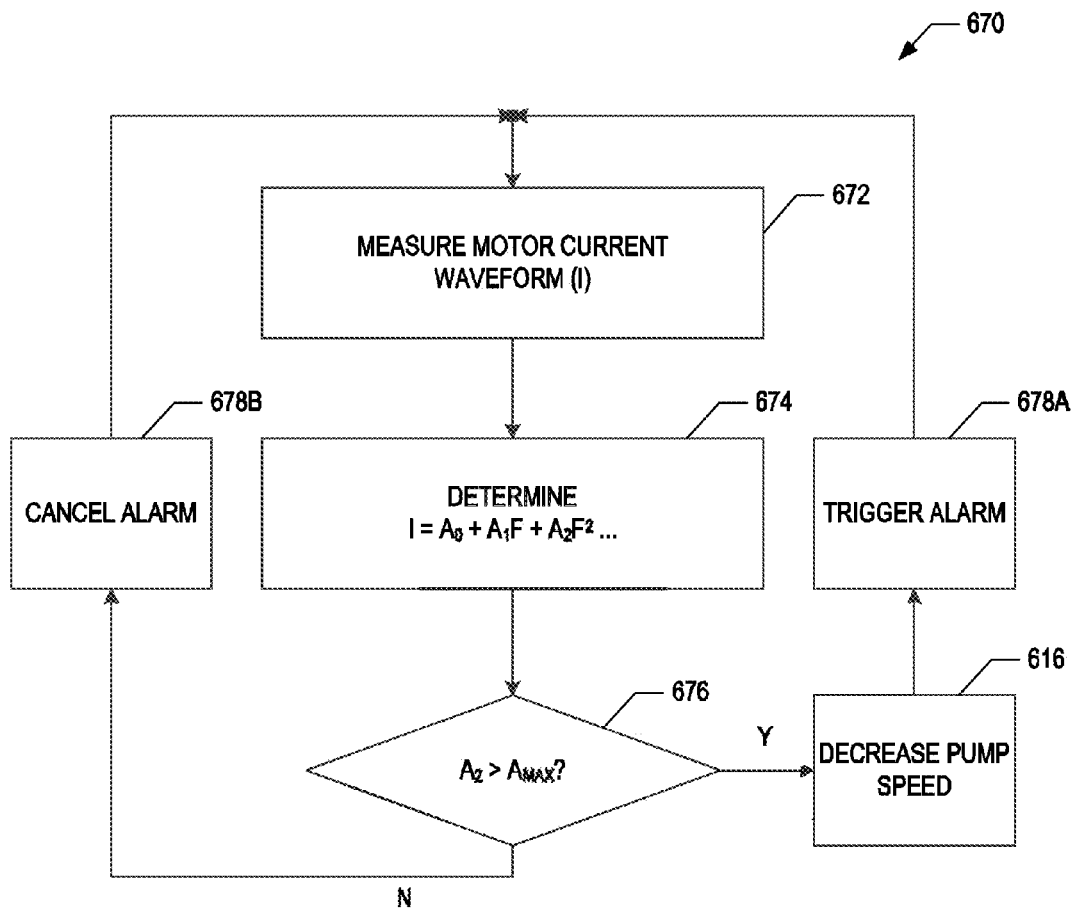
FIGS. 36F-36H are flowcharts of control system methods according to various embodiments.

Safety Features and Alarms:

The automatic control system may also include safety features to avoid hazards associated with changes in the patient's cardiovascular system or malfunctions of the pump system or pump control system. As shown in FIG. 36F, a speed control method 670 can detect characteristic changes in the motor current waveform associated with decreased preload or increase in afterload (e.g. due to thrombosis), suction, flow limitation, and imminent collapse of the vessel around the inflow conduit tip at block 672. Spectral analysis of the motor current waveform is performed using a Fourier transform at block 674. When the amplitude of the second harmonic term of the Fourier series exceeds a predetermined value at block 676, suction has occurred and collapse is deemed imminent. Pump speed is immediately decreased at block 616 and an alarm is triggered at block 678A within the control device 21. When normal operation is restored, the alarm is canceled at block 678B.

Figure 36G:
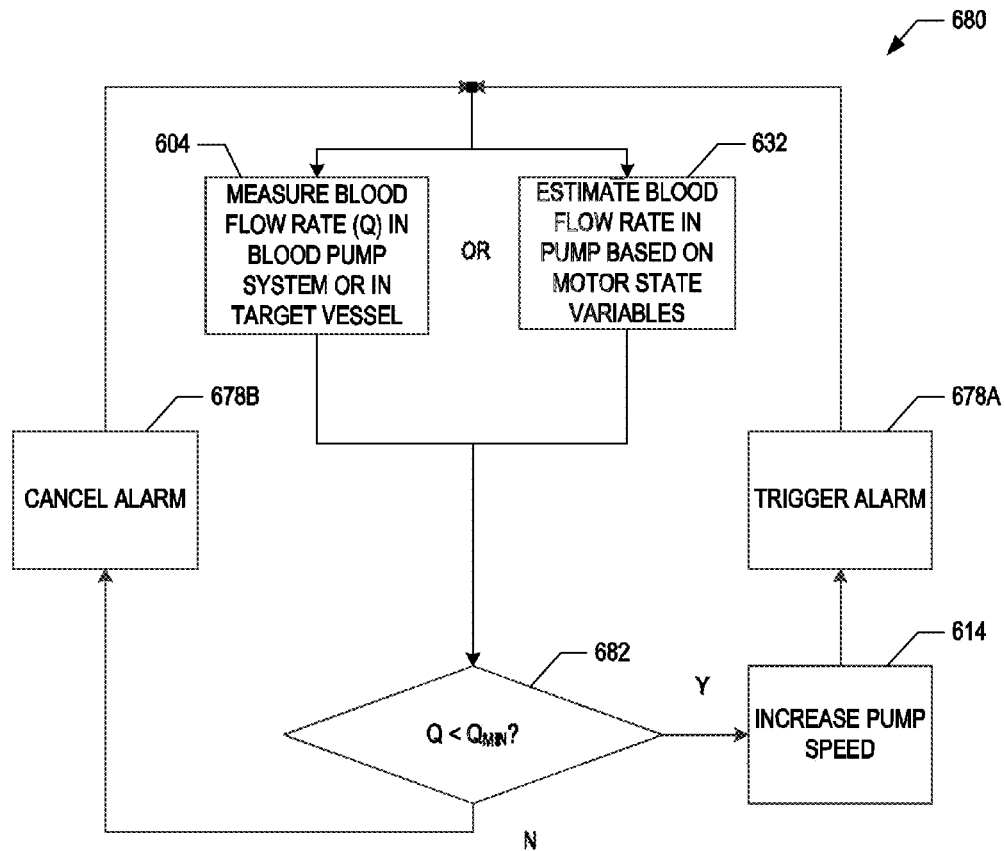

As shown in FIG. 36G, a speed control method 680 can detect low flow conditions. When the pump flow rate drops below the safe threshold level to avoid thrombosis of the pump-conduit system 10 at block 682, the pump speed is immediately increased at block 614 and an alarm is triggered at block 678A within the control device 21. When normal operation is restored, the alarm is canceled at block 678B.

Figure 36H:
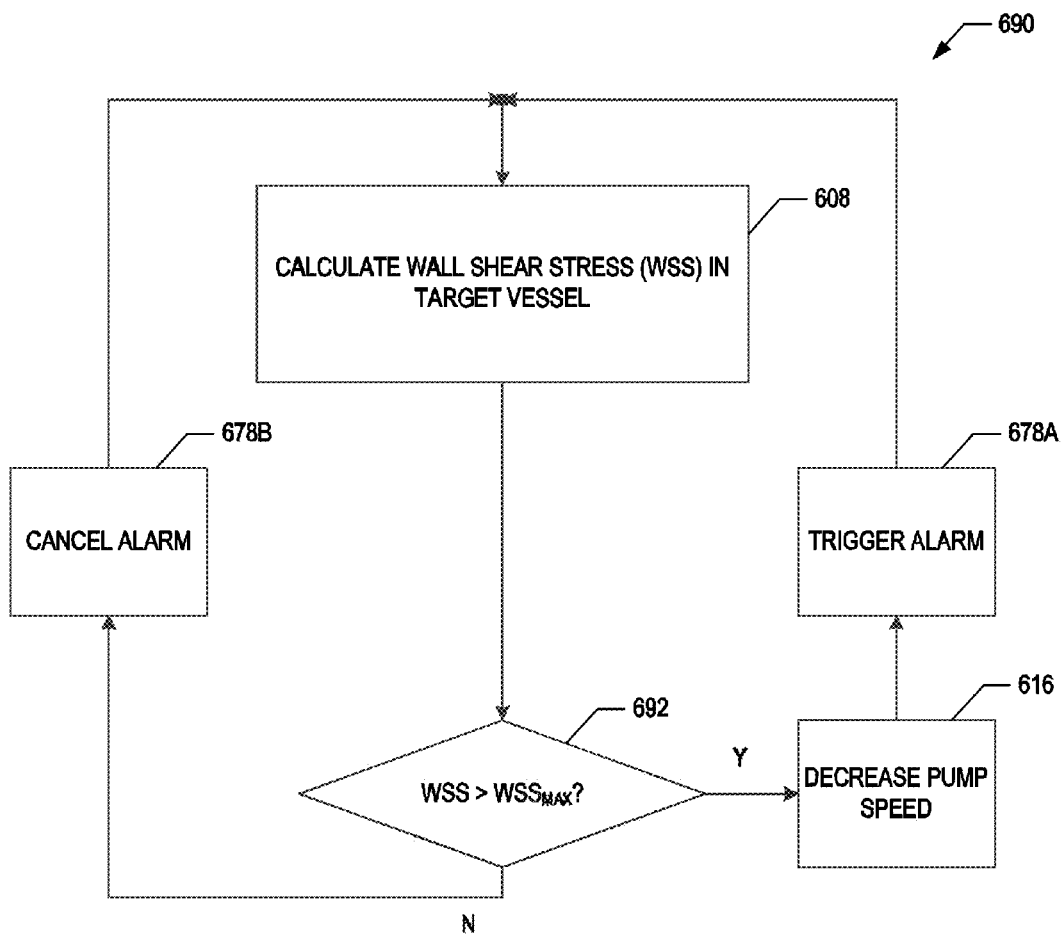

As shown in FIG. 36H, a speed control method 690 can detect high wall shear stress conditions. When the WSS rises above the safe threshold level to avoid damage to the vessel endothelium at block 692, the pump speed is immediately decreased at block 616 and an alarm is triggered at block 678A within the control device 21. When normal operation is restored, the alarm is canceled at block 678B.

In yet another embodiment in which the inflow conduit 20 is connected to an artery and the outflow conduit 30 is connected to a vein, the control system 14 monitors and modifies the pulsatility of blood flow that is discharged into the accepting vein. For example, the control system 14 can monitor the electrocardiogram or monitor the cyclic changes in the pulse wave of blood coming into the blood pump system. During ventricular contraction and pulse wave propagation, the control system can decrease the rotational speed of the pump. During systole and after the pulse wave has passed, the control system can increase the rotational speed of the pump. In this manner, pulsatility in the blood entering the accepting vein can be reduced. Alternatively, the pulsatility of the blood in the accepting vein may be periodically checked manually, as may be accomplished with ultrasound, and the pump may be manually adjusted, for example, by tuning the head-flow characteristics of the pump, adding a compliance reservoir or elastic reservoir (a segmental or a diffuse change) to the pump inflow or outflow, or modulating the pump speed. Other adjustments may also be made. Alternatively, a compliance reservoir or elastic reservoir can be added to the inflow or outflow conduits at the time of implantation of the blood pump system.

In certain embodiments, a patient controller portion of the control system 14 may incorporate means for patients and care providers to make immediate changes in pump speed in response to urgent or emergent events, such as bleeding or pain. For example, the patient or care provider may stop the pump with an emergency stop function or may change the pump operation to a "safe mode" wherein the pump speed is reduced such that conduit pressure and blood flow is reduced but the blood flow through the pump system remains at a level sufficient for thrombosis free operation. These means may further comprise a system to provide instruction to the patient or care providers, such as to seek immediate medical care at the nearest hospital or clinic.

In various other embodiments, the control system 14 is monitored and adjusted manually or with a software program or application encoded on a computer-readable medium and executable by the processor 24, or other automated systems. The computer-readable medium may include volatile media, nonvolatile media, removable media, non-removable media, and/or another available medium that can be accessed by control system 14. By way of example and not limitation, the computer-readable medium may include computer storage media and communication media. Computer storage media includes memory, volatile media, nonvolatile media, removable media, and/or non-removable media implemented in a method or technology for storage of information, such as computer readable instructions, data structures, program modules, or other data.

The software program may include executable instructions to automatically adjust the pump speed to maintain the desired amount of blood flow, mean blood velocity or velocity, and mean WSS in the vessel segment to be treated (the "target vessel" or the "target blood vessel") in which a persistent increase in overall diameter and lumen diameter, or length, is desired, whether it is a donating artery, a donating vein, an accepting artery, or an accepting vein. Alternatively, the overall diameter, lumen diameter, length, and blood flow in the target vessel may be periodically checked manually, as may be accomplished with ultrasound, and the pump may be manually adjusted, for example, by tuning the head-flow characteristics of the pump or modulating the pump speed. Other adjustments may also be made.

In one embodiment, the mean blood velocity is determined by calculating an average of multiple discrete measurements of blood velocity by summing the discrete measurements and dividing the total by the number of measurements. Mean blood velocity can be calculated by taking measurements over a period of milliseconds, seconds, 1 minute, 5 minutes, 15 minutes, 30 minutes, 1 hour, or multiple hours.

In another embodiment, the mean WSS is determined by making a series of discrete measurements, making multiple discrete determinations of WSS (using those measurements), summing the discrete WSS determinations, and dividing the total by the number of determinations. Mean WSS can be calculated by taking measurements and making discrete WSS determinations over a period of seconds, 1 minute, 5 minutes, 15 minutes, 30 minutes, 1 hour, or multiple hours.

In one embodiment, the control system 14 receives information from sensor 22 in communication with the blood pump 25. In other embodiments, the control system 14 receives information from a sensor 22 in communication with an inflow conduit 20 or an outflow conduit 30 or in a vessel in fluid communication the inflow or outflow conduit. In various embodiments, all or portions of the control system 14 may be located within the pump body 25, while in other embodiments all or a portion of the control system may be located within the conduits, or within the control device 21.

The systems and methods described herein increase the mean WSS level in peripheral veins and arteries. Normal mean WSS for veins ranges between 0.076 Pa and 0.76 Pa. The systems described herein are configured to increase the mean WSS level in the accepting peripheral vein to a range between 0.76 Pa and 23 Pa, preferably to a range between 2.5 Pa and 10 Pa. Normal mean WSS for arteries ranges between 0.3 Pa and 1.5 Pa. For artery dilation, the systems and methods described herein increase the mean WSS level to a range between 1.5 Pa and 23 Pa, preferably to a range between 2.5 Pa and 10 Pa. In certain instances, sustained mean WSS less than 0.76 Pa in veins or less than 1.5 Pa in arteries may increase the overall diameter and lumen diameter of these vessels but the extent and rate of this increase is not likely to be clinically meaningful or compatible with routine clinical practice. Sustained mean WSS greater than 23 Pa in arteries or veins is likely to cause denudation (loss) of the endothelium of the blood vessels, or damage to the endothelium, which is known to retard dilation of blood vessels in response to increases in mean blood velocity and mean WSS. Pumping blood in a manner that increases mean WSS to the desired range for preferably 1 day to 84 days, and more preferably between about 7 and 42 days, for example, produces a persistent increase in the overall diameter and lumen diameter in an accepting vein, a donating vein, or a donating artery such that veins and arteries that were initially ineligible or suboptimal for use as a hemodialysis access sites or bypass grafts due to small vein or artery diameter become usable or more optimal. The blood pumping process may be monitored and adjusted periodically. For example, the pump may be adjusted over a period of minutes, hours, 1 day, 3 days, 1 week, or multiple weeks to account for changes in the peripheral vein or artery (such as a persistent increase in the overall diameter and lumen diameter) prior to achieving the desired persistent dilation.

Referring to FIGS. 37-40, a system 10 to increase the overall diameter and lumen diameter of veins and arteries is illustrated as used for a patient 1. In FIG. 37, the system 10 draws deoxygenated venous blood from the patient's venous system and discharges that blood into the accepting peripheral vessel 700. The system 10 also increases the mean velocity of blood in the accepting peripheral vessel 700 and increases the mean WSS exerted on the endothelium of the accepting peripheral vessel 700, to increase the overall diameter and lumen diameter of the accepting peripheral vessel 700 located, for example, in an arm or leg. The diameter of blood vessels such as peripheral veins can be determined by measuring the diameter of the lumen, which is the open space at the center of blood vessel where blood is flowing or by measuring the diameter of the overall vessel, which includes the open space and the walls of the blood vessel.

The invention also relates to simultaneously and persistently increasing the overall diameter and lumen diameter of a peripheral vein or artery by directing blood into or out of the peripheral vein or artery, thereby increasing the mean velocity of the blood in the peripheral vein or artery and increasing the mean WSS on the endothelium of the peripheral vein or artery. Systems are described wherein the mean velocity of the blood in a peripheral vein or artery and the mean WSS on the endothelium of the peripheral vein or artery is increased by using a blood pump system. Preferably, the pump directs blood into the peripheral vein, wherein the pumped blood has reduced pulsatility, such as when the pulse pressure is lower than blood in a peripheral artery.

The system 10 is suitable to maintain a flow rate preferably between 50 mL/min and 2500 mL/min and optionally between 50 mL/min and 1500 mL/min or between 100 mL/min and 1000 mL/min while also maintaining a pressure range in the outflow conduit between 10 mmHg and 350 mmHg, preferably between 25 mmHg and 100 mmHg. As previously described, the control system 14 may be optimized to maintain a steady mean wall shear stress of between 0.76 Pa and 23 Pa, preferably between 2.5 Pa and 10 Pa or between 2.5 Pa and 7.5 Pa, in peripheral veins such that the overall diameter and lumen diameter of the peripheral veins are persistently increased by as much as 5% to more than 500%.

The systems described herein also increase the mean velocity of blood in peripheral veins. At rest, the mean velocity of blood in the cephalic vein in humans (with an average lumen diameter of 2.4±0.5 mm) is generally between 5 to 9 cm/s (0.05 to 0.09 m/s). For the systems described herein, the mean velocity of blood in the peripheral vein is increased to a range between 5 cm/s and 235 cm/s (0.05 and 2.35 m/s), preferably to a range between 15 cm/s and 100 cm/s (0.15 m/s and 1.0 m/s), depending on the initial overall diameter or lumen diameter of peripheral accepting vein and the final overall or lumen diameter that is desired. The systems described herein also increase the mean velocity of blood in peripheral arteries. At rest, the mean velocity of blood in the brachial artery in humans (with an average lumen diameter of 3.7±0.7 mm) is generally between 10 and 15 cm/s (0.1 and 0.15 m/s). For the systems and methods described herein, the mean velocity of blood in the peripheral artery is increased to a range between 15 cm/s and 360 cm/s (0.1 and 3.6 m/s), preferably to a range between 25 cm/s and 160 cm/s (0.25 and 1.6 m/s), depending on the initial overall diameter or lumen diameter of artery the final overall or lumen diameter that is desired.

Preferably, the mean blood velocity is increased for between 1 day and 84 days, or preferably, between 7 and 42 days, to induce a persistent increase in the overall diameter and lumen diameter in the peripheral accepting vein, peripheral accepting artery, peripheral donating vein, or peripheral donating artery such that veins and arteries that were initially ineligible or suboptimal for use as a hemodialysis access site or bypass graft due to a small vein or artery diameter become usable. This can also be accomplished by intermittently increasing mean blood velocity during the treatment period, with intervening periods of normal mean blood velocity.

Studies have shown that baseline hemodynamic forces and changes in hemodynamic forces within veins and arteries play a vital role in determining the overall diameter and lumen diameter, and the length of those veins and arteries. For example, persistent increases in mean blood velocity and mean WSS can lead to a persistent increase in the lumen diameter and overall diameter, and length, of veins and arteries. The elevated mean blood velocity and mean WSS are sensed by endothelial cells, which trigger signaling mechanisms that result in stimulation of vascular smooth muscle cells, attraction of monocytes and macrophages, and synthesis and release of proteases capable of degrading components of the extracellular matrix such as collagen and elastin. As such, the present invention relates to increasing mean blood velocity and mean WSS for a period of time sufficient to result in vein and artery remodeling and an increase in the overall diameter and the lumen diameter, and length, of the veins and arteries.

The systems described herein increase the mean WSS level in a peripheral vein or artery. Normal mean WSS for veins ranges between 0.076 Pa and 0.76 Pa. The systems described herein increase the mean WSS level in veins to a range between 0.76 Pa and 23 Pa, preferably to a range between 2.5 Pa and 10 Pa. Normal mean WSS for arteries ranges between 0.3 Pa and 1.5 Pa. To persistently increase the overall diameter and lumen diameter of arteries, the systems and methods described herein increase the mean WSS level to a range between 1.5 Pa and 23 Pa, preferably to a range between 2.5 Pa and 10 Pa. Preferably, the mean WSS is increased for between 1 days and 84 days, or preferably, between 7 and 42 days, to induce a persistent increase in the overall diameter and lumen diameter in the peripheral accepting vein, peripheral accepting artery, peripheral donating vein, or peripheral donating artery such that veins and arteries that were initially ineligible or suboptimal for use as a hemodialysis access site or bypass graft due to a small vein and artery diameter become usable. This can also be accomplished by intermittently increasing mean WSS during the treatment period, with intervening periods of normal mean WSS.

In some circumstances, sustained periods of mean WSS levels in the peripheral veins lower than 0.76 Pa or in peripheral arteries lower than 1.5 Pa may result in increased overall diameter and lumen diameter of these veins and arteries, but the extent and rate of this increase is not likely to be clinically meaningful or compatible with routine clinical practice. Sustained mean WSS levels in peripheral veins and arteries higher than about 23 Pa are likely to cause denudation (loss) of the endothelium of the veins or damage to the endothelium of the veins. Denudation of the endothelium or damage to the endothelium of blood vessels is known to reduce the increase in overall diameter and lumen diameter of blood vessels in the setting of increased in mean blood velocity and mean WSS. The increased mean WSS induces sufficient persistent increase in the overall diameter and lumen diameter, or length, in the veins and arteries, such that those that were initially ineligible or suboptimal for use as a hemodialysis access site or bypass graft due to a small vein or artery diameter become usable or more optimal. The diameter of the peripheral accepting vein, peripheral accepting artery, peripheral donating vein, or peripheral donating artery can be determined intermittently, such as every 1 day, 3 days, 1 week, or multiple weeks for example, to allow for pump speed adjustment in order to optimize the rate and extent of the persistent increase in the overall diameter and lumen diameter of the vein and artery during the treatment period.

The systems described herein also increase the mean velocity of blood in peripheral veins. At rest, the mean velocity of blood in the cephalic vein in humans (with an average lumen diameter of 2.4±0.5 mm) is generally between 5 and 9 cm/s (0.05 and 0.09 m/s). For the systems described herein, the mean velocity of blood in the peripheral vein is increased to a range between 5 cm/s and 235 cm/s (0.05 and 2.35 m/s), preferably to a range between 15 cm/s and 100 cm/s (0.15 m/s and 1.0 m/s), depending on the initial overall diameter or lumen diameter of the peripheral accepting vein and the desired final overall diameter and lumen diameter of the peripheral accepting vein. The systems described herein also increase the mean velocity of blood in peripheral arteries. At rest, the mean velocity of blood in the brachial artery in humans (with an average lumen diameter of 3.7±0.7 mm) is generally between 10-15 cm/s (0.1 and 0.15 m/s). For the systems and methods described herein, the mean velocity of blood in the peripheral artery is increased to a range between 15 cm/s and 360 cm/s (0.1 and 3.6 m/s), preferably to a range between 25 cm/s and 160 cm/s (0.25 and 1.6 m/s), depending on the initial overall diameter or lumen diameter of the peripheral artery and the desired final overall diameter or lumen diameter of the peripheral artery. Preferably, the mean blood velocity is increased for between 1 day and 84 days, or preferably, between 7 and 42 days, to induce a persistent increase in the overall diameter and the lumen diameter, or length, of the peripheral accepting vein, peripheral accepting artery, peripheral donating vein, or peripheral donating artery such that veins and arteries that were initially ineligible or suboptimal for use as a hemodialysis access site or bypass graft due to a small vein or artery diameter or inadequate length become usable. Mean blood velocity levels in the peripheral accepting or donating vein lower than 5 cm/s to 15 cm/s (0.05 m/s to 0.15 m/s) or mean blood velocity levels in the peripheral accepting or donating artery lower than 15 cm/s to 25 cm/s (0.15 m/s to 0.25 m/s) may result in increased overall diameter and lumen diameter of these veins and arteries, but the extent and rate of this increase is not likely to be clinically meaningful or compatible with routine clinical practice. Mean blood velocity levels in the peripheral accepting or donating vein higher than 160 cm/s to 235 cm/s (0.16 m/s to 2.35 m/s) or mean blood velocity levels in the peripheral accepting or donating artery higher than 250 cm/s to 360 cm/s (0.25 m/s to 0.36 m/s) are likely to cause denudation (loss) of the endothelium of the veins or damage to the endothelium of veins. Denudation or damage of the endothelium of blood vessels is known to reduce the increase in the overall diameter and lumen diameter of blood vessels observed in the setting of increased mean blood velocity. The increased mean blood velocity in the desired range and for a sufficient period of time induces sufficient persistent increase in the overall diameter and lumen diameter, or length, in the veins and arteries, such that those that were initially ineligible or suboptimal for use as a hemodialysis access site or bypass graft due to a small vein or artery diameter or inadequate length become usable. The overall diameter or lumen diameter of the peripheral accepting vein, peripheral accepting artery, peripheral donating vein, and peripheral donating artery can be determined intermittently, such as every minute(s), hour(s), 1 day, 3 days, 1 week, or multiple weeks for example, to allow for pump speed adjustment in order to optimize the rate and extent of the persistent increase in the overall diameter and lumen diameter of the vein and artery during the treatment period.

In one embodiment shown in FIG. 34, the system 10 includes the blood pump 25, the pair of conduits 12, and the control device 21 for moving deoxygenated venous blood from a donating vein or location in the venous system of a patient to a peripheral accepting vein. In various embodiments, the peripheral accepting vein may be a cephalic vein, radial vein, median vein, ulnar vein, antecubital vein, median cephalic vein, median basilic vein, basilic vein, brachial vein, lesser saphenous vein, greater saphenous vein, femoral vein, or other veins. Other veins that might be useful in the creation of a hemodialysis access site or bypass graft or other veins useful for other vascular surgery procedures requiring the use of veins may be used. The conduits 12 move the deoxygenated blood to the peripheral accepting vein. The persistently elevated mean velocity of the blood and the elevated mean WSS in the peripheral vessel causes a persistent and progressive increase in the overall diameter and lumen diameter of the peripheral accepting vein. Thus, the system 10 of the present invention advantageously increases the diameter or length of the peripheral vein 4 so that it can be used, for example, to construct an hemodialysis access site (such as an AVF or AVG), a bypass graft, or used in another clinical setting where a vein of a certain diameter or length is needed, as determined by one skilled in the art.

As used herein, deoxygenated blood is blood that has passed through the capillary system and had oxygen removed by the surrounding tissues and then passed into the venous system. A peripheral vein, as used herein, means any vein with a portion residing outside of the chest, abdomen, or pelvis. In the embodiment shown in FIG. 37A, the peripheral accepting vein 712 is the cephalic vein. However, in other embodiments, the peripheral accepting vein may be a radial vein, median vein, ulnar vein, antecubital vein, median cephalic vein, median basilic vein, basilic vein, brachial vein, lesser saphenous vein, greater saphenous vein, femoral vein, or other veins. In addition to a peripheral vein, other veins that might be useful in the creation of a hemodialysis access site or bypass graft or other veins useful for other vascular surgery procedures requiring the use of veins may also be used as accepting veins, such as those residing in the chest, abdomen, and pelvis.

Figure 37B:
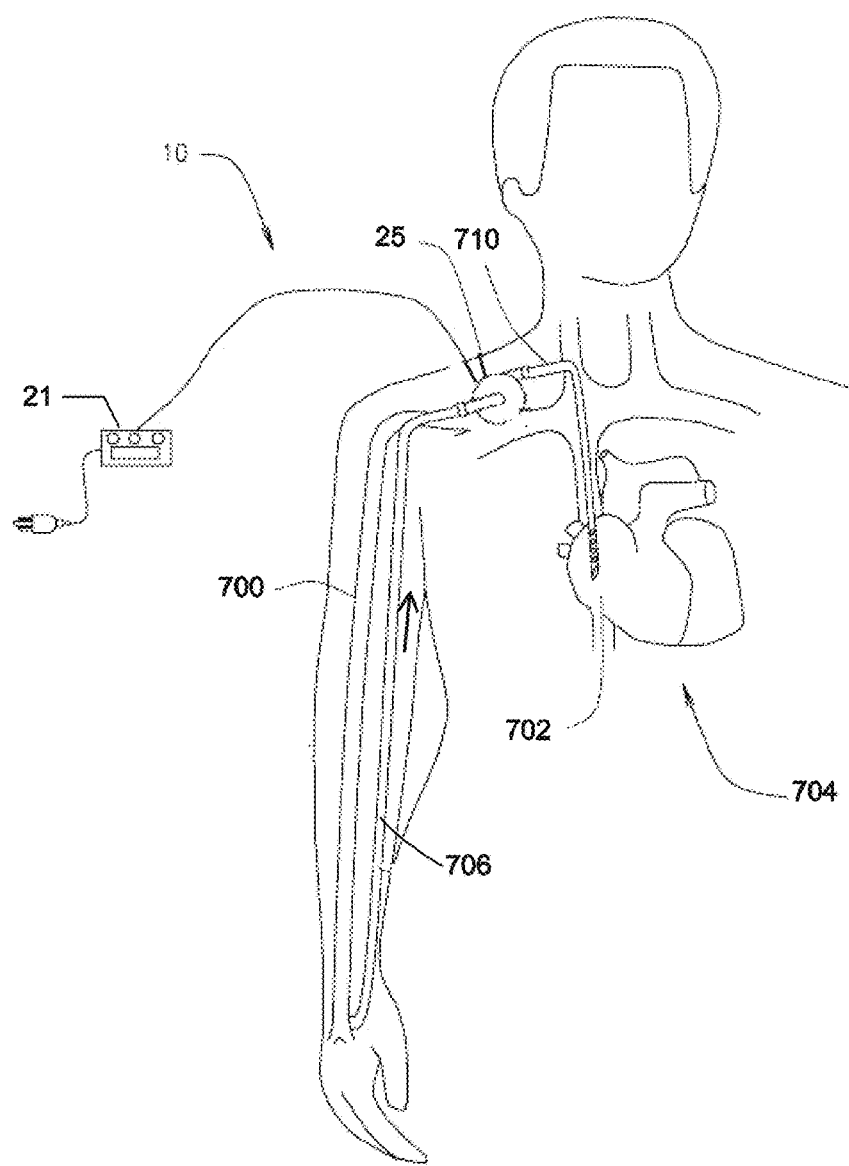
FIG. 37B is a view of the pump system as applied to a circulatory system of a patient according to a second embodiment.

FIG. 37B illustrates another embodiment for using the system 10 to increase the overall diameter and lumen diameter of a blood vessel. In this embodiment, the system 10 is configured to remove deoxygenated blood from a donating vein 700 and move the blood to the superior vena cava or right atrium 702 of the heart 704. As shown, an inflow conduit 706 is connected in fluid communication with the donating vein 700, in this case the cephalic vein. In one embodiment, the connection may be made using a short ePTFE segment of the inflow conduit 706 that is used to secure the inflow conduit 706 to the donating vein 700 while the remaining segment of the inflow conduit is made using polyurethane. In other embodiments, at least a portion of the inflow conduit or the outflow conduit further comprises nitinol, for kink and compression resistance. As shown, one end of the outflow conduit 710 is connected to the blood pump 25 while the other end of the outflow conduit is fluidly connected to the superior vena cava and the right atrium 702 by an intravascular portion. For the embodiment of FIG. 37, a blood pump is used increase the rate at which blood moves from the donating vein 700 to the superior vena cava and right atrium 702 of the heart 704 in order to achieve a desired elevated level of mean blood velocity and elevated level of mean WSS in the donating vein 700. The pump is operated at a rate and for a time sufficient to result in a desired persistent increase in the overall diameter and lumen diameter of the donating vein, such as a 10% increase, a 25% increase, a 50% increase, or an increase of 100% or more from the starting diameter. In a further embodiment, one or more venous valves between the junction of the inflow conduit 706 and the donating vein 700, and the right atrium 702 may be rendered incompetent or less competent (using any of the methods available to one skilled in the art) to allow blood to flow in a retrograde fashion in the donating vein 700 and then into the inflow conduit 706.

Figure 38:
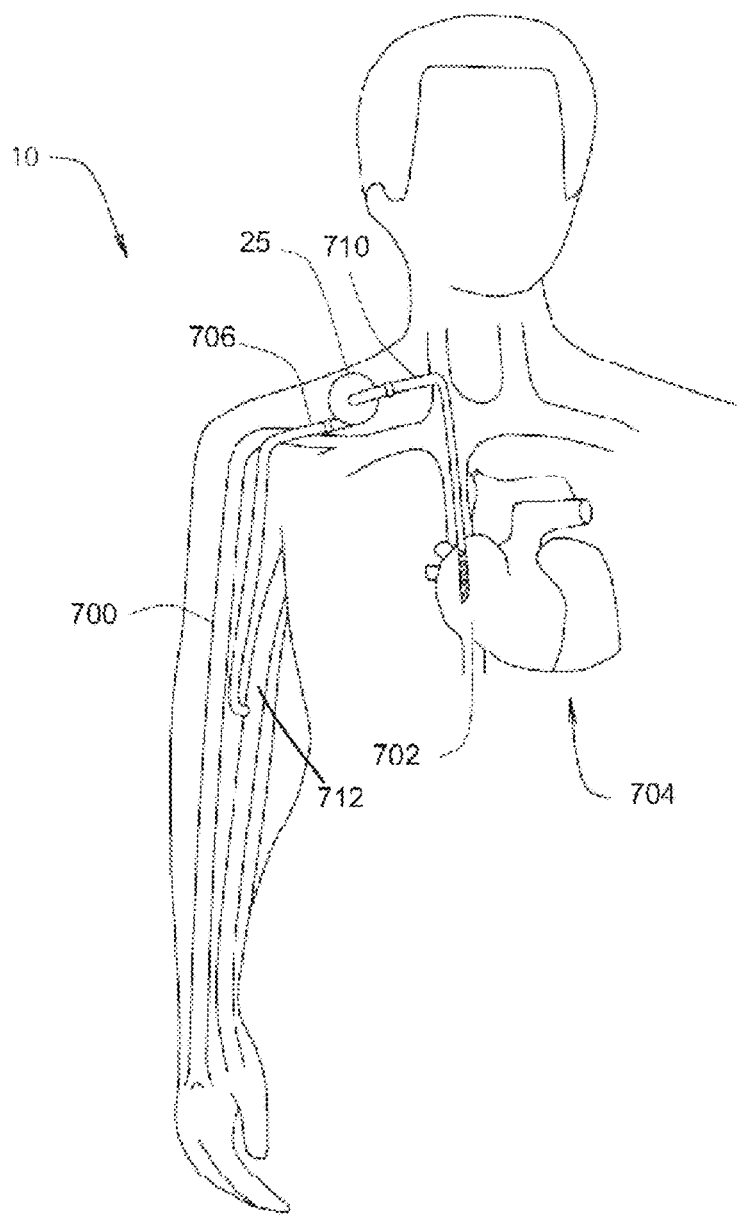
FIG. 38 is a schematic view of the pump system as applied to a circulatory system of a patient according to a third embodiment.

FIG. 38 illustrates another embodiment for using the system 10 to increase the overall diameter and lumen diameter of a blood vessel. In this embodiment, the system 10 is configured to remove oxygenated blood from a donating artery 712 (in this case the brachial artery) and move the blood to the superior vena cava and right atrium 702 of the heart 704. As shown, an inflow conduit 706 is connected in fluid communication with the donating artery 712. In one embodiment, the connection may be made using a short ePTFE segment of the inflow conduit 706 that is used to secure the inflow conduit to the donating artery 712 while the remaining segment of the inflow conduit is made using polyurethane. In other embodiments, one or both segments of the inflow conduit 706 further comprise nitinol, such as for kink and compression resistance. As shown, one end of the outflow conduit 710 is connected to the blood pump 25 while the other end of the outflow conduit is fluidly connected to the superior vena cava and the right atrium 702 by an intravascular portion. For the embodiment of FIG. 38, a blood pump is used increase the rate at which blood moves from the donating artery 712 to the right atrium 702 of the heart 704 in order to achieve a desired elevated level of mean blood velocity and elevated mean level of WSS in the donating artery 712. The pump is operated at a rate and for a time sufficient to result in a desired persistent increase in the overall diameter and lumen diameter of the donating artery, such as a 10% increase, a 25% increase, a 50% increase, or an increase of 100% or more from the starting diameter.

In other embodiments, oxygenated arterial blood may be moved from a donating artery to an accepting location. Donating arteries may include, but are not limited to, a radial artery, ulnar artery, interosseous artery, brachial artery, anterior tibial artery, posterior tibial artery, peroneal artery, popliteal artery, profunda artery, superficial femoral artery, or femoral artery.

Figure 39:
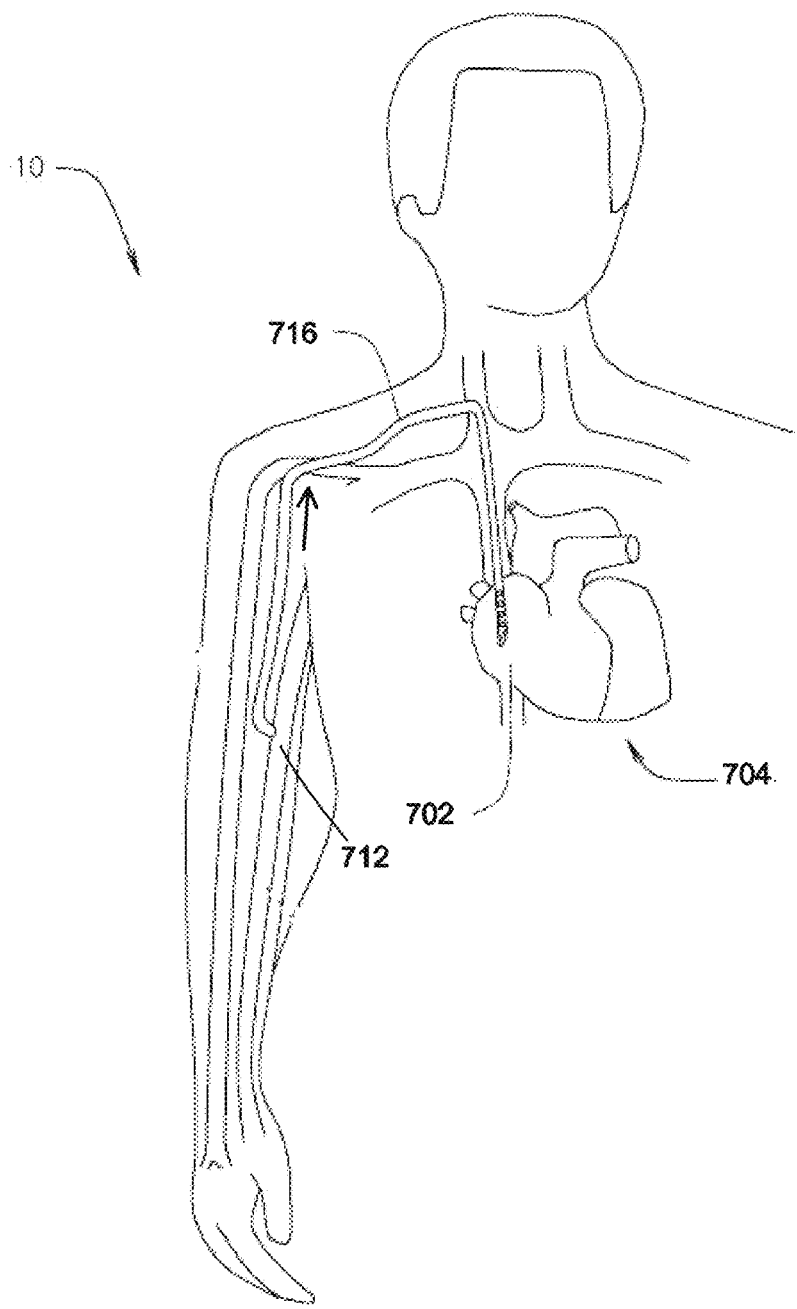
FIG. 39 is a schematic view of the system without a pump as applied to a circulatory system of a patient according to a fourth embodiment.

FIG. 39 illustrates another embodiment for using the system 10 to increase the overall diameter and lumen diameter of a blood vessel. In this embodiment, the system 10 is configured to remove oxygenated blood from a donating artery 712 (in this case the brachial artery) and move the blood to the superior vena cava and right atrium 702 of the heart 704. As shown, a conduit 716 is connected in fluid communication with the donating artery 712. In one embodiment, the connection may be made using a short ePTFE segment of the conduit 716 that is used to secure the inflow conduit to the donating artery 712 while the remaining segment of the inflow conduit is made using polyurethane. In other embodiments, one or both segments of the conduit 716 further comprise nitinol, such as for kink and compression resistance. For the embodiment of FIG. 39, there is no pump and blood moves passively from the higher pressure donating artery 712 to the lower pressure superior vena cava and right atrium 702, and the conduit 716 is configured in length and lumen diameter to achieve a desired elevated level of mean blood velocity and mean WSS in the donating artery 712. The conduit 716 remains in place for a time sufficient to result in a desired persistent increase in the overall diameter and lumen diameter of the donating artery 712, such as a 10% increase, a 25% increase, a 50% increase, or an increase of 100% or more from the starting diameter.

Figure 40:
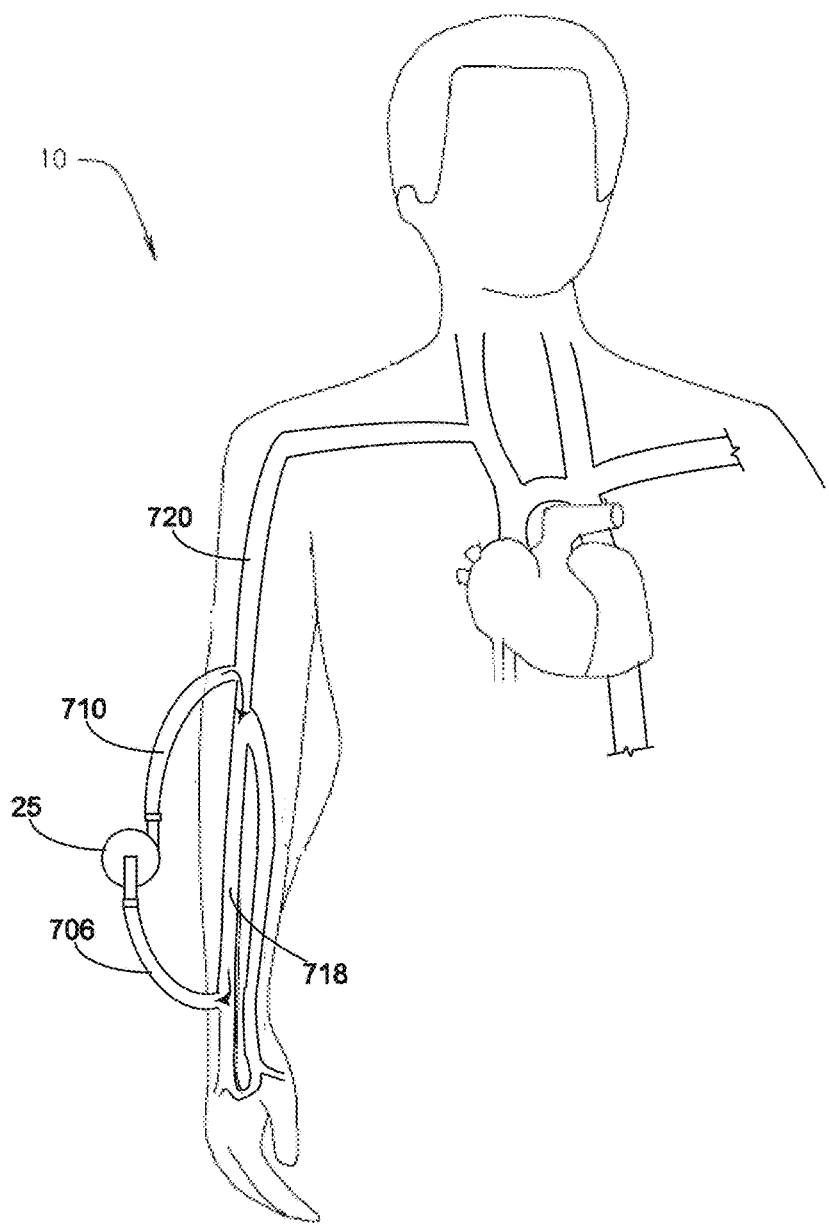
FIG. 40 is a schematic view of the pump system as applied to a circulatory system of a patient according to a fifth embodiment.

FIG. 40 illustrates another embodiment for using the system 10 to increase the overall diameter and lumen diameter of a peripheral artery. In this embodiment, the system 10 is configured to remove oxygenated blood from a target artery 718, such as the radial artery, and move the blood to an accepting artery 720, such as the brachial artery. As shown, an inflow conduit 706 is connected in fluid communication with the target artery 718. In one embodiment, the connection between the inflow conduit 706 and an artery or the outflow conduit 710 and an artery may be made using a short ePTFE segment of the respective conduit that is used to fluidly connect the inflow conduit to the target artery 718 or the outflow conduit 710 that is fluidly connected to the accepting artery 720, while the remaining segments of the inflow and outflow conduits can be made using polyurethane. In other embodiments, one or both segments of the inflow conduit 706 or the outflow conduit 710 further comprise nitinol, such as for kink and compression resistance.

As shown, one end of the outflow conduit 710 is connected to the blood pump 25 while the other end of the outflow conduit is fluidly connected to the accepting artery 720. For the embodiment of FIG. 40, the blood pump 25 is used increase the rate at which blood is withdrawn from the target artery 718 in order to achieve a desired elevated level of mean blood velocity and elevated mean level of WSS in the target artery. The pump is operated at a rate and for a time sufficient to result in a desired persistent increase in the overall diameter and lumen diameter of the target artery 718, such as a 10% increase, a 25% increase, a 50% increase, or an increase of 100% or more from the starting diameter.

Referring now to FIGS. 44A-D, the pump system 10 may also be used to increase the return of venous blood from a lower extremity to the heart, reduce lower extremity venous hypertension, and heal venous ulcers by pumping venous blood from the lower extremity, such as a leg, to another location in the venous circulation, in this case the superior vena cava and the right atrium.

In one embodiment, as shown in FIG. 45A, the inflow conduit 20 includes a nitinol support structure, a hydrophilic coating, and a bonded ePTFE segment 503 that is configured for forming an anastomosis 290 to the femoral vein 292. Collapse and occlusion at the inflow conduit tip may be prevented by the use of a suction detection algorithm, as shown in FIG. 36F, to adjust pump speed and/or a coil-reinforced ePTFE graft section, as shown in FIG. 31, to resist collapse under negative pressures. The outflow conduit 30 also includes a nitinol support structure, a hydrophilic coating, and an unreinforced segment 509 with side discharge holes configured for insertion into the superior vena cava and right atrium, as shown in FIG. 45B.

Various configurations of the control device 21 may be employed. For example, the pump system 10 may be controlled by a small portable control device 21 optimized for use by ambulatory patients, as shown in FIG. 46A, which may be worn by the patient on a belt, in a pocket, or carried in a carrying case during treatment. The portable control device 21 may contain rechargeable batteries to provide power to the pump 25 through the lead 120. The control device 21 may also provide system status information to the patient and adjust the pump speed and other system parameters based on the patient's body position (e.g. standing or supine, etc.) or the blood pressure in an inflow conduit 20, an outflow conduit 30, in a vein segment adjacent to the inflow conduit or outflow conduit. In another embodiment, the control device 21 may be a larger base unit optimized for use by non-ambulatory patients in hospitals or clinics, or nighttime use at home by ambulatory patients, as shown in FIG. 46B, and may be configured for placement on a table when powered by AC mains or on a cart when powered by rechargeable batteries.

Figure 44B:
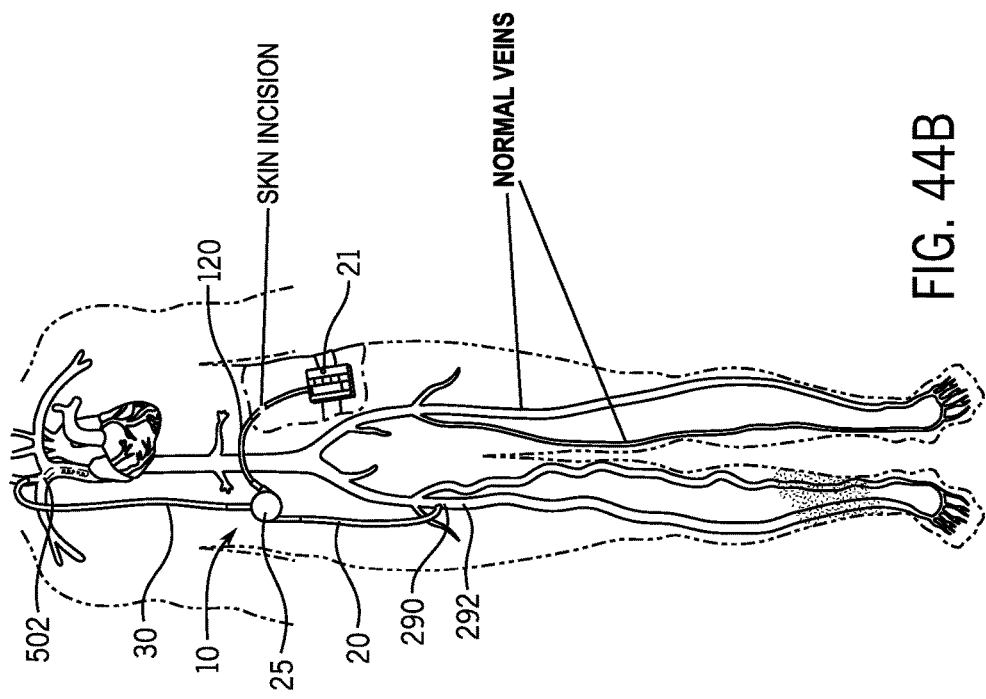
FIGS. 44A-D are schematic views of the pump system as applied to the lower extremity venous system of a patient for the treatment of venous hypertension and venous ulcer.
Figure 44A:
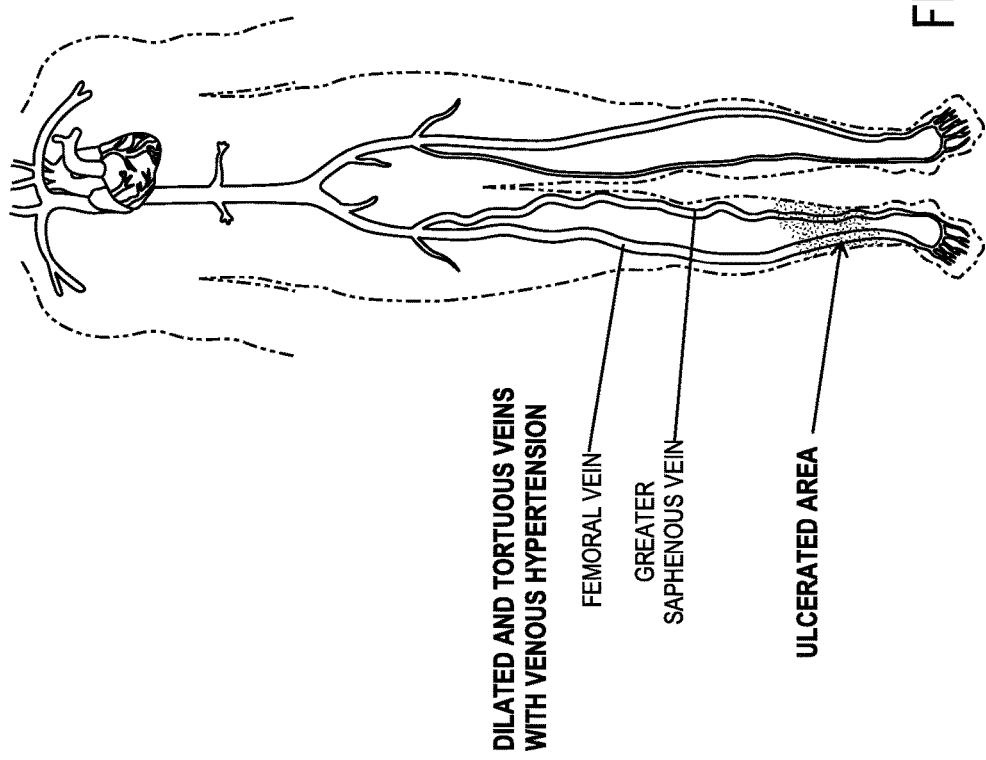
Figure 44C:
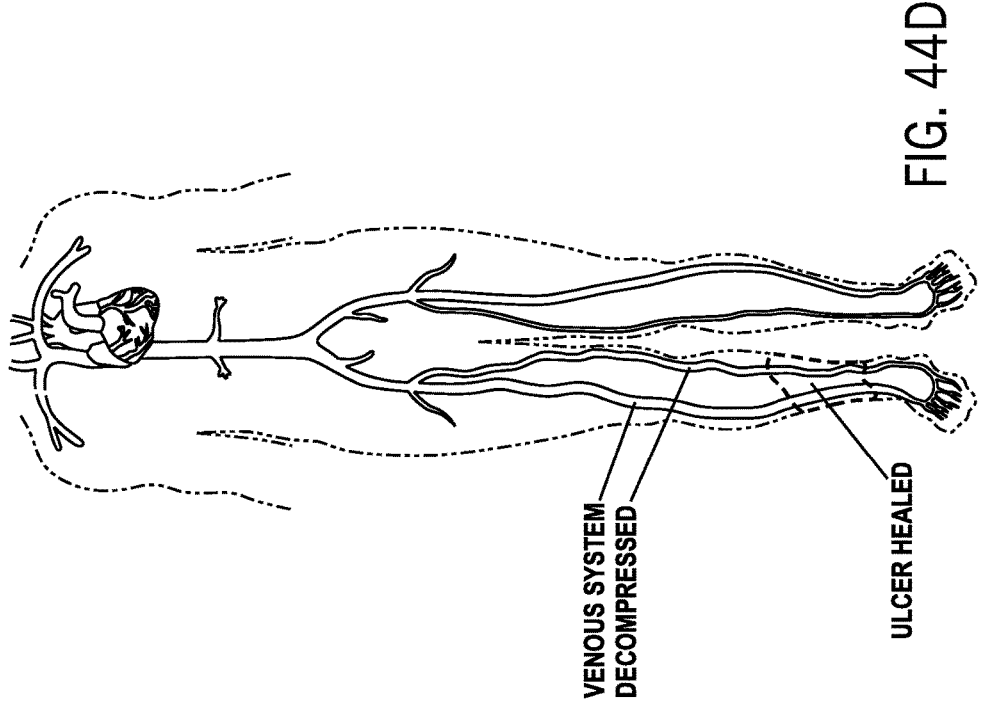
Figure 44D:
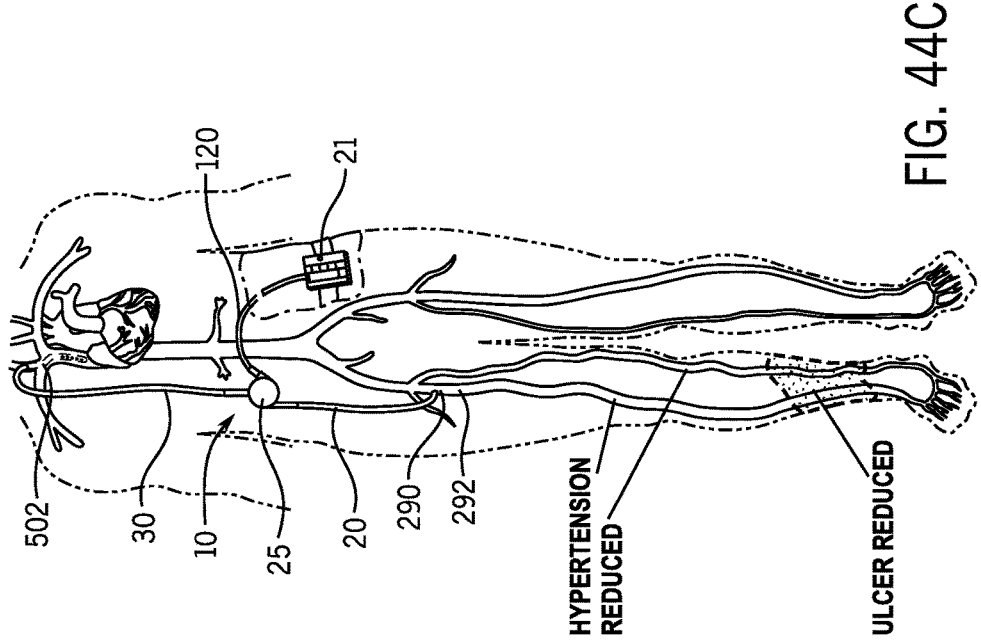

In one aspect, the pump system 10 may convey venous blood from a lower extremity to another location in the venous system in order to reduce lower extremity venous pressure, and assist in healing of an ulceration after approximately three months of use, as shown in FIG. 44C. The pump system 10 may be removed after the ulcer has fully healed, as shown in FIG. 44D.

In various embodiments of the control device 21, as shown in FIGS. 46A-B, the processor 24 for controlling the pump 25 may be located within the pump. Placing the processor 24 within the pump 25 reduces wiring located within the power cord 120. This reduction improves the ability to detect the commutation timing via the back-EMF that comes from the un-driven leg of the three-phase motor coil configuration.

Figure 47A:
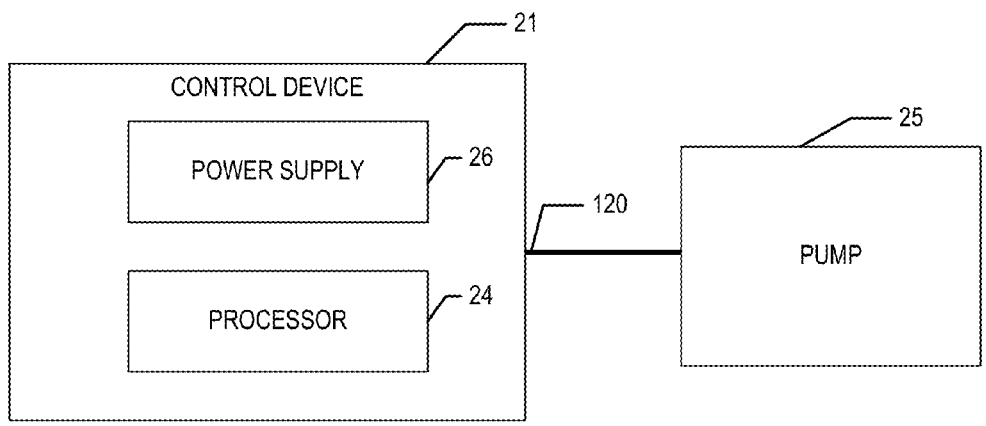
FIGS. 47A-B are block diagrams of various arrangements a control device and a blood pump, where a motor drive processor may be located in the control device or in the body of the blood pump.

One embodiment of the control device 21, as shown in FIG. 46B, that includes a base unit powered by AC mains and optimized for hospital or clinic use by non-ambulatory patients, is tethered to the blood pump 25 by a cable 120, as illustrated in FIG. 47A. In this embodiment, the processor 24 and power supply 26 are located within the control device 21. As the long cable 120 may act as an antenna, any motor commutation signals generated at the blood pump 25 to be received at the control device 21 and likewise, any AC motor current pulses generated at the control device to be receives at the blood pump, are highly susceptible to radio frequency (RF) noise. Therefore, attention must be given to RF shielding and the grounding of components to ensure reliable operation.

Figure 47B:
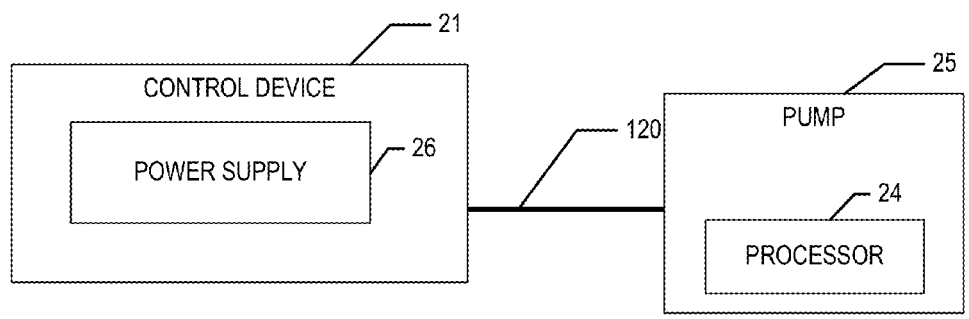

In embodiments of the control device 21 and pump 25, where the processor 24 is in closer proximity to the pump, whether either located within the blood pump body 105, as shown in FIG. 47B, or at least connected inline between the cable 120 and the blood pump, the effects of RF noise are diminished. In these embodiments, the DC current provided over the cable 120 is less affected by RF noise.

In other embodiments of the control device 21, as shown in FIG. 46A, that include a portable, battery-powered unit optimized for use by ambulatory patients, a shorter length of cable 120 that is less susceptible to RF noise is used. Therefore, the processor 24 may be located in either the control device 21 or the pump 25.

Example Studies and Experiments

In a series of in vivo feasibility studies, embodiments of the AFE System were implanted in pigs. In particular, the AFE system was placed in communication with the left jugular vein and the left hindlimb lateral saphenous vein (SV). In one study, various hemodynamic parameters including the mean right atrial pressure (RAP), mean pulmonary artery pressure (PAP), oxygen ($O_2$) saturation, arterial blood pressure (ABP), and pump flow were measured in an acute study of a 21 kg pig. During the acute study, pump flows of 100-500 mL/min induced no changes in the hemodynamic parameters or cardiac function from baseline values.

Figure 49:
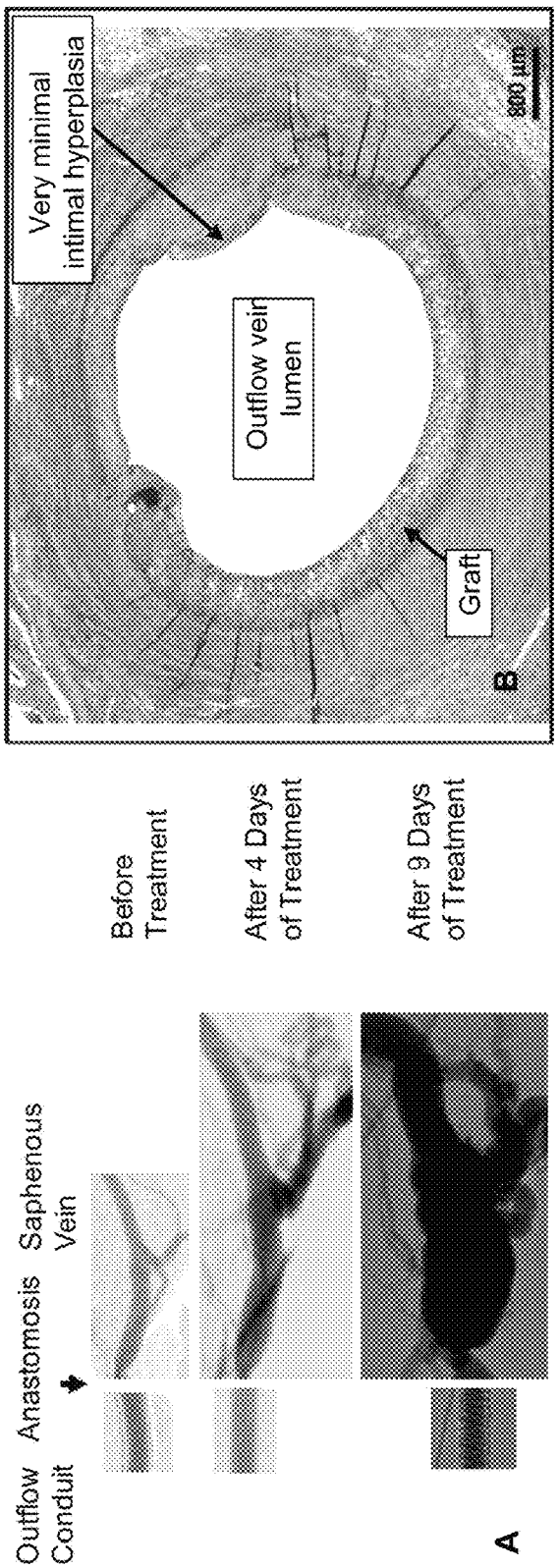
FIGS. 49A-B are angiographic and histological results from an in vivo feasibility study of the AFE System.

Another study consisted of a chronic study of an anticoagulated 28 kg pig, the lateral saphenous vein was treated for 9 days with a WSS dose of approximately 4 Pa. During the chronic study, pump flow increased from 270 mL/min on Day 0 to 947 mL/min on Day 9, and the outflow segment of the saphenous vein dilated from 3.7 mm to 13.8 mm, as shown in FIG. 49A, without angiographic evidence of stenosis. A necropsy performed on Day 9 showed a dilated saphenous vein that was elongated and easily mobilized. Histology demonstrated extensive dilatory remodeling and very minimal intimal hyperplasia, as illustrated in FIG. 49B.

In order to compare results with the AFE System to the current standard of care arteriovenous fistula (AVF), a study was performed wherein the lateral saphenous vein was mobilized and connected to the femoral artery by a side (artery) to end (vein) anastomosis to make an AVF. The diameter and blood flow of the AVF outflow vein was determined over 4 weeks by ultrasound and angiography. All four of the AVFs that were created failed to mature by KDOQI criteria (6 mm vein diameter and 600 mL/min blood flow) due to the development of severe intimal hyperplasia and stenosis in the outflow vein segment adjacent to the artery. By week 4, one AVF was occluded and the other three AVFs were nearly occluded.

A chronic study was completed on anticoagulated pigs weighing 20-25 kg wherein an arteriovenous fistula was made between the femoral artery and the mobilized lateral saphenous vein bilaterally in 2 pigs (n=4 arteriovenous fistulas).

The results of these pilot studies demonstrated the efficacy of the AFE System to dilate and mature peripheral veins in vivo. In particular, the studies demonstrated the a vein dilation of approximately 10.1 mm, roughly equal to a 275% increase, was achievable after nine days of treatment with a maintained WSS of 4 Pa, with little intimal hyperplasia formation in the treated, dilated vein. These results with the AFE System stand in contrast to results with the standard of care AVF wherein vein dilation was poor and AVF blood flow was limited by the appearance of sever intimal hyperplasia and stenosis in the outflow vein.

Figure 54:
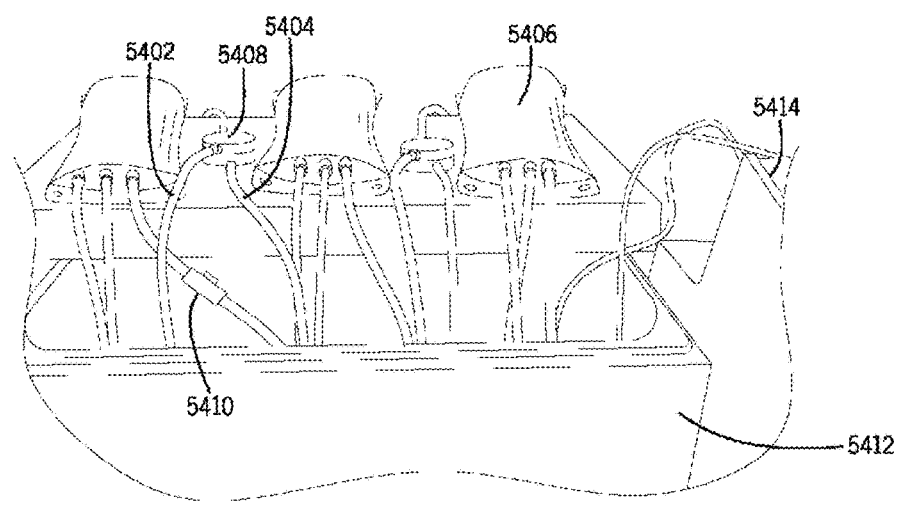
FIG. 54 is a photograph of an experimental circulatory loop used during various studies and experiments according to one embodiment.

In another study, the hemolytic properties of extracorporeal blood pump (EBP) units, including one similar to the pump 25, were evaluated both before and after a series of hydraulic performance tests. As a benchmark, the hemolytic properties of the EBP test units were assessed. A closed mock circulatory, non-pulsatile test loop was constructed for each pump in the hemolysis test. An example of the closed mock loop used during the study is shown in FIG. 54. Each loop comprised 4 mm ID PVC tubing (Tygon stock #AAC1S1518) for inflow & outflow conduits 5402 and 5404, a reservoir 5406, and a pump 5408. The inflow and outflow conduits measured 0.5 m in length. Bovine blood collected by venipuncture and stored in a bag with CPDA-1 was used within 48 hours (Lampire, CN#7200805) in compliance with ASTM F1830-97. The blood was transferred into other blood bags (1 L, Sorin Group #00-700-1001) which were used as reservoirs, each containing three ports 5410 used as the inlet, outlet, and sampling conduits. Straight barbed connectors were used to securely connect the tubing to the reservoir ports. A water bath 5412 was adjusted to 37° C. BBS was pumped through each pump and circuit for 30 minutes to rinse out the systems prior to testing. Prior to the testing, the reservoirs were supported above the water bath with the inflow and outflow conduits suspended in the bath to warm circulating blood to 37° C., as shown in FIG. 54

Pumps tested in the hemolysis analysis were the Medtronic BP-50, a pump used for pediatric cardiopulmonary bypass (CPB) and extracorporeal oxygenation (ECMO), and EBP test units. Pump speeds were selected to maintain a flow rate of 500 mL/min. The speed of each EBP was controlled via an mPBU, while the speed of the BP-50 5414 was maintained using a console (Medtronic Biomedicus 540 Bioconsole). Flow in each loop was measured using a custom ultrasonic flow sensor (Transonic Systems model ME3PXL) blood at 37° C. and a flow meter (Transonic Systems model TS410). Each hemolysis test ran for 6 hours, with 3-5 mL samples collected from each pump in 15 minute intervals. A colorimetric assay was used to characterize blood damage using the methods previously described. Results were plotted as plasma free hemoglobin (PFH) concentration over time, and the slope of the best fit line was used to calculate hemolysis rates. These studies were conducted three times on each pump both before and after the life test. After each hemolysis study, the pumps were flushed with room temperature blood bank saline.

Hemolysis results were calculated as the milligram normalized index of hemolysis (mg N.I.H.), based on ASTM F-1841, the preferred measurement for data comparison across the literature, and BP-50 units. BP-50 units account for day-to-day and animal-to-animal variations in blood fragility by normalizing the EBP hemolysis rate using the BP-50 test results obtained on the same day using the same blood source. It is derived by dividing the EBP mg N.I.H. rate by the BP-50 mg N.I.H rate. mg N.I.H is determined by the formula:

$$\text{mg N.I.H.} = \Delta\text{free } Hb \times V \times (100-Ht)/100 \times 100/(Q \times T);$$

where mg PFH added per 100 ml of blood pumped is corrected for plasma volume and normalized by flow rate and run time. As such higher values are expected at higher flow rates if the pumps are equally hemolytic. BP 50 Units are normalized by using mg NIH of BP-50 at same flow rate using the same blood source.

Figure 55:
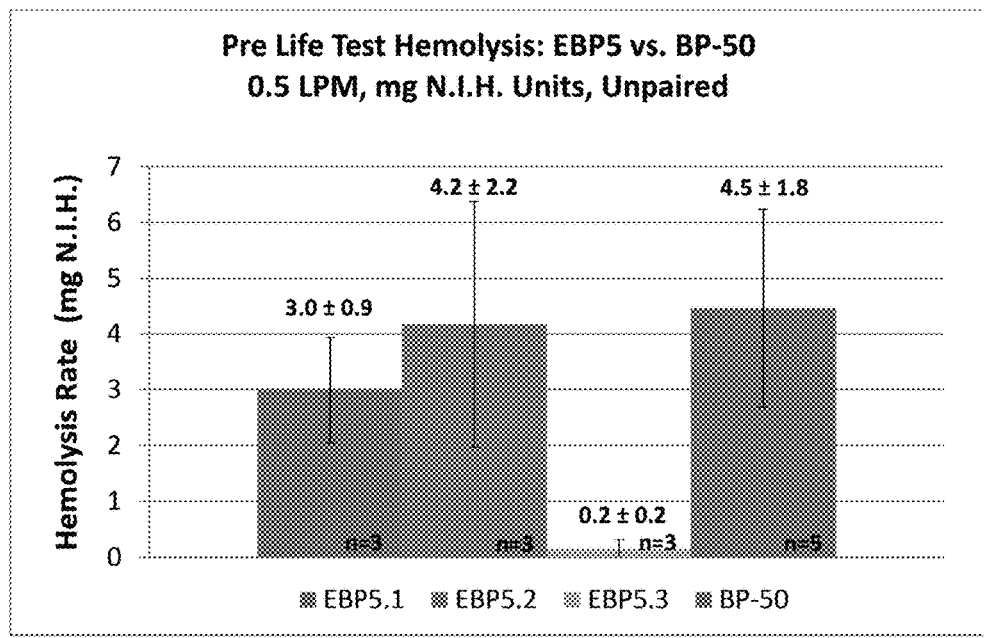
FIG. 55 is a graph depicting the unpaired results for test pumps units comparing BP-50 against mg N.I.H. Units.
Figure 56:
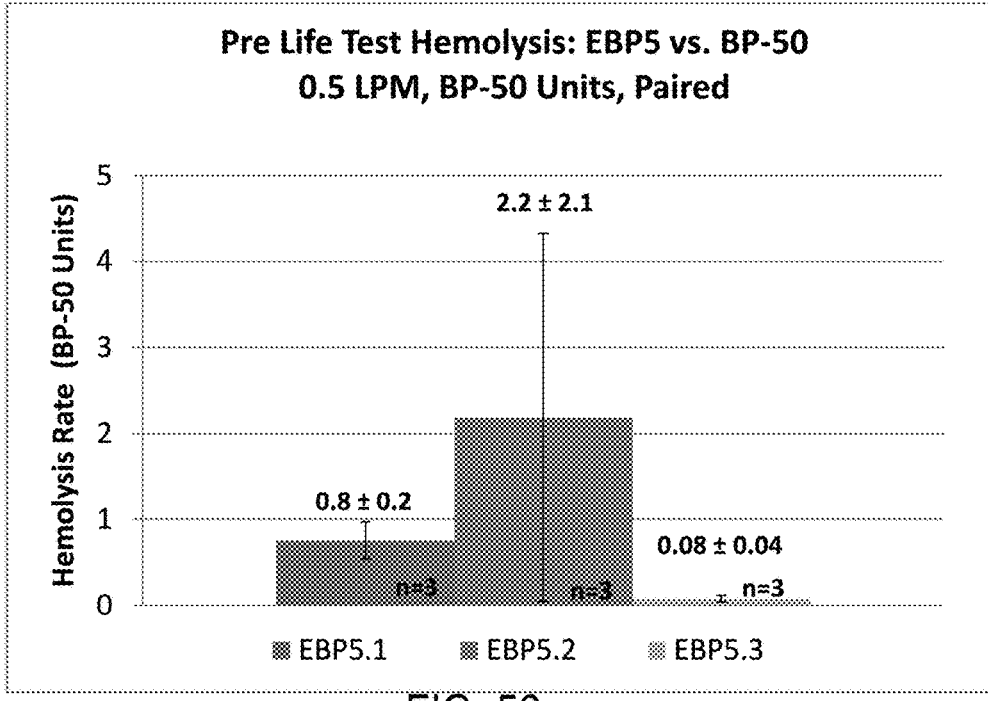
FIG. 56 is a chart depicting paired results of a hemolysis test using test pumps units against BP-50 Units.
Figure 57:
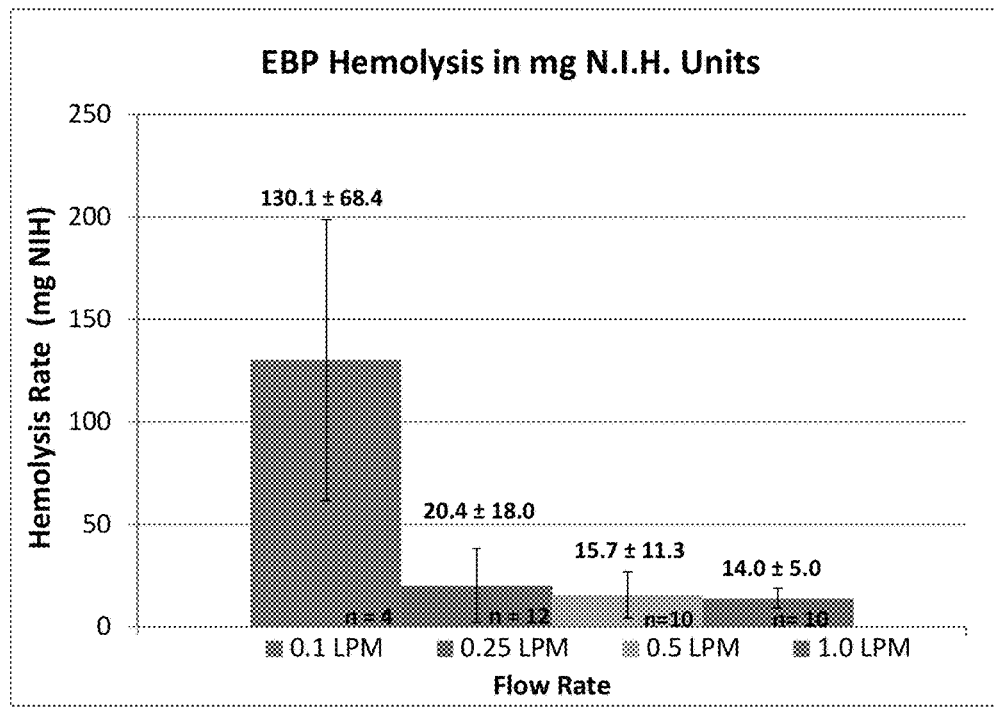
FIG. 57 is a chart depicting test pump hemolysis at various flow rates expressed in mg N.I.H. units according to one embodiment
Figure 58:
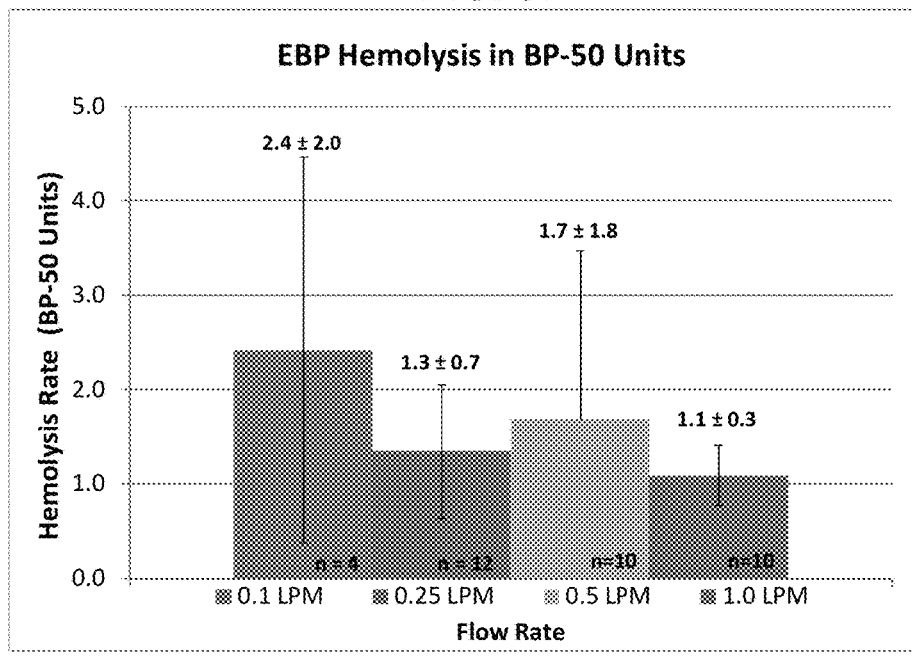
FIG. 58 is a chart depicting test pump hemolysis at various flow rates expressed in BP-50 units according to one embodiment.

FIG. 55 shows the unpaired results for EBPs compared with BP-50 against mg N.I.H. Units. FIG. 56 shows the paired results of the Pre Life Test Hemolysis Results for EBPs against BP-50 Units. FIG. 57 is a chart depicting test pump hemolysis at various flow rates expressed in mg N.I.H. units, while FIG. 58 is a chart depicting test pump hemolysis at various flow rates expressed in BP-50 units.

Several studies were conducted to determine the optimal distances for the gaps 540 and 542 between the impeller and the impeller casing. These gaps are preferably optimized to limit the destruction of red blood cells (RBCs) by exposure to shear stress, as a result of hemolysis. In addition, it is desirable to achieve a hydrodynamic bearing effect in the upper gap to counter the hydrostatic force of pressure acting on the bottom surface of the rotor and reduce forces on the upper bearing. The upper and lower rotor-housing gaps were therefore selected to provide minimal hemolysis and maximal hydrodynamic bearing effect for the EBPs whose application requires a design point speed, flow, and pressure head of 3800 RPM, 538 mL/min, and 125 mmHg and an ideal operating flow range of 50-1250 mL/min.

In highly simplified models of blood damage, hemolysis is a power law function of shear stress and exposure time. RBCs can tolerate high shear stresses (>100 Pa) for short exposure times (<1 s). In a laminar flow between a rotating plate and a parallel stationary plate, shear stress increases directly with surface velocity and inversely with gap width. Small gaps on the order of the RBC diameter (10 μm) exclude RBCs and limit hemolysis. Large gaps on the order of 1 mm are associated with recirculation that can extend exposure times and promote hemolysis. Through computational fluid dynamics modeling of the EBP, upper gaps of 50, 75 μm, and 125 μm were tested and a lower gap of 250 μm was tested to evaluate hemolysis. In practice, these gaps have manufacturing tolerances, and manufacturing methods are developed on a situational basis to limit the tolerances for these gap distances as low as possible, practical or economical.

For the first study described below, EBPs were built with target rotor-housing upper gaps of 125±50 μm and target rotor-housing lower gaps of 250±50 μm. The machined components had tolerances of ±100 μm. An average 3 measurements of total (i.e. upper+lower) gap on assembled pump was reported. Conical housing or rotor surfaces were lapped to achieve the target total gap. The upper bearing gap was set by potting the upper bearing.

In vitro hemolysis tests of EBP prototypes with a 125 μm upper gap and a 250 μm lower gap demonstrated hemolysis rates averaging 14-130 mg N.I.H. (or mg plasma free hemoglobin added per 100 L of blood pumped) across the 100-1000 mL/min operating range of pump flows (shown in FIG. 57). This compares favorably with concurrent tests of the FDA-approved Medtronic Model BP-50 Bio-Pump® Centrifugal Blood Pump across the same flow range, with the EBP demonstrating normalized hemolysis rates of 1.1-2.4 BP-50 units (shown in FIG. 58).

In vitro hemolysis tests of EBP prototypes with a 50 µm upper gap demonstrated hemolysis rates averaging 3.0-4.2 mg N.I.H. (or mg plasma free hemoglobin added per 100 L of blood pumped) while operating at 500 mL/min (shown in FIG. 55). This compares favorably with concurrent tests of the FDA-approved Medtronic Model BP-50 Bio-Pump® Centrifugal Blood Pump at the same flow rate, with the EBP demonstrating normalized hemolysis rates of 0.8-2.0 BP-50 units (shown in FIG. 56).

In vitro hemolysis tests of EBP prototypes with a 100 µm upper gap demonstrated hemolysis rates averaging 0.2 mg N.I.H. (or mg plasma free hemoglobin added per 100 L of blood pumped) while operating at 500 mL/min (shown in FIG. 55). This compares favorably with concurrent tests of the FDA-approved Medtronic Model BP-50 Bio-Pump® Centrifugal Blood Pump at the same flow rate, with the EBP demonstrating normalized hemolysis rates of <0.1 BP-50 units (shown in FIG. 56).

Hydrodynamic bearing effects arise when a fluid film between a moving and stationary surface converges in the direction of sliding. Fluid is drawn into and through the film by the moving surface. The pressure within the fluid film is proportional to surface speed times fluid viscosity and to the inverse square of film thickness. Hydrodynamic bearing forces between the surfaces are proportional to the area over which this pressure acts.

The upper surfaces of the 7 impeller blades of the EBP have a combined area of 96.1 $mm^2$ (with reference to FIG. 4G). In vitro bearing load studies of EBP prototypes without motor backplates demonstrate unloading of the upper bearing at 4000 RPM for upper gaps of 0-175 µm (Shown in FIG. 4H).

Based on the above analyses and testing, the upper and lower rotor-housing gaps in this embodiment of the EBP are in the range of 25-225 µm and 150-350 µm, respectively, or preferably in the range of 75-175 µm and 200-300 µm, respectively, or nominally 100 µm and 250 µm, respectively.

An arteriovenous fistula (AVF) is created when a direct surgical connection is made between an artery and vein. In order to attempt to make an AVF for use as a vascular access site for routine hemodialysis, the patient generally needs a peripheral vein with a diameter >2.5-3.0 mm. After creation, the "inflow" artery and the "outflow" vein that comprise the AVF need to dilate and the blood flow in the AVF outflow vein needs to increase for the AVF to mature and become usable for hemodialysis. According to criteria established by the National Kidney Foundation (KDOQI) for an AVF to be deemed mature, the outflow vein must dilate to at least 6 mm and the outflow vein blood flow must increase to at least 600 mL/min.

Figure 59:
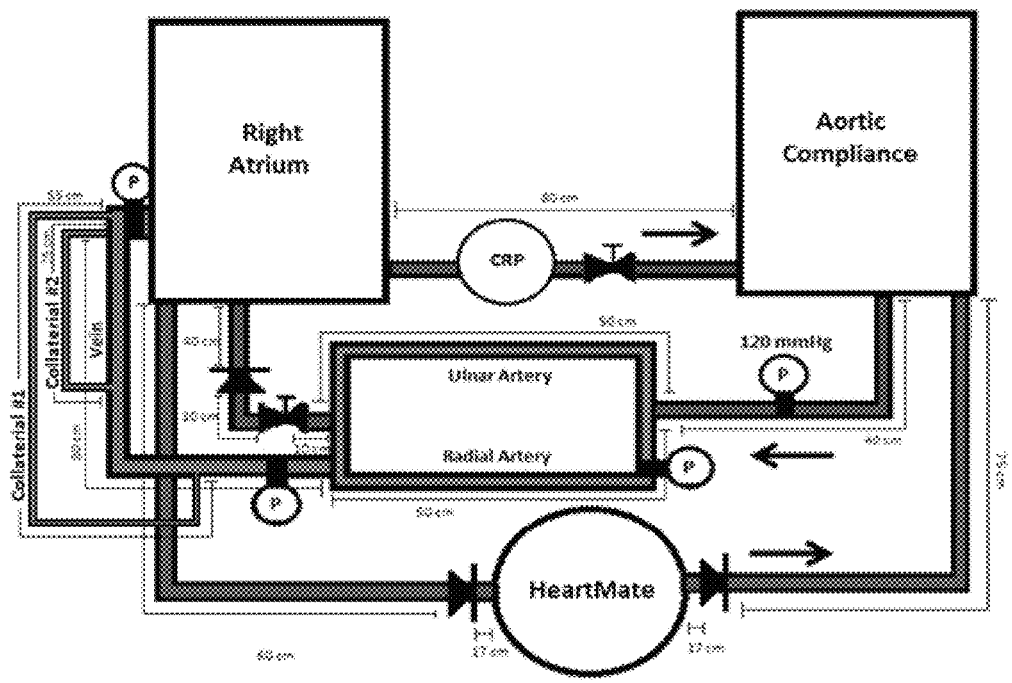
FIG. 59 is a mock test loop of a forearm AVF mock loop according to one embodiment.
Figure 60:
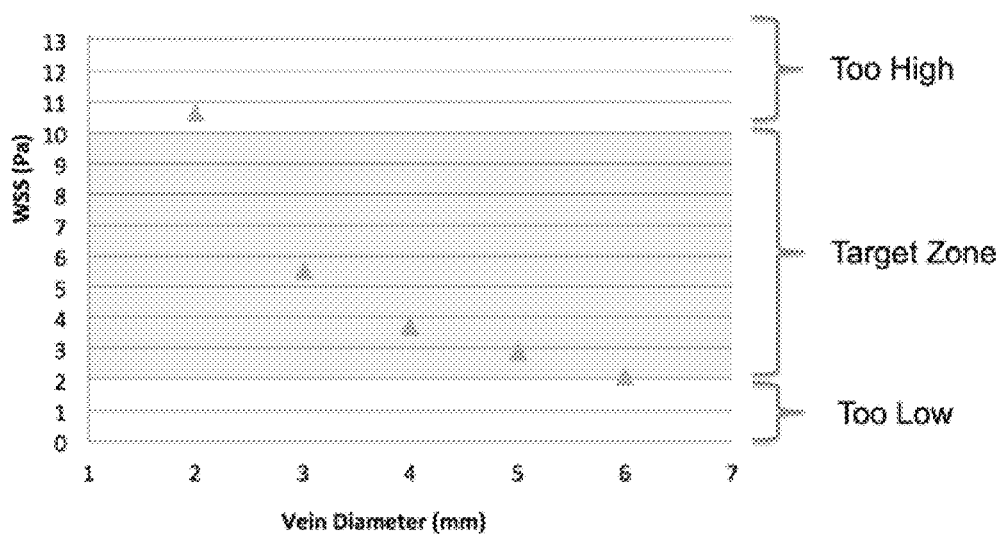
FIG. 60 is a graph depicting WSS doses against vein diameter according to one embodiment.

Using the mock AVF loop shown in FIG. 59. a bench top experiment was performed to evaluate the effect of AVF outflow vein diameter on AVF outflow vein wall shear stress (WSS) when the inflow artery starting diameter was 4 mm (ID). A HeartMate 2000 IP LVAS was used to generate MAP=120 mmHg in the mock circulatory loop. Approximately 50 cm of Tygon tubing of 4 mm ID was used to simulate the AVF inflow radial artery. Approximately 80 cm of Tygon tubing was used to simulate the AVF outflow cephalic vein with diameters of 2, 3, 4, 5, or 6 mm ID. A Transonic (TS410/ME3PXL) ultrasonic flow sensor was used to determine blood flow rates in the AVF outflow vein. NETech (Digimano 200-2000IN) pressure sensors were placed at the pump inlet, pump outlet, and conduit-vein anastomosis. A 35% glycerine in tap water solution @ 22° C. was used to simulate blood. As shown in FIG. 60, AVF outflow vein WSS levels vary widely with AVF outflow vein diameters demonstrating that arterial blood pressure and vessel diameters determine AVF outflow vein WSS levels, factors which cannot be effectively controlled during AVF creation and maturation.

Figure 53:
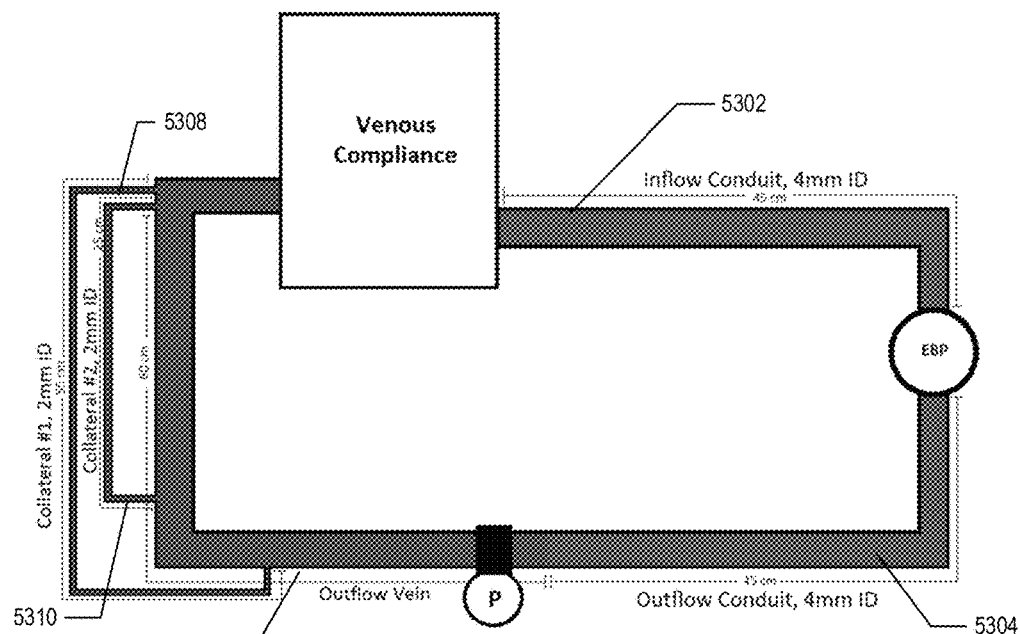
FIG. 53 is an illustration of a mock circulatory loop used during various studies and experiments according to one embodiment.
Figure 61:
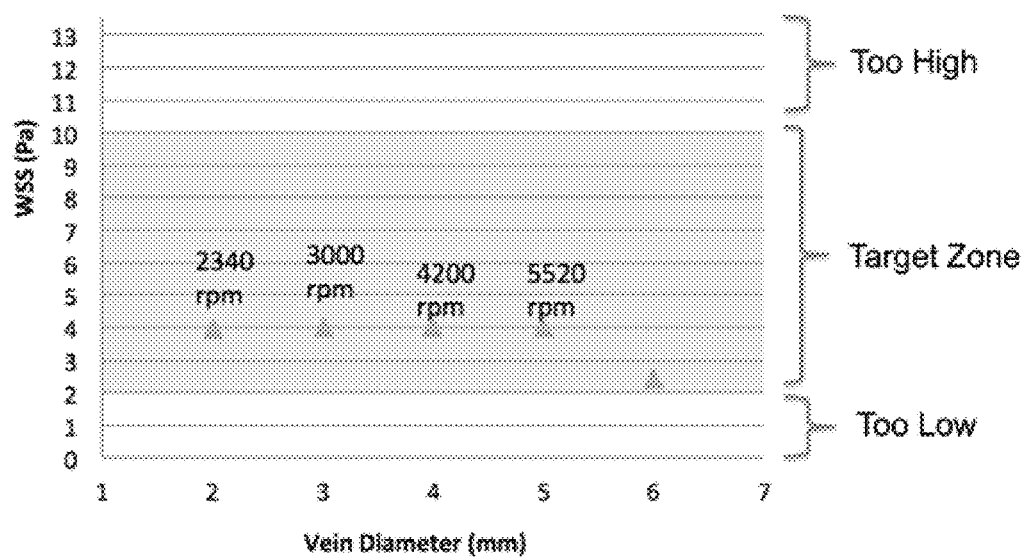
FIG. 61 is a graph depicting WSS doses against vein diameter according to another embodiment.

Using a mock AVF loop shown in FIG. 53, a bench top experiment was performed to evaluate the effect of AFE System pump speed and AFE System outflow vein diameter on AFE System outflow vein wall shear stress (WSS). The test loop includes inflow and outflow conduits 5302 and 5304, a mock outflow vein 5306 and mock collateral vessels 5308 and 5310. A 1 L reservoir was used to simulate venous system Approximately 45 cm of 4 mm ID Tygon tubing was used to simulate the AFE System inflow and outflow conduits. Approximately 80 cm of Tygon tubing was used to simulate the outflow vein with diameters of 2, 3, 4, 5, or 6 mm ID. A Transonic (TS410/ME3PXL) ultrasonic flow sensor was used to determine blood flow rates in the AVF outflow vein. NETech (Digimano 200-2000IN) pressure sensors were placed at the pump inlet, pump outlet, and conduit-vein anastomosis. A 35% glycerine in tap water solution @ 22° C. was used to simulate blood. As shown in FIG. 61, a consistent WSS dose of 4 Pa could be administered to the AFE System outflow vein with vein diameters up to 5 mm by varying the speed of the pump.

While the invention has been explained in relation to exemplary aspects and embodiments, it is to be understood that various modifications thereof will become apparent to those skilled in the art upon reading the description. Therefore, it is to be understood that the invention disclosed herein is intended to cover such modifications as fall within the scope of the appended claims.

What is claimed is:

1. A blood pump system comprising:
   a centrifugal blood pump with an operating range between 50 milliliters per minute and 1500 milliliters per minute, comprising:
   a pump housing defining a pump inlet to receive blood and direct blood onto an impeller, the pump housing having a top pivot bearing extending from a top of the housing into the inlet, and a bottom pivot bearing extending from a bottom of the housing into the interior space of the housing, wherein an axial load can be shared between the top pivot bearing and the bottom pivot bearing,
   the impeller suspended within the housing, the impeller having:
      an impeller pivot having a first end to engage the top pivot and a second end to engage the bottom pivot;
      a plurality of blades on the top surface of the impeller and extending radially away from a center of the impeller, the blades to force blood received at the inlet through the pump housing and to the outlet; and,
      at least one lumen extending parallel to a central axis of the impeller from the bottom surface through the impeller to a top surface;
   at least one magnet mechanically engaged to the impeller; and
   an electric motor, formed from a magnet assembly comprising the at least one magnet and an electric coil assembly, to magnetically engage the at least one magnet, wherein the electric motor rotates the at least one magnet and the impeller; and a first conduit having a first proximal end and a first distal end, the first proximal end configured for a fluid communication with the pump inlet and the first distal end configured for placement within the lumen of a donating vessel;

a second conduit having a second proximal end and a second distal end, the second proximal end configured for a fluid communication with the pump outlet and the second distal end configured for placement within the lumen of a peripheral vein; and wherein at least one of the first conduit or the second conduit comprises a reinforcement segment of a shape memory material, a self-expanding material, or a radially expansive material formed in a braid or coil pattern.

2. The blood pump system of claim 1, wherein the pump inlet comprises an inflow diffuser.

3. The blood pump system of claim 1, wherein a portion of the top pivot bearing, the bottom pivot bearing, or the impeller pivot comprises alumina.

4. The blood pump system of claim 3, wherein a portion of the top pivot bearing, the bottom pivot bearing, or the impeller pivot further comprises zirconia.

5. The blood pump system of claim 3, wherein a portion of the top pivot bearing, the bottom pivot bearing, or the impeller pivot further comprises silicon carbide.

6. The blood pump system of claim 1, wherein a portion of the top pivot bearing, the bottom pivot bearing, or both pivot bearings comprises polyethylene.

7. The blood pump system of claim 6, wherein the polyethylene is an ultrahigh molecular weight polyethylene.

8. The blood pump system of claim 1, wherein the pump housing further comprises a top bezel where the top pivot bearing extends from a top of the housing into the inlet, and a bottom bezel where the bottom pivot bearing extends from a bottom of the housing into the interior space of the housing.

9. The blood pump system of claim 1, wherein the ratio of the summed area of a top surface of the blades to the total area of the rotor top surface, including the top surface of the blades, is less than one of 0.5, 0.4, 0.3, 0.2, 0.15, and 0.10.

10. The blood pump system of claim 1, wherein a first gap between the impeller and a top portion of the housing is in a first range between 0.05 mm and 0.3 mm.

11. The blood pump system of claim 1, wherein a second gap between the impeller and the bottom of the housing is in a second range between 0.1 mm and 0.5 mm.

12. The blood pump system of claim 1, comprising a ferromagnetic backplate to magnetically engage the at least one magnet.

13. The blood pump system of claim 12, wherein the electric coil assembly is positioned between the ferromagnetic backplate and the at least one magnet.

14. The blood pump system of claim 12, wherein a portion of the impeller pivot is in contact with the top pivot bearing and an axial force of the portion of the impeller pivot on the top pivot bearing is less than one of 3 N, 2.2 N or 1 N when an impeller speed is less than or equal to 6000 rpm.

15. The blood pump system of claim 1, further comprising one or more side ports in fluid communication with at least one conduit.

16. The blood pump system of claim 15, wherein the one or more side ports are configured to enable the insertion of guidewires and catheters into the conduits.

17. The blood pump system of claim 15, wherein one or more side ports may be secured to the pump using radially-compressive connectors.

18. The blood pump system of claim 1, wherein the blood pump comprises polycarbonate or polyetheretherketone.

19. The blood pump system of claim 1, wherein one or both conduits comprise polyurethane or silicone.

20. The blood pump system of claim 19, wherein the polyurethane is Pellethane or Carbothane.

21. The blood pump system of claim 20, wherein the Carbothane is PC-3575 Carbothane.

22. The blood pump system of claim 1, wherein the shape memory material is nitinol wire.

23. The blood pump system of claim 1, wherein at least one blood-contacting surface of the blood pump, conduits, or side ports comprises an antithrombotic coating.

24. The blood pump system of claim 23, wherein the antithrombotic coating comprises heparin.

25. The blood pump system of claim 1, wherein one or both conduits may be secured to the pump using radially-compressive connectors.

26. The blood pump system of claim 1, further comprising one or more attachable conduit cuffs to engage at least one of the first conduit or the second conduit.

27. The blood pump system of claim 26, wherein each of the one or more attachable conduit cuffs comprises an upper portion and a lower portion configured to mechanically engage, wherein when engaged the upper portion and lower portion define a channel to receive a conduit in fluid communication with the blood pump.

28. The blood pump system of claim 26, wherein the conduit cuffs comprise Dacron or polyester velour.

29. The blood pump system of claim 1, wherein 10% or less of the impeller top surface area forms a hydrodynamic bearing during operation.

30. The blood pump system of claim 29, wherein a portion of the impeller pivot is in contact with the top pivot bearing and an axial force of the portion of the impeller pivot on the top pivot bearing is less than one of 3 N, 2.2 N or 1 N when an impeller speed is less than or equal to 6000 rpm.

31. The blood pump system of claim 1, wherein 10% to 50% of the impeller top surface area forms a hydrodynamic bearing during operation.

32. The blood pump system of claim 31, wherein a portion of the impeller pivot is in contact with the top pivot bearing and an axial force of the portion of the impeller pivot on the top pivot bearing is less than one of 3 N, 2.2 N or 1 N when an impeller speed is less than or equal to 6000 rpm.

33. The blood pump system of claim 1, wherein 50% or more of the impeller top surface area forms a hydrodynamic bearing during operation.

34. The blood pump system of claim 33, wherein a portion of the impeller pivot is in contact with the bottom pivot bearing and an axial force of the portion of the impeller pivot on the bottom pivot bearing is greater than 0.1 N, 0.5 N, 1 N, 2 N, 3 N, 4 N, 5 N, 7.5 N, and 10 N when an impeller speed is 0 rpm.

35. The blood pump system of claim 34, wherein a portion of the impeller pivot is in contact with the bottom pivot bearing and the axial force of the portion of the impeller pivot on the bottom pivot bearing is between 2 N and 8 N when the impeller speed is 0 rpm.

36. The blood pump system of claim 33, wherein a portion of the impeller pivot is in contact with the top pivot bearing and an axial force of the portion of the impeller pivot on the top pivot bearing is less than one of 3 N, 2.2 N or 1 N when an impeller speed is less than or equal to 6000 rpm.

37. The blood pump system of claim 1, wherein a portion of the impeller pivot is in contact with the top pivot bearing and an axial force of the portion of the impeller pivot on the top pivot bearing is less than one of 3 N, 2.2 N or 1 N when an impeller speed is less than or equal to 6000 rpm.

38. The blood pump system of claim 1, wherein the operating range is between 100 milliliters per minute and 1000 milliliters per minute.

39. The blood pump system of claim 38, wherein a rate of hemolysis across a flow range of 100 milliliters per minute to 1000 milliliters per minute is less than 20 mg N.I.H.

* * * * *